US011725059B2

(12) United States Patent
Brentjens et al.

(10) Patent No.: US 11,725,059 B2
(45) Date of Patent: *Aug. 15, 2023

(54) ANTIBODIES TARGETING B-CELL MATURATION ANTIGEN AND METHODS OF USE

(71) Applicants: MEMORIAL SLOAN KETTERING CANCER CENTER, New York, NY (US); EUREKA THERAPEUTICS, INC., Emeryville, CA (US)

(72) Inventors: Renier J. Brentjens, New York, NY (US); Eric L. Smith, New York, NY (US); Cheng Liu, Emeryville, CA (US)

(73) Assignees: MEMORIAL SLOAN KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 17/173,716

(22) Filed: Feb. 11, 2021

(65) Prior Publication Data

US 2022/0315660 A1  Oct. 6, 2022

Related U.S. Application Data

(63) Continuation of application No. 16/732,089, filed on Dec. 31, 2019, now Pat. No. 10,947,314, which is a continuation of application No. 15/613,986, filed on Jun. 5, 2017, now Pat. No. 10,562,972, which is a continuation of application No. PCT/US2015/064119, filed on Dec. 4, 2015.

(60) Provisional application No. 62/088,246, filed on Dec. 5, 2014.

(51) Int. Cl.
| | |
|---|---|
| *A61K 39/395* | (2006.01) |
| *C07K 16/28* | (2006.01) |
| *C07K 14/705* | (2006.01) |
| *A61K 47/68* | (2017.01) |
| *A61P 35/00* | (2006.01) |
| *G01N 33/68* | (2006.01) |

(52) U.S. Cl.
CPC ...... *C07K 16/2878* (2013.01); *A61K 47/6849* (2017.08); *A61P 35/00* (2018.01); *C07K 14/70575* (2013.01); *C07K 16/2896* (2013.01); *G01N 33/6863* (2013.01); *C07K 2317/21* (2013.01); *C07K 2317/24* (2013.01); *C07K 2317/34* (2013.01); *C07K 2317/622* (2013.01); *C07K 2317/92* (2013.01); *C07K 2319/21* (2013.01); *C07K 2319/30* (2013.01); *C07K 2319/42* (2013.01); *G01N 2333/70578* (2013.01)

(58) Field of Classification Search
None
See application file for complete search history.

(56) References Cited

U.S. PATENT DOCUMENTS

| | | | |
|---|---|---|---|
| 4,956,778 A | 9/1990 | Naito | |
| 5,091,513 A | 2/1992 | Huston et al. | |
| 5,132,405 A | 7/1992 | Huston et al. | |
| 7,083,785 B2 | 8/2006 | Browning et al. | |
| 7,605,236 B2 | 10/2009 | Ruben et al. | |
| 8,399,645 B2 | 3/2013 | Campana et al. | |
| 8,497,118 B2 | 7/2013 | Jensen | |
| 8,802,374 B2 | 8/2014 | Jensen | |
| 9,034,324 B2 | 5/2015 | Kalled et al. | |
| 9,243,058 B2 * | 1/2016 | Armitage | C07K 16/18 |
| 10,562,972 B2 | 2/2020 | Brentjens et al. | |
| 10,821,135 B2 | 11/2020 | Brentjens et al. | |
| 10,918,665 B2 | 2/2021 | Brentjens et al. | |
| 10,947,314 B2 | 3/2021 | Brentjens et al. | |
| 11,000,549 B2 | 5/2021 | Brentjens et al. | |
| 11,066,475 B2 | 7/2021 | Sather et al. | |
| 2005/0196754 A1 | 9/2005 | Drmanac et al. | |
| 2009/0169562 A1 | 7/2009 | Throsby et al. | |
| 2011/0117093 A1 | 5/2011 | Ruben et al. | |
| 2012/0082661 A1 | 4/2012 | Kalled et al. | |
| 2013/0336964 A1 | 12/2013 | Rovati et al. | |
| 2014/0161828 A1 | 6/2014 | Armitage et al. | |
| 2014/0193433 A1 | 7/2014 | Borges et al. | |
| 2014/0243504 A1 | 8/2014 | Davis et al. | |
| 2015/0051266 A1 | 2/2015 | Kochenderfer | |
| 2016/0046724 A1 | 2/2016 | Brogdon et al. | |
| 2017/0226216 A1 | 8/2017 | Morgan et al. | |
| 2018/0360880 A1 | 12/2018 | Brentjens et al. | |
| 2019/0161553 A1 | 5/2019 | Sather et al. | |
| 2021/0324100 A1 | 10/2021 | Sather et al. | |
| 2021/0393690 A1 | 12/2021 | Blythe et al. | |

FOREIGN PATENT DOCUMENTS

| | | |
|---|---|---|
| CN | 107827989 A | 3/2018 |
| EP | 1 468 694 A1 | 10/2004 |
| JP | 2011-178691 A | 9/2011 |
| WO | WO 2008/116149 A2 | 9/2008 |

(Continued)

OTHER PUBLICATIONS

U.S. Appl. No. 15/613,638 (US 2018/0360880), filed Jan. 19, 2018 (Dec. 20, 2018).
U.S. Appl. No. 15/613,986 (U.S. Pat. No. 10,562,972), filed Jun. 5, 2017 (Feb. 18, 2020).
U.S. Appl. No. 16/732,089 (U.S. Pat. No. 10,947,314), filed Dec. 31, 2019 (Mar. 16, 2021).
U.S. Appl. No. 15/613,638, dated Jan. 12, 2021 Issue Fee Payment.
U.S. Appl. No. 15/613,638, dated Oct. 15, 2020 Notice of Allowance.

(Continued)

*Primary Examiner* — Meera Natarajan
(74) *Attorney, Agent, or Firm* — Baker Botts L.L.P.

(57) ABSTRACT

The presently disclosed subject matter provides antibodies that bind to B-cell maturation antigen (BCMA) and methods of using the same.

40 Claims, 12 Drawing Sheets

Specification includes a Sequence Listing.

(56) References Cited

FOREIGN PATENT DOCUMENTS

| WO | WO 2010/054007 A1 | 5/2010 |
|---|---|---|
| WO | WO 2010/104949 A2 | 9/2010 |
| WO | WO 2011/085103 A2 | 7/2011 |
| WO | WO 2012/066058 A1 | 5/2012 |
| WO | WO 2012/079000 A1 | 6/2012 |
| WO | WO 2012/143498 A1 | 10/2012 |
| WO | WO 2013/072406 A1 | 5/2013 |
| WO | WO 2013/072415 A1 | 5/2013 |
| WO | WO 2013/154760 A1 | 10/2013 |
| WO | WO 2014/087010 A1 | 6/2014 |
| WO | WO 2014/089335 A2 | 6/2014 |
| WO | WO 2014/134165 A1 | 9/2014 |
| WO | WO 2014/191128 A1 | 12/2014 |
| WO | WO 2015/142675 A2 | 9/2015 |
| WO | WO 2015/157391 A1 | 10/2015 |
| WO | WO 2015/158671 A1 | 10/2015 |
| WO | WO 2016/014565 A2 | 1/2016 |
| WO | WO 2016/014789 A2 | 1/2016 |
| WO | WO 2016/090320 A1 | 6/2016 |
| WO | WO 2016/090327 A2 | 6/2016 |
| WO | WO 2016/094304 A2 | 6/2016 |
| WO | WO 2017/041143 A1 | 3/2017 |
| WO | WO 2017/087547 A1 | 5/2017 |
| WO | WO 2018/197675 A1 | 11/2018 |
| WO | WO 2018/204427 A1 | 11/2018 |
| WO | WO 2020/092848 A2 | 5/2020 |

OTHER PUBLICATIONS

U.S. Appl. No. 15/613,638, dated Sep. 3, 2020 Request for Continued Examination (RCE).
U.S. Appl. No. 15/613,638, dated Jun. 24, 2020 Notice of Allowance.
U.S. Appl. No. 15/613,638, dated Jun. 4, 2020 Response to Non-Final Office Action.
U.S. Appl. No. 15/613,638, dated Apr. 30, 2020 Non-Final Office Action.
U.S. Appl. No. 15/613,638, dated Jan. 27, 2020 Response to Restriction/Election.
U.S. Appl. No. 15/613,638, dated Oct. 25, 2019 Requirement for Restriction/Election.
U.S. Appl. No. 15/613,986, dated Dec. 31, 2019 Issue Fee Payment.
U.S. Appl. No. 15/613,986, dated Oct. 2, 2019 Notice of Allowance.
U.S. Appl. No. 15/613,986, dated Sep. 19, 2019 Request for Continued Examination (RCE).
U.S. Appl. No. 15/613,986, dated Jul. 11, 2019 Notice of Allowance.
U.S. Appl. No. 15/613,986, dated May 21, 2019 Response to Non-Final Office Action.
U.S. Appl. No. 15/613,986, dated Feb. 21, 2019 Non-Final Office Action.
U.S. Appl. No. 15/613,986, dated Jan. 31, 2019 Response to Non-Final Office Action and Request for Continued Examination.
U.S. Appl. No. 15/613,986, dated Nov. 2, 2018 Notice of Allowance.
U.S. Appl. No. 15/613,986, dated Aug. 3, 2018 Response to Non-Final Office Action.
U.S. Appl. No. 16/732,089, dated Feb. 10, 2021 Issue Fee Payment.
U.S. Appl. No. 16/732,089, dated Nov. 12, 2020 Notice of Allowance.
U.S. Appl. No. 16/732,089, dated Sep. 3, 2020 Request for Continued Examination (RCE).
U.S. Appl. No. 16/732,089, dated Jun. 26, 2020 Notice of Allowance.
U.S. Appl. No. 16/732,089, dated Jun. 4, 2020 Response to Non-Final Office Action.
U.S. Appl. No. 16/732,089, dated Mar. 9, 2020 Non-Final Office Action.
U.S. Appl. No. 16/178,571, filed Nov. 1, 2018, Sather, et al. (not submitted herewith pursuant to the waiver of 37 C.F. R. § 1.98(a)(2)(iii) issued by the Office dated Sep. 21, 2004)).
U.S. Appl. No. 15/613,638, dated Jan. 12, 2012 Issue Fee Payment.
Ali et al., "T cells expressing an anti-B-cell maturation antigen chimeric antigen receptor cause remissions of multiple myeloma," Blood 128(13):1688-1700 (2016).
Allen, "Ligand-Targeted Therapeutics in Anticancer Therapy," Nat. Rev. Cancer 2:750-763 (2002).
Altschul et al., "Basic Local Alignment Search Tool," J. Mol. Biol. 215(3):403-410 (1990).
Altschul et al., "Gapped BLAST and PSI-BLAST: a new generation of protein database search programs," Nucleic Acids Res. 25(17):3389-3402 (1997).
Amon et al., "Monoclonal Antibodies for Immunotargeting Of Drugs In Cancer Therapy," in Monoclonal Antibodies and Cancer Therapy, Reisfeld et al. (eds.), pp. 243-256 (Alan R. Liss, Inc. 1985).
Azinovic et al., "Survival benefit associated with human anti-mouse antibody (HAMA) in patients with B-cell malignancies," Cancer Immunol Immunother 55:1451-1458 (2006).
Bataille et al., "The phenotype of normal, reactive and malignant plasma cells. Identification of 'many and multiple myelomas' and of new targets for myeloma therapy," Haematologica 91:1234-1240 (2006).
Bertilaccio et al., "Low-Dose Lenalidomide Improves CAR-Based Immunotherapy In CLL By Reverting T-Cell Defects In Vivo," Blood 122:4171 (2013).
Bird et al., "Single-Chain Antigen-Binding Proteins," Science 242(4877):423-426 (1988).
Boyd et al., "The Clinical Impact and Molecular Biology of del(17p) in Multiple Myeloma Treated with Conventional or Thalidomide-Based Therapy," Genes, Chromosomes & Cancer 50:765-774 (2011).
Brennan et al., "Preparation of Bispecific Antibodies by Chemical Recombination of Monoclonal Immunoglobulin G$_{1}$ Fragments," Science 229(4708):81-83 (1985).
Brentjens et al., "CD19-Targeted T Cells Rapidly Induce Molecular Remissions in Adults with Chemotherapy-Refractory Acute Lymphoblastic Leukemia," Science Translational Medicine 5:177ra38 (2013).
Brentjens et al., "Eradication of systemic B-cell tumors by genetically targeted human T lymphocytes co-stimulated by CD80 and interleukin-15," Nature Medicine 9(3):279-286 (2003).
Brentjens et al., "Genetically Targeted T cells Eradicate Systemic Acute Lymphoblastic Leukemia Xenografts," Clin Cancer Res. 13(18):5426-5435 (2007).
Brentjens et al., "Safety and persistence of adoptively transferred autologous CD19-targeted T cells in patients with relapsed or chemotherapy refractory B-cell leukemias," Blood 118(18):4817-4828 (2011).
Brocks et al., "A TNF receptor antagonistic scFv, which is not secreted in mammalian cells, is expressed as a soluble mono- and bivalent scFv derivative in insect cells," Immunotechnology 3:173-184 (1997).
Caron et al., "Engineered Humanized Dimeric Forms of IgG are More Effective Antibodies," J Exp. Med 176:1191-1195 (1992).
Carpenter et al., "B-cell Maturation Antigen is a Promising Target for Adoptive T-cell Therapy of Multiple Myeloma," Clin Cancer Res. 19(8):2048-2060 (2013).
Casset et al., "A peptide mimetic of an anti-CD4 monoclonal antibody by rational design," Biochemical and Biophysical Research Communications 307:198-205 (2003).
Chen et al., "Selection and Analysis of an Optimized Anti-VEGF Antibody: Crystal Structure of an Affinity-matured Fab in Complex with Antigen," J. Mol. Biol. 293:865-881 (1999).
Cheri et al. (J. Mol. Bio. (1999) 293, 865-881) (Year: 1999).
Clinical Trial Identifier NCT02215967, "Study of T Cells Targeting B-Cell Maturation Antigen for Previously Treated Multiple Myeloma," first posted Aug. 13, 2014, accessible at https://clinicaltrials.gov/ct2/show/NCT02215967.

(56) References Cited

OTHER PUBLICATIONS

Clinical Trial Identifier NCT02546167, "CART-BCMA Cells for Multiple Myeloma," Retrieved on https://clinicaltrials.gov/ct2/show/NCT02546167. Retrieved on Oct. 22, 2018.
Coico (Koyko) et al., "Immunology," translation from English, edited by N.B Serebryanaya, Mosow, "Akademiya," 2008, p. 37 (in Russian with English translation).
Creative Biomart, Anti-Human TNFRSF17 scFv Stable Cell Line-CHO. (Aug. 30, 2013) [according to the properties of the posted document] (Retrieved from the Internet Mar. 23, 2016: <http://www.creativebiomart.net/pdf/CSC-P0544,TNFRSF17.pdf>); p. 1.
Cuesta et al., "Multivalent antibodies: when design surpasses evolution," Trends in Biotechnology 28:355-362 (2010).
Davila et al., "Efficacy and Toxicity Management of 19-28z CAR T Cell Therapy in B Cell Acute Lymphoblastic Leukemia," Science Translational Medicine 6:224ra25 (2014).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084 (2002).
Dimopoulos et al. "Current treatment landscape for relapsed and/or refractory multiple myeloma," Nat Rev Clin Oncol (2015) 12:42-54.
Dondelinger et al., "Understanding the Significance and Implications of Antibody Numbering and Antigen-Binding Surface/Residue Definition," Frontiers in Immunology, pp. 1-15 (2018).
Dudley et al., "Adoptive Cell Therapy for Patients With Metastatic Melanoma: Evaluation of Intensive Myeloablative Chemoradiation Preparative Regimens," J Clin Oncol. 26(32):5233-5239 (2008).
Examination Report (Communication pursuant to Article 94(3) EPC) dated Apr. 2, 2020 for European Patent Application No. 15864826.1.
Extended European Search Report dated Jul. 24, 2018 in Application No. EP 15864826.
Extended European Search Report dated Jul. 17, 2018 in Application No. 15864646.3.
Fife et al., "Inhibition of T cell activation and autoimmune diabetes using a B cell surface-linked CTLA-4 agonist," J Clin Invst 116(8):2252-2261 (2006).
Flatman et al., "Process analytics for purification of monoclonal antibodies," J Chromatogr. B 848:79-87 (2007).
Frigyesi et al., "Robust isolation of malignant plasma cells in multiple myeloma," Blood 123(9):1336-1340 (2014).
Gade et al., "Targeted Elimination of Prostate Cancer by Genetically Directed Human T Lymphocytes," Cancer Res. 65:9080-9088 (2005).
Gahrton et al., "Allogeneic Bone Marrow Transplantation in Multiple Myeloma," The N. Engl. J. Med 325(18):1267-1273 (1991).
Garfall et al., "Immunotherapy with Chimeric Antigen Receptors for Multiple Myeloma," Discov Med., 17(91):37-46 (2014).
Gershoni et al., "Epitope mapping—The first step in developing epitope-based vaccines," Biod, Adis International Ltd, 21(3):145-156 (2007).
Giomarelli et al., "Inhibition of thrombin-induced platelet aggregation using human single-chain Fv antibodies specific for TREM-like transcript-1," Thromb Haemost 97:955-963 (2007).
Glennie et al., "Preparation and performance of bispecific F(ab' gamma)2 antibody containing thioether-linked Fab' gamma fragments," J. Immunol. 139:2367-2375 (1987).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia 1(2):123-127 (1999).
Harris et al., "Crystallographic Structure of an Intact IgG1 Monoclonal Antibody," Journal of Molecular Biology 275:861-872 (1998).
Hellstrom et al., "Antibodies for Drug Delivery," in Controlled Drug Delivery (2nd Ed.), Robinson et al. (eds.), pp. 623-653 (Marcel Dekker, Inc. 1987).

Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Hollyman et al., "Manufacturing Validation of Biologically Functional T Cells Targeted to CD19 Antigen for Autologous Adoptive Cell Therapy," J. Immunother 32(2):169-180 (2009).
Hunder et al., "Treatment of Metastatic Melanoma with Autologous CD4+ T Cells against NY-ESO-1," N. Engl. J. Med 358(25):2698-2703 (2008).
Huston et al., "Protein engineering of antibody binding sites: Recovery of specific activity in an anti-digoxin single-chain Fv analogue produced in *Escherichia coli*," PNAS USA 85:5879-5883 (1988).
International Search Report dated Mar. 3, 2016 in International Application No. PCT/US15/64112.
International Search Report dated May 31, 2016 in International Application No. PCT/US15/64119.
Kabat et al., Sequences of Proteins of Immunological Interest, 4th Edition, U.S. Department of Health and Human Services, National Institutes of Health (1987).
Kabat et al., Sequences of Proteins of Immunological Interest, vol. 1, Fifth Edition, U.S. Department of Health and Human Services, NIH Publication No. 91-3242 (1991).
Karpovsky et al., "Production of Target-Specific Effector Cells Using Hetero-Cross-Linked Aggregates Containing Anti-Target Cell And Anti-Fcγ Receptor Antibodies," J. Exp. Med. 160:1686-1701 (1984).
Kershaw et al., "Gene-Engineered T Cells as a Superior Adjuvant Therapy for Metastatic Cancer," J Immunol 173:2143-2150 (2004).
Klechevsky et al., "Antitumor activity of immunotoxins with T-cell receptor-like specificity against human melanoma xenografts," Cancer Res 68(15):6360-6367 (2008).
Kochenderfer et al., "Adoptive transfer of syngeneic T cells transduced with a chimeric antigen receptor that recognizes murine CD19 can eradicate lymphoma and normal B cells," Blood, 116(19):3875-3886 (2010).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Kuester et al., "Pharmacokinetics of Monoclonal Antibodies," in Pharmacokinetics and Pharmacodynamics of Biotech Drugs, ed. Bernd Meibohm, Wiley-VHC, chapter 3, p. 45-91 (2006).
Lammirimaki et al. (JBC 2001, 276:36687-36694) (Year: 2001).
Ledbetter et al., "Agonistic Activity of a CD40-Specific Single-Chain Fv Constructed from the Variable Regions of mAb G28-5," Crit Rev Immunol. 17:427-435 (1997).
LeFranc et al., "IMGT unique numbering for immunoglobulin and T cell receptor variable domains and Ig superfamily V-like domains," Dev Comp Immunol 27:55-77 (2003).
Liu et al., "Heteroantibody duplexes target cells for lysis by cytotoxic T lymphocytes," PNAS USA 82:8648-8652 (1985).
Lyddane et al., "Cutting Edge: CD28 Controls Dominant Regulatory T Cell Activity during Active Immunization," J. Immunol. 176:3306-3310 (2006).
MacCallum et al., "Antibody-antigen Interactions: Contact Analysis and Binding Site Topography," J. Mol. Biol. 262:732-745 (1996).
Maher et al., "Human T-lymphocyte cytotoxicity and proliferation directed by a single chimeric TCRζ/CD28 receptor," Nat. Biotechnol. 20:70-75 (2002).
Maus et al., "T Cells Expressing Chimeric Antigen Receptors Can Cause Anaphylaxis in Humans," Cancer Immunol Res 1(1):26-31 (2013).
Maus et al., "Zoom Zoom: Racing CARs for Multiple Myeloma," Clin Cancer Res., 19(8):1917-1919(2013).
McCafferty et al., "Phage antibodies: filamentous phage displaying antibody variable domains," Nature 348:552-554 (1990).
McKay Brown et al., "Tolerance to single, but not multiple, amino acid replacements in antibody V-H CDR2: A means of minimizing B cell wastage from somatic hypermutation?" The Journal Of Immunology, The American Association Of Immunologists, 156(9):3285-3291 (1996).

(56) References Cited

OTHER PUBLICATIONS

Meibohm (Pharmacokinetics arid Pharmacodynamics of Biotech Drugs, Wiley-VHC, 2006, chapter 3, p. 45-91) (Year: 2006).
Meyers et al., "Optimal alignments in linear space," Cabios 4(1):11-17 (1988).
Moosmayer et al., "A single-chain TNF receptor antagonist is an effective inhibitor of TNF mediated cytotoxicity," Ther Immunol. 2:31-40 (1995).
Morgan et al., "Case Report of a Serious Adverse Event Following the Administration of T Cells Transduced With a Chimeric Antigen Receptor Recognizing ERBB2," Molecular Therapy 18(4):843-851 (2010).
Needleman et al., "A General Method Applicable to the Search for Similarities in the Amino Acid Sequence of Two Proteins," J. Mol. Biol. 48:443-453 (1970).
Nasonov et al., "Belimumab: advancement in treatment of Systemic Lupus Erythematosus (SLE)," Federal State Budgetary Institution 'Scientific Research Institute for Rheumatology', RAMS, Moscow, 54(5):13-19 (2012) [with full English translation].
Order, S. "Analysis, Results, And Future Prospective of The Therapeutic Use Of Radiolabeled Antibody In Cancer Therapy," in Monoclonal Antibodies For Cancer Detection And Therapy, Baldwin et al. (eds.), pp. 303-316 (Academic Press 1985).
Ozhegov, S.I. The Thesaurus of the Russian Language: 80,000 words and idioms / S.I Ozhegov and N. Yu Shvedova; Russian Academy of Sciences, Institute of the Russian Language named after V.V. Vinogradov.—4th Edition, updated—Moscow: [A TEMP}, 2006. 1:375 (with full English translation).
Padlan et al. (PNAS 1989, 86:5938-5942) (Year: 1989).
Parkman R., "Clonal Analysis of Murine Graft-vs-Host Disease. I. Phenotypic and Functional Analysis of T Lymphocyte Clones," J. Immunol. (1986) 136(10):3543-3548.
Partial Supplementary European Search Report dated May 2, 2018 in Application No. 15864646.3.
Pascalis et al. (The Journal of Immunology (2002) 169, 3076-3084) (Year: 2002).
Pastan et al., "Immunotoxins in Cancer Therapy," Curr. Opin. Investig. Drugs 3(7):1089-1091 (2002).
Paulus, "Preparation and Biomedical Applications of Bispecific Antibodies," Behring Ins. Mitt. 78:118-132 (1985).
Payne, "Progress in immunoconjugate cancer therapeutics," Cancer Cell 3:207-212 (2003).
Pegram et al., "Tumor-targeted T cells modified to secrete IL-12 eradicate systemic tumors without need for prior conditioning," Blood 119(18):4133-4141 (2012).
Persic et al., "An integrated vector system for the eukaryotic expression of antibodies or their fragments after selection from phage display libraries," Gene 187:9-18 (1997).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the β2-Adrenergic Receptor," J Biol. Chem. 278(38):36740-36747 (2003).
Queen et al., "A humanized antibody that binds to the interleukin 2 receptor," PNAS USA 86:10029-10033 (1989).
Ramadoss et al., "An Anti-B Cell Maturation Antigen Bispecific Antibody for Multiple Myeloma," J. Am. Chem. Soc., 137:5288-5291 (2015).
Riechmann et al., "Reshaping human antibodies for therapy," Nature 332:323-327 (1988).
Ritter et al., "Serological Analysis of Human Anti-Human Antibody Responses in Colon Cancer Patients Treated with Repeated Doses of Humanized Monoclonal Antibody A33," Cancer Res 61:6851-6859 (2001).
Riviere et al., "Novel Strategies for Cancer Therapy: The Potential of Genetically Modified T Lymphocytes," Curr Hematol Rep 3:290-297 (2004).
Roberts et al., "Vaccination with CD20 peptides induces a biologically active, specific immune response in mice," Blood 99:3748-3755 (2002).
Rosenberg et al., "Adoptive cell transfer: a clinical path to effective cancer immunotherapy," Nature Reviews Cancer 8:299-308 (2008).
Ruidikoff et al., "Single amino acid substitution altering antigen-binding specificity," PNAS USA 79:1979-1983 (1982).
Ryan et al., "Antibody targeting of B-cell maturation antigen on malignant plasma cells," Molecular Cancer Therapeutics 6(11):3009-3018 (2007).
Sadelain et al., "The basic principles of chimeric antigen receptor (CAR) design," Cancer Discovery 3(4):388-398 (2013).
Sadelain et al., "The promise and potential pitfalls of chimeric antigen receptors," Curr Opin Immunol 21:215-223 (2009).
Saito et al., "Drug delivery strategy utilizing conjugation via reversible disulfide linkages: role and site of cellular reducing activities," Adv. Drug Delivery Rev. 55:199-215 (2003).
Senter et al., "Selective activation of anticancer prodrugs by monoclonal antibody—enzyme conjugates," Adv. Drug Deliv. Rev. 53:247-264 (2001).
Shaughnessy et al., "A validated gene expression model of high-risk multiple myeloma is defined by deregulated expression of genes mapping to chromosome 1," Blood 109:2276-2284 (2007).
Shen et al., "Engineering Peptide Linkers for scFv Immunosensors," Anal. Chem. 80(6):1910-1917(2008).
Shieh et al., "Transgenic Expression of Single-Chain Anti-CTLA-4 Fv on 13 Cells Protects Nonobese Diabetic Mice from Autoimmune Diabetes," J Immunol 183:2277-2285 (2009).
Siegel et al., "Cancer Statistics, 2013," CA Cancer J Clin. 63:11-30 (2013).
Stephan et al., "T cell-encoded CD80 and 4-1BBL induce auto- and transcostimulation, resulting in potent tumor rejection," Nat. Med 13(12):1440-1449 (2007).
Supplemental Partial European Search Report dated May 4, 2018 in Application No. EP 15864826.
Tai et al., "Antibody-Based Therapies in Multiple Myeloma," Bone Marrow Research (2011) Article ID: 924058, 14 pages.
Tai et al., "Novel afucosylated anti-B cell maturation antigen-monomethyl auristatin F antibody-drug conjugate (GSK2857916) induces potent and selective anti-multiple myeloma activity," Blood (2014).
Tai et al., "Targeting B-cell maturation antigen in multiple myeloma," Immunotherapy 7(11):1187-1199 (2015).
Thorpe et al., "The Preparation and Cytotoxic Properties Of Antibody-Toxin Conjugates," Immunol. Rev., 62:119-158 (1982).
Thorpe, "Antibody Carriers of Cytotoxic Agents in Cancer Therapy: A Review," Monoclonal Antibodies '84: Biological and Clinical Applications, pp. 475-506 (1985).
Tjandra et al., "Development of human anti-murine antibody (HAMA) response in patients," Immunol Cell Biol. 68:367-376 (1990).
Tomimatsu et al., "Production of Human Monoclonal Antibodies against FcεRIα by a Method Combining in-vitro Immunization with Phage Display," Biosci. Biotechnol. Biochem 73(7):1465-1469 (2009).
Trail et al., "Monoclonal antibody drug immunoconjugates for targeted treatment of cancer," Cancer Immunol. Immunother. 52:328-337 (2003).
Vajdos et al. (J. Mol. Biol. (2002) 320, 415-428) (Year: 2002).
Ward et al., "Binding activities of a repertoire of single immunoglobulin variable domains secreted from *Escherichia coli*," Nature 341:544-546 (1989).
White et al. (2001, Ann. Rev. Med., 2001, 52:125-145) (Year: 2001).
Wu et al. (J. Mol. Biol. (1999) 294, 151-162) (Year: 1999).
Xie et al., "Direct demonstration of MuSK involvement in acetylcholine receptor clustering through identification of agonist ScFv," Nat Biotech 15:768-771 (1997).
Yasmina et al., "Probing the binding mechanism and affinity of tanezumab, a recombinant humanized anti-NGF monoclonal antibody, using a repertoire of biosensors," Protein Science 17:1326-1335 (2008).
Yeger, L., "Clinical Immunology and Allergology," (1990) 2nd ed., translation from German, Mosow, Meditsina in 3 volumes, vol. 1, pp. 219-222 (in Russian with English translation).

(56) References Cited

OTHER PUBLICATIONS

Zhao et al., "Characteristics of an scFv Antibody Fragment That Binds to Immunoglobulin G of Graves' Disease Patients and Inhibits Autoantibody-Mediated Thyroid-Stimulating Activity," Hyrbidoma 27(6):445-451 (2008).

Anson et al., "An improved β-galactosidase reporter gene," Journal of Biotechnology (2004) 108:17-30.

Gacerez et al., "How Chimeric Antigen Receptor Design Affects Adoptive T Cell Therapy," J Cell Physiol. (2016) 231(12):2590-2598.

Harrington et al., "Development of JCARH125: Optimization of a Fully Human Anti-Bcma CAR for Use in the Treatment of Multiple Myeloma," Blood (2017) 130:1813.

Ormhoj et al., "CARs in the lead against Multiple Myeloma," Curr Hematol Malig Rep. (2017) 12(2):119-125.

Presnyak et al., "Codon optimality is a major determinant of mRNA stability," Cell (2015) 160(6):1111-1124.

Yanagi et al., "Transcripts from a single full-length cDNA clone of hepatitis C virus are infectious when directly transfected into the liver of a chimpanzee," PNAS, vol. 94(16), Aug. 5, 1997, p. 8738-8743.

* cited by examiner

Epitope: amino acid #7-27

```
1          11         21         31         41         51
LQMAGQCSQN EYFDSLLHAC IPCQLRCSSN TPPLTCQRYC NASVTNSVKG TNA
```
(amino acids 7-27 underlined: CSQN EYFDSLLHAC IPCQLRC)

|  | 1 | 2 | 3 | 4 | 5 | 6 | 7 | 8 | 9 | 10 | 11 | 12 |
|---|---|---|---|---|---|---|---|---|---|---|---|---|
| ET140-3 mIgG | 0.084 | 0.076 | 0.086 | 0.094 | 0.08 | 0.127 | 0.381 | 0.178 | 2.249 | 0.758 | 1.067 | 2.08 |
| ET140-24 mIgG | 0.084 | 0.079 | 0.08 | 0.081 | 0.073 | 0.105 | 0.087 | 0.083 | 0.104 | 0.115 | 0.094 | 0.137 |
| ET140-54 mIgG | 0.069 | 0.076 | 0.083 | 0.073 | 0.069 | 0.095 | 0.075 | 0.073 | 0.087 | 0.087 | 0.085 | 0.139 |
| 901mIgG | 0.084 | 0.075 | 0.089 | 0.088 | 0.073 | 0.118 | 0.087 | 0.078 | 0.116 | 0.094 | 0.108 | 0.186 |
|  | 13 | 14 | 15 | 16 | 17 | 18 | 19 | 20 | 21 | 22 | 23 | 24 |
| ET140-3 mIgG | 1.027 | 0.124 | 0.328 | 0.266 | 0.155 | 0.097 | 0.098 | 0.087 | 0.089 | 0.131 | 0.113 | 0.382 |
| ET140-24 mIgG | 0.143 | 0.105 | 0.268 | 0.231 | 0.15 | 0.099 | 0.104 | 0.083 | 0.086 | 0.098 | 0.109 | 0.357 |
| ET140-54 mIgG | 0.138 | 0.104 | 0.276 | 0.263 | 0.146 | 0.105 | 0.099 | 0.081 | 0.077 | 0.111 | 0.101 | 0.325 |
| 901mIgG | 0.252 | 0.126 | 0.305 | 0.282 | 0.162 | 0.112 | 0.126 | 0.094 | 0.089 | 0.12 | 0.114 | 0.354 |

|  | 25 | 26 | 27 | 28 | 29 | 30 | 31 | 32 | 33 | 34 | 35 | 36 |
|---|---|---|---|---|---|---|---|---|---|---|---|---|
| ET140-3 mIgG | 0.583 | 0.225 | 0.12 | 0.109 | 0.109 | 0.111 | 0.107 | 0.099 | 0.116 | 0.099 | 0.072 | 0.089 |
| ET140-24 mIgG | 0.537 | 0.212 | 0.1 | 0.101 | 0.09 | 0.083 | 0.085 | 0.092 | 0.083 | 0.069 | 0.076 | 0.084 |
| ET140-54 mIgG | 0.494 | 0.2 | 0.103 | 0.093 | 0.083 | 0.08 | 0.08 | 0.092 | 0.084 | 0.07 | 0.071 | 0.085 |
| 901mIgG | 0.492 | 0.162 | 0.098 | 0.096 | 0.09 | 0.086 | 0.087 | 0.094 | 0.086 | 0.079 | 0.072 | 0.088 |
|  | 37 | 38 | 39 |  |  |  |  |  |  |  |  |  |
| ET140-3 mIgG | 0.085 | 0.08 | 0.072 | 0.074 | 0.07 | 0.066 | 0.068 | 0.072 | 0.074 | 0.065 | 0.07 | 0.069 |
| ET140-24 mIgG | 0.086 | 0.071 | 0.071 | 0.079 | 0.092 | 0.084 | 0.077 | 0.077 | 0.078 | 0.068 | 0.064 | 0.069 |
| ET140-54 mIgG | 0.083 | 0.069 | 0.074 | 0.078 | 0.065 | 0.065 | 0.07 | 0.069 | 0.066 | 0.067 | 0.069 | 0.061 |
| 901 mIgG | 0.09 | 0.075 | 0.085 | 0.083 | 0.084 | 0.078 | 0.071 | 0.075 | 0.068 | 0.066 | 0.064 | 0.066 |

FIG. 5

ANTIBODIES TARGETING B-CELL MATURATION ANTIGEN AND METHODS OF USE

CROSS-REFERENCE TO RELATED APPLICATIONS

This application is a Continuation of U.S. patent application Ser. No. 16/732,089, filed Dec. 31, 2019, which is a Continuation of U.S. patent application Ser. No. 15/613,986, filed Jun. 5, 2017, now U.S. Pat. No. 10,562,927, which is a Continuation of International Application Serial No. PCT/US2015/064119, filed Dec. 4, 2015, which claims priority to U.S. Provisional Patent Application Ser. No. 62/088,246, filed Dec. 5, 2014, the contents of each of which are incorporated by reference in their entireties, and to each of which priority is claimed.

SEQUENCE LISTING

The specification further incorporates by reference the Sequence Listing submitted herewith via EFS on Feb. 11, 2021. Pursuant to 37 C.F.R. § 1.52(e)(5), the Sequence Listing text file, identified as 072734_1207_SL.txt, is 143,945 bytes and was created on Feb. 11, 2021. The Sequence Listing electronically filed herewith, does not extend beyond the scope of the specification and thus does not contain new matter.

FIELD OF THE INVENTION

The presently disclosed subject matter relates to antibodies that bind to B-cell maturation antigen (BCMA), and methods of using the same.

BACKGROUND

BCMA is involved in B cell differentiation and signaling and is known to be expressed on non-malignant differentiated B cells and plasma cells. Several groups have confirmed surface expression of BCMA on multiple myeloma (MM), with one group finding it as an alternative to CD138 as a FACS marker for malignant plasma cells from fresh or frozen patient bone marrow samples with mean relative mean fluorescence intensity (MFI) between 9-16 (n=35) (Frigyesi, I., et al. Robust isolation of malignant plasma cells in multiple myeloma. Blood 123, 1336-1340 (2014); Tai, Y. T., et al. Novel afucosylated anti-B cell maturation antigen-monomethyl auristatin F antibody-drug conjugate (GSK2857916) induces potent and selective anti-multiple myeloma activity. Blood (2014)). Given the significant role for BCMA in multiple myeloma, antibodies that recognize BCMA, and methods of using such agents, are desired.

SUMMARY

The presently disclosed subject matter provides antibodies that bind to a B-cell maturation antigen (BCMA), and methods of using the same.

In certain embodiments, the presently disclosed subject matter provides an isolated antibody, or an antigen-binding fragment thereof, comprising a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 1, 5, 9, 13, 17, 21, 25, 29, 33, 37, 41, 45, 49, 53, 57, 61, and 65, wherein the antibody, or an antigen-binding fragment thereof specifically binds to human BCMA. The presently disclosed subject matter provides an isolated antibody, or an antigen-binding fragment thereof, comprising a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS:2, 6, 10, 14, 18, 22, 26, 30, 34, 38, 42, 46, 50, 54, 58, 62, and 66, wherein the antibody or antigen-binding fragment thereof specifically binds to human BCMA. Furthermore, the presently disclosed subject matter provides an isolated antibody, or an antigen-binding fragment thereof, comprising (a) a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 1, 5, 9, 13, 17, 21, 25, 29, 33, 37, 41, 45, 49, 53, 57, 61, and 65; and (b) a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOS: 2, 6, 10, 14, 18, 22, 26, 30, 34, 38, 42, 46, 50, 54, 58, 62, and 66, wherein the antibody or antigen-binding fragment thereof specifically binds to human BCMA.

In addition, the presently disclosed subject matter provides an isolated antibody, or an antigen-binding fragment thereof, comprising a heavy chain variable region comprising an amino acid sequence selected from the group consisting of SEQ ID NOS: 1, 5, 9, 13, 17, 21, 25, 29, 33, 37, 41, 45, 49, 53, 57, 61, 65, and conservative modifications thereof, wherein the antibody or antigen-binding fragment thereof specifically binds to human BCMA. The presently disclosed subject matter provides an isolated antibody, or an antigen-binding fragment thereof, comprising a light chain variable region comprising an amino acid sequence selected from the group consisting of SEQ ID NOS:2, 6, 10, 14, 18, 22, 26, 30, 34, 38, 42, 46, 50, 54, 58, 62, 66, and conservative modifications thereof, wherein the antibody, or antigen-binding fragment thereof specifically binds to human BCMA. Furthermore, the presently disclosed subject matter provides an isolated antibody, or an antigen-binding fragment thereof, comprising (a) a heavy chain variable region comprising an amino acid sequence selected from the group consisting of SEQ ID NOS: 1, 5, 9, 13, 17, 21, 25, 29, 33, 37, 41, 45, 49, 53, 57, 61, 65, and conservative modifications thereof; and (b) a light chain variable region comprising an amino acid sequence selected from the group consisting of SEQ ID NOS: 6, 10, 14, 18, 22, 26, 30, 34, 38, 42, 46, 50, 54, 58, 62, 66, and conservative modifications thereof, wherein the antibody, or antigen-binding fragment thereof specifically binds to human BCMA.

The presently disclosed subject matter provides an isolated antibody, or an antigen-binding fragment thereof, comprising a heavy chain variable region and a light chain variable region, wherein the heavy chain variable region and the light chain variable region are selected from the group consisting of: (a) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:1, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:2; (b) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:5, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:6; (c) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:9, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:10; (d) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:13, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:14; (e) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:17, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:18; (f) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:21, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:22; (g) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:25, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:26; (h) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:29, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:30; (i) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:33, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:34; (j) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:37, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:38; (k) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:41, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:42; (l) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:45, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:46; (m) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:49, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:50; (n) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:53, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:54; (o) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:57, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:58; (p) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:61, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:62; and (q) a heavy chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:65, and a light chain variable region comprising amino acids having a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequence set forth in SEQ ID NO:66, wherein the antibody or antigen-binding portion thereof specifically binds to human BCMA.

In certain embodiments, the antibody or antigen-binding fragment comprises: (a) a heavy chain variable region comprising amino acids having a sequence set forth in SEQ ID NO:1, and a light chain variable region comprising amino acids having a sequence set forth in SEQ ID NO:2; (b) a heavy chain variable region comprising amino acids having a sequence set forth in SEQ ID NO:5, and a light chain variable region comprising amino acids having a sequence set forth in SEQ ID NO:6; (c) a heavy chain variable region comprising amino acids having a sequence set forth in SEQ ID NO:9, and a light chain variable region comprising amino acids having a sequence set forth in SEQ ID NO:10; (d) a heavy chain variable region comprising amino acids having a sequence set forth in SEQ ID NO:13, and a light chain variable region comprising amino acids having a sequence set forth in SEQ ID NO:14; (e) a heavy chain variable region comprising amino acids having a sequence set forth in SEQ ID NO:17, and a light chain variable region comprising amino acids having a sequence set forth in SEQ ID NO:18; (f) a heavy chain variable region comprising amino acids having a sequence set forth in SEQ ID NO:21, and a light chain variable region comprising amino acids having a sequence set forth in SEQ ID NO:22; (g) a heavy chain variable region comprising amino acids having a sequence set forth in SEQ ID NO:25, and a light chain variable region comprising amino acids having a sequence set forth in SEQ ID NO:26; (h) a heavy chain variable region comprising amino acids having a sequence set forth in SEQ ID NO:29, and a light chain variable region comprising amino acids having a sequence set forth in SEQ ID NO:30; (i) a heavy chain variable region comprising amino acids having a sequence set forth in SEQ ID NO:33, and a light chain variable region comprising amino acids having a sequence set forth in SEQ ID NO:34; (j) a heavy chain variable region comprising amino acids having a sequence set forth in SEQ ID NO:37, and a light chain variable region comprising amino acids having a sequence set forth in SEQ ID NO:38; (k) a heavy chain variable region comprising amino acids having a sequence set forth in SEQ ID NO:41, and a light chain variable region comprising amino acids having a sequence set forth in SEQ ID NO:42; (l) a heavy chain variable region comprising amino acids having a sequence set forth in SEQ ID NO:45, and a light chain variable region comprising amino acids having a sequence set forth in SEQ ID NO:46; (m) a heavy chain variable region comprising amino acids having a sequence set forth in SEQ ID NO:49, and a light chain variable region comprising amino acids having a sequence set forth in SEQ ID NO:50; (n) a heavy chain variable region comprising amino acids having a sequence set forth in SEQ ID NO:53, and a light chain variable region comprising amino acids having a sequence set forth in SEQ ID NO:54; (o) a heavy chain variable region comprising amino acids having a sequence set forth in SEQ ID NO:57, and a light chain variable region comprising amino acids having a sequence set forth in SEQ ID NO:58; (p) a heavy chain variable region comprising amino acids having a sequence set forth in SEQ ID NO:61, and a light chain variable region comprising amino acids having a sequence set forth in SEQ ID NO:62; or (q) a heavy chain variable region comprising amino acids having a sequence set forth in SEQ ID NO:65, and a light chain variable region comprising amino acids having a sequence set forth in SEQ ID NO:66.

The presently disclosed subject matter also provides an isolated antibody or antigen-binding fragment thereof comprising a heavy chain variable region that comprises CDR1, CDR2, and CDR3 domains; and a light chain variable region that comprises CDR1, CDR2, and CDR3 domains, wherein the heavy chain variable region and light chain variable region CDR3 domains are selected from the group consisting of:

(a) a heavy chain variable region CDR3 comprising amino acids having the sequence set forth in SEQ ID NO: 91 and conservative modifications thereof; and a light chain variable region CDR3 comprising amino acids having the sequence set forth in SEQ ID NO: 94 and conservative modifications thereof;

(b) a heavy chain variable region CDR3 comprising amino acids having the sequence set forth in SEQ ID NO: 97 and conservative modifications thereof; and a light chain variable region CDR3 comprising amino acids having the sequence set forth in SEQ ID NO: 100 and conservative modifications thereof;

(c) a heavy chain variable region CDR3 comprising amino acids having the sequence set forth in SEQ ID NO: 103 and conservative modifications thereof; and a light chain variable region CDR3 comprising amino acids having the sequence set forth in SEQ ID NO:106 and conservative modifications thereof;

(d) a heavy chain variable region CDR3 comprising amino acids having the sequence set forth in SEQ ID NO: 109 and conservative modifications thereof; and a light chain variable region CDR3 comprising amino acids having the sequence set forth in SEQ ID NO: 112 and conservative modifications thereof;

(e) a heavy chain variable region CDR3 comprising amino acids having the sequence set forth in SEQ ID NO:115 and conservative modifications thereof; and a light chain variable region CDR3 comprising amino acids having the sequence set forth in SEQ ID NO:118 and conservative modifications thereof;

(f) a heavy chain variable region CDR3 comprising amino acids having the sequence set forth in SEQ ID NO: 121 and conservative modifications thereof; and a light chain variable region CDR3 comprising amino acids having the sequence set forth in SEQ ID NO: 124 and conservative modifications thereof;

(g) a heavy chain variable region CDR3 comprising amino acids having the sequence set forth in SEQ ID NO: 127 and conservative modifications thereof; and a light chain variable region CDR3 comprising amino acids having the sequence set forth in SEQ ID NO: 130 and conservative modifications thereof;

(h) a heavy chain variable region CDR3 comprising amino acids having the sequence set forth in SEQ ID NO: 133 and conservative modifications thereof; and a light chain variable region CDR3 comprising amino acids having the sequence set forth in SEQ ID NO:136 and conservative modifications thereof;

(i) a heavy chain variable region CDR3 comprising amino acids having the sequence set forth in SEQ ID NO: 139 and conservative modifications thereof; and a light chain variable region CDR3 comprising amino acids having the sequence set forth in SEQ ID NO: 142 and conservative modifications thereof;

(j) a heavy chain variable region CDR3 comprising amino acids having the sequence set forth in SEQ ID NO:145 and conservative modifications thereof; and a light chain variable region CDR3 comprising amino acids having the sequence set forth in SEQ ID NO:148 and conservative modifications thereof;

(k) a heavy chain variable region CDR3 comprising amino acids having the sequence set forth in SEQ ID NO: 151 and conservative modifications thereof; and a light chain variable region CDR3 comprising amino acids having the sequence set forth in SEQ ID NO: 154 and conservative modifications thereof;

(l) a heavy chain variable region CDR3 comprising amino acids having the sequence set forth in SEQ ID NO: 157 and conservative modifications thereof; and a light chain variable region CDR3 comprising amino acids having the sequence set forth in SEQ ID NO:160 and conservative modifications thereof;

(m) a heavy chain variable region CDR3 comprising amino acids having the sequence set forth in SEQ ID NO: 163 and conservative modifications thereof; and a light chain variable region CDR3 comprising amino acids having the sequence set forth in SEQ ID NO: 166 and conservative modifications thereof;

(n) a heavy chain variable region CDR3 comprising amino acids having the sequence set forth in SEQ ID NO: 169 and conservative modifications thereof; and a light chain variable region CDR3 comprising amino acids having the sequence set forth in SEQ ID NO: 172 and conservative modifications thereof;

(o) a heavy chain variable region CDR3 comprising amino acids having the sequence set forth in SEQ ID NO: 175 and conservative modifications thereof; and a light chain variable region CDR3 comprising amino acids having the sequence set forth in SEQ ID NO: 178 and conservative modifications thereof;

(p) a heavy chain variable region CDR3 comprising amino acids having the sequence set forth in SEQ ID NO: 181 and conservative modifications thereof; and a light chain variable region CDR3 comprising amino acids having the sequence set forth in SEQ ID NO: 184 and conservative modifications thereof; and (q) a heavy chain variable region CDR3 comprising amino acids having the sequence set forth in SEQ ID NO:187 and conservative modifications thereof; and a light chain variable region CDR3 comprising amino acids having the sequence set forth in SEQ ID NO:190 and conservative modifications thereof;

wherein the antibody or antigen-binding portion thereof specifically binds to BCMA.

In certain embodiments, the heavy chain variable region and light chain variable region CDR2 domains the antibody or antigen-binding portion thereof are selected from the group consisting of:

(a) a heavy chain variable region CDR2 comprising amino acids having the sequence set forth in SEQ ID NO:90 and conservative modifications thereof; and a light chain variable region CDR2 comprising amino acids having the sequence set forth in SEQ ID NO: 93 and conservative modifications thereof;

(b) a heavy chain variable region CDR2 comprising amino acids having the sequence set forth in SEQ ID NO: 96 and conservative modifications thereof; and a light chain variable region CDR2 comprising amino acids having the sequence set forth in SEQ ID NO: 99 and conservative modifications thereof;

(c) a heavy chain variable region CDR2 comprising amino acids having the sequence set forth in SEQ ID NO: 102 and conservative modifications thereof; and a light chain variable region CDR2 comprising amino acids having the sequence set forth in SEQ ID NO: 105 and conservative modifications thereof;

(d) a heavy chain variable region CDR2 comprising amino acids having the sequence set forth in SEQ ID NO: 108 and conservative modifications thereof; and a light chain variable region CDR2 comprising amino acids having the sequence set forth in SEQ ID NO: 111 and conservative modifications thereof;

(e) a heavy chain variable region CDR2 comprising amino acids having the sequence set forth in SEQ ID NO: 114 and conservative modifications thereof; and a light chain variable region CDR2 comprising amino acids having the sequence set forth in SEQ ID NO: 117 and conservative modifications thereof;

(f) a heavy chain variable region CDR2 comprising amino acids having the sequence set forth in SEQ ID NO: 120 and conservative modifications thereof; and a light chain variable region CDR2 comprising amino acids having the sequence set forth in SEQ ID NO: 123 and conservative modifications thereof;

(g) a heavy chain variable region CDR2 comprising amino acids having the sequence set forth in SEQ ID NO: 126 and conservative modifications thereof; and a light chain variable region CDR2 comprising amino acids having the sequence set forth in SEQ ID NO: 129 and conservative modifications thereof;

(h) a heavy chain variable region CDR2 comprising amino acids having the sequence set forth in SEQ ID NO: 132 and conservative modifications thereof; and a light chain variable region CDR2 comprising amino acids having the sequence set forth in SEQ ID NO: 135 and conservative modifications thereof;

(i) a heavy chain variable region CDR2 comprising amino acids having the sequence set forth in SEQ ID NO: 138 and conservative modifications thereof; and a light chain variable region CDR2 comprising amino acids having the sequence set forth in SEQ ID NO: 141 and conservative modifications thereof;

(j) a heavy chain variable region CDR2 comprising amino acids having the sequence set forth in SEQ ID NO:144 and conservative modifications thereof; and a light chain variable region CDR2 comprising amino acids having the sequence set forth in SEQ ID NO:147 and conservative modifications thereof;

(k) a heavy chain variable region CDR2 comprising amino acids having the sequence set forth in SEQ ID NO: 150 and conservative modifications thereof; and a light chain variable region CDR2 comprising amino acids having the sequence set forth in SEQ ID NO: 153 and conservative modifications thereof;

(l) a heavy chain variable region CDR2 comprising amino acids having the sequence set forth in SEQ ID NO:156 and conservative modifications thereof; and a light chain variable region CDR2 comprising amino acids having the sequence set forth in SEQ ID NO:159 and conservative modifications thereof;

(m) a heavy chain variable region CDR2 comprising amino acids having the sequence set forth in SEQ ID NO:162 and conservative modifications thereof; and a light chain variable region CDR2 comprising amino acids having the sequence set forth in SEQ ID NO:165 and conservative modifications thereof;

(n) a heavy chain variable region CDR2 comprising amino acids having the sequence set forth in SEQ ID NO: 168 and conservative modifications thereof; and a light chain variable region CDR2 comprising amino acids having the sequence set forth in SEQ ID NO: 171 and conservative modifications thereof;

(o) a heavy chain variable region CDR2 comprising amino acids having the sequence set forth in SEQ ID NO: 174 and conservative modifications thereof; and a light chain variable region CDR2 comprising amino acids having the sequence set forth in SEQ ID NO: 177 and conservative modifications thereof;

(p) a heavy chain variable region CDR2 comprising amino acids having the sequence set forth in SEQ ID NO: 180 and conservative modifications thereof; and a light chain variable region CDR2 comprising amino acids having the sequence set forth in SEQ ID NO: 183 and conservative modifications thereof; and (q) a heavy chain variable region CDR2 comprising amino acids having the sequence set forth in SEQ ID NO: 186 and conservative modifications thereof; and a light chain variable region CDR2 comprising amino acids having the sequence set forth in SEQ ID NO: 189 and conservative modifications thereof.

In certain embodiments, the heavy chain variable region and light chain variable region CDR1 domains of the antibody or antigen-binding portion thereof are selected from the group consisting of:

(a) a heavy chain variable region CDR1 comprising amino acids having the sequence set forth in SEQ ID NO:89 and conservative modifications thereof; and a light chain variable region CDR1 comprising amino acids having the sequence set forth in SEQ ID NO: 92 and conservative modifications thereof;

(b) a heavy chain variable region CDR1 comprising amino acids having the sequence set forth in SEQ ID NO:95 and conservative modifications thereof; and a light chain variable region CDR1 comprising amino acids having the sequence set forth in SEQ ID NO:98 and conservative modifications thereof;

(c) a heavy chain variable region CDR1 comprising amino acids having the sequence set forth in SEQ ID NO:101 and conservative modifications thereof; and a light chain variable region CDR1 comprising amino acids having the sequence set forth in SEQ ID NO:104 and conservative modifications thereof;

(d) a heavy chain variable region CDR1 comprising amino acids having the sequence set forth in SEQ ID NO:107 and conservative modifications thereof; and a light chain variable region CDR1 comprising amino acids having the sequence set forth in SEQ ID NO:110 and conservative modifications thereof;

(e) a heavy chain variable region CDR1 comprising amino acids having the sequence set forth in SEQ ID NO:113 and conservative modifications thereof; and a light chain variable region CDR1 comprising amino acids having the sequence set forth in SEQ ID NO:116 and conservative modifications thereof;

(f) a heavy chain variable region CDR1 comprising amino acids having the sequence set forth in SEQ ID NO:119 and conservative modifications thereof; and a light chain variable region CDR1 comprising amino acids having the sequence set forth in SEQ ID NO:122 and conservative modifications thereof;

(g) a heavy chain variable region CDR1 comprising amino acids having the sequence set forth in SEQ ID NO:125 and conservative modifications thereof; and a light chain variable region CDR1 comprising amino acids having the sequence set forth in SEQ ID NO:128 and conservative modifications thereof;

(h) a heavy chain variable region CDR1 comprising amino acids having the sequence set forth in SEQ ID NO:131 and conservative modifications thereof; and a light chain variable region CDR1 comprising amino acids having the sequence set forth in SEQ ID NO:134 and conservative modifications thereof;

(i) a heavy chain variable region CDR1 comprising amino acids having the sequence set forth in SEQ ID NO:137 and conservative modifications thereof; and a light chain variable region CDR1 comprising amino acids having the sequence set forth in SEQ ID NO:140 and conservative modifications thereof;

(j) a heavy chain variable region CDR1 comprising amino acids having the sequence set forth in SEQ ID NO:143 and conservative modifications thereof; and a light chain variable region CDR1 comprising amino acids having the sequence set forth in SEQ ID NO:146 and conservative modifications thereof;

(k) a heavy chain variable region CDR1 comprising amino acids having the sequence set forth in SEQ ID NO:149 and conservative modifications thereof; and a light chain variable region CDR1 comprising amino acids having the sequence set forth in SEQ ID NO:152 and conservative modifications thereof;

(l) a heavy chain variable region CDR1 comprising amino acids having the sequence set forth in SEQ ID NO:155 and conservative modifications thereof; and a light chain variable region CDR1 comprising amino acids having the sequence set forth in SEQ ID NO:158 and conservative modifications thereof;

(m) a heavy chain variable region CDR1 comprising amino acids having the sequence set forth in SEQ ID NO:161 and conservative modifications thereof; and a light chain variable region CDR1 comprising amino acids having the sequence set forth in SEQ ID NO:164 and conservative modifications thereof;

(n) a heavy chain variable region CDR1 comprising amino acids having the sequence set forth in SEQ ID NO:167 and conservative modifications thereof; and a light chain variable region CDR1 comprising amino acids having the sequence set forth in SEQ ID NO:170 and conservative modifications thereof;

(o) a heavy chain variable region CDR1 comprising amino acids having the sequence set forth in SEQ ID NO:173 and conservative modifications thereof; and a light chain variable region CDR1 comprising amino acids having the sequence set forth in SEQ ID NO:176 and conservative modifications thereof;

(p) a heavy chain variable region CDR1 comprising amino acids having the sequence set forth in SEQ ID NO:179 and conservative modifications thereof; and a light chain variable region CDR1 comprising amino acids having the sequence set forth in SEQ ID NO:182 and conservative modifications thereof; and (q) a heavy chain variable region CDR1 comprising amino acids having the sequence set forth in SEQ ID NO:185 and conservative modifications thereof; and a light chain variable region CDR1 comprising amino acids having the sequence set forth in SEQ ID NO:188 and conservative modifications thereof.

In certain embodiments, one or more of the CDR sequences have up to about 3 amino acid substitutions. In certain embodiments, one or more of the CDR sequences have up to about 5 amino acid substitutions.

Furthermore, the presently disclosed subject matter provides an isolated antibody, or an antigen-binding portion thereof, comprising:

(a) a heavy chain variable region CDR1 comprising amino acids having the sequence set forth in SEQ ID NO: 89; a heavy chain variable region CDR2 comprising amino acids having the sequence set forth in SEQ ID NO: 90; and a heavy chain variable region CDR3 comprising amino acids having the sequence set forth in SEQ ID NO: 91;

(b) a heavy chain variable region CDR1 comprising amino acids having the sequence set forth in SEQ ID NO: 95; a heavy chain variable region CDR2 comprising amino acids having the sequence set forth in SEQ ID NO: 96; and a heavy chain variable region CDR3 comprising amino acids having the sequence set forth in SEQ ID NO: 97;

(c) a heavy chain variable region CDR1 comprising amino acids having the sequence set forth in SEQ ID NO: 101; a heavy chain variable region CDR2 comprising amino acids having the sequence set forth in SEQ ID NO: 102; and a heavy chain variable region CDR3 comprising amino acids having the sequence set forth in SEQ ID NO: 103;

(d) a heavy chain variable region CDR1 comprising amino acids having the sequence set forth in SEQ ID NO: 107; a heavy chain variable region CDR2 comprising amino acids having the sequence set forth in SEQ ID NO: 108; and a heavy chain variable region CDR3 comprising amino acids having the sequence set forth in SEQ ID NO: 109;

(e) a heavy chain variable region CDR1 comprising amino acids having the sequence set forth in SEQ ID NO: 113; a heavy chain variable region CDR2 comprising amino acids having the sequence set forth in SEQ ID NO: 114; and a heavy chain variable region CDR3 comprising amino acids having the sequence set forth in SEQ ID NO: 115;

(f) a heavy chain variable region CDR1 comprising amino acids having the sequence set forth in SEQ ID NO: 119; a heavy chain variable region CDR2 comprising amino acids having the sequence set forth in SEQ ID NO: 120; and a heavy chain variable region CDR3 comprising amino acids having the sequence set forth in SEQ ID NO: 121;

(g) a heavy chain variable region CDR1 comprising amino acids having the sequence set forth in SEQ ID NO: 125; a heavy chain variable region CDR2 comprising amino acids having the sequence set forth in SEQ ID NO: 126; and a heavy chain variable region CDR3 comprising amino acids having the sequence set forth in SEQ ID NO: 127;

(h) a heavy chain variable region CDR1 comprising amino acids having the sequence set forth in SEQ ID NO: 131; a heavy chain variable region CDR2 comprising amino acids having the sequence set forth in SEQ ID NO: 132; and a heavy chain variable region CDR3 comprising amino acids having the sequence set forth in SEQ ID NO: 133;

(i) a heavy chain variable region CDR1 comprising amino acids having the sequence set forth in SEQ ID NO: 137; a heavy chain variable region CDR2 comprising amino acids having the sequence set forth in SEQ ID NO: 138; and a heavy chain variable region CDR3 comprising amino acids having the sequence set forth in SEQ ID NO: 139;

(j) a heavy chain variable region CDR1 comprising amino acids having the sequence set forth in SEQ ID NO: 143; a heavy chain variable region CDR2 comprising amino acids having the sequence set forth in SEQ ID NO: 144; and a heavy chain variable region CDR3 comprising amino acids having the sequence set forth in SEQ ID NO: 145;

(k) a heavy chain variable region CDR1 comprising amino acids having the sequence set forth in SEQ ID NO: 149; a heavy chain variable region CDR2 comprising amino acids having the sequence set forth in SEQ ID NO: 150; and a heavy chain variable region CDR3 comprising amino acids having the sequence set forth in SEQ ID NO: 151;

(l) a heavy chain variable region CDR1 comprising amino acids having the sequence set forth in SEQ ID NO: 155 a heavy chain variable region CDR2 comprising amino acids having the sequence set forth in SEQ ID NO: 156; and a heavy chain variable region CDR3 comprising amino acids having the sequence set forth in SEQ ID NO: 157;

(m) a heavy chain variable region CDR1 comprising amino acids having the sequence set forth in SEQ ID NO: 161; a heavy chain variable region CDR2 comprising amino acids having the sequence set forth in SEQ ID NO: 162; and a heavy chain variable region CDR3 comprising amino acids having the sequence set forth in SEQ ID NO: 163;

(n) a heavy chain variable region CDR1 comprising amino acids having the sequence set forth in SEQ ID NO: 167; a heavy chain variable region CDR2 comprising amino acids having the sequence set forth in SEQ ID NO: 168; and a heavy chain variable region CDR3 comprising amino acids having the sequence set forth in SEQ ID NO: 169;

(o) a heavy chain variable region CDR1 comprising amino acids having the sequence set forth in SEQ ID NO: 173; a heavy chain variable region CDR2 comprising amino acids having the sequence set forth in SEQ ID NO: 174; and a heavy chain variable region CDR3 comprising amino acids having the sequence set forth in SEQ ID NO: 175;

(p) a heavy chain variable region CDR1 comprising amino acids having the sequence set forth in SEQ ID NO: 179; a heavy chain variable region CDR2 comprising amino acids having the sequence set forth in SEQ ID NO:180; and a heavy chain variable region CDR3 comprising amino acids having the sequence set forth in SEQ ID NO: 181; or (q) a heavy chain variable region CDR1 comprising amino acids having the sequence set forth in SEQ ID NO: 185; a heavy chain variable region CDR2 comprising amino acids having the sequence set forth in SEQ ID NO: 186; and a heavy chain variable region CDR3 comprising amino acids having the sequence set forth in SEQ ID NO: 187.

Additionally, the presently disclosed subject matter provides an isolated antibody, or an antigen-binding portion thereof, comprising:

(a) a light chain variable region CDR1 comprising amino acids having the sequence set forth in SEQ ID NO: 92; a light chain variable region CDR2 comprising amino acids having the sequence set forth in SEQ ID NO:93; and a light chain variable region CDR3 comprising amino acids having the sequence set forth in SEQ ID NO: 94;

(b) a light chain variable region CDR1 comprising amino acids having the sequence set forth in SEQ ID NO: 98; a light chain variable region CDR2 comprising amino acids having the sequence set forth in SEQ ID NO:99; and a light chain variable region CDR3 comprising SEQ ID NO: 100;

(c) a light chain variable region CDR1 comprising amino acids having the sequence set forth in SEQ ID NO: 104; a light chain variable region CDR2 comprising amino acids having the sequence set forth in SEQ ID NO:105; and a light chain variable region CDR3 comprising amino acids having the sequence set forth in SEQ ID NO: 106;

(d) a light chain variable region CDR1 comprising amino acids having the sequence set forth in SEQ ID NO: 110; a light chain variable region CDR2 comprising SEQ ID NO:111; and a light chain variable region CDR3 comprising amino acids having the sequence set forth in SEQ ID NO: 112;

(e) a light chain variable region CDR1 comprising amino acids having the sequence set forth in SEQ ID NO: 116; a light chain variable region CDR2 comprising amino acids having the sequence set forth in SEQ ID NO:117; and a light chain variable region CDR3 comprising amino acids having the sequence set forth in SEQ ID NO: 118;

(f) a light chain variable region CDR1 comprising amino acids having the sequence set forth in SEQ ID NO: 122; a light chain variable region CDR2 comprising amino acids having the sequence set forth in SEQ ID NO:123; and a light chain variable region CDR3 comprising amino acids having the sequence set forth in SEQ ID NO: 124;

(g) a light chain variable region CDR1 comprising amino acids having the sequence set forth in SEQ ID NO: 128; a light chain variable region CDR2 comprising amino acids having the sequence set forth in SEQ ID NO:129; and a light chain variable region CDR3 comprising amino acids having the sequence set forth in SEQ ID NO: 130;

(h) a light chain variable region CDR1 comprising amino acids having the sequence set forth in SEQ ID NO: 134; a light chain variable region CDR2 comprising amino acids having the sequence set forth in SEQ ID NO:135; and a light chain variable region CDR3 comprising SEQ ID NO: 136;

(i) a light chain variable region CDR1 comprising amino acids having the sequence set forth in SEQ ID NO: 140; a light chain variable region CDR2 comprising amino acids having the sequence set forth in SEQ ID NO:141; and a light chain variable region CDR3 comprising amino acids having the sequence set forth in SEQ ID NO: 142;

(j) a light chain variable region CDR1 comprising amino acids having the sequence set forth in SEQ ID NO: 146; a light chain variable region CDR2 comprising amino acids having the sequence set forth in SEQ ID NO:147; and a light chain variable region CDR3 comprising amino acids having the sequence set forth in SEQ ID NO: 148;

(k) a light chain variable region CDR1 comprising amino acids having the sequence set forth in SEQ ID NO: 152; a light chain variable region CDR2 comprising amino acids having the sequence set forth in SEQ ID NO:153; and a light chain variable region CDR3 comprising amino acids having the sequence set forth in SEQ ID NO: 154;

(l) a light chain variable region CDR1 comprising amino acids having the sequence set forth in SEQ ID NO: 158 a light chain variable region CDR2 comprising amino acids having the sequence set forth in SEQ ID NO:159; and a light chain variable region CDR3 comprising amino acids having the sequence set forth in SEQ ID NO: 160;

(m) a light chain variable region CDR1 comprising amino acids having the sequence set forth in SEQ ID NO: 164; a light chain variable region CDR2 comprising amino acids having the sequence set forth in SEQ ID NO:165; and a light chain variable region CDR3 comprising amino acids having the sequence set forth in SEQ ID NO: 166;

(n) a light chain variable region CDR1 comprising amino acids having the sequence set forth in SEQ ID NO: 170; a light chain variable region CDR2 comprising amino acids having the sequence set forth in SEQ ID NO: 171; and a light chain variable region CDR3 comprising amino acids having the sequence set forth in SEQ ID NO: 172;

(o) a light chain variable region CDR1 comprising amino acids having the sequence set forth in SEQ ID NO: 176; a light chain variable region CDR2 comprising amino acids having the sequence set forth in SEQ ID NO: 177; and a light chain variable region CDR3 comprising amino acids having the sequence set forth in SEQ ID NO: 178;

(p) a light chain variable region CDR1 comprising amino acids having the sequence set forth in SEQ ID NO: 182; a light chain variable region CDR2 comprising amino acids having the sequence set forth in SEQ ID NO: 183; and a light chain variable region CDR3 comprising amino acids having the sequence set forth in SEQ ID NO: 184; or (q) a light chain variable region CDR1 comprising amino acids having the sequence set forth in SEQ ID NO: 188; a light chain variable region CDR2 comprising amino acids having the sequence set forth in SEQ ID NO: 189; and a light chain variable region CDR3 comprising amino acids having the sequence set forth in SEQ ID NO: 190.

The presently disclosed subject matter also provides an isolated antibody, or an antigen-binding portion thereof, comprising:

(a) a heavy chain variable region CDR1 comprising amino acids having the sequence set forth in SEQ ID NO: 89; a heavy chain variable region CDR2 comprising amino acids having the sequence set forth in SEQ ID NO: 90; a heavy chain variable region CDR3 comprising amino acids having the sequence set forth in SEQ ID NO: 91; a light chain variable region CDR1 comprising amino acids having the sequence set forth in SEQ ID NO: 92; a light chain variable region CDR2 comprising amino acids having the sequence set forth in SEQ ID NO: 93; and a light chain variable region CDR3 comprising amino acids having the sequence set forth in SEQ ID NO: 94;

(b) a heavy chain variable region CDR1 comprising amino acids having the sequence set forth in SEQ ID NO: 95; a heavy chain variable region CDR2 comprising amino acids having the sequence set forth in SEQ ID NO: 96; a heavy chain variable region CDR3 comprising amino acids having the sequence set forth in SEQ ID NO: 97; a light chain variable region CDR1 comprising amino acids having the sequence set forth in SEQ ID NO: 98; a light chain variable region CDR2 comprising amino acids having the sequence set forth in SEQ ID NO: 99; and a light chain variable region CDR3 comprising amino acids having the sequence set forth in SEQ ID NO: 100;

(c) a heavy chain variable region CDR1 comprising amino acids having the sequence set forth in SEQ ID NO: 101; a heavy chain variable region CDR2 comprising amino acids having the sequence set forth in SEQ ID NO: 102; a heavy chain variable region CDR3 comprising amino acids having the sequence set forth in SEQ ID NO: 103; a light chain variable region CDR1 comprising amino acids having the sequence set forth in SEQ ID NO: 104; a light chain variable region CDR2 comprising amino acids having the sequence set forth in SEQ ID NO: 105; and a light chain variable region CDR3 comprising amino acids having the sequence set forth in SEQ ID NO: 106;

(d) a heavy chain variable region CDR1 comprising amino acids having the sequence set forth in SEQ ID NO: 107; a heavy chain variable region CDR2 comprising amino acids having the sequence set forth in SEQ ID NO: 108; a heavy chain variable region CDR3 comprising amino acids having the sequence set forth in SEQ ID NO: 109; a light chain variable region CDR1 comprising amino acids having the sequence set forth in SEQ ID NO: 110; a light chain variable region CDR2 comprising amino acids having the sequence set forth in SEQ ID NO: 111; and a light chain variable region CDR3 comprising amino acids having the sequence set forth in SEQ ID NO: 112;

(e) a heavy chain variable region CDR1 comprising amino acids having the sequence set forth in SEQ ID NO: 113; a heavy chain variable region CDR2 comprising amino acids having the sequence set forth in SEQ ID NO: 114; a heavy chain variable region CDR3 comprising amino acids having the sequence set forth in SEQ ID NO: 115; a light chain variable region CDR1 comprising amino acids having the sequence set forth in SEQ ID NO: 116; a light chain variable region CDR2 comprising amino acids having the sequence set forth in SEQ ID NO: 117; and a light chain variable region CDR3 comprising amino acids having the sequence set forth in SEQ ID NO: 118;

(f) a heavy chain variable region CDR1 comprising amino acids having the sequence set forth in SEQ ID NO: 119; a heavy chain variable region CDR2 comprising amino acids having the sequence set forth in SEQ ID NO: 120; a heavy chain variable region CDR3 comprising amino acids having the sequence set forth in SEQ ID NO: 121; a light chain variable region CDR1 comprising amino acids having the sequence set forth in SEQ ID NO: 122; a light chain variable region CDR2 comprising amino acids having the sequence set forth in SEQ ID NO: 123; and a light chain variable region CDR3 comprising amino acids having the sequence set forth in SEQ ID NO: 124;

(g) a heavy chain variable region CDR1 comprising amino acids having the sequence set forth in SEQ ID NO: 125; a heavy chain variable region CDR2 comprising amino acids having the sequence set forth in SEQ ID NO: 126; a heavy chain variable region CDR3 comprising amino acids having the sequence set forth in SEQ ID NO: 127; a light chain variable region CDR1 comprising amino acids having the sequence set forth in SEQ ID NO: 128; a light chain variable region CDR2 comprising amino acids having the sequence set forth in SEQ ID NO: 129; and a light chain variable region CDR3 comprising amino acids having the sequence set forth in SEQ ID NO: 130;

(h) a heavy chain variable region CDR1 comprising amino acids having the sequence set forth in SEQ ID NO: 131; a heavy chain variable region CDR2 comprising amino acids having the sequence set forth in SEQ ID NO: 132; a heavy chain variable region CDR3 comprising amino acids having the sequence set forth in SEQ ID NO: 133; a light chain variable region CDR1 comprising amino acids having the sequence set forth in SEQ ID NO: 134; a light chain variable region CDR2 comprising amino acids having the sequence set forth in SE ID NO: 135; and a light chain variable region CDR3 comprising amino acids having the sequence set forth in SEQ ID NO: 136;

(i) a heavy chain variable region CDR1 comprising amino acids having the sequence set forth in SEQ ID NO: 137; a heavy chain variable region CDR2 comprising amino acids having the sequence set forth in SEQ ID NO: 138; a heavy chain variable region CDR3 comprising amino acids having the sequence set forth in SEQ ID NO: 139; a light chain variable region CDR1 comprising amino acids having the sequence set forth in SEQ ID NO: 140; a light chain variable region CDR2 comprising amino acids having the sequence set forth in SEQ ID NO: 141; and a light chain variable region CDR3 comprising amino acids having the sequence set forth in SEQ ID NO: 142;

(j) a heavy chain variable region CDR1 comprising amino acids having the sequence set forth in SEQ ID NO: 143; a heavy chain variable region CDR2 comprising amino acids having the sequence set forth in SEQ ID NO: 144; a heavy chain variable region CDR3 comprising amino acids having the sequence set forth in SEQ ID NO: 145; a light chain variable region CDR1 comprising amino acids having the sequence set forth in SEQ ID NO: 146; a light chain variable region CDR2 comprising amino acids having the sequence set forth in SE ID NO: 147; and a light chain variable region CDR3 comprising amino acids having the sequence set forth in SEQ ID NO: 148;

(k) a heavy chain variable region CDR1 comprising amino acids having the sequence set forth in SEQ ID NO: 149; a heavy chain variable region CDR2 comprising amino acids having the sequence set forth in SEQ ID NO: 150; a heavy chain variable region CDR3 comprising amino acids having the sequence set forth in SEQ ID NO: 151; a light chain variable region CDR1 comprising amino acids having the sequence set forth in SEQ ID NO: 152; a light chain variable region CDR2 comprising amino acids having the sequence set forth in SEQ ID NO: 153; and a light chain variable region CDR3 comprising amino acids having the sequence set forth in SEQ ID NO: 154;

(l) a heavy chain variable region CDR1 comprising amino acids having the sequence set forth in SEQ ID NO: 155; a heavy chain variable region CDR2 comprising amino acids having the sequence set forth in SEQ ID NO: 156; a heavy chain variable region CDR3 comprising amino acids having the sequence set forth in SEQ ID NO: 157; a light chain variable region CDR1 comprising amino acids having the sequence set forth in SEQ ID NO: 158; a light chain variable region CDR2 comprising amino acids having the sequence set forth in SEQ ID NO: 159; and a light chain variable region CDR3 comprising amino acids having the sequence set forth in SEQ ID NO: 160;

(m) a heavy chain variable region CDR1 comprising amino acids having the sequence set forth in SEQ ID NO: 161; a heavy chain variable region CDR2 comprising amino acids having the sequence set forth in SEQ ID NO: 162; a heavy chain variable region CDR3 comprising amino acids having the sequence set forth in SEQ ID NO: 163; a light chain variable region CDR1 comprising amino acids having the sequence set forth in SEQ ID NO: 164; a light chain variable region CDR2 comprising amino acids having the sequence set forth in SEQ ID NO:165; and a light chain variable region CDR3 comprising amino acids having the sequence set forth in SEQ ID NO: 166;

(n) a heavy chain variable region CDR1 comprising amino acids having the sequence set forth in SEQ ID NO: 167; a heavy chain variable region CDR2 comprising amino acids having the sequence set forth in SEQ ID NO: 168; a heavy chain variable region CDR3 comprising amino acids having the sequence set forth in SEQ ID NO: 169; a light chain variable region CDR1 comprising amino acids having the sequence set forth in SEQ ID NO: 170; a light chain variable region CDR2 comprising amino acids having the sequence set forth in SEQ ID NO: 171; and a light chain variable region CDR3 comprising amino acids having the sequence set forth in SEQ ID NO: 172;

(o) a heavy chain variable region CDR1 comprising amino acids having the sequence set forth in SEQ ID NO: 173; a heavy chain variable region CDR2 comprising amino acids having the sequence set forth in SEQ ID NO: 174; a heavy chain variable region CDR3 comprising amino acids having the sequence set forth in SEQ ID NO: 175; a light chain variable region CDR1 comprising amino acids having the sequence set forth in SEQ ID NO: 176; a light chain variable region CDR2 comprising amino acids having the sequence set forth in SEQ ID NO: 177; and a light chain variable region CDR3 comprising amino acids having the sequence set forth in SEQ ID NO: 178;

(p) a heavy chain variable region CDR1 comprising amino acids having the sequence set forth in SEQ ID NO: 179; a heavy chain variable region CDR2 comprising amino acids having the sequence set forth in SEQ ID NO: 180; a heavy chain variable region CDR3 comprising amino acids having the sequence set forth in SEQ ID NO: 181; a light chain variable region CDR1 comprising amino acids having the sequence set forth in SEQ ID NO: 182; a light chain variable region CDR2 comprising amino acids having the sequence set forth in SEQ ID NO: 183; and a light chain variable region CDR3 comprising amino acids having the sequence set forth in SEQ ID NO: 184; or (q) a heavy chain variable region CDR1 comprising amino acids having the sequence set forth in SEQ ID NO: 185; a heavy chain variable region CDR2 comprising amino acids having the sequence set forth in SEQ ID NO: 186; a heavy chain variable region CDR3 comprising amino acids having the sequence set forth in SEQ ID NO: 187; a light chain variable region CDR1 comprising amino acids having the sequence set forth in SEQ ID NO: 188; a light chain variable region CDR2 comprising amino acids having the sequence set forth in SEQ ID NO: 189; and a light chain variable region CDR3 comprising amino acids having the sequence set forth in SEQ ID NO: 190.

In certain embodiments, the antibody or antigen-binding portion thereof binds to human BMCA with a binding affinity ($K_D$) of from about $1 \times 10^{-9}$ M to about $1 \times 10^{-8}$ M. In certain embodiments, the antibody, or antigen-binding portion thereof binds to a human BCMA comprising the amino acid sequence set forth in SEQ ID NO: 71. In certain embodiments, the antibody or antigen-binding portion thereof binds to an epitope region comprising amino acids 14-22 of SEQ ID NO:71. For example, the antibody or antigen-binding portion thereof comprises a $V_H$ comprising amino acids having the sequence set forth in SEQ ID NO:21 and a $V_L$ comprising amino acids having the sequence set forth in SEQ ID NO:22, For example, the antibody or antigen-binding portion thereof comprises a $V_H$ CDR1 comprising amino acids having the sequence set forth in SEQ ID NO:119, a $V_H$ CDR2 comprising amino acids having the sequence set forth in SEQ ID NO:120, a $V_H$ CDR3 comprising amino acids having the sequence set forth in SEQ ID NO:121, a $V_L$ CDR1 comprising amino acids having the sequence set forth in SEQ ID NO:122, a $V_L$ CDR2 comprising amino acids having the sequence set forth in SEQ ID NO:123, and a $V_L$ CDR3 comprising amino acids having the sequence set forth in SEQ ID NO:124.

The presently disclosed subject matter provides an isolated antibody, or an antigen-binding portion thereof, which cross-competes for binding to human BCMA with any of the above-described antibody or antigen-binding portion thereof. The presently disclosed subject matter provides an isolated antibody, or an antigen-binding portion thereof, which binds to the same epitope on human BCMA as any of the above-described antibody or antigen-binding portion thereof.

Furthermore, the presently disclosed subject matter provides an isolated antibody, or an antigen-binding portion thereof, which cross-competes for binding to human BCMA with a reference antibody or reference antigen-binding portion thereof comprising: (a) a heavy chain variable region comprising amino acids having a sequence set forth in SEQ ID NO:1, and a light chain variable region comprising amino acids having a sequence set forth in SEQ ID NO:2; (b) a heavy chain variable region comprising amino acids having a sequence set forth in SEQ ID NO:5, and a light chain variable region comprising amino acids having a sequence set forth in SEQ ID NO:6; (c) a heavy chain variable region comprising amino acids having a sequence set forth in SEQ ID NO:9, and a light chain variable region comprising amino acids having a sequence set forth in SEQ ID NO:10; (d) a heavy chain variable region comprising amino acids having a sequence set forth in SEQ ID NO:13, and a light chain variable region comprising amino acids having a sequence set forth in SEQ ID NO:14; (e) a heavy chain variable region comprising amino acids having a sequence set forth in SEQ ID NO:17, and a light chain variable region comprising amino acids having a sequence set forth in SEQ ID NO:18; (f) a heavy chain variable region comprising amino acids having a sequence set forth in SEQ ID NO:21, and a light chain variable region comprising amino acids having a sequence set forth in SEQ ID NO:22; (g) a heavy chain variable region comprising amino acids having a sequence set forth in SEQ ID NO:25, and a light chain variable region comprising amino acids having a sequence set forth in SEQ ID NO:26; (h) a heavy chain variable region comprising amino acids having a sequence set forth in SEQ ID NO:29, and a light chain variable region comprising amino acids having a sequence set forth in SEQ ID NO:30; (i) a heavy chain variable region comprising amino acids having a sequence set forth in SEQ ID NO:33, and a light chain variable region comprising amino acids having a sequence set forth in SEQ ID NO:34; (j) a heavy chain variable region comprising amino acids having a sequence set forth in SEQ ID NO:37, and a light chain variable region comprising amino acids having a sequence set forth in SEQ ID NO:38; (k) a heavy chain variable region comprising amino acids having a sequence set forth in SEQ ID NO:41, and a light chain variable region comprising amino acids having a sequence set forth in SEQ ID NO:42; (l) a heavy chain variable region comprising amino acids having a sequence set forth in SEQ ID NO:45, and a light chain variable region comprising amino acids having a sequence set forth in SEQ ID NO:46; (m) a heavy chain variable region comprising amino acids having a sequence set forth in SEQ ID NO:49, and a light chain variable region comprising amino acids having a sequence set forth in SEQ ID NO:50; (n) a heavy chain variable region comprising amino acids having a sequence set forth in SEQ ID NO:53, and a light chain variable region comprising amino acids having a sequence set forth in SEQ ID NO:54; (o) a heavy chain variable region comprising amino acids having a sequence set forth in SEQ ID NO:57, and a light chain variable region comprising amino acids having a sequence set forth in SEQ ID NO:58; (p) a heavy chain variable region comprising amino acids having a sequence set forth in SEQ ID NO:61, and a light chain variable region comprising amino acids having a sequence set forth in SEQ ID NO:62; or (q) a heavy chain variable region comprising amino acids having a sequence set forth in SEQ ID NO:65, and a light chain variable region comprising amino acids having a sequence set forth in SEQ ID NO:66.

In addition, the presently disclosed subject matter provides an isolated antibody, or an antigen-binding portion thereof, which binds to the same epitope on human BCMA as a reference antibody or reference antigen-binding portion thereof comprising: (a) a heavy chain variable region comprising amino acids having a sequence set forth in SEQ ID NO:1, and a light chain variable region comprising amino acids having a sequence set forth in SEQ ID NO:2; (b) a heavy chain variable region comprising amino acids having a sequence set forth in SEQ ID NO:5, and a light chain variable region comprising amino acids having a sequence set forth in SEQ ID NO:6; (c) a heavy chain variable region comprising amino acids having a sequence set forth in SEQ ID NO:9, and a light chain variable region comprising amino acids having a sequence set forth in SEQ ID NO:10; (d) a heavy chain variable region comprising amino acids having a sequence set forth in SEQ ID NO:13, and a light chain variable region comprising amino acids having a sequence set forth in SEQ ID NO:14; (e) a heavy chain variable region comprising amino acids having a sequence set forth in SEQ ID NO:17, and a light chain variable region comprising amino acids having a sequence set forth in SEQ ID NO:18; (f) a heavy chain variable region comprising amino acids having a sequence set forth in SEQ ID NO:21, and a light chain variable region comprising amino acids having a sequence set forth in SEQ ID NO:22; (g) a heavy chain variable region comprising amino acids having a sequence set forth in SEQ ID NO:25, and a light chain variable region comprising amino acids having a sequence set forth in SEQ ID NO:26; (h) a heavy chain variable region comprising amino acids having a sequence set forth in SEQ ID NO:29, and a light chain variable region comprising amino acids having a sequence set forth in SEQ ID NO:30; (i) a heavy chain variable region comprising amino acids having a sequence set forth in SEQ ID NO:33, and a light chain variable region comprising amino acids having a sequence set forth in SEQ ID NO:34; (j) a heavy chain variable region comprising amino acids having a sequence set forth in SEQ ID NO:37, and a light chain variable region comprising amino acids having a sequence set forth in SEQ ID NO:38; (k) a heavy chain variable region comprising amino acids having a sequence set forth in SEQ ID NO:41, and a light chain variable region comprising amino acids having a sequence set forth in SEQ ID NO:42; (l) a heavy chain variable region comprising amino acids having a sequence set forth in SEQ ID NO:45, and a light chain variable region comprising amino acids having a sequence set forth in SEQ ID NO:46; (m) a heavy chain variable region comprising amino acids having a sequence set forth in SEQ ID NO:49, and a light chain variable region comprising amino acids having a sequence set forth in SEQ ID NO:50; (n) a heavy chain variable region comprising amino acids having a sequence set forth in SEQ ID NO:53, and a light chain variable region comprising amino acids having a sequence set forth in SEQ ID NO:54; (o) a heavy chain variable region comprising amino acids having a sequence set forth in SEQ ID NO:57, and a light chain variable region comprising amino acids having a sequence set forth in SEQ ID NO:58; (p) a heavy chain variable region comprising amino acids having a sequence set forth in SEQ ID NO:61, and a light chain variable region comprising amino acids having a sequence set forth in SEQ ID NO:62; or (q) a heavy chain variable region comprising amino acids having a sequence set forth in SEQ ID NO:65, and a light chain variable region comprising amino acids having a sequence set forth in SEQ ID NO:66.

In certain embodiments, the cross-competing antibody, or antigen-binding portion thereof binds to a human BCMA comprising the amino acid sequence set forth in SEQ ID NO: 71. In certain embodiments, the cross-competing antibody, or antigen-binding portion thereof binds to an epitope region comprising amino acids 14-22 of SEQ ID NO:71. For example, the reference antibody or antigen-binding portion thereof comprises a $V_H$ comprising amino acids having the sequence set forth in SEQ ID NO:21 and a $V_L$ comprising amino acids having the sequence set forth in SEQ ID NO:22, For example, the reference antibody or antigen-binding portion comprises a $V_H$ CDR1 comprising amino acids having the sequence set forth in SEQ ID NO:119, a $V_H$ CDR2 comprising amino acids having the sequence set forth in SEQ ID NO:120, a $V_H$ CDR3 comprising amino acids having the sequence set forth in SEQ ID NO:121, a $V_L$ CDR1 comprising amino acids having the sequence set forth in SEQ ID NO:122, a $V_L$ CDR2 comprising amino acids having the sequence set forth in SEQ ID NO:123, and a $V_L$ CDR3 comprising amino acids having the sequence set forth in SEQ ID NO:124.

The presently disclosed subject matter also provides an isolated antibody, or antigen-binding fragment thereof, comprising an amino acid sequence selected from the group consisting of SEQ ID NOS: 72-88.

In certain embodiments, the antibody or antigen-binding fragment thereof comprises a human variable region framework region. In certain embodiments, the antibody or antigen-binding fragment thereof is fully human or an antigen-binding fragment thereof. In certain embodiments, the antibody or antigen-binding fragment thereof is a chimeric antibody or an antigen-binding fragment thereof. In certain embodiments, the antibody or antigen-binding portion thereof is a humanized antibody or an antigen-binding fragment thereof. In certain embodiments, the antigen-binding fragment of the antibody is an Fab, Fab', F(ab')2, Fv or single chain Fv (scFv).

The presently disclosed subject matter also provides a composition comprising the antibody or antigen-binding fragment thereof disclosed herein, and a pharmaceutically acceptable carrier.

In addition, the presently disclosed subject matter provides an immunoconjugate comprising the antibody or antigen-binding fragment thereof disclosed herein, linked to a therapeutic agent. In certain embodiments, the therapeutic agent is a drug, cytotoxin, or a radioactive isotope. The presently disclosed subject matter also provides a composition comprising such immunoconjugate and a pharmaceutically acceptable carrier.

Furthermore, the presently disclosed subject matter provides a bispecific molecule comprising the antibody or antigen-binding fragment thereof disclosed herein, linked to a second functional moiety. In certain embodiments, the second functional moiety has a different binding specificity than the antibody or antigen binding fragment thereof. In certain embodiments, the second functional moiety has a binding specificity for an immune cell. In certain embodiments, the second functional moiety has a binding specificity for CD3. The presently disclosed subject matter also provides a composition comprising such bispecific molecule and a pharmaceutically acceptable carrier.

In addition, the presently disclosed subject matter provides an isolated nucleic acid that encodes the antibody or antigen-binding fragment thereof disclosed herein, an expression vector comprising such nucleic acid molecule, and a host cell comprising such expression vector.

Furthermore, the presently disclosed subject matter provides a method for detecting BCMA in a whole cell or tissue. In certain embodiments, the method comprises: contacting a cell or tissue with the antibody or antigen-binding fragment thereof disclosed herein, wherein said antibody or antigen-binding fragment thereof comprises a detectable label; and determining the amount of the labeled antibody or antigen-binding fragment thereof bound to said cell or tissue by measuring the amount of detectable label associated with said cell or tissue, wherein the amount of bound antibody or antigen-binding fragment thereof indicates the amount of BCMA in said cell or tissue.

Furthermore, the presently disclosed subject matter provides a method of treating a tumor in a subject. In certain embodiments, the method comprises: administering an effective amount of the antibody or antigen-binding fragment thereof disclosed herein to the subject, thereby inducing death of a tumor cell in the subject. In certain embodiments, the method reduces the number of the tumor cells. In certain embodiments, the method reduces the tumor size. In certain embodiments, the method eradicates the tumor in the subject. In certain embodiments, the subject is a human.

In addition, the presently disclosed subject matter provides use of the antibody or antigen-binding fragment disclosed herein for the treatment of a tumor, and the antibody or antigen-binding fragment thereof disclosed herein for use in treating a tumor in a subject.

Furthermore, the presently disclosed subject matter provides a kit for treating a tumor, comprising the antibody or antigen-binding fragment thereof disclosed herein. In certain embodiments, the kit further comprises written instructions for using the antibody or antigen-binding fragment thereof for treating a subject having a tumor.

In certain embodiments, the tumor is selected from the group consisting of multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the tumor is multiple myeloma.

BRIEF DESCRIPTION OF THE FIGURES

The following Detailed Description, given by way of example, but not intended to limit the invention to specific embodiments described, may be understood in conjunction with the accompanying drawings.

FIG. 5 depicts epitope mapping of ET140-3, ET140-24, and ET140-54.

DETAILED DESCRIPTION OF EMBODIMENTS OF THE INVENTION

Figure 1:
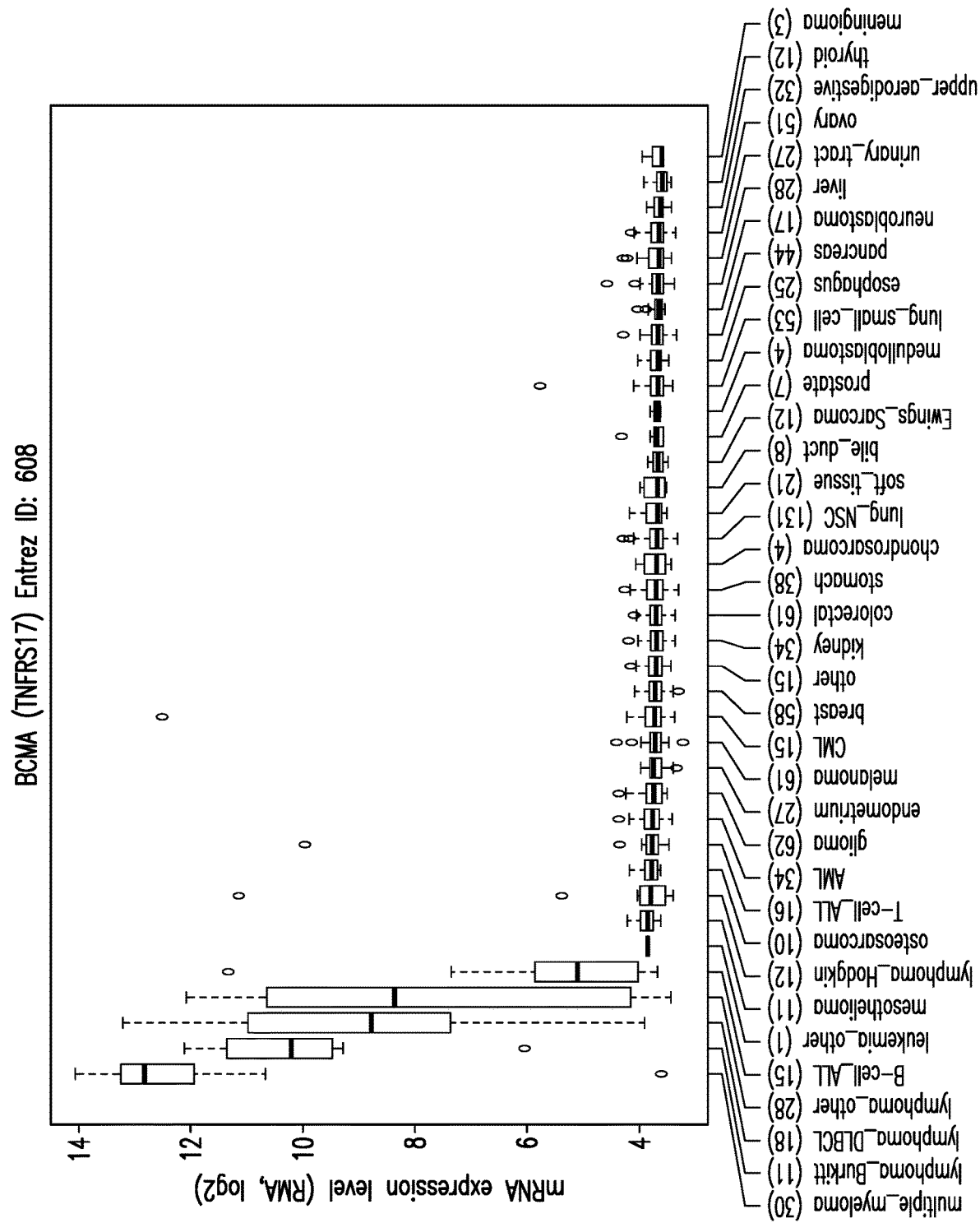
FIG. 1 depicts the human BCMA expression in various tissues.
Figure 1:
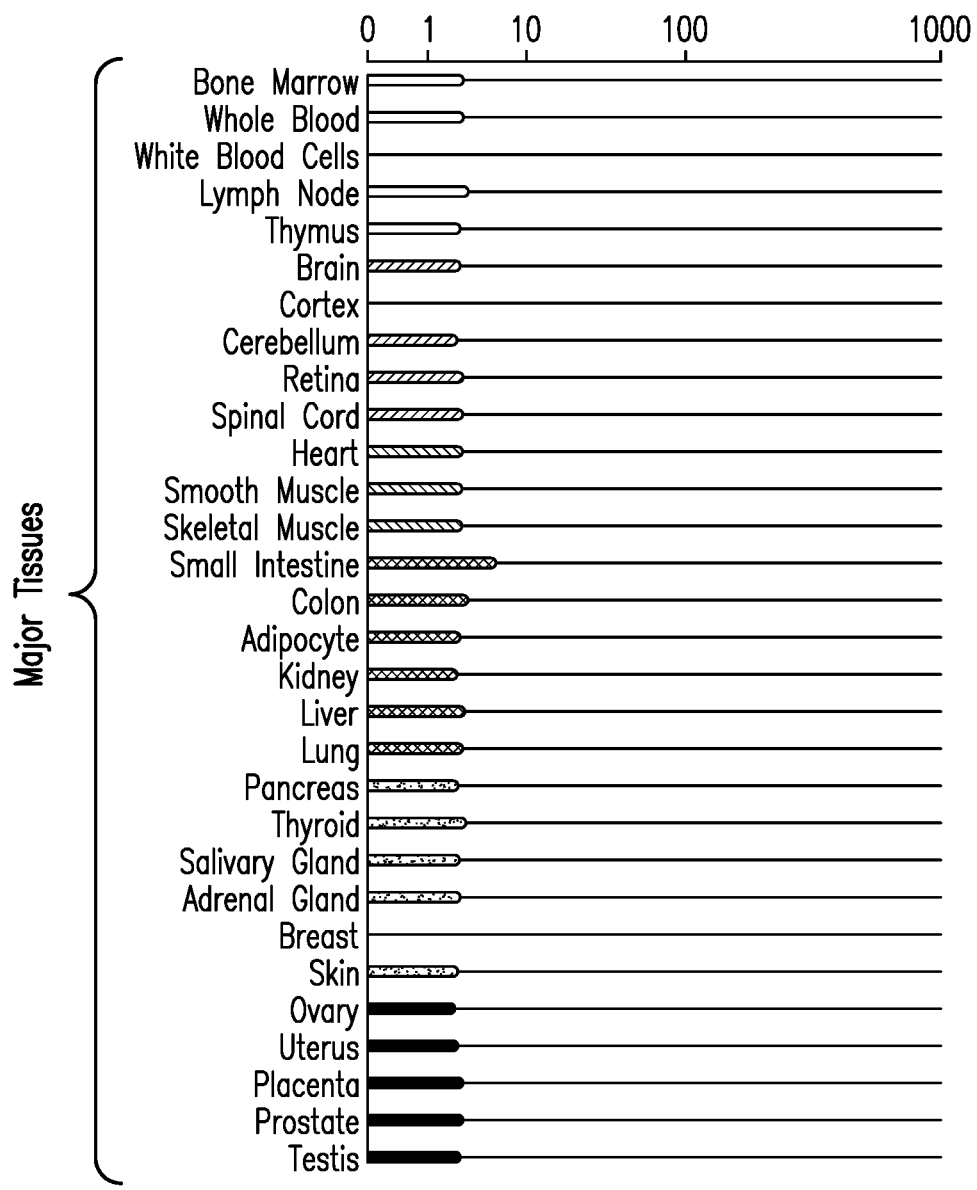
Figure 1:
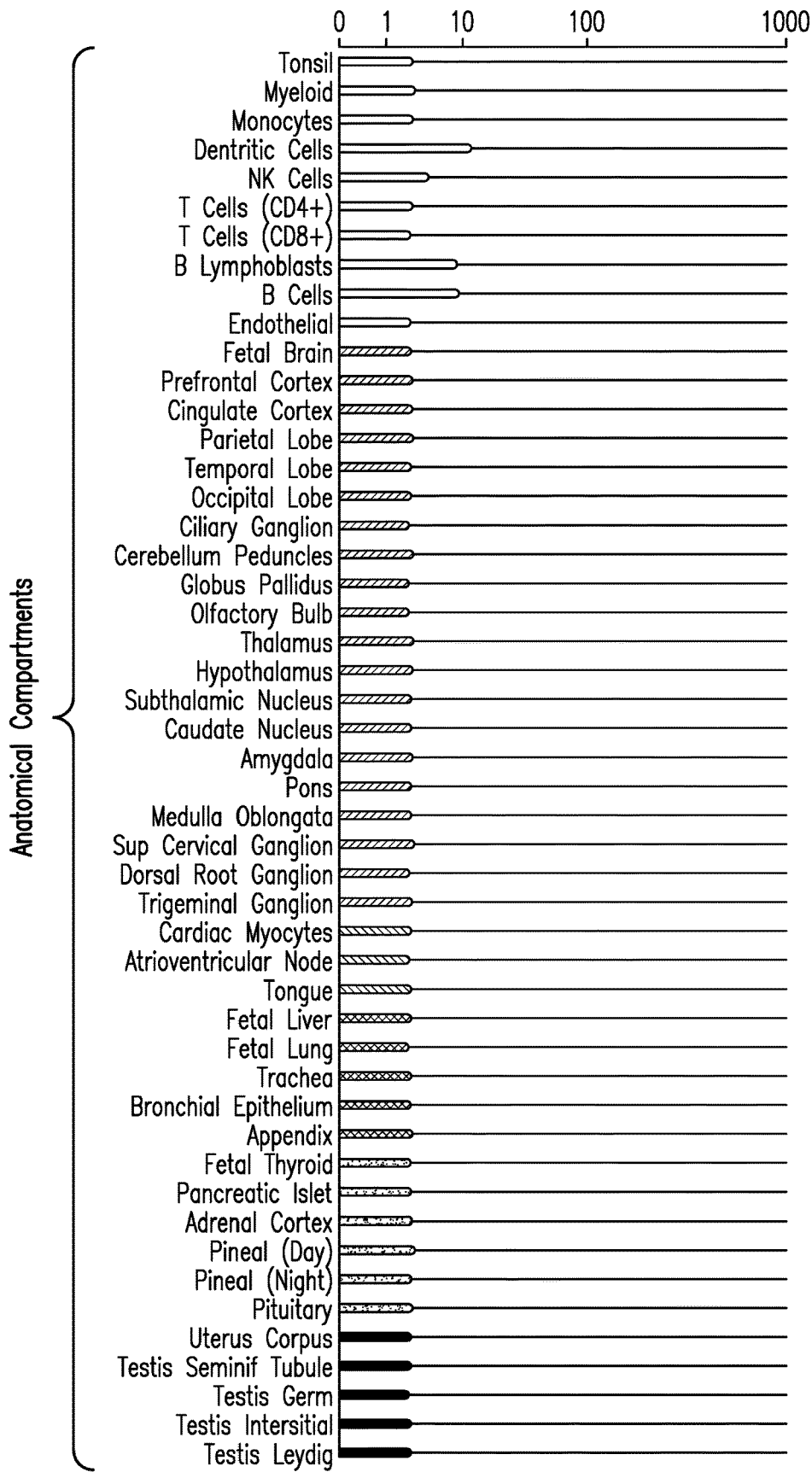

All publications, patents and other references cited herein are incorporated by reference in their entirety into the present disclosure.

In practicing the presently disclosed subject matter, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001;

Recombinant Antibodies for Immunotherapy, Melvyn Little, ed. Cambridge University Press 2009; Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

Definitions

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding portion, that is, has a strong affinity to another molecule to which it binds. Antigen-binding proteins encompass antibodies, chimeric antigen receptors (CARs) and fusion proteins.

"Antibody" and "antibodies" as those terms are known in the art refer to antigen binding proteins of the immune system. The term "antibody" as referred to herein includes whole, full length antibodies having an antigen-binding region, and any fragment thereof in which the "antigen-binding portion" or "antigen-binding region" is retained, or single chains, for example, single chain variable fragment (scFv), thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant (CH) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the presently disclosed subject matter may include amino acid residues not encoded by human germline immunoglobulin sequences (e.g., mutations introduced by random or site-specific mutagenesis in vitro or by somatic mutation in vivo).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline $V_H$ and $V_L$ sequences, may not naturally exist within the human antibody germline repertoire in vivo.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human BCMA" is intended to refer to an antibody that binds to human BCMA with a $K_D$ of about $5 \times 10^{-7}$ M or less, about $1 \times 10^{-7}$ M or less, about $5 \times 10^{-8}$ M or less, about $1 \times 10^{-8}$ M or less, about $5 \times 10^{-9}$ M or less, about $1 \times 10^{-9}$ M or less, about $5 \times 10^{-10}$ M or less, about $1 \times 10^{-10}$ M or less, about $5 \times 10^{-11}$ M or less, or about $1 \times 10^{-11}$ M or less.

An "antibody that competes for binding" or "antibody that cross-competes for binding" with a reference antibody for binding to an antigen, e.g., BCMA, refers to an antibody that blocks binding of the reference antibody to the antigen (e.g., BCMA) in a competition assay by 50% or more, and conversely, the reference antibody blocks binding of the antibody to the antigen (e.g., BCMA) in a competition assay by 50% or more. An exemplary competition assay is described in "Antibodies", Harlow and Lane (Cold Spring Harbor Press, Cold Spring Harbor, N.Y.).

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen (e.g., a BMCA polypeptide)."

The term "antigen-binding portion" or "antigen-binding region" of an antibody, as used herein, refers to that region or portion of the antibody that binds to the antigen and which confers antigen specificity to the antibody; fragments of antigen-binding proteins, for example, antibodies includes one or more fragments of an antibody that retain the ability to specifically bind to an antigen (e.g., a BCMA polypeptide). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., 1988 Science 242:423-426; and Huston et al., 1988 Proc. Natl. Acad. Sci. 85:5879-5883. These antibody fragments are obtained using conventional techniques known to those of skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

The terms "BCMA" and "B-cell maturation antigen" are used interchangeably, and include variants, isoforms, species homologs of human BCMA, and analogs having at least one common epitope with BCMA (e.g., human BCMA). An exemplary human BCMA sequence can be found under Entrez Gene Accession No.: NP 001183.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker. In certain embodiments, the linker comprises amino acids having the sequence set forth in SEQ ID NO:191 as provided below:

[SEQ ID NO: 191]
GGGGSGGGGSGGGGS.

In certain embodiments, the nucleic acid sequence encoding the amino acid sequence of SEQ ID NO:191 is set forth in SEQ ID NO:192, which is provided below:

[SEQ ID NO: 192]
GGTGGAGGTGGATCAGGTGGAGGTGGATCTGGTGGAGGTGGATCT.

In certain embodiments, the linker comprises amino acids having the sequence set forth in SEQ ID NO:69 as provided below.

[SEQ ID NO: 69]
SRGGGGSGGGGSGGGGSLEMA

In certain embodiments, the nucleic acid sequence encoding the amino acid sequence of SEQ ID NO:69 is set forth in SEQ ID NO:70, which is provided below:

[SEQ ID NO: 70]
tctagaggtggtggtggtagcggcggcggcggctctggtggtggtggatcc ctcgagatggcc In certain embodiments, the linker comprises amino acids having the following sequence GGGGS [SEQ ID NO:193].

In certain embodiments, the linker comprises amino acids having the following sequence SGGSGGS [SEQ ID NO:194].

In certain embodiments, the linker comprises amino acids having the following sequence GGGGSGGGS [SEQ ID NO:195].

In certain embodiments, the linker comprises amino acids having the following sequence GGGGSGGGGS [SEQ ID NO:196].

In certain embodiments, the linker comprises amino acids having the following sequence GGGGSGGGGSGGGGGGGS [SEQ ID NO:197].

In certain embodiments, the linker comprises amino acids having the following sequence GGGGSGGGGSGGGGSGGGGS [SEQ ID NO:198].

In certain embodiments, the linker comprises amino acids having the following sequence GGGGSGGGGSGGGGSGGGGSGGGGS [SEQ ID NO:199].

In certain embodiments, the linker comprises amino acids having the following sequence GGGGSGGGGSGGGGSGGGGSGGGGSGGGGS [SEQ ID NO:200].

In certain embodiments, the linker comprises amino acids having the following sequence GGGGSGGGGSGGGGSGGGGSGGGGSGGGGSGGGGS [SEQ ID NO:201].

In certain embodiments, the linker comprises amino acids having the following sequence EPKSCDKTHTCPPCP [SEQ ID NO:202].

In certain embodiments, the linker comprises amino acids having the following sequence GGGGSGGGSEPKSCDKTHTCPPCP [SEQ ID NO:203].

In certain embodiments, the linker comprises amino acids having the following sequence

[SEQ ID NO: 204]
ELKTPLGDTTHTCPRCPEPKSCDTPPPCPRCPEPKSCDTPPPCPRCPEPKS

CDTPPPCPRCP.

In certain embodiments, the linker comprises amino acids having the following sequence GSGSGS [SEQ ID NO:205].

In certain embodiments, the linker comprises amino acids having the following sequence AAA [SEQ ID NO:206].

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$," refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

""CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise three heavy chain and three light chain CDRs or CDR regions in the variable region. CDRs provide the majority of contact residues for the binding of the antibody to the antigen or epitope.

An "isolated antibody" is one which has been separated from a component of its natural environment. In certain embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

An "isolated nucleic acid encoding an antibody" (including references to a specific antibody, e.g. an anti-KLB antibody) refers to one or more nucleic acid molecules encoding antibody heavy and light chains (or fragments thereof), including such nucleic acid molecule(s) in a single vector separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "immunoconjugate" is an antibody conjugated to one or more heterologous molecule(s), including, but not limited to, a cytotoxic agent.

An "effective amount" of an agent, e.g., an anti-BCMA antibody or an antigen-binding fragment thereof, a pharmaceutical composition comprising thereof, refers to an amount effective, at dosages and for periods of time necessary, to achieve the desired therapeutic or prophylactic result, e.g., treating a tumor (e.g., multiple myeloma).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibodies of the presently disclosed subject matter are used to delay development of a disease or to slow the progression of a disease, e.g., a tumor (multiple myeloma).

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As described herein, any concentration range, percentage range, ratio range or integer range is to be understood to include the value of any integer within the recited range and, when appropriate, fractions thereof (such as one tenth and one hundredth of an integer), unless otherwise indicated.

Anti-BCMA Antibodies

The antibodies of the presently disclosed subject matter are characterized by particular functional features or properties of the antibodies. For example, the antibodies bind specifically to BCMA (e.g., bind to human BCMA and may cross-react with BCMA from other species, such as mouse). In certain embodiments, an antibody of the presently disclosed subject matter binds to BCMA with high affinity, for example with a $K_D$ of $1 \times 10^{-6}$ M or less, e.g., about $1 \times 10^{-7}$ M or less, about $1 \times 10^{-8}$ M or less, about $1 \times 10^{-9}$ M or less, about $1 \times 10^{-10}$ M or less, or about $1 \times 10^{-11}$ M or less. In certain embodiments, a presently disclosed anti-BCMA antibody binds to BCMA (e.g., human BCMA) with a $K_D$ of from about $1 \times 10^{-11}$ M to about $1 \times 10^{-6}$ M, e.g., from about $1 \times 10^{-11}$ M to about $1 \times 10^{-10}$ M, from about $1 \times 10^{-10}$ M to about $1 \times 10^{-9}$ M, from $1 \times 10^{-9}$ M to about $1 \times 10^{-8}$ M, from about $1 \times 10^{-8}$ M to about $1 \times 10^{-7}$ M, or from about $1 \times 10^{-7}$ M to about $1 \times 10^{-6}$ M. In certain embodiments, a presently disclosed anti-BCMA antibody binds to BCMA (e.g., human BCMA) with a $K_D$ of about $1 \times 10^{-8}$ M or less. In certain embodiments, a presently disclosed anti-BCMA antibody binds to BCMA (e.g., human BCMA) with a $K_D$ of from about $1 \times 10^{-9}$ M to about $1 \times 10^{-8}$ M. In certain embodiments, a presently disclosed anti-BCMA antibody binds to BCMA (e.g., human BCMA) with a $K_D$ of from about $1 \times 10^{-9}$ M to about $1.5 \times 10^{-9}$ M. In certain embodiments, a presently disclosed anti-BCMA antibody binds to BCMA (e.g., human BCMA) with a $K_D$ of about $1.2 \times 10^{-9}$ M. In certain embodiments, a presently disclosed anti-BCMA antibody binds to BCMA (e.g., human BCMA) with a $K_D$ of from about $4 \times 10^{-9}$ M to about $5 \times 10^{-9}$ M. In certain embodiments, a presently disclosed anti-BCMA antibody binds to BCMA (e.g., human BCMA) with a $K_D$ of about $5 \times 10^{-9}$ M. In certain embodiments, a presently disclosed anti-BCMA antibody binds to BCMA (e.g., human BCMA) with a $K_D$ of about $4.8 \times 10^{-9}$ M. In certain embodiments, a presently disclosed anti-BCMA antibody binds to BCMA (e.g., human BCMA) with a $K_D$ of from about $8 \times 10^{-9}$ M to about $9 \times 10^{-9}$ M. In certain embodiments, a presently disclosed anti-BCMA antibody binds to BCMA (e.g., human BCMA) with a $K_D$ of about $8 \times 10^{-9}$ M. In certain embodiments, a presently disclosed anti-BCMA antibody binds to BCMA (e.g., human BCMA) with a $K_D$ of about $8.1 \times 10^{-9}$ M.

The heavy and light chains of an antibody of the presently disclosed subject matter can be full-length (e.g., an antibody can include at least one (e.g., one or two) complete heavy chains, and at least one (e.g., one or two) complete light chains) or can include an antigen-binding portion (a Fab, F(ab)$_2$, Fv or a single chain Fv fragment ("scFv")). In certain embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

1. Single-Chain Variable Fragments (scFvs)

In some embodiments, the presently disclosed subject matter includes antibodies that have the scFv sequence fused to one or more constant domains to form an antibody with an Fc region of a human immunoglobulin to yield a bivalent protein, increasing the overall avidity and stability of the antibody. In addition, the Fc portion allows the direct conjugation of other molecules, including but not limited to fluorescent dyes, cytotoxins, radioisotopes etc. to the antibody for example, for use in antigen quantitation studies, to immobilize the antibody for affinity measurements, for targeted delivery of a therapeutic agent, to test for Fc-mediated cytotoxicity using immune effector cells and many other applications.

The results presented here highlight the specificity, sensitivity and utility of the antibodies of the invention in targeting a BCMA polypeptide.

The molecules of the invention are based on the identification and selection of single chain variable fragments (scFvs) using phage display, the amino acid sequence of which confers the molecules' specificity for a BCMA polypeptide of interest and forms the basis of all antigen binding proteins of the disclosure. The scFv, therefore, can be used to design a diverse array of "antibody" molecules, including, for example, full length antibodies, fragments thereof, such as Fab and F(ab')$_2$, minibodies, fusion proteins, including scFv-Fc fusions, multivalent antibodies, that is, antibodies that have more than one specificity for the same antigen or different antigens, for example, bispecific antibodies, tribodies, etc. (see Cuesta et al., Multivalent antibodies: when design surpasses evolution. Trends in Biotechnology 28:355-362 2010).

In certain embodiments, the antigen-binding protein is a full length antibody, the heavy and light chains of an antibody of the presently disclosed subject matter can be full-length (e.g., an antibody can include at least one, and preferably two, complete heavy chains, and at least one, and preferably two, complete light chains) or can include an antigen-binding portion (a Fab, F(ab')$_2$, Fv or a single chain Fv fragment ("scFv")). In certain embodiments, the antibody heavy chain constant region is chosen from, e.g., IgG1, IgG2, IgG3, IgG4, IgM, IgA1, IgA2, IgD, and IgE. In certain embodiments, the immunoglobulin isotype is selected from IgG1, IgG2, IgG3, and IgG4, more particularly, IgG1 (e.g., human IgG1). The choice of antibody isotype can depend on the immune effector function that the antibody is designed to elicit.

In constructing a recombinant immunoglobulin, appropriate amino acid sequences for constant regions of various immunoglobulin isotypes and methods for the production of a wide array of antibodies are known to those of skill in the art.

In certain embodiments, the antibody or other antigen binding protein is an anti-BCMA scFv or an antigen-binding fragment thereof having an antigen-binding region that comprises the amino acid sequence of SEQ ID NO: 72 and specifically binds to a BCMA polypeptide (e.g., a BCMA polypeptide having the amino acid sequence SEQ ID NO:71 provided below, or fragments thereof), which is designated as ET140-192 (also referred to as "ET140-42").

[SEQ ID NO: 71]
MLQMAGQCSQNEYFDSLLHACIPCQLRCSSNTPPLTCQRYCNASVTNSVKG

TNAILWTCLGLSLITSLAVFVLMFLLRKINSEPLKDEFKNTGSGLLGMANI

DLEKSRTGDEIILPRGLEYTVEECTCEDCIKSKPKVDSDHCFPLPAMEEGA

TILVTTKTNDYCKSLPAALSATEIEKSISAR

In certain embodiments, the anti-BCMA scFv antibody comprises a heavy chain variable region comprising amino acids having the sequence set forth in SEQ ID NO:1 and a light chain variable region comprising amino acids having the sequence set forth in SEQ ID NO:2, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with $V_H$ and $V_L$ regions or CDRs selected from Table 1. In certain embodiments, the anti-BCMA scFv comprises a $V_H$ comprising amino acids having the sequence set forth in SEQ ID NO:1, as shown in Table 1. In certain embodiments, the anti-BCMA scFv comprises a $V_L$ comprising amino acids having the sequence set forth in SEQ ID NO:2, as shown in Table 1. In certain embodiments, the anti-BCMA scFv comprises a $V_H$ comprising amino acids having the sequence set forth in SEQ ID NO:1 and a $V_L$ comprising amino acids having the sequence set forth in SEQ ID NO:2, as shown in Table 1. In certain embodiments, the anti-BCMA scFv comprises a $V_H$ CDR1 comprising amino acids having the sequence set forth in SEQ ID NO:89 or conservative modifications thereof, a $V_H$ CDR2 comprising amino acids having the sequence set forth in SEQ ID NO:90 or conservative modifications thereof, and a $V_H$ CDR3 comprising amino acids having the sequence set forth in SEQ ID NO:91 or conservative modifications thereof, as shown in Table 1. In certain embodiments, the anti-BCMA scFv comprises a $V_L$ CDR1 comprising amino acids having the sequence set forth in SEQ ID NO:92 or conservative modifications thereof, a $V_L$ CDR2 comprising amino acids having the sequence set forth in SEQ ID NO:93 or conservative modifications thereof, and a $V_L$ CDR3 comprising amino acids having the sequence set forth in SEQ ID NO:94 or conservative modifications thereof, as shown in Table 1. In certain embodiments, the anti-BCMA scFv comprises a $V_H$ CDR1 comprising amino acids having the sequence set forth in SEQ ID NO:89 or conservative modifications thereof, a $V_H$ CDR2 comprising amino acids having the sequence set forth in SEQ ID NO:90 or conservative modifications thereof, a $V_H$ CDR3 comprising amino acids having the sequence set forth in SEQ ID NO:91 or conservative modifications thereof, a $V_L$ CDR1 comprising amino acids having the sequence set forth in SEQ ID NO:92 or conservative modifications thereof, a $V_L$ CDR2 comprising amino acids having the sequence set forth in SEQ ID NO:93 or conservative modifications thereof, and a $V_L$ CDR3 comprising amino acids having the sequence set forth in SEQ ID NO:94 or conservative modifications thereof, as shown in Table 1. In certain embodiments, the anti-BCMA scFv comprises a $V_H$ CDR1 comprising amino acids having the sequence set forth in SEQ ID NO:89, a $V_H$ CDR2 comprising amino acids having the sequence set forth in SEQ ID NO:90, a $V_H$ CDR3 comprising amino acids having the sequence set forth in SEQ ID NO:91, a $V_L$ CDR1 comprising amino acids having the sequence set forth in SEQ ID NO:92, a $V_L$ CDR2 comprising amino acids having the sequence set forth in SEQ ID NO:93, and a $V_L$ CDR3 comprising amino acids having the sequence set forth in SEQ ID NO:94.

TABLE 1

| Antigen | A BCMA polypeptide having the amino acid sequence of SEQ ID NO: 71 | | |
|---|---|---|---|
| CDRs | 1 | 2 | 3 |
| $V_H$ | VSSNSAAWN [SEQ ID NO: 89] | YRSKWYN [SEQ ID NO: 90] | ARQGYSYYGYSDV [SEQ ID NO: 91] |
| $V_L$ | SSNIGHND [SEQ ID NO: 92] | FDD [SEQ ID NO: 93] | AAWDGSLNAFV [SEQ ID NO: 94] |
| Full $V_H$ | QVQLQQSGPGLVKPSQTLSLTCAISGDSVSSNSAAWNWIRQSPSRGLEWLGRT YYRSKWYNDYAVSVKSRITINPDTSKNQFSLQLNSVTPEDTAVYYCARQGYSY YGYSDVWGQGTLVTVSS [SEQ ID NO: 1] | | |
| DNA | Caggtacagctgcagcagtcaggtccaggactggtgaagccctcgcagaccctctcactcacctgtgccatctccggggac agtgtctctagcaacagtgctgcttggaactggatcaggcagtccccatcgagaggccttgagtggctgggaaggacatacta caggtccaagtggtataatgattatgcagtatctgtgaaaagtcgaataaccatcaacccagacacatccaagaaccagttctc cctgcagctgaactctgtgactcccgaggacacggctgtgtattactgtgcgcgccagggttactcttactacggttactctgat gtttggggtcaaggtactctggtgaccgtctcctca [SEQ ID NO: 3] | | |
| Full $V_L$ | QSVLTQPPSVSVAPRQRVTISCSGSSSNIGHNDVSWYQHLPGKAPRLLIYFDDLL PSGVSDRFSASKSGTSASLAISGLQSEDEADYYCAAWDGSLNAFVFGTGTKVT VLG [SEQ ID NO: 2] | | |

TABLE 1-continued

| Antigen | A BCMA polypeptide having the amino acid sequence of SEQ ID NO: 71 | | |
|---|---|---|---|
| CDRs | 1 | 2 | 3 |
| DNA | Cagtctgtgctgactcagccaccctcggtgtctgtagccccaggcagagggtcaccatctcgtgttctggaagcagctccaa<br>catcggacataatgatgtaagctggtaccagcatctcccagggaaggctcccagactcctcatctattttgatgacctgctgccg<br>tcaggggtctctgaccgattctctgcctccaagtctggcacctcagcctccctggccatcagtgggctccagtctgaggatgag<br>gctgattattactgtgcagcatgggatggcagcctgaatgcctttgtcttcggaactgggaccaaggtcaccgtcctaggt<br>[SEQ ID NO: 4] | | |
| scFv | QSVLTQPPSVSVAPRQRVTISCSGSSSNIGHNDVSWYQHLPGKAPRLLIYFDDLL<br>PSGVSDRFSASKSGTSASLAISGLQSEDEADYYCAAWDGSLNAFVFGTGTKVT<br>VLGSRGGGGSGGGGSGGGGSLEMAQVQLQQSGPGLVKPSQTLSLTCAISGDSV<br>SSNSAAWNWIRQSPSRGLEWLGRTYYRSKWYNDYAVSVKSRITINPDTSKNQF<br>SLQLNSVTPEDTAVYYCARQGYSYYGYSDVWGQGTLVTVSS [SEQ ID NO: 72] | | |

In certain embodiments, the antibody or other antigen binding protein is an anti-BCMA scFv or an antigen-binding fragment thereof having an antigen-binding region that comprises the amino acid sequence of SEQ ID NO:73 and specifically binds to a BCMA polypeptide (e.g., a BCMA polypeptide having the amino acid sequence SEQ ID NO:71, or fragments thereof), which is designated as ET140-197 (also referred to as "ET140-47").

In certain embodiments, the anti-BCMA scFv antibody comprises a heavy chain variable region comprising amino acids having the sequence set forth in SEQ ID NO:5 and a light chain variable region comprising amino acids having the sequence set forth in SEQ ID NO:6, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with $V_H$ and $V_L$ regions or CDRs selected from Table 2. In certain embodiments, the anti-BCMA scFv comprises a $V_H$ comprising amino acids having the sequence set forth in SEQ ID NO:5, as shown in Table 2. In certain embodiments, the anti-BCMA scFv comprises a $V_L$ comprising amino acids having the sequence set forth in SEQ ID NO:6, as shown in Table 2. In certain embodiments, the anti-BCMA scFv comprises a $V_H$ comprising amino acids having the sequence set forth in SEQ ID NO:5 and a $V_L$ comprising amino acids having the sequence set forth in SEQ ID NO:6, as shown in Table 2. In certain embodiments, the anti-BCMA scFv comprises a $V_H$ CDR1 comprising amino acids having the sequence set forth in SEQ ID NO:95 or conservative modifications thereof, a $V_H$ CDR2 comprising amino acids having the sequence set forth in SEQ ID NO:96 or conservative modifications thereof, and a $V_H$ CDR3 comprising amino acids having the sequence set forth in SEQ ID NO:97 or conservative modifications thereof, as shown in Table 2. In certain embodiments, the anti-BCMA scFv comprises a $V_L$ CDR1 comprising amino acids having the sequence set forth in SEQ ID NO:98 or conservative modifications thereof, a $V_L$ CDR2 comprising amino acids having the sequence set forth in SEQ ID NO:99 or conservative modifications thereof, and a $V_L$ CDR3 comprising amino acids having the sequence set forth in SEQ ID NO:100 or conservative modifications thereof, as shown in Table 2. In certain embodiments, the anti-BCMA scFv comprises a $V_H$ CDR1 comprising amino acids having the sequence set forth in SEQ ID NO:95 or conservative modifications thereof, a $V_H$ CDR2 comprising amino acids having the sequence set forth in SEQ ID NO:96 or conservative modifications thereof, a $V_H$ CDR3 comprising amino acids having the sequence set forth in SEQ ID NO:97 or conservative modifications thereof, a $V_L$ CDR1 comprising amino acids having the sequence set forth in SEQ ID NO:98 or conservative modifications thereof, a $V_L$ CDR2 comprising amino acids having the sequence set forth in SEQ ID NO:99 or conservative modifications thereof, and a $V_L$ CDR3 comprising amino acids having the sequence set forth in SEQ ID NO:100 or conservative modifications thereof, as shown in Table 2. In certain embodiments, the extracellular antigen-binding domain comprises a $V_H$ CDR1 comprising amino acids having the sequence set forth in SEQ ID NO:95, a $V_H$ CDR2 comprising amino acids having the sequence set forth in SEQ ID NO:96, a $V_H$ CDR3 comprising amino acids having the sequence set forth in SEQ ID NO:97, a $V_L$ CDR1 comprising amino acids having the sequence set forth in SEQ ID NO:98, a $V_L$ CDR2 comprising amino acids having the sequence set forth in SEQ ID NO:99, and a $V_L$ CDR3 comprising amino acids having the sequence set forth in SEQ ID NO:100.

TABLE 2

| Antigen | A BCMA polypeptide having the amino acid sequence of SEQ ID NO: 71 | | |
|---|---|---|---|
| CDRs | 1 | 2 | 3 |
| $V_H$ | VSSNSAAWN [SEQ ID NO: 95] | YRSKWYN [SEQ ID NO: 96] | ARYGFSGSRFYDT [SEQ ID NO: 97] |
| $V_L$ | SSNIGNNA [SEQ ID NO: 98] | FDD [SEQ ID NO: 99] | AAWDDSLNGYV [SEQ ID NO: 100] |
| Full $V_H$ | QVQLQQSGPGLVKPSQTLSLTCAISGDSVSSNSAAWNWIRQSPSRGLEWLGRTY<br>YRSKWYNDYAVSVKSRITINPDTSKNQFSLQLNSVTPEDTAVYYCARYGFSGSR<br>FYDTWGQGTLVTVSS [SEQ ID NO: 5] | | |

TABLE 2-continued

| Antigen | A BCMA polypeptide having the amino acid sequence of SEQ ID NO: 71 | | |
|---|---|---|---|
| CDRs | 1 | 2 | 3 |

DNA
Caggtacagctgcagcagtcaggtccaggactggtgaagccctcgcagaccctctcactcacctgtgccatctccggggaca
gtgtctctagcaacagtgctgcttggaactggatcaggcagtccccatcgagaggccttgagtggctgggaaggacatactaca
ggtccaagtggtataatgattatgcagtatctgtgaaaagtcgaataaccatcaacccagacacatccaagaaccagttctccctg
cagctgaactctgtgactcccgaggacacggctgtgtattactgtgcgcgctacggtttctctggttctcgtttctacgatacttggg
gtcaaggtactctggtgaccgtctcctca [SEQ ID NO: 7]

Full V<sub>L</sub>
QPVLTQPPSVSEAPRQRVTISCSGSSSNIGNNAVNWYQQLPGKAPKLLIYFDDLLS
SGVSDRFSGSKSGTSASLAISGLQSEDEADYYCAAWDDSLNGYVFGTGTKVTVL
G [SEQ ID NO: 6]

DNA
Cagcctgtgctgactcagccaccctcggtgtctgaagcccccaggcagagggtcaccatctcctgttctggaagcagctccaa
catcggaaataatgctgtaaactggtaccagcagctcccaggaaaggctcccaaactcctcatctattttgatgatctgctgtcctc
aggggtctctgaccgattctctggctccaagtctggcacctcagcctccctggccatcagtgggctccagtctgaagatgaggct
gattattactgtgcagcatgggatgacagcctgaatggttatgtcttcggaactgggaccaaggtcaccgtcctaggt [SEQ
ID NO: 8]

scFv
QPVLTQPPSVSEAPRQRVTISCSGSSSNIGNNAVNWYQQLPGKAPKLLIYFDDLLS
SGVSDRFSGSKSGTSASLAISGLQSEDEADYYCAAWDDSLNGYVFGTGTKVTVL
GSRGGGGSGGGGSGGGGSLEMAQVQLQQSGPGLVKPSQTLSLTCAISGDSVSSN
SAAWNWIRQSPSRGLEWLGRTYYRSKWYNDYAVSVKSRITINPDTSKNQFSLQL
NSVTPEDTAVYYCARYGFSGSRFYDTWGQGTLVTVSS [SEQ ID NO: 73]

In certain embodiments, the antibody or other antigen binding protein is an anti-BCMA scFv or an antigen-binding fragment thereof having an antigen-binding region that comprises the amino acid sequence of SEQ ID NO:74 and specifically binds to a BCMA polypeptide (e.g., a BCMA polypeptide having the amino acid sequence SEQ ID NO:71, or fragments thereof), which is designated as ET140-180 (also referred to as "ET140-30").

In certain embodiments, the anti-BCMA scFv antibody comprises a heavy chain variable region comprising amino acids having the sequence set forth in SEQ ID NO:9 and a light chain variable region comprising amino acids having the sequence set forth in SEQ ID NO:10, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V<sub>H</sub> and V<sub>L</sub> regions or CDRs selected from Table 3. In certain embodiments, the anti-BCMA scFv comprises a V<sub>H</sub> comprising amino acids having the sequence set forth in SEQ ID NO:9, as shown in Table 3. In certain embodiments, the anti-BCMA scFv comprises a V<sub>L</sub> comprising amino acids having the sequence set forth in SEQ ID NO:10, as shown in Table 3. In certain embodiments, the anti-BCMA scFv comprises a V<sub>H</sub> comprising amino acids having the sequence set forth in SEQ ID NO:9 and a V<sub>L</sub> comprising amino acids having the sequence set forth in SEQ ID NO:10, as shown in Table 3. In certain embodiments, the anti-BCMA scFv comprises a V<sub>H</sub> CDR1 comprising amino acids having the sequence set forth in SEQ ID NO:101 or conservative modifications thereof, a V<sub>H</sub> CDR2 comprising amino acids having the sequence set forth in SEQ ID NO:102 or conservative modifications thereof, and a V<sub>H</sub> CDR3 comprising amino acids having the sequence set forth in SEQ ID NO:103 or conservative modifications thereof, as shown in Table 3. In certain embodiments, the anti-BCMA scFv comprises a V<sub>L</sub> CDR1 comprising amino acids having the sequence set forth in SEQ ID NO:104 or conservative modifications thereof, a V<sub>L</sub> CDR2 comprising amino acids having the sequence set forth in SEQ ID NO:105 or conservative modifications thereof, and a V<sub>L</sub> CDR3 comprising amino acids having the sequence set forth in SEQ ID NO:106 or conservative modifications thereof, as shown in Table 3. In certain embodiments, the anti-BCMA scFv comprises a V<sub>H</sub> CDR1 comprising amino acids having the sequence set forth in SEQ ID NO:101 or conservative modifications thereof, a V<sub>H</sub> CDR2 comprising amino acids having the sequence set forth in SEQ ID NO:102 or conservative modifications thereof, a V<sub>H</sub> CDR3 comprising amino acids having the sequence set forth in SEQ ID NO:103 or conservative modifications thereof, a V<sub>L</sub> CDR1 comprising amino acids having the sequence set forth in SEQ ID NO:104 or conservative modifications thereof, a V<sub>L</sub> CDR2 comprising amino acids having the sequence set forth in SEQ ID NO:105 or conservative modifications thereof, and a V<sub>L</sub> CDR3 comprising amino acids having the sequence set forth in SEQ ID NO:106 or conservative modifications thereof, as shown in Table 3. In certain embodiments, the extracellular antigen-binding domain comprises a V<sub>H</sub> CDR1 comprising amino acids having the sequence set forth in SEQ ID NO:101, a V<sub>H</sub> CDR2 comprising amino acids having the sequence set forth in SEQ ID NO:102, a V<sub>H</sub> CDR3 comprising amino acids having the sequence set forth in SEQ ID NO:103, a V<sub>L</sub> CDR1 comprising amino acids having the sequence set forth in SEQ ID NO:104, a V<sub>L</sub> CDR2 comprising amino acids having the sequence set forth in SEQ ID NO:105, and a V<sub>L</sub> CDR3 comprising amino acids having the sequence set forth in SEQ ID NO:106.

TABLE 3

| Antigen | A BCMA polypeptide having the amino acid sequence of SEQ ID NO: 71 | | |
|---|---|---|---|
| CDRs | 1 | 2 | 3 |
| V$_H$ | GGTFSSYA [SEQ ID NO: 101] | IIPILGIA [SEQ ID NO: 102] | ARSGYSKSIVSYMDY [SEQ ID NO: 103] |
| V$_L$ | SSNIGSNV [SEQ ID NO: 104] | RNN [SEQ ID NO: 105] | AAWDDSLSGYV [SEQ ID NO: 106] |
| Full V$_H$ | EVQLVQSGAEVKKPGSSVKVSCKASGGTFSSYAISWVRQAPGQGLEWMGRIIPIL GIANYAQKFQGRVTMTEDTSTDTAYMELSSLRSEDTAVYYCARSGYSKSIVSYM DYWGQGTLVTVSS [SEQ ID NO: 9] | | |
| DNA | Gaggtccagctggtgcagtctggagctgaggtgaagaagcctgggcctcggtgaaggtctcctgcaaggcttctggaggca ccttcagcagctatgctatcagctgggtgcgacaggcccctggacaagggcttgagtggatgggaaggatcatccctatccttg gtatagcaaactacgcacagaagttccagggcagagtcaccatgaccgaggacacatctacagacacagcctacatggagct gagcagcctgagatctgaggacacggccgtgtattactgtgcgcgctctggt- tactctaaatctatcgtttcttacatggattactgg ggtcaaggtactctggtgaccgtctcctca [SEQ ID NO: 11] | | |
| Full V$_L$ | LPVLTQPPSTSGTPGQRVTVSCSGSSSNIGSNVVFWYQQLPGTAPKLVIYRNNQR PSGVPDRFSVSKSGTSASLAISGLRSEDEADYYCAAWDDSLSGYVFGTGTKVTV LG [SEQ ID NO: 10] | | |
| DNA | Ctgcctgtgctgactcagccccctccacgtctgggaccccgggcagagggtcaccgtctcttgttctggaagcagctccaa catcggaagtaatgttgtattctggtaccagcagctcccaggcacgccccaaacttgtcatctataggaataatcaacggccct caggggtccctgaccgattctctgtctccaagtctggcacctcagcctccctggccatcagtgggctccggtccgaggacgagg ctgattattattgtgcagcttgggatgacagcctgagtggttatgtcttcggaactgggaccaaggtcaccgtcctaggt [SEQ ID NO: 12] | | |
| scFv | LPVLTQPPSTSGTPGQRVTVSCSGSSSNIGSNVVFWYQQLPGTAPKLVIYRNNQR PSGVPDRFSVSKSGTSASLAISGLRSEDEADYYCAAWDDSLSGYVFGTGTKVTV LGSRGGGGSGGGGSGGGGSLEMAEVQLVQSGAEVKKPGSSVKVSCKASGGTFS SYAISWVRQAPGQGLEWMGRIIPILGIANYAQKFQGRVTMTEDTSTDTAYMELS SLRSEDTAVYYCARSGYSKSIVSYMDYWGQGTLVTVSS [SEQ ID NO: 74] | | |

In certain embodiments, the antibody or other antigen binding protein is an anti-BCMA scFv or an antigen-binding fragment thereof having an antigen-binding region that comprises the amino acid sequence of SEQ ID NO:75 and specifically binds to a BCMA polypeptide (e.g., a BCMA polypeptide having the amino acid sequence SEQ ID NO:71, or fragments thereof), which is designated as ET140-172 (also referred to as "ET140-22").

In certain embodiments, the anti-BCMA scFv antibody comprises a heavy chain variable region comprising amino acids having the sequence set forth in SEQ ID NO:13 and a light chain variable region comprising amino acids having the sequence set forth in SEQ ID NO:14, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V$_H$ and V$_L$ regions or CDRs selected from Table 4. In certain embodiments, the anti-BCMA scFv comprises a V$_H$ comprising amino acids having the sequence set forth in SEQ ID NO:13, as shown in Table 4. In certain embodiments, the anti-BCMA scFv comprises a V$_L$ comprising amino acids having the sequence set forth in SEQ ID NO:14, as shown in Table 4. In certain embodiments, the anti-BCMA scFv comprises a V$_H$ comprising amino acids having the sequence set forth in SEQ ID NO:13 and a V$_L$ comprising amino acids having the sequence set forth in SEQ ID NO:14, as shown in Table 4. In certain embodiments, the anti-BCMA scFv comprises a V$_H$ CDR1 comprising amino acids having the sequence set forth in SEQ ID NO:107 or conservative modifications thereof, a V$_H$ CDR2 comprising amino acids having the sequence set forth in SEQ ID NO:108 or conservative modifications thereof, and a V$_H$ CDR3 comprising amino acids having the sequence set forth in SEQ ID NO:109 or conservative modifications thereof, as shown in Table 4. In certain embodiments, the anti-BCMA scFv comprises a V$_L$ CDR1 comprising amino acids having the sequence set forth in SEQ ID NO:110 or conservative modifications thereof, a V$_L$ CDR2 comprising amino acids having the sequence set forth in SEQ ID NO:111 or conservative modifications thereof, and a V$_L$ CDR3 comprising amino acids having the sequence set forth in SEQ ID NO:112 or conservative modifications thereof, as shown in Table 4. In certain embodiments, the anti-BCMA scFv comprises a V$_H$ CDR1 comprising amino acids having the sequence set forth in SEQ ID NO:107 or conservative modifications thereof, a V$_H$ CDR2 comprising amino acids having the sequence set forth in SEQ ID NO:108 or conservative modifications thereof, a V$_H$ CDR3 comprising amino acids having the sequence set forth in SEQ ID NO:109 or conservative modifications thereof, a V$_L$ CDR1 comprising amino acids having the sequence set forth in SEQ ID NO:110 or conservative modifications thereof, a V$_L$ CDR2 comprising amino acids having the sequence set forth in SEQ ID NO:111 or conservative modifications thereof, and a V$_L$ CDR3 comprising amino acids having the sequence set forth in SEQ ID NO:112 or conservative modifications thereof, as shown in Table 4. In certain embodiments, the extracellular antigen-binding domain comprises a V$_H$ CDR1 comprising amino acids having the sequence set forth in SEQ ID NO:107, a V$_H$ CDR2 comprising amino acids having the sequence set forth in SEQ ID NO:108, a V$_H$ CDR3 comprising amino acids having the sequence set forth in SEQ ID NO:109, a V$_L$ CDR1 comprising amino acids having the sequence set forth in SEQ ID NO:110, a V$_L$ CDR2 comprising amino acids having the sequence set forth in SEQ ID NO:111, and a V$_L$ CDR3 comprising amino acids having the sequence set forth in SEQ ID NO:112.

TABLE 4

| Antigen | A BCMA polypeptide having the amino acid sequence of SEQ ID NO: 71 | | |
|---|---|---|---|
| CDRs | 1 | 2 | 3 |
| V$_H$ | GYTFTSYY [SEQ ID NO: 107] | INPSGGST [SEQ ID NO: 108] | ARSQWGGVLDY [SEQ ID NO: 109] |
| V$_L$ | SSNIGARYD [SEQ ID NO: 110] | GNN [SEQ ID NO: 111] | QSYDSSLSASV [SEQ ID NO: 112] |
| Full V$_H$ | EVQLVQSGAEVKKPGASVKVSCKASGYTFTSYYMHWVRQAPGQGLEWMGIINP SGGSTSYAQKFQGRVTMTRDTSTSTVYMELSSLRSEDTAVYYCARSQWGGVLD YWGQGTLVTVSS [SEQ ID NO: 13] | | |
| DNA | Gaggtccagctggtacagtctggggctgaggtgaagaagcctgggcctcagtgaaggtttcctgcaaggcatctggataca ccttcaccagctactatatgcactgggtgcgacaggcccctggacaagggcttgagtggatgggaataatcaaccctagtggtg gtagcacaagctacgcacagaagttccagggcagagtcaccatgaccagggacacgtccacgagcacagtctacatggagct gagcagcctgagatctgaggacacggccgtgtattactgtgcgcgctctcagtggggtggtgttctggattactggggtcaaggt actctggtgaccgtctcctca [SEQ ID NO: 15] | | |
| Full V$_L$ | QSVVTQPPSVSGAPGQRVTISCSGSSSNIGARYDVQWYQQLPGTAPKLLIFGNNN RPSGVPDRFSGSKSGTSASLAITGLQAEDEADYYCQSYDSSLSASVFGGGTKLTV LG [SEQ ID NO: 14] | | |
| DNA | Cagtctgtcgtgacgcagccgccctcagtgtctggggcccagggcagagggtcaccatctcctgcagtgggagcagctcca acatcggggcacgttatgatgttcagtggtaccagcagcttccaggaacagcccccaaactcctcatctttggtaacaacaatcg gccctcaggggtccctgaccgattctctggctccaagtctggcacgtcagcctccctggccatcactgggctccaggctgagga tgaggctgattattactgccagtcctatgacagcagcctgagtgcttcggtgttcggcggagggaccaagctgaccgtcctaggt [SEQ ID NO: 16] | | |
| scFv | QSVVTQPPSVSGAPGQRVTISCSGSSSNIGARYDVQWYQQLPGTAPKLLIFGNNN RPSGVPDRFSGSKSGTSASLAITGLQAEDEADYYCQSYDSSLSASVFGGGTKLTV LGSRGGGGSGGGGSGGGGSLEMAEVQLVQSGAEVKKPGASVKVSCKASGYTFT SYYMHWVRQAPGQGLEWMGIINPSGGSTSYAQKFQGRVTMTRDTSTSTVYMEL SSLRSEDTAVYYCARSQWGGVLDYWGQGTLVTVSS [SEQ ID NO: 75] | | |

In certain embodiments, the antibody or other antigen binding protein is an anti-BCMA scFv or an antigen-binding fragment thereof having an antigen-binding region that comprises the amino acid sequence of SEQ ID NO:76 and specifically binds to a BCMA polypeptide (e.g., a BCMA polypeptide having the amino acid sequence SEQ ID NO:71, or fragments thereof)—which is designated as ET140-157 (also referred to as "ET140-7").

In certain embodiments, the anti-BCMA scFv antibody comprises a heavy chain variable region comprising amino acids having the sequence set forth in SEQ ID NO:17 and a light chain variable region comprising amino acids having the sequence set forth in SEQ ID NO:18, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V$_H$ and V$_L$ regions or CDRs selected from Table 5. In certain embodiments, the anti-BCMA scFv comprises a V$_H$ comprising amino acids having the sequence set forth in SEQ ID NO:17, as shown in Table 5. In certain embodiments, the anti-BCMA scFv comprises a V$_L$ comprising amino acids having the sequence set forth in SEQ ID NO:18, as shown in Table 5. In certain embodiments, the anti-BCMA scFv comprises a V$_H$ comprising amino acids having the sequence set forth in SEQ ID NO:17 and a V$_L$ comprising amino acids having the sequence set forth in SEQ ID NO:18, as shown in Table 5. In certain embodiments, the anti-BCMA scFv comprises a V$_H$ CDR1 comprising amino acids having the sequence set forth in SEQ ID NO:113 or conservative modifications thereof, a V$_H$ CDR2 comprising amino acids having the sequence set forth in SEQ ID NO:114 or conservative modifications thereof, and a V$_H$ CDR3 comprising amino acids having the sequence set forth in SEQ ID NO:115 or conservative modifications thereof, as shown in Table 5. In certain embodiments, the anti-BCMA scFv comprises a V$_L$ CDR1 comprising amino acids having the sequence set forth in SEQ ID NO:116 or conservative modifications thereof, a V$_L$ CDR2 comprising amino acids having the sequence set forth in SEQ ID NO:117 or conservative modifications thereof, and a V$_L$ CDR3 comprising amino acids having the sequence set forth in SEQ ID NO:118 or conservative modifications thereof, as shown in Table 5. In certain embodiments, the anti-BCMA scFv comprises a V$_H$ CDR1 comprising amino acids having the sequence set forth in SEQ ID NO:113 or conservative modifications thereof, a V$_H$ CDR2 comprising amino acids having the sequence set forth in SEQ ID NO:114 or conservative modifications thereof, a V$_H$ CDR3 comprising amino acids having the sequence set forth in SEQ ID NO:115 or conservative modifications thereof, a V$_L$ CDR1 comprising amino acids having the sequence set forth in SEQ ID NO:116 or conservative modifications thereof, a V$_L$ CDR2 comprising amino acids having the sequence set forth in SEQ ID NO:117 or conservative modifications thereof, and a V$_L$ CDR3 comprising amino acids having the sequence set forth in SEQ ID NO:118 or conservative modifications thereof, as shown in Table 5. In certain embodiments, the extracellular antigen-binding domain comprises a V$_H$ CDR1 comprising amino acids having the sequence set forth in SEQ ID NO:113, a V$_H$ CDR2 comprising amino acids having the sequence set forth in SEQ ID NO:114, a V$_H$ CDR3 comprising amino acids having the sequence set forth in SEQ ID NO:115, a V$_L$ CDR1 comprising amino acids having the sequence set forth in SEQ ID NO:116, a V$_L$ CDR2 comprising amino acids having the sequence set forth in SEQ ID NO:117, and a V$_L$ CDR3 comprising amino acids having the sequence set forth in SEQ ID NO:118.

TABLE 5

| Antigen | A BCMA polypeptide having the amino acid sequence of SEQ ID NO: 71 | | |
|---|---|---|---|
| CDRs | 1 | 2 | 3 |
| V$_H$ | GGTFSSYA [SEQ ID NO: 113] | IIPILGIA [SEQ ID NO: 114] | ARTGYESWGSYEVIDR [SEQ ID NO: 115] |
| V$_L$ | SSNIGSNT [SEQ ID NO: 116] | SNN [SEQ ID NO: 117] | AAWDDSLNGVV [SEQ ID NO: 118] |
| Full V$_H$ | QVQLVESGAEVKKPGSSVKVSCKASGGTFSSYAISWVRQAPGQGLEWMGRIIPIL GIANYAQKFQGRVTITADESTSTAYMELSSLRSEDTAVYYCARTGYESWGSYEV IDRWGQGTLVTVSS [SEQ ID NO: 17] | | |
| DNA | Caggtgcagctggtggagtctggggctgaggtgaagaagcctgggtcctcggtgaaggtctcctgcaaggcttctggaggca ccttcagcagctatgctatcagctgggtgcgacaggcccctggacaagggcttgagtggatgggaaggatcatccctatccttg gtatagcaaactacgcacagaagttccagggcagagtcacgattaccgcggacgaatccacgagcacagcctacatggagct gagcagcctgagatctgaggacacggccgtatattactgtgcgcgcactggttacgaatcttggggttcttacgaagttatcgatc gttggggtcaaggtactctggtgaccgtctcctca [SEQ ID NO: 19] | | |
| Full V$_L$ | QAVLTQPPSASGTPGQRVTISCSGSSSNIGSNTVNWYRQLPGTAPKLLIYSNNQRP SGVPDRFSGSKSGTSASLAISGLQSEDEADYYCAAWDDSLNGVVFGGGTKLTVL G [SEQ ID NO: 18] | | |
| DNA | Caggctgtgctgactcagccaccctcagcgtctgggaccccgggcagagggtcaccatctcttgttctggaagcagctccaa catcggaagtaatactgtaaactggtaccggcagctcccaggaacggcccccaaactcctcatctatagtaataatcagcggcc ctcagggg tccctgaccgattctctggctccaagtctggcacctcagcctccctggccatcagtgggctccagtctgaggatga ggctgattattactgtgcagcatgggatgacagcctgaatggtgtggtattcggcggagggaccaagctgaccgtcctaggt [SEQ ID NO: 20] | | |
| scFv | QAVLTQPPSASGTPGQRVTISCSGSSSNIGSNTVNWYRQLPGTAPKLLIYSNNQRP SGVPDRFSGSKSGTSASLAISGLQSEDEADYYCAAWDDSLNGVVFGGGTKLTVL GSRGGGGSGGGGSGGGGSLEMAQVQLVESGAEVKKPGSSVKVSCKASGGTFSS YAISWVRQAPGQGLEWMGRIIPILGIANYAQKFQGRVTITADESTSTAYMELSSL RSEDTAVYYCARTGYESWGSYEVIDRWGQGTLVTVSS [SEQ ID NO: 76] | | |

In certain embodiments, the antibody or other antigen binding protein is an anti-BCMA scFv or an antigen-binding fragment thereof having an antigen-binding region that comprises the amino acid sequence of SEQ ID NO:77 and specifically binds to a BCMA polypeptide (e.g., a BCMA polypeptide having the amino acid sequence SEQ ID NO:71, or fragments thereof), which is designated as ET140-153 (also referred to as "ET140-3").

In certain embodiments, the anti-BCMA scFv antibody comprises a heavy chain variable region comprising amino acids having the sequence set forth in SEQ ID NO:21 and a light chain variable region comprising amino acids having the sequence set forth in SEQ ID NO:22, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V$_H$ and V$_L$ regions or CDRs selected from Table 6. In certain embodiments, the anti-BCMA scFv comprises a V$_H$ comprising amino acids having the sequence set forth in SEQ ID NO:21, as shown in Table 6. In certain embodiments, the anti-BCMA scFv comprises a V$_L$ comprising amino acids having the sequence set forth in SEQ ID NO:22, as shown in Table 6. In certain embodiments, the anti-BCMA scFv comprises a V$_H$ comprising amino acids having the sequence set forth in SEQ ID NO:21 and a V$_L$ comprising amino acids having the sequence set forth in SEQ ID NO:22, as shown in Table 6. In certain embodiments, the anti-BCMA scFv comprises a V$_H$ CDR1 comprising amino acids having the sequence set forth in SEQ ID NO:119 or conservative modifications thereof, a V$_H$ CDR2 comprising amino acids having the sequence set forth in SEQ ID NO:120 or conservative modifications thereof, and a V$_H$ CDR3 comprising amino acids having the sequence set forth in SEQ ID NO:121 or conservative modifications thereof, as shown in Table 6. In certain embodiments, the anti-BCMA scFv comprises a V$_L$ CDR1 comprising amino acids having the sequence set forth in SEQ ID NO:122 or conservative modifications thereof, a V$_L$ CDR2 comprising amino acids having the sequence set forth in SEQ ID NO:123 or conservative modifications thereof, and a V$_L$ CDR3 comprising amino acids having the sequence set forth in SEQ ID NO:124 or conservative modifications thereof, as shown in Table 6. In certain embodiments, the anti-BCMA scFv comprises a V$_H$ CDR1 comprising amino acids having the sequence set forth in SEQ ID NO:119 or conservative modifications thereof, a V$_H$ CDR2 comprising amino acids having the sequence set forth in SEQ ID NO:120 or conservative modifications thereof, a V$_H$ CDR3 comprising amino acids having the sequence set forth in SEQ ID NO:121, a V$_L$ CDR1 comprising amino acids having the sequence set forth in SEQ ID NO:122 or conservative modifications thereof, a V$_L$ CDR2 comprising amino acids having the sequence set forth in SEQ ID NO:123 or conservative modifications thereof, and a V$_L$ CDR3 comprising amino acids having the sequence set forth in SEQ ID NO:124 or conservative modifications thereof, as shown in Table 6. In certain embodiments, the extracellular antigen-binding domain comprises a V$_H$ CDR1 comprising amino acids having the sequence set forth in SEQ ID NO:119, a V$_H$ CDR2 comprising amino acids having the sequence set forth in SEQ ID NO:120, a V$_H$ CDR3 comprising amino acids having the sequence set forth in SEQ ID NO:121, a V$_L$ CDR1 comprising amino acids having the sequence set forth in SEQ ID NO:122, a V$_L$ CDR2 comprising amino acids having the sequence set forth in SEQ ID NO:123, and a V$_L$ CDR3 comprising amino acids having the sequence set forth in SEQ ID NO:124.

TABLE 6

| Antigen | A BCMA polypeptide having the amino acid sequence of SEQ ID NO: 71 | | |
|---|---|---|---|
| CDRs | 1 | 2 | 3 |
| $V_H$ | GGTFSSYA [SEQ ID NO: 119] | IIPILGIA [SEQ ID NO: 120] | ARGGYYSHDMWSED [SEQ ID NO: 121] |
| $V_L$ | SSNIGSNS [SEQ ID NO: 122] | SNN [SEQ ID NO: 123] | ATWDDNLNVHYV [SEQ ID NO: 124] |
| Full $V_H$ | QVQLVQSGAEVKKPGSSVKVSCKASGGTFSSYAISWVRQAPGQGLEWMGRIIPILGIANYAQKFQGRVTITADKSTSTAYMELSSLRSEDTAVYYCARGGYYSHDMWSEDWGQGTLVTVSS [SEQ ID NO: 211] | | |
| DNA | Caggtgcagctggtgcagtctggggctgaggtgaagaagcctgggtcctcggtgaaggtctcctgcaaggcttctggaggcaccttcagcagctatgctatcagctgggtgcgacaggcccctggacaagggctctgagtggatgggaaggatcatccctatccttggtatagcaaactacgcacagaagttccagggcagagtcacgattaccgcggacaaatccacgagcacagcctacatggagctgagcagcctgagatctgaggacacggccgtgtattactgtgcgcgcggtggttactactctcatgacatggtctgaagattggggtcaaggtactctggtgaccgtctcctca [SEQ ID NO: 23] | | |
| Full $V_L$ | LPVLTQPPSASGTPGQRVTISCSGRSSNIGSNSVNWYRQLPGAAPKLLIYSNNQRPPGVPVRFSGSKSGTSASLAISGLQSEDEATYYCATWDDNLNVHYVFGTGTKVTVLG [SEQ ID NO: 22] | | |
| DNA | Ctgcctgtgctgactcagccaccctcagcgtctgggaccccgggcagagggtcaccatctcttgttctggacgcagttccaacatcgggagtaattctgttaactggtatcgacaactcccaggagcggccccccaaactcctcatctatagtaataatcagcggccccagggggtccctgtgcgattctctggctccaagtctggcacctcagcctccctggccatcagtgggctccagtctgaagatgaggccacttattactgtgcaacatgggatgacaatctgaatgttcactatgtcttcggaactgggaccaaggtcaccgtcctaggt [SEQ ID NO: 24] | | |
| scFv | LPVLTQPPSASGTPGQRVTISCSGRSSNIGSNSVNWYRQLPGAAPKLLIYSNNQRPPGVPVRFSGSKSGTSASLAISGLQSEDEATYYCATWDDNLNVHYVFGTGTKVTVLGSRGGGGSGGGGSGGGGSLEMAQVQLVQSGAEVKKPGSSVKVSCKASGGTFSSYAISWVRQAPGQGLEWMGRIIPILGIANYAQKFQGRVTITADKSTSTAYMELSSLRSEDTAVYYCARGGYYSHDMWSEDWGQGTLVTVSS [SEQ ID NO: 77] | | |

In certain embodiments, the antibody or other antigen binding protein is an anti-BCMA scFv or an antigen-binding fragment thereof having an antigen-binding region that comprises the amino acid sequence of SEQ ID NO:78 and specifically binds to a BCMA polypeptide (e.g., a BCMA polypeptide having the amino acid sequence SEQ ID NO:71, or fragments thereof), which is designated as ET140-201 (also referred to as "ET140-51").

In certain embodiments, the anti-BCMA scFv antibody comprises a heavy chain variable region comprising amino acids having the sequence set forth in SEQ ID NO:25 and a light chain variable region comprising amino acids having the sequence set forth in SEQ ID NO:26, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with $V_H$ and $V_L$ regions or CDRs selected from Table 7. In certain embodiments, the anti-BCMA scFv comprises a $V_H$ comprising amino acids having the sequence set forth in SEQ ID NO:25, as shown in Table 7. In certain embodiments, the anti-BCMA scFv comprises a $V_L$ comprising amino acids having the sequence set forth in SEQ ID NO:26, as shown in Table 7. In certain embodiments, the anti-BCMA scFv comprises a $V_H$ comprising amino acids having the sequence set forth in SEQ ID NO:25 and a $V_L$ comprising amino acids having the sequence set forth in SEQ ID NO:26, as shown in Table 7. In certain embodiments, the anti-BCMA scFv comprises a $V_H$ CDR1 comprising amino acids having the sequence set forth in SEQ ID NO:125 or conservative modifications thereof, a $V_H$ CDR2 comprising amino acids having the sequence set forth in SEQ ID NO:126 or conservative modifications thereof, and a $V_H$ CDR3 comprising amino acids having the sequence set forth in SEQ ID NO:127 or conservative modifications thereof, as shown in Table 7. In certain embodiments, the anti-BCMA scFv comprises a $V_L$ CDR1 comprising amino acids having the sequence set forth in SEQ ID NO:128 or conservative modifications thereof, a $V_L$ CDR2 comprising amino acids having the sequence set forth in SEQ ID NO:129 or conservative modifications thereof, and a $V_L$ CDR3 comprising amino acids having the sequence set forth in SEQ ID NO:130 or conservative modifications thereof, as shown in Table 7. In certain embodiments, the anti-BCMA scFv comprises a $V_H$ CDR1 comprising amino acids having the sequence set forth in SEQ ID NO:125 or conservative modifications thereof, a $V_H$ CDR2 comprising amino acids having the sequence set forth in SEQ ID NO:126 or conservative modifications thereof, a $V_H$ CDR3 comprising amino acids having the sequence set forth in SEQ ID NO:127 or conservative modifications thereof, a $V_L$ CDR1 comprising amino acids having the sequence set forth in SEQ ID NO:128 or conservative modifications thereof, a $V_L$ CDR2 comprising amino acids having the sequence set forth in SEQ ID NO:129 or conservative modifications thereof, and a $V_L$ CDR3 comprising amino acids having the sequence set forth in SEQ ID NO:130 or conservative modifications thereof, as shown in Table 7. In certain embodiments, the extracellular antigen-binding domain comprises a $V_H$ CDR1 comprising amino acids having the sequence set forth in SEQ ID NO:125, a $V_H$ CDR2 comprising amino acids having the sequence set forth in SEQ ID NO:126, a $V_H$ CDR3 comprising amino acids having the sequence set forth in SEQ ID NO:127, a $V_L$ CDR1 comprising amino acids having the sequence set forth in SEQ ID NO:128, a $V_L$ CDR2 comprising amino acids having the sequence set forth in SEQ ID NO:129, and a V_L CDR3 comprising amino acids having the sequence set forth in SEQ ID NO:130.

TABLE 7

| Antigen | A BCMA polypeptide having the amino acid sequence of SEQ ID NO: 71 | | |
|---|---|---|---|
| CDRs | 1 | 2 | 3 |
| V_H | GGSISNSNW [SEQ ID NO: 125] | IYHSGST [SEQ ID NO: 126] | ARRDNWKTPTTKID GFDI [SEQ ID NO: 127] |
| V_L | SGYSNYK [SEQ ID NO: 128] | VGTGGIVG [SEQ ID NO: 129] | GADHGSGSNFVYV SEQ ID NO: 130] |
| Full V_H | QVQLQESGPGLVKPSGTLSLTCGVSGGSISNSNWWSWVRQPPGKGLEWIGEIYH SGSTKYNPSLRSRVTISVDKSKNQFSLKLSSVTAADTAVYYCARRDNWKTPTTKI DGFDIWGQGTMVTVSS [SEQ ID NO: 25] | | |
| DNA | Caggtgcagctgcaggagtcgggcccaggactggtgaagccttcggggaccctgtccctcacctgcggtgtctctggtggct ccatcagcaatagtaactggtggagttgggtccgccagcccccgggaaggggctggagtggattggggaaatctatcatagt gggagcaccaagtacaacccgtccctcaggagtcgagtcaccatatcagtagacaagtccaagaaccagttctccctaaaattg agctctgtgaccgccgcggacacggccgtatattactgtgcgagacgagataactggaagaccccactaccaaaattgatggt tttgatatctggggccaagggacaatggtcaccgtctcttca [SEQ ID NO: 27] | | |
| Full V_L | QPVLTQPPSASASLGASVTLTCTLSSGYSNYKVDWYQQRPGKGPRFVMRVGTG GIVGSKGDGIPDRFSVLGSGLNRYLTIKNIQEEDEGDYHCGADHGSGSNFVYVFG TGTKVTVLG [SEQ ID NO: 26] | | |
| DNA | Cagcctgtgctgactcagccaccttctgcatcagcctccctgggagcctcggtcacactcacctgcaccctgagcagcggcta cagtaattataaagtggactggtaccagcagagaccagggaagggccccggtttgtgatgcgagtgggcactggtgggattg tgggatccaaggggatggcatccctgatcgcttctcagtcttgggctcaggcctgaatcggtacctgaccatcaagaacatcca ggaagaagatgagggtgactatcactgtggggcagaccatggcagtgggagcaacttcgtgtatgtcttcggaactgggacca aggtcaccgtcctaggt [SEQ ID NO: 28] | | |
| scFv | QPVLTQPPSASASLGASVTLTCTLSSGYSNYKVDWYQQRPGKGPRFVMRVGTG GIVGSKGDGIPDRFSVLGSGLNRYLTIKNIQEEDEGDYHCGADHGSGSNFVYVFG TGTKVTVLGSRGGGGSGGGGSGGGGSLEMAQVQLQESGPGLVKPSGTLSLTCG VSGGSISNSNWWSWVRQPPGKGLEWIGEIYHSGSTKYNPSLRSRVTISVDKSKNQ FSLKLSSVTAADTAVYYCARRDNWKTPTTKIDGFDIWGQGTMVTVSS [SEQ ID NO: 78] | | |

In certain embodiments, the antibody or other antigen binding protein is an anti-BCMA scFv or an antigen-binding fragment thereof having an antigen-binding region that comprises the amino acid sequence of SEQ ID NO:79 and specifically binds to a BCMA polypeptide (e.g., a BCMA polypeptide having the amino acid sequence SEQ ID NO:71, or fragments thereof), which is designated as ET140-167 (also referred to as "ET140-17").

In certain embodiments, the anti-BCMA scFv antibody comprises a heavy chain variable region comprising amino acids having the sequence set forth in SEQ ID NO:29 and a light chain variable region comprising amino acids having the sequence set forth in SEQ ID NO:30, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V_H and V_L regions or CDRs selected from Table 8. In certain embodiments, the anti-BCMA scFv comprises a V_H comprising amino acids having the sequence set forth in SEQ ID NO:29, as shown in Table 8. In certain embodiments, the anti-BCMA scFv comprises a V_L comprising amino acids having the sequence set forth in SEQ ID NO:30, as shown in Table 8. In certain embodiments, the anti-BCMA scFv comprises a V_H comprising amino acids having the sequence set forth in SEQ ID NO:29 and a V_L comprising amino acids having the sequence set forth in SEQ ID NO:30, as shown in Table 8. In certain embodiments, the anti-BCMA comprises a V_H CDR1 comprising amino acids having the sequence set forth in SEQ ID NO:131 or conservative modifications thereof, a V_H CDR2 comprising amino acids having the sequence set forth in SEQ ID NO:132 or conservative modifications thereof, and a V_H CDR3 comprising amino acids having the sequence set forth in SEQ ID NO:133 or conservative modifications thereof, as shown in Table 8. In certain embodiments, the anti-BCMA scFv comprises a V_L CDR1 comprising amino acids having the sequence set forth in SEQ ID NO:134 or conservative modifications thereof, a V_L CDR2 comprising amino acids having the sequence set forth in SEQ ID NO:135 or conservative modifications thereof, and a V_L CDR3 comprising amino acids having the sequence set forth in SEQ ID NO:136 or conservative modifications thereof, as shown in Table 8. In certain embodiments, the anti-BCMA scFv comprises a V_H CDR1 comprising amino acids having the sequence set forth in SEQ ID NO:131 or conservative modifications thereof, a V_H CDR2 comprising amino acids having the sequence set forth in SEQ ID NO:132 or conservative modifications thereof, a V_H CDR3 comprising amino acids having the sequence set forth in SEQ ID NO:133 or conservative modifications thereof, a V_L CDR1 comprising amino acids having the sequence set forth in SEQ ID NO:134 or conservative modifications thereof, a V_L CDR2 comprising amino acids having the sequence set forth in SEQ ID NO:135 or conservative modifications thereof, and a V_L CDR3 comprising amino acids having the sequence set forth in SEQ ID NO:136 or conservative modifications thereof, as shown in Table 8. In certain embodiments, the extracellular antigen-binding domain comprises a V_H CDR1 comprising amino acids having the sequence set forth in SEQ ID NO:131, a V_H CDR2 comprising amino acids having the sequence set forth in SEQ ID NO:132, a V_H CDR3 comprising amino acids having the sequence set forth in SEQ ID NO:133, a V_L CDR1 comprising amino acids having the sequence set forth in SEQ ID NO:134, a V_L CDR2 comprising amino acids having the sequence set forth in SEQ ID NO:135, and a V_L CDR3 comprising amino acids having the sequence set forth in SEQ ID NO:136.

having the sequence set forth in SEQ ID NO:34, as shown in Table 9. In certain embodiments, the anti-BCMA scFv comprises a V_H CDR1 comprising amino acids having the sequence set forth in SEQ ID NO:137 or conservative modifications thereof, a V_H CDR2 comprising amino acids having the sequence set forth in SEQ ID NO:138 or con-

TABLE 8

| Antigen | A BCMA polypeptide having the amino acid sequence of SEQ ID NO: 71 | | |
|---|---|---|---|
| CDRs | 1 | 2 | 3 |
| V_H | GYTFTGYY [SEQ ID NO: 131] | INPNSGGT [SEQ ID NO: 132] | ARSQWGSSWDY [SEQ ID NO: 133] |
| V_L | QSISSY [SEQ ID NO: 134] | AAS [SEQ ID NO: 135] | QQSYSTPPT [SEQ ID NO: 136] |
| Full V_H | QVQLVQSGAEVKKPGASVKVSCKASGYTFTGYYMHWVRQAPGQGLEWMGWI NPNSGGTNYAQKFQGRVTMTRDTSISTAYMELSRLRSDDTAVYYCARSQWGSS WDYWGQGTLVTVSS [SEQ ID NO: 29] | | |
| DNA | Caggtccagctggtacagtctggggctgaggtgaagaagcctggggcctcagtgaaggtctcctgcaaggcttctggatacac cttcaccggctactatatgcactgggtgcgacaggcccctggacaagggcttgagtggatgggatggatcaaccctaacagtg gtggcacaaactatgcacagaagtttcagggcagggtcaccatgaccagggacacgtccatcagcacagcctacatggagct gagcaggctgagatctgacgacacggccgtgtattactgtgcgcgctctcagtggggttcttcttgggattactggggtcaaggt actctggtgaccgtctcctca [SEQ ID NO: 311 | | |
| Full V_L | DIQLTQSPSSLSASVGDRVTITCRASQSISSYLNWYQQKPGKAPKLLIYAASSLQS GVPSRFSGSGSGTDFTLTISSLQPEDFATYYCQQSYSTPPTFGQGTKVEIKR [SEQ ID NO: 30] | | |
| DNA | Gacatccagttgacccagtctccatcctccctgtctgcatctgtaggagacagagtcaccatcacttgccgggcaagtcagagc attagcagctatttaaattggtatcagcagaaaccagggaaagccctaagctcctgatctatgctgcatccagtttgcaaagtgg ggtcccatcaaggttcagtggcagtggatctgggacagatttcactctcaccatcagcagtctgcaacctgaagattttgcaactt actactgtcaacagagttacagtacccctccgacgttcggccaagggaccaaggtggagatcaaacgt [SEQ ID NO: 32] | | |
| scFv | DIQLTQSPSSLSASVGDRVTITCRASQSISSYLNWYQQKPGKAPKLLIYAASSLQS GVPSRFSGSGSGTDFTLTISSLQPEDFATYYCQQSYSTPPTFGQGTKVEIKRSRGG GGSGGGGSGGGGSLEMAQVQLVQSGAEVKKPGASVKVSCKASGYTFTGYYMH WVRQAPGQGLEWMGWINPNSGGTNYAQKFQGRVTMTRDTSISTAYMELSRLR SDDTAVYYCARSQWGSSWDYWGQGTLVTVSS [SEQ ID NO: 79] | | |

In certain embodiments, the antibody or other antigen binding protein is an anti-BCMA scFv or an antigen-binding fragment thereof having an antigen-binding region that comprises the amino acid sequence of SEQ ID NO:80 and specifically binds to a BCMA polypeptide (e.g., a BCMA polypeptide having the amino acid sequence SEQ ID NO:71, or fragments thereof), which is designated as ET140-163 (also referred to as "ET140-13").

In certain embodiments, the anti-BCMA scFv antibody comprises a heavy chain variable region comprising amino acids having the sequence set forth in SEQ ID NO:33 and a light chain variable region comprising amino acids having the sequence set forth in SEQ ID NO:34, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V_H and V_L regions or CDRs selected from Table 9. In certain embodiments, the anti-BCMA scFv comprises a V_H comprising amino acids having the sequence set forth in SEQ ID NO:33, as shown in Table 9. In certain embodiments, the anti-BCMA scFv comprises a V_L comprising amino acids having the sequence set forth in SEQ ID NO:34, as shown in Table 9. In certain embodiments, the anti-BCMA scFv comprises a V_H comprising amino acids having the sequence set forth in SEQ ID NO:33 and a V_L comprising amino acids servative modifications thereof, and a V_H CDR3 comprising amino acids having the sequence set forth in SEQ ID NO:139 or conservative modifications thereof, as shown in Table 9. In certain embodiments, the anti-BCMA scFv comprises a V_L CDR1 comprising amino acids having the sequence set forth in SEQ ID NO:140 or conservative modifications thereof, a V_L CDR2 comprising amino acids having the sequence set forth in SEQ ID NO:141 or conservative modifications thereof, and a V_L CDR3 comprising amino acids having the sequence set forth in SEQ ID NO:142 or conservative modifications thereof, as shown in Table 9. In certain embodiments, the anti-BCMA scFv comprises a V_H CDR1 comprising amino acids having the sequence set forth in SEQ ID NO:137 or conservative modifications thereof, a V_H CDR2 comprising amino acids having the sequence set forth in SEQ ID NO:138 or conservative modifications thereof, a V_H CDR3 comprising amino acids having the sequence set forth in SEQ ID NO:139 or conservative modifications thereof, a V_L CDR1 comprising amino acids having the sequence set forth in SEQ ID NO:140 or conservative modifications thereof, a V_L CDR2 comprising amino acids having the sequence set forth in SEQ ID NO:141 or conservative modifications thereof, and a V_L CDR3 comprising amino acids having the sequence set forth in SEQ ID NO:142 or conservative modifications thereof, as shown in Table 9. In certain embodiments, the extracellular antigen-binding domain comprises a V_H CDR1 comprising amino acids having the sequence set forth in SEQ ID NO:137, a V$_H$ CDR2 comprising amino acids having the sequence set forth in SEQ ID NO:138, a V$_H$ CDR3 comprising amino acids having the sequence set forth in SEQ ID NO:139, a V$_L$ CDR1 comprising amino acids having the sequence set forth in SEQ ID NO:140, a V$_L$ CDR2 comprising amino acids having the sequence set forth in SEQ ID NO:141, and a V$_L$ CDR3 comprising amino acids having the sequence set forth in SEQ ID NO:142.

in Table 10. In certain embodiments, the anti-BCMA scFv comprises a V$_H$ comprising amino acids having the sequence set forth in SEQ ID NO:37 and a V$_L$ comprising amino acids having the sequence set forth in SEQ ID NO:38, as shown in Table 10. In certain embodiments, the anti-BCMA scFv comprises a V$_H$ CDR1 comprising amino acids having the sequence set forth in SEQ ID NO:143 or conservative modifications thereof, a V$_H$ CDR2 comprising amino acids

TABLE 9

| Antigen | A BCMA polypeptide having the amino acid sequence of SEQ ID NO: 71 | | |
|---|---|---|---|
| CDRs | 1 | 2 | 3 |
| V$_H$ | GYTFTGYY [SEQ ID NO: 137] | INPNSGGT [SEQ ID NO: 138] | ARSSYHLYGYDS [SEQ ID NO: 139] |
| V$_L$ | NDYTNYK [SEQ ID NO: 140] | VGPGGIVG [SEQ ID NO: 141] | GADHGTGSNFVYV [SEQ ID NO: 142] |
| Full V$_H$ | EVQLVESGAEVKKPGASVKVSCKASGYTFTGYYMHWVRQAPGQGLEWMGWI NPNSGGTNYAQKFQGRVTMTRDTSISTAYMELSRLRSDDTAVYYCARSSYHLY GYDSWGQGTLVTVSS [SEQ ID NO: 33] | | |
| DNA | Gaggtgcagctggtggagtccggggctgaggtgaagaagcctggggcctcagtgaaggtctcctgcaaggcttctggataca ccttcaccggctactatatgcactgggtgcgacaggcccctggacaagggcttgagtggatgggatggatcaaccctaacagt ggtggcacaaactatgcacagaagtttcagggcagggtcaccatgaccagggacacgtccatcagcacagcctacatggagc tgagcaggctgagatctgacgacacggccgtatattactgtgcgcgctcttcttaccatctgtacggttacgattcttggggtcaag gtactctggtgaccgtctcctca [SEQ ID NO: 35] | | |
| Full V$_L$ | QPVLTQPPSASASLGASVTLTCTLSNDYTNYKVDWYQQRPGKGPRFVMRVGPG GIVGSKGDGIPDRFSVLGSGLNRYLTIKNIQEEDESDYHCGADHGTGSNFVYVFG GGTKLTVLG [SEQ ID NO: 34] | | |
| DNA | Cagcctgtgctgactcagccacccttctgcatcagcctccctgggagcctcggtcactctcacctgcaccctgagcaacgactac actaattataaagtggactggtaccagcagagaccagggaagggccccggtttgtgatgcgagtgggccctggtgggattgt gggatccaaggggatggcatccctgatcgcttctcagtcttgggctcaggcctgaatcgatacctgaccatcaagaacatcca ggaggaggatgagagtgactaccactgtggggcggaccatggcaccgggagcaacttcgtgtacgtgttcggcggagggac caagctgaccgtcctaggt [SEQ ID NO: 36] | | |
| scFv | QPVLTQPPSASASLGASVTLTCTLSNDYTNYKVDWYQQRPGKGPRFVMRVGPG GIVGSKGDGIPDRFSVLGSGLNRYLTIKNIQEEDESDYHCGADHGTGSNFVYVFG GGTKLTVLGSRGGGGSGGGGSGGGGSLEMAEVQLVESGAEVKKPGASVKVSCK ASGYTFTGYYMHWVRQAPGQGLEWMGWINPNSGGTNYAQKFQGRVTMTRDT SISTAYMELSRLRSDDTAVYYCARSSYHILYGYDSWGQGTLVTVSS [SEQ ID NO: 80] | | |

In certain embodiments, the antibody or other antigen binding protein is an anti-BCMA scFv or an antigen-binding fragment thereof having an antigen-binding region that comprises the amino acid sequence of SEQ ID NO:81 and specifically binds to a BCMA polypeptide (e.g., a BCMA polypeptide having the amino acid sequence SEQ ID NO:71, or fragments thereof), which is designated as ET140-207 (also referred to as "ET140-57").

In certain embodiments, the anti-BCMA scFv antibody comprises a heavy chain variable region comprising amino acids having the sequence set forth in SEQ ID NO:37 and a light chain variable region comprising amino acids having the sequence set forth in SEQ ID NO:38, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-BCMA scFv antibody is a scFv-Fc fusion protein or full length human IgG with V$_H$ and V$_L$ regions or CDRs selected from Table 10. In certain embodiments, the anti-BCMA scFv comprises a V$_H$ comprising amino acids having the sequence set forth in SEQ ID NO:37, as shown in Table 10. In certain embodiments, the anti-BCMA scFv comprises a V$_L$ comprising amino acids having the sequence set forth in SEQ ID NO:38, as shown in Table 10. In certain embodiments, the anti-BCMA scFv comprises a V$_H$ CDR1 comprising amino acids having the sequence set forth in SEQ ID NO:143 or conservative modifications thereof, a V$_H$ CDR2 comprising amino acids having the sequence set forth in SEQ ID NO:144 or conservative modifications thereof, and a V$_H$ CDR3 comprising amino acids having the sequence set forth in SEQ ID NO:145 or conservative modifications thereof, as shown in Table 10. In certain embodiments, the anti-BCMA scFv comprises a V$_L$ CDR1 comprising amino acids having the sequence set forth in SEQ ID NO:146 or conservative modifications thereof, a V$_L$ CDR2 comprising amino acids having the sequence set forth in SEQ ID NO:147 or conservative modifications thereof, and a V$_L$ CDR3 comprising amino acids having the sequence set forth in SEQ ID NO:148 or conservative modifications thereof, as shown in Table 10. In certain embodiments, the anti-BCMA scFv comprises a V$_H$ CDR1 comprising amino acids having the sequence set forth in SEQ ID NO:143 or conservative modifications thereof, a V$_H$ CDR2 comprising amino acids having the sequence set forth in SEQ ID NO:144 or conservative modifications thereof, a V$_H$ CDR3 comprising amino acids having the sequence set forth in SEQ ID NO:145 or conservative modifications thereof, a V$_L$ CDR1 comprising amino acids having the sequence set forth in SEQ ID NO:146 or conservative modifications thereof, a V$_L$ CDR2 comprising amino acids having the sequence set forth in SEQ ID NO:147 or conservative modifications thereof, and a V$_L$ CDR3 comprising amino acids having the sequence set forth in SEQ ID NO:148 or conservative modifications thereof, as shown in Table 10. In certain embodiments, the extracellular antigen-binding domain comprises a V$_H$ CDR1 comprising amino acids having the sequence set forth in SEQ ID NO:143, a V$_H$ CDR2 comprising amino acids having the sequence set forth in SEQ ID NO:144, a V$_H$ CDR3 comprising amino acids having the sequence set forth in SEQ ID NO:145, a V$_L$ CDR1 comprising amino acids having the sequence set forth in SEQ ID NO:146, a V$_L$ CDR2 comprising amino acids having the sequence set forth in SEQ ID NO:147, and a V$_L$ CDR3 comprising amino acids having the sequence set forth in SEQ ID NO:148.

prising amino acids having the sequence set forth in SEQ ID NO:41, as shown in Table 11. In certain embodiments, the anti-BCMA scFv comprises a V$_L$ comprising amino acids having the sequence set forth in SEQ ID NO:42, as shown in Table 11. In certain embodiments, the anti-BCMA scFv comprises a V$_H$ comprising amino acids having the sequence set forth in SEQ ID NO:41 and a V$_L$ comprising amino acids having the sequence set forth in SEQ ID NO:42, as shown in Table 11. In certain embodiments, the anti-BCMA scFv comprises a V$_H$ CDR1 comprising amino acids having the sequence set forth in SEQ ID NO:149 or conservative modifications thereof, a V$_H$ CDR2 comprising amino acids

TABLE 10

| Antigen | A BCMA polypeptide having the amino acid sequence of SEQ ID NO: 71 | | |
|---|---|---|---|
| CDRs | 1 | 2 | 3 |
| V$_H$ | GGTFSSYA [SEQ ID NO: 143] | IIPIFSTA [SEQ ID NO: 144] | ARQPWTWYSPYDQ [SEQ ID NO: 145] |
| V$_L$ | SGYSNYK [SEQ ID NO: 146] | VDTGGIVG [SEQ ID NO: 147] | GADHGSGSNFVWV [SEQ ID NO: 148] |
| Full V$_H$ | QVQLVQSGAEVKKPGSSVKVSCKASGGTFSSYAISWVRQAPGQGLEWMGGIIPI FSTANYAQKFQGRVTMTTDTSTSTAYMELRSLRSDDTAVYYCARQPWTWYSPY DQWGQGTLVTVSS [SEQ ID NO: 37] | | |
| DNA | Caggtgcagctggtgcagtctggggctgaggtgaagaagcctgggtcctcggtgaaggtctcctgcaaggcttctggaggca ccttcagcagctatgctatcagctgggtgcgacaggcccctggacaagggcttgagtggatgggagggatcatccctatcttta gtacagcaaactacgcacagaagttccagggcagagtcaccatgaccacagacacatccacgagcacagcctacatggagct gaggagcctgagatctgacgacacggccgtgtattactgtgcgcgccagccgtggacttggtactctccgtacgatcagtggg gtcaaggtactctggtgaccgtctcctca [SEQ ID NO: 39] | | |
| Full V$_L$ | QPVLTQPPSASASLGASVTLTCTLSSGYSNYKVDWYQQRPGKGPRFLMRVDTGG IVGSKGDGIPDRFSVSGSGLNRYLTIKNIQEEDESDYHCGADHGSGSNFVWVFGG GTKLTVLG [SEQ ID NO: 38] | | |
| DNA | Cagcctgtgctgactcagccacctctgcatcagcctccctgggagcctcggtcacactcacctgcaccctgagcagcggcta cagtaattataaagtggactggtatcaacagagaccagggaagggcccccggtttctgatgcgagtagacaccggtgggattgt gggatccaaggggggatggcatccctgatcgcttctcagtctcgggctcaggtctgaatcggtacctgaccatcaagaacattca ggaagaggatgagagtgactaccactgtggggcagaccatggcagtggggagcaacttcgtgtgggtgttcggcggagggac caagctgaccgtcctaggt [SEQ ID NO: 40] | | |
| scFv | QPVLTQPPSASASLGASVTLTCTLSSGYSNYKVDWYQQRPGKGPRFLMRVDTGG IVGSKGDGIPDRFSVSGSGLNRYLTIKNIQEEDESDYHCGADHGSGSNFVWVFGG GTKLTVLGSRGGGGSGGGGSGGGGSLEMAQVQLVQSGAEVKKPGSSVKVSCK ASGGTFSSYAISWVRQAPGQGLEWMGGIIPIFSTANYAQKFQGRVTMTTDTSTST AYMELRSLRSDDTAVYYCARQPWTWYSPYDQWGQGTLVTVSS [SEQ ID NO: 81] | | |

In certain embodiments, the antibody or other antigen binding protein is an anti-BCMA scFv or an antigen-binding fragment thereof having an antigen-binding region that comprises the amino acid sequence of SEQ ID NO:82 and specifically binds to a BCMA polypeptide (e.g., a BCMA polypeptide having the amino acid sequence SEQ ID NO:71, or fragments thereof), which is designated as ET140-165 (also referred to as "ET140-15").

In certain embodiments, the anti-BCMA scFv antibody comprises a heavy chain variable region comprising amino acids having the sequence set forth in SEQ ID NO:41 and a light chain variable region comprising amino acids having the sequence set forth in SEQ ID NO:42, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V$_H$ and V$_L$ regions or CDRs selected from Table 11. In certain embodiments, the anti-BCMA scFv comprises a V$_H$ com-having the sequence set forth in SEQ ID NO: 150 or conservative modifications thereof, and a V$_H$ CDR3 comprising amino acids having the sequence set forth in SEQ ID NO: 151 or conservative modifications thereof, as shown in Table 11. In certain embodiments, the anti-BCMA scFv comprises a V$_L$ CDR1 comprising amino acids having the sequence set forth in SEQ ID NO: 152 or conservative modifications thereof, a V$_L$ CDR2 comprising amino acids having the sequence set forth in SEQ ID NO: 153 or conservative modifications thereof, and a V$_L$ CDR3 comprising amino acids having the sequence set forth in SEQ ID NO: 154 or conservative modifications thereof, as shown in Table 11. In certain embodiments, the anti-BCMA scFv comprises a V$_H$ CDR1 comprising amino acids having the sequence set forth in SEQ ID NO: 147 or conservative modifications thereof, a V$_H$ CDR2 comprising amino acids having the sequence set forth in SEQ ID NO: 150 or conservative modifications thereof, a V$_H$ CDR3 comprising amino acids having the sequence set forth in SEQ ID NO: 151 or conservative modifications thereof, a V$_L$ CDR1 comprising amino acids having the sequence set forth in SEQ ID NO: 152 or conservative modifications thereof, a $V_L$ CDR2 comprising amino acids having the sequence set forth in SEQ ID NO: 153 or conservative modifications thereof, and a $V_L$ CDR3 comprising amino acids having the sequence set forth in SEQ ID NO: 154 or conservative modifications thereof, as shown in Table 11. In certain embodiments, the extracellular antigen-binding domain comprises a $V_H$ CDR1 comprising amino acids having the sequence set forth in SEQ ID NO: 149, a $V_H$ CDR2 comprising amino acids having the sequence set forth in SEQ ID NO: 150, a $V_H$ CDR3 comprising amino acids having the sequence set forth in SEQ ID NO: 151, a $V_L$ CDR1 comprising amino acids having the sequence set forth in SEQ ID NO: 152, a $V_L$ CDR2 comprising amino acids having the sequence set forth in SEQ ID NO: 153, and a $V_L$ CDR3 comprising amino acids having the sequence set forth in SEQ ID NO: 154.

scFv-Fc fusion protein or full length human IgG with $V_H$ and $V_L$ regions or CDRs selected from Table 12. In certain embodiments, the anti-BCMA scFv comprises a $V_H$ comprising amino acids having the sequence set forth in SEQ ID NO:45, as shown in Table 12. In certain embodiments, the anti-BCMA scFv comprises a $V_L$ comprising amino acids having the sequence set forth in SEQ ID NO:46, as shown in Table 12. In certain embodiments, the anti-BCMA scFv comprises a $V_H$ comprising amino acids having the sequence set forth in SEQ ID NO:45 and a $V_L$ comprising amino acids having the sequence set forth in SEQ ID NO:46, as shown in Table 12. In certain embodiments, the anti-BCMA scFv comprises a $V_H$ CDR1 comprising amino acids having the sequence set forth in SEQ ID NO:155 or conservative modifications thereof, a $V_H$ CDR2 comprising amino acids having the sequence set forth in SEQ ID NO: 156 or

TABLE 11

| Antigen | A BCMA polypeptide having the amino acid sequence of SEQ ID NO: 71 | | |
| --- | --- | --- | --- |
| CDRs | 1 | 2 | 3 |
| $V_H$ | GFTFSTYA [SEQ ID NO: 149] | ITPGGDRT [SEQ ID NO: 150] | ARYYGYMIDM [SEQ ID NO: 151] |
| $V_L$ | QSLLHSNGYNY [SEQ ID NO: 152] | LGS [SEQ ID NO: 153] | MQALQTPLT [SEQ ID NO: 154] |
| Full $V_H$ | EVQLVETGGGLVQPGGSLRLSCAASGFTFSTYAMTWVRQAPGKGLEWVSAITP GGDRTYYADSVKGRFTISRDNSRNTLYLQMNSLRAEDTAVYYCARYYGYMIDM WGQGTLVTVSS [SEQ ID NO: 41] | | |
| DNA | Gaggtgcagctggtggagactggggggaggcctggtacagcctggggggtccctgagactctcctgtgctgcctctggattca cctttagcacctatgccatgacctgggtccgccaggctccagggaaggggctggagtgggtctcagctattactcctggtggtg atcgcacatactacgcagactccgtgaagggccgtttcactatctccagagacaattccaggaacacgctgtatctgcaaatgaa cagcctgagagccgaggacacggccgtatattactgtgcgcgctactacggttacatgatcgatatgtggggtcaaggtactctg gtgaccgtctcctca [SEQ ID NO: 43] | | |
| Full $V_L$ | DVVMTQSPLSLPVTPGEPASISCRSSQSLLHSNGYNYLDWYLQKPGQSPQLLIYL GSNRASGVPDRFSGSGSGTDFTLKISRVEAEDVGVYYCMQALQTPLTFGGGTKV EIKR [SEQ ID NO: 42] | | |
| DNA | Gatgttgtgatgactcagtctccactctccctgcccgtcacccctggagagccggcctccatctcctgcaggtctagtcagagcc tcctgcatagtaatggatacaactatttggattggtacctgcagaagccagggcagtctccacagctcctgatctatttgggttctaa tcgggcctccggggtccctgacaggttcagtggcagtggatcaggcacagattttacactgaaaatcagcagagtggaggctg aggatgttggggtttattactgcatgcaagctctacaaactcctctcactttcggcggagggaccaaggtggaaatcaaacgt [SEQ ID NO: 44] | | |
| scFv | DVVMTQSPLSLPVTPGEPASISCRSSQSLLHSNGYNYLDWYLQKPGQSPQLLIYL GSNRASGVPDRFSGSGSGTDFTLKISRVEAEDVGVYYCMQALQTPLTFGGGTKV EIKRSRGGGGSGGGGSGGGGSLEMAEVQLVETGGGLVQPGGSLRLSCAASGFTF STYAMTWVRQAPGKGLEWVSAITPGGDRTYYADSVKGRFTISRDNSRNTLYLQ MNSLRAEDTAVYYCARYYGYMIDMWGQGTLVTVSS [SEQ ID NO: 82] | | |

In certain embodiments, the antibody or other antigen binding protein is an anti-BCMA scFv or an antigen-binding fragment thereof having an antigen-binding region that comprises the amino acid sequence of SEQ ID NO:83 and specifically binds to a BCMA polypeptide (e.g., a BCMA polypeptide having the amino acid sequence SEQ ID NO:71, or fragments thereof), which is designated as ET140-188 (also referred to as "ET140-38").

In certain embodiments, the anti-BCMA scFv antibody comprises a heavy chain variable region comprising amino acids having the sequence set forth in SEQ ID NO:45 and a light chain variable region comprising amino acids having the sequence set forth in SEQ ID NO:46, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a conservative modifications thereof, and a $V_H$ CDR3 comprising amino acids having the sequence set forth in SEQ ID NO: 157 or conservative modifications thereof, as shown in Table 12. In certain embodiments, the anti-BCMA scFv comprises a $V_L$ CDR1 comprising amino acids having the sequence set forth in SEQ ID NO: 158 or conservative modifications thereof, a $V_L$ CDR2 comprising amino acids having the sequence set forth in SEQ ID NO: 159 or conservative modifications thereof, and a $V_L$ CDR3 comprising amino acids having the sequence set forth in SEQ ID NO: 160 or conservative modifications thereof, as shown in Table 12. In certain embodiments, the anti-BCMA scFv comprises a $V_H$ CDR1 comprising amino acids having the sequence set forth in SEQ ID NO: 155 or conservative modifications thereof, a $V_H$ CDR2 comprising amino acids having the sequence set forth in SEQ ID NO: 156 or conservative modifications thereof, a $V_H$ CDR3 comprising amino acids having the sequence set forth in SEQ ID NO:

157 or conservative modifications thereof, a V_L CDR1 comprising amino acids having the sequence set forth in SEQ ID NO: 158 or conservative modifications thereof, a V_L CDR2 comprising amino acids having the sequence set forth in SEQ ID NO: 159 or conservative modifications thereof, and a V_L CDR3 comprising amino acids having the sequence set forth in SEQ ID NO: 160 or conservative modifications thereof, as shown in Table 12. In certain embodiments, the extracellular antigen-binding domain comprises a V_H CDR1 comprising amino acids having the sequence set forth in SEQ ID NO: 155, a V_H CDR2 comprising amino acids having the sequence set forth in SEQ ID NO: 156, a V_H CDR3 comprising amino acids having the sequence set forth in SEQ ID NO: 157, a V_L CDR1 comprising amino acids having the sequence set forth in SEQ ID NO: 158, a V_L CDR2 comprising amino acids having the sequence set forth in SEQ ID NO: 159, and a V_L CDR3 comprising amino acids having the sequence set forth in SEQ ID NO: 160.

acids having the sequence set forth in SEQ ID NO:69. In certain embodiments, the anti-BCMA scFv antibody is a scFv-Fc fusion protein or full length human IgG with V_H and V_L regions or CDRs selected from Table 13. In certain embodiments, the anti-BCMA scFv comprises a V_H comprising amino acids having the sequence set forth in SEQ ID NO:49, as shown in Table 13. In certain embodiments, the anti-BCMA scFv comprises a V_L comprising amino acids having the sequence set forth in SEQ ID NO:50, as shown in Table 13. In certain embodiments, the anti-BCMA scFv comprises a V_H comprising amino acids having the sequence set forth in SEQ ID NO:49 and a V_L comprising amino acids having the sequence set forth in SEQ ID NO:50, as shown in Table 13. In certain embodiments, the anti-BCMA scFv comprises a V_H CDR1 comprising amino acids having the sequence set forth in SEQ ID NO:161 or conservative modifications thereof, a V_H CDR2 comprising amino acids having the sequence set forth in SEQ ID NO: 162 or

TABLE 12

| Antigen | A BCMA polypeptide having the amino acid sequence of SEQ ID NO: 71 | | |
|---|---|---|---|
| CDRs | 1 | 2 | 3 |
| V_H | GYTFTGYY [SEQ ID NO: 155] | INPNSGGT [SEQ ID NO: 156] | ARSQWGGTYDY [SEQ ID NO: 157] |
| V_L | SSNIGSNT [SEQ ID NO: 158] | SNN [SEQ ID NO: 159] | AAWDDSLNGWV [SEQ ID NO: 160] |
| Full V_H | QMQLVQSGAEVKKPGASVKVSCKASGYTFTGYYVHWLRQAPGQGLEWMGWI NPNSGGTNNAQEFQGRITMTRDTSINTAYMELSRLRSDDTAVYYCARSQWGGT YDYWGQGTLVTVSS [SEQ ID NO: 45] | | |
| DNA | Cagatgcagctggtgcagtctggggctgaggtgaagaagcctggggcctcagtgaaggtctcctgcaaggcttctggataca ccttcaccggctattatgtacactggttgcgacaggcccctggacaagggcttgagtggatgggttggatcaacccta acagtgg cggcacaaacaatgcacaggagtttcaaggcaggatcaccatgaccagggacacgtccatcaacacagcctacatggagctg agcaggctgagatctgacgacacggccgtgtattactgtgcgcgctctcagtggggtggtacttacgattactggggtcaaggta ctctggtgaccgtctcctca [SEQ ID NO: 47] | | |
| Full V_L | SYVLTQPPSASGTPGQRVTISCSGSSSNIGSNTVNWYQQVPGTAPKLLIYSNNQRP SGVPDRFSGSKSGASASLAISWLQSEDEADYYCAAWDDSLNGWVFGGGTKLTV LG [SEQ ID NO: 46] | | |
| DNA | Tcctatgtgctgactcagccacccttcagcgtctgggaccccgggcagagggtcaccatctcttgttctggaagcagctccaac atcggaagtaatactgtaaactggtaccagcaggtcccaggaacggcccccaaactcctcatctatagtaataatcagcggccct cagggggtccctgaccgattctctggctccaagtctggcgcctcagcctccctggccatcagttggctccagtctgaggatgagg ctgattattactgtgcagcatgggatgacagcctgaatggttgggtgttcggcggagggaccaagctgaccgtcctaggt [SEQ ID NO: 48] | | |
| scFv | SYVLTQPPSASGTPGQRVTISCSGSSSNIGSNTVNWYQQVPGTAPKLLIYSNNQRP SGVPDRFSGSKSGASASLAISWLQSEDEADYYCAAWDDSLNGWVFGGGTKLTV LGSRGGGGSGGGGSGGGGSLEMAQMQLVQSGAEVKKPGASVKVSCKASGYTF TGYYVHWLRQAPGQGLEWMGWINPNSGGTNNAQEFQGRITMTRDTSINTAYM ELSRLRSDDTAVYYCARSQWGGTYDYWGQGTLVTVSS [SEQ ID NO: 83] | | |

In certain embodiments, the antibody or other antigen binding protein is an anti-BCMA scFv or an antigen-binding fragment thereof having an antigen-binding region that comprises the amino acid sequence of SEQ ID NO:84 and specifically binds to a BCMApolypeptide (e.g., a BCMA polypeptide having the amino acid sequence SEQ ID NO:71, or fragments thereof), which is designated as ET140-196 (also referred to as "ET140-46").

In certain embodiments, the anti-BCMA scFv antibody comprises a heavy chain variable region comprising amino acids having the sequence set forth in SEQ ID NO:49 and a light chain variable region comprising amino acids having the sequence set forth in SEQ ID NO:50, optionally with (iii) a linker sequence, for example a linker peptide, between the heavy chain variable region and the light chain variable region. In certain embodiments, the linker comprises amino conservative modifications thereof, and a V_H CDR3 comprising amino acids having the sequence set forth in SEQ ID NO: 163 or conservative modifications thereof, as shown in Table 13. In certain embodiments, the anti-BCMA scFv comprises a V_L CDR1 comprising amino acids having the sequence set forth in SEQ ID NO: 164 or conservative modifications thereof, a V_L CDR2 comprising amino acids having the sequence set forth in SEQ ID NO:165 or conservative modifications thereof, and a V_L CDR3 comprising amino acids having the sequence set forth in SEQ ID NO:166 or conservative modifications thereof, as shown in Table 13. In certain embodiments, the anti-BCMA scFv comprises a V_H CDR1 comprising amino acids having the sequence set forth in SEQ ID NO: 161 or conservative modifications thereof, a V_H CDR2 comprising amino acids having the sequence set forth in SEQ ID NO: 162 or conservative modifications thereof, a $V_H$ CDR3 comprising amino acids having the sequence set forth in SEQ ID NO: 163 or conservative modifications thereof, a $V_L$ CDR1 comprising amino acids having the sequence set forth in SEQ ID NO: 164 or conservative modifications thereof, a $V_L$ CDR2 comprising amino acids having the sequence set forth in SEQ ID NO:165 or conservative modifications thereof, and a $V_L$ CDR3 comprising amino acids having the sequence set forth in SEQ ID NO:166 or conservative modifications thereof, as shown in Table 13. In certain embodiments, the extracellular antigen-binding domain comprises a $V_H$ CDR1 comprising amino acids having the sequence set forth in SEQ ID NO: 161, a $V_H$ CDR2 comprising amino acids having the sequence set forth in SEQ ID NO: 162, a $V_H$ CDR3 comprising amino acids having the sequence set forth in SEQ ID NO: 163, a $V_L$ CDR1 comprising amino acids having the sequence set forth in SEQ ID NO: 164, a $V_L$ CDR2 comprising amino acids having the sequence set forth in SEQ ID NO:165, and a $V_L$ CDR3 comprising amino acids having the sequence set forth in SEQ ID NO:166.

heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with $V_H$ and $V_L$ regions or CDRs selected from Table 14. In certain embodiments, the anti-BCMA scFv comprises a $V_H$ comprising amino acids having the sequence set forth in SEQ ID NO:53, as shown in Table 14. In certain embodiments, the anti-BCMA scFv comprises a $V_L$ comprising amino acids having the sequence set forth in SEQ ID NO:54, as shown in Table 14. In certain embodiments, the anti-BCMA scFv comprises a $V_H$ comprising amino acids having the sequence set forth in SEQ ID NO:53 and a $V_L$ comprising amino acids having the sequence set forth in SEQ ID NO:54, as shown in Table 14. In certain embodiments, the anti-BCMA scFv comprises a $V_H$ CDR1 comprising amino acids having the sequence set forth in SEQ ID NO:167 or conservative modifications thereof, a $V_H$ CDR2 comprising amino acids having the sequence set forth in SEQ ID NO:168 or con-

TABLE 13

| Antigen | A BCMA polypeptide having the amino acid sequence of SEQ ID NO: 71 | | |
| --- | --- | --- | --- |
| CDRs | 1 | 2 | 3 |
| $V_H$ | GYDFTTYW [SEQ ID NO: 161] | IYPGDSDT [SEQ ID NO: 162] | ARMWTFSQDG [SEQ ID NO: 163] |
| $V_L$ | SSNIGSYT [SEQ ID NO: 164] | SNN [SEQ ID NO: 165] | AAWDDSLNGYV [SEQ ID NO: 166] |
| Full $V_H$ | EVQLVQSGAEVKKPGESLKISCKGSGYDFTTYWIGWVRQMPGKGLEWMGIIYP GDSDTRYSPSVRGRVTISADKSINTAYLQWSSLEASDTAMYYCARMWTFSQDG WGQGTLVTVSS [SEQ ID NO: 49] | | |
| DNA | gaggtgcagctggtgcagtctggagcagaggtgaaaaagccgggggagtctctgaagatctcctgtaagggttctggatatga ctttaccacctactggatcgggtgggtgcgccagatgcccgggaagggcctggagtggatggggatcatctatcctggtgactc tgataccagatacagcccgtccgtccgaggccgggtcaccatctcagccgacaagtccatcaacaccgcctatttgcagtgga gtagcctggaggcctccgacaccgccatgtattactgtgcgcgcatgtggactttctctcaggatggttggggtcaaggtactctg gtgaccgtctcctca [SEQ ID NO: 51] | | |
| Full $V_L$ | QAVLTQPPSASGTPGQRVTISCSGSSSNIGSYTVSWYQQLPGTAPKFLIYSNNQRP SGVPDRFSGSKSGTSASLAISGLQSEDEADYYCAAWDDSLNGYVFGTGTKVTVL G [SEQ ID NO: 50] | | |
| DNA | Caggctgtgctgactcagccaccctcagcgtctggaccccgggcagagggtcaccatctcttgttctggaagcagctccaa catcggaagttatactgtaagctggtaccagcaactcccaggaacggccccaaattcctcatctattctaataatcagcggccct caggggtccctgaccgattctctggctccaagtctggcacctcagcctcctggccatcagtgggctccagtctgaggatgagg ctgattattactgtgctgcatgggatgacagcctgaatggttatgtcttcggaactgggaccaaggtcaccgtcctaggt [SEQ ID NO: 52] | | |
| scFv | QAVLTQPPSASGTPGQRVTISCSGSSSNIGSYTVSWYQQLPGTAPKFLIYSNNQRP SGVPDRFSGSKSGTSASLAISGLQSEDEADYYCAAWDDSLNGYVFGTGTKVTVL GSRGGGGSGGGGSGGGGSLEMAEVQLVQSGAEVKKPGESLKISCKGSGYDFTT YWIGWVRQMPGKGLEWMGIIYPGDSDTRYSPSVRGRVTISADKSINTAYLQWSS LEASDTAMYYCARMWTFSQDGWGQGTLVTVSS [SEQ ID NO: 84] | | |

In certain embodiments, the antibody or other antigen binding protein is an anti-BCMA scFv or an antigen-binding fragment thereof having an antigen-binding region that comprises the amino acid sequence of SEQ ID NO:85 and specifically binds to a BCMA polypeptide (e.g., a BCMA polypeptide having the amino acid sequence SEQ ID NO:71, or fragments thereof), which is designated as ET140-204 (also referred to as "ET140-54").

In certain embodiments, the anti-BCMA scFv antibody comprises a heavy chain variable region comprising amino acids having the sequence set forth in SEQ ID NO:53 and a light chain variable region comprising amino acids having the sequence set forth in SEQ ID NO:54, optionally with (iii) a linker sequence, for example a linker peptide, between the servative modifications thereof, and a $V_H$ CDR3 comprising amino acids having the sequence set forth in SEQ ID NO:169 or conservative modifications thereof, as shown in Table 14. In certain embodiments, the anti-BCMA scFv comprises a $V_L$ CDR1 comprising amino acids having the sequence set forth in SEQ ID NO: 170 or conservative modifications thereof, a $V_L$ CDR2 comprising amino acids having the sequence set forth in SEQ ID NO: 171 or conservative modifications thereof, and a $V_L$ CDR3 comprising amino acids having the sequence set forth in SEQ ID NO: 172 or conservative modifications thereof, as shown in Table 14. In certain embodiments, the anti-BCMA scFv comprises a $V_H$ CDR1 comprising amino acids having the sequence set forth in SEQ ID NO: 167 or conservative modifications thereof, a $V_H$ CDR2 comprising amino acids having the sequence set forth in SEQ ID NO: 168 or conservative modifications thereof, a $V_H$ CDR3 comprising amino acids having the sequence set forth in SEQ ID NO: 169 or conservative modifications thereof, a $V_L$ CDR1 comprising amino acids having the sequence set forth in SEQ ID NO: 170 or conservative modifications thereof, a $V_L$ CDR2 comprising amino acids having the sequence set forth in SEQ ID NO: 171 or conservative modifications thereof, and a $V_L$ CDR3 comprising amino acids having the sequence set forth in SEQ ID NO: 172 or conservative modifications thereof, as shown in Table 14. In certain embodiments, the extracellular antigen-binding domain comprises a $V_H$ CDR1 comprising amino acids having the sequence set forth in SEQ ID NO: 167, a $V_H$ CDR2 comprising amino acids having the sequence set forth in SEQ ID NO: 168, a $V_H$ CDR3 comprising amino acids having the sequence set forth in SEQ ID NO: 169, a $V_L$ CDR1 comprising amino acids having the sequence set forth in SEQ ID NO: 170, a $V_L$ CDR2 comprising amino acids having the sequence set forth in SEQ ID NO: 171, and a $V_L$ CDR3 comprising amino acids having the sequence set forth in SEQ ID NO: 172.

a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with $V_H$ and $V_L$ regions or CDRs selected from Table 15. In certain embodiments, the anti-BCMA scFv comprises a $V_H$ comprising amino acids having the sequence set forth in SEQ ID NO:57, as shown in Table 15. In certain embodiments, the anti-BCMA scFv comprises a $V_L$ comprising amino acids having the sequence set forth in SEQ ID NO:58, as shown in Table 15. In certain embodiments, the anti-BCMA scFv comprises a $V_H$ comprising amino acids having the sequence set forth in SEQ ID NO:57 and a $V_L$ comprising amino acids having the sequence set forth in SEQ ID NO:58, as shown in Table 15. In certain embodiments, the anti-BCMA scFv comprises a $V_H$ CDR1 comprising amino acids having the sequence set forth in SEQ ID NO:173 or conservative modifications thereof, a $V_H$ CDR2 comprising amino acids having the sequence set forth in SEQ ID NO: 174 or conservative modifications thereof, and a $V_H$ CDR3 com-

TABLE 14

| Antigen | A BCMA polypeptide having the amino acid sequence of SEQ ID NO: 71 | | |
|---|---|---|---|
| CDRs | 1 | 2 | 3 |
| $V_H$ | GYTFIDYY [SEQ ID NO: 167] | INPNSGGT [SEQ ID NO: 168] | ARSQRDGYMDY [SEQ ID NO: 169] |
| $V_L$ | ISCTGTSSD [SEQ ID NO: 170] | EDS [SEQ ID NO: 171] | SSNTRSSTLV [SEQ ID NO: 172] |
| Full $V_H$ | EVQLVQSGAEMKKPGASLKLSCKASGYTFIDYYVYWMRQAPGQGLESMGWIN PNSGGTNYAQKFQGRVTMTRDTSISTAYMELSRLRSDDTAMYYCARSQRDGYM DYWGQGTLVTVSS [SEQ ID NO: 53] | | |
| DNA | Gaagtgcagctggtgcagtctggggctgagatgaagaagcctgggggcctcactgaagctctcctgcaaggcttctggatacac cttcatcgactactatgtatactggatgcgacaggcccctggacaagggcttgagtccatgggatggatcaaccctaacagtggt ggcacaaactatgcacagaagtttcagggcagggtcaccatgaccagggacacgtccatcagcacagcctacatggagctga gcaggctgagatctgacgacaccgccatgtattactgtgcgcgctcccagcgtgacggttacatggattactggggtcaaggta ctctggtgaccgtctcctca [SEQ ID NO: 55] | | |
| Full $V_L$ | QSALTQPASVSASPGQSIAISCTGTSSDVGWYQQHPGKAPKLMIYEDSKRPSGVS NRFSGSKSGNTASLTISGLQAEDEADYYCSSNTRSSTLVFGGGTKLTVLG [SEQ ID NO: 54] | | |
| DNA | Caatctgccctgactcagcctgcctccgtgtctgcgtctcctggacagtcgatcgccatctcctgcactggaaccagcagtgac gttggttggtatcaacagcacccaggcaaagcccccaaactcatgatttatgaggacagtaagcggccctcaggggtttctaatc gcttctctggctccaagtctggcaacacggcctccctgaccatctctgggctccaggctgaggacgaggctgattattactgcag ctcaaatacaagaagcagcactttggtgttcggcggagggaccaagctgaccgtcctaggt [SEQ ID NO: 56] | | |
| scFv | QSALTQPASVSASPGQSIAISCTGTSSDVGWYQQHPGKAPKLMIYEDSKRPSGVS NRFSGSKSGNTASLTISGLQAEDEADYYCSSNTRSSTLVFGGGTKLTVLGSRGGG GSGGGGSGGGGSLEMAEVQLVQSGAEMKKPGASLKLSCKASGYTFIDYYVYW MRQAPGQGLESMGWINPNSGGTNYAQKFQGRVTMTRDTSISTAYMELSRLRSD DTAMYYCARSQRDGYMDYWGQGTLVTVSS [SEQ ID NO: 85] | | |

In certain embodiments, the antibody or other antigen binding protein is an anti-BCMA scFv or an antigen-binding fragment thereof having an antigen-binding region that comprises the amino acid sequence of SEQ ID NO:86 and specifically binds to a BCMA polypeptide (e.g., a BCMA polypeptide having the amino acid sequence SEQ ID NO:71, or fragments thereof), which is designated as ET140-190 (also referred to as "ET140-40").

In certain embodiments, the anti-BCMA scFv antibody comprises a heavy chain variable region comprising amino acids having the sequence set forth in SEQ ID NO:57 and a light chain variable region comprising amino acids having the sequence set forth in SEQ ID NO:58, optionally with (iii) prising amino acids having the sequence set forth in SEQ ID NO: 175 or conservative modifications thereof, as shown in Table 15. In certain embodiments, the anti-BCMA scFv comprises a $V_L$ CDR1 comprising amino acids having the sequence set forth in SEQ ID NO: 176 or conservative modifications thereof, a $V_L$ CDR2 comprising amino acids having the sequence set forth in SEQ ID NO: 177 or conservative modifications thereof, and a $V_L$ CDR3 comprising amino acids having the sequence set forth in SEQ ID NO: 178 or conservative modifications thereof, as shown in Table 15. In certain embodiments, the anti-BCMA scFv comprises a $V_H$ CDR1 comprising amino acids having the sequence set forth in SEQ ID NO: 173 or conservative modifications thereof, a V$_H$ CDR2 comprising amino acids having the sequence set forth in SEQ ID NO: 174 or conservative modifications thereof, a V$_H$ CDR3 comprising amino acids having the sequence set forth in SEQ ID NO: 175 or conservative modifications thereof, a V$_L$ CDR1 comprising amino acids having the sequence set forth in SEQ ID NO: 176 or conservative modifications thereof, a V$_L$ CDR2 comprising amino acids having the sequence set forth in SEQ ID NO: 177 or conservative modifications thereof, and a V$_L$ CDR3 comprising amino acids having the sequence set forth in SEQ ID NO: 178 or conservative modifications thereof, as shown in Table 15. In certain embodiments, the extracellular antigen-binding domain comprises a V$_H$ CDR1 comprising amino acids having the sequence set forth in SEQ ID NO: 173, a V$_H$ CDR2 comprising amino acids having the sequence set forth in SEQ ID NO: 174, a V$_H$ CDR3 comprising amino acids having the sequence set forth in SEQ ID NO: 175, a V$_L$ CDR1 comprising amino acids having the sequence set forth in SEQ ID NO: 176, a V$_L$ CDR2 comprising amino acids having the sequence set forth in SEQ ID NO: 177, and a V$_L$ CDR3 comprising amino acids having the sequence set forth in SEQ ID NO: 178.

the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with V$_H$ and V$_L$ regions or CDRs selected from Table 16. In certain embodiments, the anti-BCMA scFv comprises a V$_H$ comprising amino acids having the sequence set forth in SEQ ID NO:61, as shown in Table 16. In certain embodiments, the anti-BCMA scFv comprises a V$_L$ comprising amino acids having the sequence set forth in SEQ ID NO:62, as shown in Table 16. In certain embodiments, the anti-BCMA scFv comprises a V$_H$ comprising amino acids having the sequence set forth in SEQ ID NO:61 and a V$_L$ comprising amino acids having the sequence set forth in SEQ ID NO:62, as shown in Table 16. In certain embodiments, the anti-BCMA scFv comprises a V$_H$ CDR1 comprising amino acids having the sequence set forth in SEQ ID NO:179 or conservative modifications thereof, a V$_H$ CDR2 comprising amino acids having the sequence set forth in SEQ ID NO: 180 or

TABLE 15

| Antigen | A BCMA polypeptide having the amino acid sequence of SEQ ID NO: 71 | | |
|---|---|---|---|
| CDRs | 1 | 2 | 3 |
| V$_H$ | GYTFTDYY [SEQ ID NO: 173] | INPNSGGT [SEQ ID NO: 174] | ARSPYSGVLDK [SEQ ID NO: 175] |
| V$_L$ | SSNIGAGFD [SEQ ID NO: 176] | GNS [SEQ ID NO: 177] [SEQ ID NO: 178] | QSYDSSLSGYV |
| Full V$_H$ | QVQLVQSGAEVKKPGASVKVSCKASGYTFTDYYMHWVRQAPGQRLEWMGWIN PNSGGTNYAQKFQDRITVTRDTSSNTGYMELTRLRSDDTAVYYCARSPYSGVLD KWGQGTLVTVSS [SEQ ID NO: 57] | | |
| DNA | Caggtccagctggtacagtctggggctgaggtgaagaagcctggggcctcagtgaaggtctcctgcaaggcttctggatacacc ttcaccgactactatatgcactgggtgcgacaggcccctggacaacggcttgagtggatgggatggatcaacccctaacagtggtg gcacaaactatgcacagaagtttcaggacaggatcaccgtgaccagggacacctccagcaacacaggctacatggagctgacc aggctgagatctgacgacacggccgtgtattactgtgcgcgctctccgtactctggtgttctggataaatggggtcaaggtactctg gtgaccgtctcctca [SEQ ID NO: 59] | | |
| Full V$_L$ | QSVLTQPPSVSGAPGQRVTISCTGSSSNIGAGFDVHWYQQLPGTAPKLLIYGNSNR PSGVPDRFSGSKSGTSASLAITGLQAEDEADYYCQSYDSSLSGYVFGTGTKVTVL G [SEQ ID NO: 58] | | |
| DNA | Cagtctgtgctgacgcagccgccctcagtgtctggggcccccagggcagagggtcaccatctcctgcactgggagcagctccaa catcggggcaggttttgatgtacactggtaccagcagcttccaggaacagcccccaaactcctcatctatggtaacagcaatcggc cctcaggggtccctgaccgattctctggctccaagtctggcacctcagcctccctggccatcactgggctccaggctgaggatga ggctgattattactgccagtcctatgacagcagcctgagtggttatgtcttcggaactgggaccaaggtcaccgtcctaggt [SEQ ID NO: 60] | | |
| ScFv | QSVLTQPPSVSGAPGQRVTISCTGSSSNIGAGFDVHWYQQLPGTAPKLLIYGNSNR PSGVPDRFSGSKSGTSASLAITGLQAEDEADYYCQSYDSSLSGYVFGTGTKVTVL GSRGGGGSGGGGSGGGGSLEMAQVQLVQSGAEVKKPGASVKVSCKASGYTFTD YYMHWVRQAPGQRLEWMGWINPNSGGTNYAQKFQDRITVTRDTSSNTGYMELT RLRSDDTAVYYCARSPYSGVLDKWGQGTLVTVSS [SEQ ID NO: 86] | | |

In certain embodiments, the antibody or other antigen binding protein is an anti-BCMA scFv or an antigen-binding fragment thereof having an antigen-binding region that comprises the amino acid sequence of SEQ ID NO: 87 and specifically binds to a BCMA polypeptide (e.g., a BCMA polypeptide having the amino acid sequence SEQ ID NO:71, or fragments thereof), which is designated as ET140-187 (also referred to as "ET140-37").

In certain embodiments, the anti-BCMA scFv antibody comprises a heavy chain variable region comprising amino acids having the sequence set forth in SEQ ID NO:61 and a light chain variable region comprising amino acids having conservative modifications thereof, and a V$_H$ CDR3 comprising amino acids having the sequence set forth in SEQ ID NO: 181 or conservative modifications thereof, as shown in Table 16. In certain embodiments, the anti-BCMA scFv comprises a V$_L$ CDR1 comprising amino acids having the sequence set forth in SEQ ID NO: 182 or conservative modifications thereof, a V$_L$ CDR2 comprising amino acids having the sequence set forth in SEQ ID NO: 183 or conservative modifications thereof, and a V$_L$ CDR3 comprising amino acids having the sequence set forth in SEQ ID NO: 184 or conservative modifications thereof, as shown in Table 16. In certain embodiments, the anti-BCMA scFv comprises a $V_H$ CDR1 comprising amino acids having the sequence set forth in SEQ ID NO: 179 or conservative modifications thereof, a $V_H$ CDR2 comprising amino acids having the sequence set forth in SEQ ID NO: 180 or conservative modifications thereof, a $V_H$ CDR3 comprising amino acids having the sequence set forth in SEQ ID NO: 181 or conservative modifications thereof, a $V_L$ CDR1 comprising amino acids having the sequence set forth in SEQ ID NO: 182 or conservative modifications thereof, a $V_L$ CDR2 comprising amino acids having the sequence set forth in SEQ ID NO: 183 or conservative modifications thereof, and a $V_L$ CDR3 comprising amino acids having the sequence set forth in SEQ ID NO: 184 or conservative modifications thereof, as shown in Table 16. In certain embodiments, the extracellular antigen-binding domain comprises a $V_H$ CDR1 comprising amino acids having the sequence set forth in SEQ ID NO: 179, a $V_H$ CDR2 comprising amino acids having the sequence set forth in SEQ ID NO: 180, a $V_H$ CDR3 comprising amino acids having the sequence set forth in SEQ ID NO: 181, a $V_L$ CDR1 comprising amino acids having the sequence set forth in SEQ ID NO: 182, a $V_L$ CDR2 comprising amino acids having the sequence set forth in SEQ ID NO: 183 and a $V_L$ CDR3 comprising amino acids having the sequence set forth in SEQ ID NO: 184.

acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, the anti-BCMA scFv antibody is a scFv-Fc fusion protein or full length human IgG with $V_H$ and $V_L$ regions or CDRs selected from Table 17. In certain embodiments, the anti-BCMA scFv comprises a $V_H$ comprising amino acids having the sequence set forth in SEQ ID NO:65, as shown in Table 17. In certain embodiments, the anti-BCMA scFv comprises a $V_L$ comprising amino acids having the sequence set forth in SEQ ID NO:66, as shown in Table 17. In certain embodiments, the anti-BCMA scFv comprises a $V_H$ comprising amino acids having the sequence set forth in SEQ ID NO:65 and a $V_L$ comprising amino acids having the sequence set forth in SEQ ID NO:66, as shown in Table 17. In certain embodiments, the anti-BCMA scFv comprises a $V_H$ CDR1 comprising amino acids having the sequence set forth in SEQ ID NO:185 or conservative modifications thereof, a $V_H$ CDR2 comprising amino acids having the sequence set forth in SEQ ID NO: 186 or

TABLE 16

| Antigen | A BCMA polypeptide having the amino acid sequence of SEQ ID NO: 71 | | |
| --- | --- | --- | --- |
| CDRs | 1 | 2 | 3 |
| $V_H$ | GGTFSSYA [SEQ ID NO: 179] | IIPILGTA [SEQ ID NO: 180] | ARSGYGSYRWED S [SEQ ID NO: 181] |
| $V_L$ | SSNIGSNY [SEQ ID NO: 182] | SNN [SEQ ID NO: 183] | AAWDDSLSASYV [SEQ ID NO: 184] |
| Full $V_H$ | QVQLVQSGAEVKKPGSSVKVSCKASGGTFSSYAISWVRQAPGQGLEWMGRIIPIL GTANYAQKFQGRVTITADESTSTAYMELSSLRSEDTAVYYCARSGYGSYRWEDS WGQGTLVTVSS [SEQ ID NO: 61] | | |
| DNA | Caggtgcagctggtgcagtctggggctgaggtgaagaagcctgggtcctcggtgaaggtctcctgcaaggcttctggaggcac cttcagcagctatgctatcagctgggtgcgacaggcccctggacaagggcttgagtggatgggaaggatcatccctatccttggt acagcaaactacgcacagaagttccagggcagagtcacgattaccgcggacgaatccacgagcacagcctacatggagctga gcagcctgagatctgaggacacggccgtgtattactgtgcgcgctctggttacggttcttaccgttgggaagattcttgggtcaag gtactctggtgaccgtctcctca [SEQ ID NO: 63] | | |
| Full $V_L$ | QAVLTQPPSASGTPGQRVTISCSGSSSNIGSNYVFWYQQLPGTAPKLLIYSNNQRPS GVPDRFSGSKSGTSASLAISGLRSEDEADYYCAAWDDSLSASYVFGTGTKVTVLG [SEQ ID NO: 62] | | |
| DNA | Caggctgtgctgactcagccaccctcagcgtctgggaccccgggcagagggtcaccatctcttgttctggaagcagctccaac atcggaagtaattacgtattctggtaccagcagctcccaggaacggcccccaaactcctcatctatagtaataatcagcggccctca ggggtccctgaccgattctctggctccaagtctggcacctcagcctccctggccatcagtgggctccggtccgaggatgaggctg attattactgtgcagcatgggatgacagcctgagtgcctcttatgttttcggaactgggaccaaggtcaccgtcctaggt [SEQ ID NO: 64] | | |
| scFv | QAVLTQPPSASGTPGQRVTISCSGSSSNIGSNYVFWYQQLPGTAPKLLIYSNNQRPS GVPDRFSGSKSGTSASLAISGLRSEDEADYYCAAWDDSLSASYVFGTGTKVTVLG SRGGGGSGGGGSGGGGSLEMAQVQLVQSGAEVKKPGSSVKVSCKASGGTFSSYA ISWVRQAPGQGLEWMGRIIPILGTANYAQKFQGRVTITADESTSTAYMELSSLRSE DTAVYYCARSGYGSYRWEDSWGQGTLVTVSS [SEQ ID NO: 87] | | |

In certain embodiments, the antibody or other antigen binding protein is an anti-BCMA scFv or an antigen-binding fragment thereof having an antigen-binding region that comprises the amino acid sequence of SEQ ID NO:88 and specifically binds to a BCMA polypeptide (e.g., a BCMA polypeptide having the amino acid sequence SEQ ID NO:71, or fragments thereof), which is designated as ET140-174 (also referred to as "ET140-24").

In certain embodiments, the anti-BCMA scFv antibody comprises a heavy chain variable region comprising amino conservative modifications thereof, and a $V_H$ CDR3 comprising amino acids having the sequence set forth in SEQ ID NO: 187 or conservative modifications thereof, as shown in Table 17. In certain embodiments, the anti-BCMA scFv comprises a $V_L$ CDR1 comprising amino acids having the sequence set forth in SEQ ID NO: 188 or conservative modifications thereof, a $V_L$ CDR2 comprising amino acids having the sequence set forth in SEQ ID NO: 189 or conservative modifications thereof, and a $V_L$ CDR3 comprising amino acids having the sequence set forth in SEQ ID NO: 190 or conservative modifications thereof, as shown in Table 17. In certain embodiments, the anti-BCMA scFv comprises a $V_H$ CDR1 comprising amino acids having the sequence set forth in SEQ ID NO: 185 or conservative modifications thereof, a $V_H$ CDR2 comprising amino acids having the sequence set forth in SEQ ID NO: 186 or conservative modifications thereof, a $V_H$ CDR3 comprising amino acids having the sequence set forth in SEQ ID NO: 187 or conservative modifications thereof, a $V_L$ CDR1 comprising amino acids having the sequence set forth in SEQ ID NO: 188 or conservative modifications thereof, a $V_L$ CDR2 comprising amino acids having the sequence set forth in SEQ ID NO: 189 or conservative modifications thereof, and a $V_L$ CDR3 comprising amino acids having the sequence set forth in SEQ ID NO: 190 or conservative modifications thereof, as shown in Table 17. In certain embodiments, the extracellular antigen-binding domain comprises a $V_H$ CDR1 comprising amino acids having the sequence set forth in SEQ ID NO: 185, a $V_H$ CDR2 comprising amino acids having the sequence set forth in SEQ ID NO: 186, a $V_H$ CDR3 comprising amino acids having the sequence set forth in SEQ ID NO: 187, a $V_L$ CDR1 comprising amino acids having the sequence set forth in SEQ ID NO: 188, a $V_L$ CDR2 comprising amino acids having the sequence set forth in SEQ ID NO: 189, and a $V_L$ CDR3 comprising amino acids having the sequence set forth in SEQ ID NO: 190.

between the heavy chain variable region and the light chain variable region, and an His-tag and an HA-tag. In certain embodiments, the amino acid sequence of the His-tag and HA-tag comprises the amino acid sequence of SEQ ID NO:246, which is provided below:

[SEQ ID NO: 246]
TSGQAGQHHHHHHGAYPYDVPDYAS

The nucleotide sequence encoding SEQ ID NO: 246 is SEQ ID NO: 247, which is provided below:

[SEQ ID NO: 247]
ACTAGTGGCCAGGCCGGCCAGCACCATCACCATCACCATGGCGCATACC

CGTACGACGTTCCGGACTACGCTTCT

2. Monoclonal Antibodies

The presently disclosed subject matter provides human antibodies (e.g., human monoclonal antibodies) that specifically bind to BCMA (e.g., human BCMA) and were isolated and structurally characterized as described in Example 2. The $V_H$ amino acid sequences of human anti-BCMA antibodies ET140-192 (also referred to as "ET140-42"), ET140-197 (also referred to as "ET140-47"), ET140-180 (also referred to as "ET140-30"), ET140-172 (also referred to as "ET140-22"), ET140-157 (also referred to as "ET140-7"), ET140-153 (also referred to as "ET140-3"), ET140-201 (also referred to as "ET140-51"), ET140-167 (also referred to as "ET140-17"), ET140-163 (also referred to as "ET140-13"), ET140-207 (also referred to as "ET140-57"), ET140-

TABLE 17

| Antigen | A BCMA polypeptide having the amino acid sequence of SEQ ID NO: 71 | | |
|---|---|---|---|
| CDRs | 1 | 2 | 3 |
| $V_H$ | GYSFTSYW [SEQ ID NO: 185] | IYPGDSDT [SEQ ID NO: 186] | ARYSGSFDN [SEQ ID NO: 187] |
| $V_L$ | SSNIGSHS [SEQ ID NO: 188] | TNN [SEQ ID NO: 189] | AAWDGSLNGLV [SEQ ID NO: 190] |
| Full $V_H$ | EVQLVQSGAEVKKPGESLKISCKGSGYSFTSYWIGWVRQMPGKGLEWMGIIYPG DSDTRYSPSFQGHVTISADKSISTAYLQWSSLKASDTAMYYCARYSGSFDNWGQ GTLVTVSS [SEQ ID NO: 65] | | |
| DNA | Gaggtgcagctggtgcagtctggagcagaggtgaaaaagcccggggagtctctgaagatctcctgtaagggttctggataca gctttaccagctactggatcggctgggtgcgccagatgcccgggaaaggcctggagtggatggggatcatctatcctggtgact ctgataccagatacagcccgtccttccaaggccacgtcaccatctcagctgacaagtccatcagcactgcctacctgcagtgga gcagcctgaaggcctcggacaccgccatgtattactgtgcgcgctactctggttcttttcgataactggggtcaaggtactctggtg accgtctcctca [SEQ ID NO: 67] | | |
| Full $V_L$ | SYELTQPPSASGTPGQRVTMSCSGTSSNIGSHSVNWYQQLPGTAPKWYTNNQR PSGVPDRFSGSKSGTSASLAISGLQSEDEADYYCAAWDGSLNGLVFGGGTKLTV LG [SEQ ID NO: 66] | | |
| DNA | Tcctatgagctgactcagccacccctcagcgtctgggaccccgggcagagggtcaccatgtcttgttctggaaccagtccaa catcggaagtcactctgtaaactggtaccagcagctcccaggaacggcccccaaactcctcatctatactaataatcagcggcc ctcaggggtccctgaccgattctctggctccaagtctggcacctcagcctccctggccatcagtggcctccagtctgaggatgag gctgattattactgtgcagcatgggatggcagcctgaatggtctggtattcggcggagggaccaagctgaccgtcctaggt [SEQ ID NO: 68] | | |
| scFv | SYELTQPPSASGTPGQRVTMSCSGTSSNIGSHSVNWYQQLPGTAPKLLIYTNNQR PSGVPDRFSGSKSGTSASLAISGLQSEDEADYYCAAWDGSLNGLVFGGGTKLTV LGSRGGGGSGGGGSGGGGSLEMAEVQLVQSGAEVKKPGESLKISCKGSGYSFTS YWIGWVRQMPGKGLEWMGIIYPGDSDTRYSPSFQGHVTISADKSISTAYLQWSS LKASDTAMYYCARYSGSFDNWGQGTLVTVSS [SEQ ID NO: 88] | | |

The presently disclosed subject matter further provides anti-BCMA scFv antibodies comprising a heavy chain variable region, a light chain variable region, a linker peptide 165 (also referred to as "ET140-15"), ET140-188 (also referred to as "ET140-38"), ET140-196 (also referred to as "ET140-46"), ET140-204 (also referred to as "ET140-54"), ET140-190 (also referred to as "ET140-40"), ET140-187 (also referred to as "ET140-37"), and ET140-174 (also referred to as "ET140-24") are shown in SEQ ID NOs: 1, 5, 9, 13, 17, 21, 25, 29, 33, 37, 41, 45, 49, 53, 57, 61, and 65, respectively. The $V_L$ amino acid sequences of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 are shown in SEQ ID NOs: 2, 6, 10, 14, 18, 22, 26, 30, 34, 38, 42, 46, 50, 54, 58, 62, and 66, respectively.

Given that each of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 antibodies can bind to BCMA, the $V_H$ and $V_L$ sequences can be "mixed and matched" to create other anti-BCMA binding molecules. BCMA binding of such "mixed and matched" antibodies can be tested using the binding assays known in the art, including for example, ELISAs, Western blots, RIAs, Biacore analysis. Preferably, when $V_H$ and $V_L$ chains are mixed and matched, a $V_H$ sequence from a particular $V_H/V_L$ pairing is replaced with a structurally similar $V_H$ sequence. Likewise, a $V_L$ sequence from a particular $V_H/V_L$ pairing is replaced with a structurally similar $V_L$ sequence.

In certain embodiments, the presently disclosed subject matter provides an isolated antibody, or antigen-binding portion thereof comprising: (a) a heavy chain variable region comprising an amino acid sequence selected from the group consisting of SEQ ID NOs: 1, 5, 9, 13, 17, 21, 25, 29, 33, 37, 41, 45, 49, 53, 57, 61, and 65; and (b) a light chain variable region comprising an amino acid sequence selected from the group consisting of SEQ ID NOs: 2, 6, 10, 14, 18, 22, 26, 30, 34, 38, 42, 46, 50, 54, 58, 62, and 66; wherein the antibody specifically binds BCMA, e.g., human BCMA.

Preferred heavy and light chain combinations include:

(a) a heavy chain variable region comprising amino acids having a sequence set forth in SEQ ID NO:1, and a light chain variable region comprising amino acids having a sequence set forth in SEQ ID NO:2; or (b) a heavy chain variable region comprising amino acids having a sequence set forth in SEQ ID NO:5, and a light chain variable region comprising amino acids having a sequence set forth in SEQ ID NO:6;

(c) a heavy chain variable region comprising amino acids having a sequence set forth in SEQ ID NO:9, and a light chain variable region comprising amino acids having a sequence set forth in SEQ ID NO:10;

(d) a heavy chain variable region comprising amino acids having a sequence set forth in SEQ ID NO:13, and a light chain variable region comprising amino acids having a sequence set forth in SEQ ID NO:14;

(e) a heavy chain variable region comprising amino acids having a sequence set forth in SEQ ID NO:17, and a light chain variable region comprising amino acids having a sequence set forth in SEQ ID NO:18;

(f) a heavy chain variable region comprising amino acids having a sequence set forth in SEQ ID NO:21, and a light chain variable region comprising amino acids having a sequence set forth in SEQ ID NO:22;

(g) a heavy chain variable region comprising amino acids having a sequence set forth in SEQ ID NO:25, and a light chain variable region comprising amino acids having a sequence set forth in SEQ ID NO:26;

(h) a heavy chain variable region comprising amino acids having a sequence set forth in SEQ ID NO:29, and a light chain variable region comprising amino acids having a sequence set forth in SEQ ID NO:30;

(i) a heavy chain variable region comprising amino acids having a sequence set forth in SEQ ID NO:33, and a light chain variable region comprising amino acids having a sequence set forth in SEQ ID NO:34;

(j) a heavy chain variable region comprising amino acids having a sequence set forth in SEQ ID NO:37, and a light chain variable region comprising amino acids having a sequence set forth in SEQ ID NO:38;

(k) a heavy chain variable region comprising amino acids having a sequence set forth in SEQ ID NO:41, and a light chain variable region comprising amino acids having a sequence set forth in SEQ ID NO:42;

(l) a heavy chain variable region comprising amino acids having a sequence set forth in SEQ ID NO:45, and a light chain variable region comprising amino acids having a sequence set forth in SEQ ID NO:46;

(m) a heavy chain variable region comprising amino acids having a sequence set forth in SEQ ID NO:49, and a light chain variable region comprising amino acids having a sequence set forth in SEQ ID NO:50;

(n) a heavy chain variable region comprising amino acids having a sequence set forth in SEQ ID NO:53, and a light chain variable region comprising amino acids having a sequence set forth in SEQ ID NO:54;

(o) a heavy chain variable region comprising amino acids having a sequence set forth in SEQ ID NO:57, and a light chain variable region comprising amino acids having a sequence set forth in SEQ ID NO:58;

(p) a heavy chain variable region comprising amino acids having a sequence set forth in SEQ ID NO:61, and a light chain variable region comprising amino acids having a sequence set forth in SEQ ID NO:62; or (q) a heavy chain variable region comprising amino acids having a sequence set forth in SEQ ID NO:65, and a light chain variable region comprising amino acids having a sequence set forth in SEQ ID NO:66.

In certain embodiments, the presently disclosed subject matter provides antibodies that comprise the heavy chain and light chain CDR1s, CDR2s and CDR3s of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 antibodies. The amino acid sequences of the $V_H$ CDR1s of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 are shown in SEQ ID NOs: 89, 95, 101, 107, 113, 119, 125, 131, 137, 143, 149, 155, 161, 167, 173, 179, and 185, respectively. The amino acid sequences of the $V_H$ CDR2s of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 antibodies are shown in SEQ ID NOs: 90, 96, 102, 108, 114, 120, 126, 132, 138, 144, 150, 156, 162, 168, 174, 180, and 186, respectively. The amino acid sequences of the $V_H$ CDR3s of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 are shown in SEQ ID NOs: 91, 97, 103, 109, 115, 121, 127, 133, 139, 145, 151, 157, 163, 169, 175, 181, and 187, respectively.

The amino acid sequences of the V$_L$ CDR1s of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 are shown in SEQ ID NOs: 92, 98, 104, 110, 116, 122, 128, 134, 140, 146, 152, 158, 164, 170, 176, 182, and 188, respectively. The amino acid sequences of the V$_L$ CDR2s of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 are shown in SEQ ID NOs: 93, 99, 105, 111, 117, 123, 129, 135, 141, 147, 153, 159, 165, 171, 177, 183, and 189, respectively. The amino acid sequences of the V$_L$ CDR3s of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 are shown in SEQ ID NOs: 94, 100, 106, 112, 118, 124, 130, 136, 142, 148, 154, 160, 166, 172, 178, 184, and 190, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to BCMA and that antigen-binding specificity is provided primarily by the CDR1, CDR2, and CDR3 regions, the V$_H$ CDR1, CDR2, and CDR3 sequences and V$_L$ CDR1, CDR2, and CDR3 sequences can be "mixed and matched" (i.e., CDRs from different antibodies can be mixed and match, although each antibody must contain a V$_H$ CDR1, CDR2, and CDR3 and a V L CDR1, CDR2, and CDR3) to create other anti-BCMA binding molecules. BCMA binding of such "mixed and matched" antibodies can be tested using the binding assays described above. When V$_H$ CDR sequences are mixed and matched, the CDR1, CDR2 and/or CDR3 sequence from a particular V$_H$ sequence is replaced with a structurally similar CDR sequence(s). Likewise, when V$_L$ CDR sequences are mixed and matched, the CDR1, CDR2 and/or CDR3 sequence from a particular V$_L$ sequence preferably is replaced with a structurally similar CDR sequence(s). It will be readily apparent to the ordinarily skilled artisan that novel V$_H$ and V$_L$ sequences can be created by substituting one or more V$_H$ and/or V$_L$ CDR region sequences with structurally similar sequences from the CDR sequences of the antibodies disclosed herein ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174.

In certain embodiments, the presently disclosed subject matter provides an isolated antibody, or antigen-binding portion thereof comprising:

(a) a heavy chain variable region CDR1 comprising an amino acid sequence selected from the group consisting of SEQ ID NOs: 89, 95, 101, 107, 113, 119, 125, 131, 137, 143, 149, 155, 161, 167, 173, 179, and 185;

(b) a heavy chain variable region CDR2 comprising an amino acid sequence selected from the group consisting of SEQ ID NOs: 90, 96, 102, 108, 114, 120, 126, 132, 138, 144, 150, 156, 162, 168, 174, 180, and 186;

(c) a heavy chain variable region CDR3 comprising an amino acid sequence selected from the group consisting of SEQ ID NOs: 91, 97, 103, 109, 115, 121, 127, 133, 139, 145, 151, 157, 163, 169, 175, 181, and 187;

(d) a light chain variable region CDR1 comprising an amino acid sequence selected from the group consisting of SEQ ID NOs: 92, 98, 104, 110, 116, 122, 128, 134, 140, 146, 152, 158, 164, 170, 176, 182, and 188;

(e) a light chain variable region CDR2 comprising an amino acid sequence selected from the group consisting of SEQ ID NOs: 93, 99, 105, 111, 117, 123, 129, 135, 141, 147, 153, 159, 165, 171, 177, 183, and 189; and (f) a light chain variable region CDR3 comprising an amino acid sequence selected from the group consisting of SEQ ID NOs: 94, 100, 106, 112, 118, 124, 130, 136, 142, 148, 154, 160, 166, 172, 178, 184, and 190;

wherein the antibody specifically binds BCMA, e.g., human BCMA.

In certain embodiments, the antibody comprises:
(a) a heavy chain variable region CDR1 comprising amino acids having the sequence set forth in SEQ ID NO: 89;
(b) a heavy chain variable region CDR2 comprising amino acids having the sequence set forth in SEQ ID NO: 90;
(c) a heavy chain variable region CDR3 comprising amino acids having the sequence set forth in SEQ ID NO: 91;
(d) a light chain variable region CDR1 comprising amino acids having the sequence set forth in SEQ ID NO: 92;
(e) a light chain variable region CDR2 comprising amino acids having the sequence set forth in SEQ ID NO: 93; and
(f) a light chain variable region CDR3 comprising amino acids having the sequence set forth in SEQ ID NO: 94.

In certain embodiments, the antibody comprises:
(a) a heavy chain variable region CDR1 comprising amino acids having the sequence set forth in SEQ ID NO: 95;
(b) a heavy chain variable region CDR2 comprising amino acids having the sequence set forth in SEQ ID NO: 96;
(c) a heavy chain variable region CDR3 comprising amino acids having the sequence set forth in SEQ ID NO: 97;
(d) a light chain variable region CDR1 comprising amino acids having the sequence set forth in SEQ ID NO: 98;
(e) a light chain variable region CDR2 comprising amino acids having the sequence set forth in SEQ ID NO: 99; and
(f) a light chain variable region CDR3 comprising amino acids having the sequence set forth in SEQ ID NO: 100.

In certain embodiments, the antibody comprises:
(a) a heavy chain variable region CDR1 comprising amino acids having the sequence set forth in SEQ ID NO: 101;
(b) a heavy chain variable region CDR2 comprising amino acids having the sequence set forth in SEQ ID NO: 102;
(c) a heavy chain variable region CDR3 comprising amino acids having the sequence set forth in SEQ ID NO: 103;
(d) a light chain variable region CDR1 comprising amino acids having the sequence set forth in SEQ ID NO: 104;
(e) a light chain variable region CDR2 comprising amino acids having the sequence set forth in SEQ ID NO: 105; and
(f) a light chain variable region CDR3 comprising amino acids having the sequence set forth in SEQ ID NO: 106.

In certain embodiments, the antibody comprises:
(a) a heavy chain variable region CDR1 comprising amino acids having the sequence set forth in SEQ ID NO: 107;
(b) a heavy chain variable region CDR2 comprising amino acids having the sequence set forth in SEQ ID NO: 108;
(c) a heavy chain variable region CDR3 comprising amino acids having the sequence set forth in SEQ ID NO: 109;
(d) a light chain variable region CDR1 comprising amino acids having the sequence set forth in SEQ ID NO: 110;
(e) a light chain variable region CDR2 comprising amino acids having the sequence set forth in SEQ ID NO: 111; and
(f) a light chain variable region CDR3 comprising amino acids having the sequence set forth in SEQ ID NO: 112.

In certain embodiments, the antibody comprises:
(a) a heavy chain variable region CDR1 comprising amino acids having the sequence set forth in SEQ ID NO: 113;
(b) a heavy chain variable region CDR2 comprising amino acids having the sequence set forth in SEQ ID NO: 114;
(c) a heavy chain variable region CDR3 comprising amino acids having the sequence set forth in SEQ ID NO: 115;
(d) a light chain variable region CDR1 comprising amino acids having the sequence set forth in SEQ ID NO: 116;
(e) a light chain variable region CDR2 comprising amino acids having the sequence set forth in SEQ ID NO: 117; and
(f) a light chain variable region CDR3 comprising amino acids having the sequence set forth in SEQ ID NO: 118.

In certain embodiments, the antibody comprises:
(a) a heavy chain variable region CDR1 comprising amino acids having the sequence set forth in SEQ ID NO: 119;
(b) a heavy chain variable region CDR2 comprising amino acids having the sequence set forth in SEQ ID NO: 120;
(c) a heavy chain variable region CDR3 comprising amino acids having the sequence set forth in SEQ ID NO: 121;
(d) a light chain variable region CDR1 comprising amino acids having the sequence set forth in SEQ ID NO: 122;
(e) a light chain variable region CDR2 comprising amino acids having the sequence set forth in SEQ ID NO: 123; and
(f) a light chain variable region CDR3 comprising amino acids having the sequence set forth in SEQ ID NO: 124.

In certain embodiments, the antibody comprises:
(a) a heavy chain variable region CDR1 comprising amino acids having the sequence set forth in SEQ ID NO: 125;
(b) a heavy chain variable region CDR2 comprising amino acids having the sequence set forth in SEQ ID NO: 126;
(c) a heavy chain variable region CDR3 comprising amino acids having the sequence set forth in SEQ ID NO: 127;
(d) a light chain variable region CDR1 comprising amino acids having the sequence set forth in SEQ ID NO: 128;
(e) a light chain variable region CDR2 comprising amino acids having the sequence set forth in SEQ ID NO: 129; and
(f) a light chain variable region CDR3 comprising amino acids having the sequence set forth in SEQ ID NO: 130.

In certain embodiments, the antibody comprises:
(a) a heavy chain variable region CDR1 comprising amino acids having the sequence set forth in SEQ ID NO: 131;
(b) a heavy chain variable region CDR2 comprising amino acids having the sequence set forth in SEQ ID NO: 132;
(c) a heavy chain variable region CDR3 comprising amino acids having the sequence set forth in SEQ ID NO: 133;
(d) a light chain variable region CDR1 comprising amino acids having the sequence set forth in SEQ ID NO: 134;
(e) a light chain variable region CDR2 comprising amino acids having the sequence set forth in SEQ ID NO: 135; and
(f) a light chain variable region CDR3 comprising amino acids having the sequence set forth in SEQ ID NO: 136.

In certain embodiments, the antibody comprises:
(a) a heavy chain variable region CDR1 comprising amino acids having the sequence set forth in SEQ ID NO: 137;
(b) a heavy chain variable region CDR2 comprising amino acids having the sequence set forth in SEQ ID NO: 138;
(c) a heavy chain variable region CDR3 comprising amino acids having the sequence set forth in SEQ ID NO: 139;
(d) a light chain variable region CDR1 comprising amino acids having the sequence set forth in SEQ ID NO: 140;
(e) a light chain variable region CDR2 comprising amino acids having the sequence set forth in SEQ ID NO: 141; and
(f) a light chain variable region CDR3 comprising amino acids having the sequence set forth in SEQ ID NO: 142.

In certain embodiments, the antibody comprises:
(a) a heavy chain variable region CDR1 comprising amino acids having the sequence set forth in SEQ ID NO: 143;
(b) a heavy chain variable region CDR2 comprising amino acids having the sequence set forth in SEQ ID NO: 144;
(c) a heavy chain variable region CDR3 comprising amino acids having the sequence set forth in SEQ ID NO: 145;
(d) a light chain variable region CDR1 comprising amino acids having the sequence set forth in SEQ ID NO: 146;
(e) a light chain variable region CDR2 comprising amino acids having the sequence set forth in SEQ ID NO: 147; and
(f) a light chain variable region CDR3 comprising amino acids having the sequence set forth in SEQ ID NO: 148.

In certain embodiments, the antibody comprises:
(a) a heavy chain variable region CDR1 comprising amino acids having the sequence set forth in SEQ ID NO: 149;
(b) a heavy chain variable region CDR2 comprising amino acids having the sequence set forth in SEQ ID NO: 150;
(c) a heavy chain variable region CDR3 comprising amino acids having the sequence set forth in SEQ ID NO: 151;
(d) a light chain variable region CDR1 comprising amino acids having the sequence set forth in SEQ ID NO: 152;
(e) a light chain variable region CDR2 comprising amino acids having the sequence set forth in SEQ ID NO: 153; and
(f) a light chain variable region CDR3 comprising amino acids having the sequence set forth in SEQ ID NO: 154.

In certain embodiments, the antibody comprises:
(a) a heavy chain variable region CDR1 comprising amino acids having the sequence set forth in SEQ ID NO: 155;
(b) a heavy chain variable region CDR2 comprising amino acids having the sequence set forth in SEQ ID NO: 156;
(c) a heavy chain variable region CDR3 comprising amino acids having the sequence set forth in SEQ ID NO: 157;
(d) a light chain variable region CDR1 comprising amino acids having the sequence set forth in SEQ ID NO: 158;
(e) a light chain variable region CDR2 comprising amino acids having the sequence set forth in SEQ ID NO: 159; and
(f) a light chain variable region CDR3 comprising amino acids having the sequence set forth in SEQ ID NO: 160.

In certain embodiments, the antibody comprises:
(a) a heavy chain variable region CDR1 comprising amino acids having the sequence set forth in SEQ ID NO: 161;
(b) a heavy chain variable region CDR2 comprising amino acids having the sequence set forth in SEQ ID NO: 162;
(c) a heavy chain variable region CDR3 comprising amino acids having the sequence set forth in SEQ ID NO: 163;
(d) a light chain variable region CDR1 comprising amino acids having the sequence set forth in SEQ ID NO: 164;
(e) a light chain variable region CDR2 comprising amino acids having the sequence set forth in SEQ ID NO:165; and
(f) a light chain variable region CDR3 comprising amino acids having the sequence set forth in SEQ ID NO: 166.

In certain embodiments, the antibody comprises:
(a) a heavy chain variable region CDR1 comprising amino acids having the sequence set forth in SEQ ID NO: 167;
(b) a heavy chain variable region CDR2 comprising amino acids having the sequence set forth in SEQ ID NO: 168;
(c) a heavy chain variable region CDR3 comprising amino acids having the sequence set forth in SEQ ID NO: 169;
(d) a light chain variable region CDR1 comprising amino acids having the sequence set forth in SEQ ID NO: 170;
(e) a light chain variable region CDR2 comprising amino acids having the sequence set forth in SEQ ID NO: 171; and
(f) a light chain variable region CDR3 comprising amino acids having the sequence set forth in SEQ ID NO: 172.

In certain embodiments, the antibody comprises:
(a) a heavy chain variable region CDR1 comprising amino acids having the sequence set forth in SEQ ID NO: 173;

(b) a heavy chain variable region CDR2 comprising amino acids having the sequence set forth in SEQ ID NO: 174;
(c) a heavy chain variable region CDR3 comprising amino acids having the sequence set forth in SEQ ID NO: 175;
(d) a light chain variable region CDR1 comprising amino acids having the sequence set forth in SEQ ID NO: 176;
(e) a light chain variable region CDR2 comprising amino acids having the sequence set forth in SEQ ID NO: 177; and
(f) a light chain variable region CDR3 comprising amino acids having the sequence set forth in SEQ ID NO: 178.

In certain embodiments, the antibody comprises:
(a) a heavy chain variable region CDR1 comprising amino acids having the sequence set forth in SEQ ID NO: 179;
(b) a heavy chain variable region CDR2 comprising amino acids having the sequence set forth in SEQ ID NO: 180;
(c) a heavy chain variable region CDR3 comprising amino acids having the sequence set forth in SEQ ID NO: 181;
(d) a light chain variable region CDR1 comprising amino acids having the sequence set forth in SEQ ID NO: 182;
(e) a light chain variable region CDR2 comprising amino acids having the sequence set forth in SEQ ID NO: 183; and
(f) a light chain variable region CDR3 comprising amino acids having the sequence set forth in SEQ ID NO: 184.

In certain embodiments, the antibody comprises:
(a) a heavy chain variable region CDR1 comprising amino acids having the sequence set forth in SEQ ID NO: 185;
(b) a heavy chain variable region CDR2 comprising amino acids having the sequence set forth in SEQ ID NO: 186;
(c) a heavy chain variable region CDR3 comprising amino acids having the sequence set forth in SEQ ID NO: 187;
(d) a light chain variable region CDR1 comprising amino acids having the sequence set forth in SEQ ID NO: 188;
(e) a light chain variable region CDR2 comprising amino acids having the sequence set forth in SEQ ID NO: 189; and
(f) a light chain variable region CDR3 comprising amino acids having the sequence set forth in SEQ ID NO: 190.

The constant region/framework region of the anti-BCMA antibodies disclosed herein can be altered, for example, by amino acid substitution, to modify the properties of the antibody (e.g., to increase or decrease one or more of: antigen binding affinity, Fc receptor binding, antibody carbohydrate, for example, glycosylation, fucosylation etc, the number of cysteine residues, effector cell function, effector cell function, complement function or introduction of a conjugation site).

In certain embodiments, a presently disclosed anti-BCMA antibody is a fully-human antibody, e.g., any one of ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174. Fully-human mAbs are preferred for therapeutic use in humans because murine antibodies cause an immunogenicity reaction, known as the HAMA (human anti-mouse antibodies) response (Azinovic I, et al. Survival benefit associated with human anti-mouse antibody (HAMA) in patients with B-cell malignancies. Cancer Immunol Immunother 2006; 55(12): 1451-8; Tjandra J J, et al. Development of human anti-murine antibody (HAMA) response in patients. Immunol Cell Biol 1990; 68(6):367-76), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies. Humanization methods known in the art (Riechmann L, et al. Reshaping human antibodies for therapy. Nature 1988; 332 (6162): 332:323; Queen C, et al. A humanized antibody that binds to the interleukin 2 receptor. Proc Natl Acad Sci USA 1989; 86 (24): 10029-33) can be employed to reduce the immunogenicity of murine-derived antibodies (Gerd R, et al. Serological Analysis of Human Anti-Human Antibody Responses in Colon Cancer Patients Treated with Repeated Doses of Humanized Monoclonal Antibody A33. Cancer Res 2001; 61, 6851-6859).

The use of phage display libraries has made it possible to select large numbers of Ab repertoires for unique and rare Abs against very defined epitopes (for more details on phage display see McCafferty et al., Phage antibodies: filamentous phage displaying antibody variable domains. Nature, 348: 552-554.) The rapid identification of human Fab or single chain Fv (scFV) fragments highly specific for tumor antigen-derived peptide-MHC complex molecules has thus become possible (19-22). Recently, immuno-toxins, generated by fusing TCR-like Fab specific for melanoma Ag MART-1 26-35/A2 or gp100 280-288/A2 to a truncated form of Pseudomonas endotoxin, have been shown to inhibit human melanoma growth both in vitro and in vivo (Klechevsky E, et al. Antitumor activity of immunotoxins with T-cell receptor-like specificity against human melanoma xenografts. Cancer Res 2008; 68 (15): 6360-6367). In addition, by engineering full-length mAb using the Fab fragments, it is possible to directly generate a therapeutic human mAb, bypassing months of time-consuming work, normally needed for developing therapeutic mAbs. The presently disclosed subject matter involves the development of a fully human mAb that recognizes, for example, a human BCMA polypeptide (e.g., a polypeptide having the amino acid sequence set forth in SEQ ID NO:71) for cancer therapy.

3. Homologous Antibodies

In certain embodiments, an antibody of the presently disclosed subject matter comprises heavy and light chain variable regions comprising amino acid sequences that are homologous to the amino acid sequences of the antibodies described herein (e.g., ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 antibodies), and wherein the antibodies retain the desired functional properties of the anti-BMCA antibodies of the presently disclosed subject matter.

For example, the presently disclosed subject matter provides an isolated antibody, or antigen-binding portion thereof, comprising a heavy chain variable region and a light chain variable region, wherein:

(a) the heavy chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOs: 1, 5, 9, 13, 17, 21, 25, 29, 33, 37, 41, 45, 49, 53, 57, 61, and 65;

(b) the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to an amino acid sequence selected from the group consisting of SEQ ID NOs: 2, 6, 10, 14, 18, 22, 26, 30, 34, 38, 42, 46, 50, 54, 58, 62, and 66; and wherein the antibody binds to human BCMA with a $K_D$ of $1 \times 10^{-7}$ M or less.

In certain embodiments, the $V_H$ and/or $V_L$ amino acid sequences can be at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered antibody for retained function (i.e., the binding affinity) using the binding assays described herein.

As used herein, the percent homology between two amino acid sequences is equivalent to the percent identity between the two sequences. The percent identity or homology between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See www.ncbi.nlm.nih.gov).

4. Antibodies with Conservative Modifications

In certain embodiments, an antibody of the presently disclosed subject matter comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 antibodies), or conservative modifications thereof, and wherein the antibodies retain the desired functional properties of the anti-BCMA antibodies of the presently disclosed subject matter. The presently disclosed subject matter provides an isolated antibody, or antigen-binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 91, 97, 103, 109, 115, 121, 127, 133, 139, 145, 151, 157, 163, 169, 175, 181, and 187, and conservative modifications thereof;

(b) the light chain variable region CDR3 sequence comprises an amino acid sequence selected from the group consisting of amino acid sequence of SEQ ID NOs: 94, 100, 106, 112, 118, 124, 130, 136, 142, 148, 154, 160, 166, 172, 178, 184, and 190, and conservative modifications thereof; and the antibody binds to human BCMA with a $K_D$ of $1 \times 10^{-7}$ M or less.

In certain embodiments, the heavy chain variable region CDR2 sequence comprises an amino acid sequence selected from the group consisting of amino acid sequences of SEQ ID NOs: 90, 96, 102, 108, 114, 120, 126, 132, 138, 144, 150, 156, 162, 168, 174, 180, and 186, and conservative modifications thereof; and the light chain variable region CDR2 sequence comprises an amino acid sequence selected from the group consisting of amino acid sequences of SEQ ID NOs: 93, 99, 105, 111, 117, 123, 129, 135, 141, 147, 153, 159, 165, 171, 177, 183, and 189, and conservative modifications thereof.

In certain embodiments, the heavy chain variable region CDR1 sequence comprises an amino acid sequence selected from the group consisting of amino acid sequences of SEQ ID NOs: 89, 95, 101, 107, 113, 119, 125, 131, 137, 143, 149, 155, 161, 167, 173, 179, and 185, and conservative modifications thereof; and the light chain variable region CDR1 sequence comprises an amino acid sequence selected from the group consisting of amino acid sequences of SEQ ID NOs: 92, 98, 104, 110, 116, 122, 128, 134, 140, 146, 152, 158, 164, 170, 176, 182, and 188, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. Exemplary conservative amino acid substitutions are shown in Table 18. Amino acid substitutions may be introduced into an antibody of interest and the products screened for a desired activity, e.g., retained/improved antigen binding, decreased immunogenicity, or improved ADCC or CDC. In certain embodiments, a sequence disclosed herein, e.g., a CDR sequence, a VH sequence or a VL sequence, can have up to about one, up to about two, up to about three, up to about four, up to about five, up to about six, up to about seven, up to about eight, up to about nine or up to about ten amino acid residues that are modified and/or substituted.

TABLE 18

| Original Residue | Exemplary conservative amino acid Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Amino acids may be grouped according to common side-chain properties:
  hydrophobic: Norleucine, Met, Ala, Val, Leu, Ile;
  neutral hydrophilic: Cys, Ser, Thr, Asn, Gln;
  acidic: Asp, Glu;
  basic: His, Lys, Arg;
  residues that influence chain orientation: Gly, Pro;
  aromatic: Trp, Tyr, Phe.

Non-conservative substitutions will entail exchanging a member of one of these classes for another class.

5. Anti BCMA Antibodies that Cross-Compete for Binding to BCMA with Anti-BCMA Antibodies of the Invention The presently disclosed subject matter provides antibodies that cross-compete with any of the disclosed anti-BCMA antibodies for binding to BCMA (e.g., human BCMA). For example, and not by way of limitation, the cross-competing antibodies can bind to the same epitope region, e.g., same epitope, adjacent epitope, or overlapping as any of the anti-BCMA antibodies of the presently disclosed subject matter. In certain embodiments, the reference antibody for cross-competition studies can be any one of the anti-BCMA antibodies disclosed herein, e.g., ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 antibodies.

In certain embodiments, the cross-competing antibody binds to an epitope region comprising amino acids 14-22 of SEQ ID NO: 71. In certain embodiments, the cross-competing antibody binds to one, two, three, four, five, six, or seven epitope region selected from the group consisting of amino acids 8-22, 9-23, 10-24, 11-25, 12-26, 13-27, 14-28, and 8-28 of SEQ ID NO: 71.

Such cross-competing antibodies can be identified based on their ability to cross-compete with any one of the presently disclosed anti-BCMA antibodies in standard BCMA binding assays. For example, Biacore analysis, ELISA assays or flow cytometry can be used to demonstrate cross-competition with the antibodies of the presently disclosed subject matter. The ability of a test antibody to inhibit the binding of, for example, any one of the presently disclosed anti-BMCA antibodies (e.g., ET140-192, ET140-197, ET140-180, ET140-172, ET140-157, ET140-153, ET140-201, ET140-167, ET140-163, ET140-207, ET140-165, ET140-188, ET140-196, ET140-204, ET140-190, ET140-187, and ET140-174 antibodies) to human BCMA demonstrates that the test antibody can compete with any one of the presently disclosed anti-BCMA antibodies for binding to human BCMA and thus binds to the same epitope region on human BCMA as any one of the presently disclosed anti-BCMA antibodies. In certain embodiments, the cross-competing antibody binds to the same epitope on human BCMA as any one of the presently disclosed anti-BCMA antibodies.

6. Characterization of Antibody Binding to Antigen

Antibodies of the presently disclosed subject can be tested for binding to BCMA by, for example, standard ELISA. To determine if the selected anti-BCMA antibodies bind to unique epitopes, each antibody can be biotinylated using commercially available reagents (Pierce, Rockford, Ill.). Competition studies using unlabeled monoclonal antibodies and biotinylated monoclonal antibodies can be performed using BCMA coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. Anti-BCMA human IgGs can be further tested for reactivity with BCMA antigen by Western blotting.

In certain embodiments, $K_D$ is measured by a radiolabeled antigen binding assay (MA). In certain embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)).

In certain embodiments, $K_D$ is measured using a BIACORE® surface plasmon resonance assay. For example, an assay using a BIACORE®-2000 or a BIACORE®-3000 (BIAcore, Inc., Piscataway, N.J.)

Epitope Mapping

In certain embodiments, a presently disclosed anti-BCMA antibody binds to a human BCMA polypeptide comprising the amino acid sequence set forth in SEQ ID NO: 71. In certain embodiments, a presently disclosed anti-BCMA antibody binds to one or more portion of the amino acid sequence set forth in SEQ ID NO: 71. In certain embodiments, a presently disclosed anti-BCMA antibody binds to an epitope region comprising amino acids 14-22 of SEQ ID NO: 71. In certain embodiments, a presently disclosed anti-BCMA antibody binds to one, two, three, four, five, six, or seven epitope region selected from the group consisting of amino acids 8-22, 9-23, 10-24, 11-25, 12-26, 13-27, 14-28, and 8-28 of SEQ ID NO: 71. In certain embodiments, a presently disclosed anti-BCMA antibody that binds to an epitope region comprising amino acids 14-22 of SEQ ID NO: 71 comprises a heavy chain variable region comprising amino acids having the sequence set forth in SEQ ID NO:9 and a light chain variable region comprising amino acids having the sequence set forth in SEQ ID NO:10, optionally with (iii) a linker sequence, for example a linker peptide, between the heavy chain variable region and the light chain variable region. In certain embodiments, the linker comprises amino acids having the sequence set forth in SEQ ID NO:69. In certain embodiments, a presently disclosed anti-BCMA antibody that binds to an epitope region comprising amino acids 14-22 of SEQ ID NO: 71 comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:21. In certain embodiments, a presently disclosed anti-BCMA antibody that binds to an epitope region comprising amino acids 14-22 of SEQ ID NO: 71 comprises a $V_H$ comprising amino acids having the sequence set forth in SEQ ID NO:21. In certain embodiments, a presently disclosed anti-BCMA antibody that binds to an epitope region comprising amino acids 14-22 of SEQ ID NO: 71 comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:22. In certain embodiments, a presently disclosed anti-BCMA antibody that binds to an epitope region comprising amino acids 14-22 of SEQ ID NO: 71 comprises a $V_L$ comprising amino acids having the sequence set forth in SEQ ID NO:22. In certain embodiments, a presently disclosed anti-BCMA antibody that binds to an epitope region comprising amino acids 14-22 of SEQ ID NO: 71 comprises a $V_H$ comprising amino acids having the sequence set forth in SEQ ID NO:21 and a $V_L$ comprising amino acids having the sequence set forth in SEQ ID NO:22. In certain embodiments, a presently disclosed anti-BCMA antibody that binds to an epitope region comprising amino acids 14-22 of SEQ ID NO: 71 comprises a $V_H$ CDR1 comprising amino acids having the sequence set forth in SEQ ID NO:119 or conservative modifications thereof, a $V_H$ CDR2 comprising amino acids having the sequence set forth in SEQ ID NO:120 or conservative modifications thereof, and a $V_H$ CDR3 comprising amino acids having the sequence set forth in SEQ ID NO:121 or conservative modifications thereof. In certain embodiments, a presently disclosed anti-BCMA antibody that binds to an epitope region comprising amino acids 14-22 of SEQ ID NO: 71 comprises a $V_L$ CDR1 comprising amino acids having the sequence set forth in SEQ ID NO:122 or conservative modifications thereof, a $V_L$ CDR2 comprising amino acids having the sequence set forth in SEQ ID NO:123 or conservative modifications thereof, and a $V_L$ CDR3 comprising amino acids having the sequence set forth in SEQ ID NO:124 or conservative modifications thereof. In certain embodiments, a presently disclosed anti-BCMA antibody that binds to an epitope region comprising amino acids 14-22 of SEQ ID NO: 71 comprises a $V_H$ CDR1 comprising amino acids having the sequence set forth in SEQ ID NO:119 or conservative modifications thereof, a $V_H$ CDR2 comprising amino acids having the sequence set forth in SEQ ID NO:120 or conservative modifications thereof, a $V_H$ CDR3 comprising amino acids having the sequence set forth in SEQ ID NO:121 or conservative modifications thereof, a $V_L$ CDR1 comprising amino acids having the sequence set forth in SEQ ID NO:122 or conservative modifications thereof, a $V_L$ CDR2 comprising amino acids having the sequence set forth in SEQ ID NO:123 or conservative modifications thereof, and a $V_L$ CDR3 comprising amino acids having the sequence set forth in SEQ ID NO:124 or conservative modifications thereof. In certain embodiments, a presently disclosed anti-BCMA antibody that binds to an epitope region comprising amino acids 14-22 of SEQ ID NO: 71 comprises a $V_H$ CDR1 comprising amino acids having the sequence set forth in SEQ ID NO:119, a $V_H$ CDR2 comprising amino acids having the sequence set forth in SEQ ID NO:120, a $V_H$ CDR3 comprising amino acids having the sequence set forth in SEQ ID NO:121, a $V_L$ CDR1 comprising amino acids having the sequence set forth in SEQ ID NO:122, a $V_L$ CDR2 comprising amino acids having the sequence set forth in SEQ ID NO:123, and a $V_L$ CDR3 comprising amino acids having the sequence set forth in SEQ ID NO:124. In certain embodiments, a presently disclosed anti-BCMA antibody is ET140-3 (or "ET140-153").

7. Immunoconjugates

The presently disclosed subject provides an anti-BCMA antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol (such as ricin, diphtheria, gelonin), cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, calecheamicin, aureastatin, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an anti-BCMA antibody disclosed herein include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to anti-BCMA antibody disclosed herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Anti-BCMA antibodies of the presently disclosed subject matter also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $^{90}Y$, $^{131}I$, $^{225}Ac$, $^{213}Bi$, $^{223}Ra$ and $^{227}Th$. Methods for preparing radioimmunconjugates are established in the art. Examples of radioimmunoconjugates are commercially available, including Zevalin™ (DEC Pharmaceuticals) and Bexxar™

(Corixa Pharmaceuticals), and similar methods can be used to prepare radioimmunoconjugates using the antibodies of the invention.

The antibody conjugates of the presently disclosed subject matter can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor (TNF) or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

8. Bispecific Molecules

The presently disclosed subject matter provides bispecific molecules comprising an anti-BCMA antibody, or a fragment thereof, disclosed herein. An antibody of the presently disclosed subject matter, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the presently disclosed subject matter can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, a presently disclosed anti-BCMA antibody can be functionally linked (e.g., by chemical coupling, genetic fusion, noncovalent association or otherwise) to one or more other binding molecules, such as another antibody, antibody fragment, peptide or binding mimetic, such that a bispecific molecule results.

The presently disclosed subject matter provides bispecific molecules comprising at least a first binding specificity for BCMA and a second binding specificity for a second target epitope. The second target epitope can be a BCMA epitope, or a non-BCMA epitope, e.g., a different antigen. In certain embodiments, the bispecific molecule is multispecific, the molecule can further include a third binding specificity. Where a first portion of a bispecific antibody binds to an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In certain embodiments, bispecific antibodies, therefore, are able to form a link between effector cells, for example, T cells and tumor cells, thereby enhancing effector function. In certain embodiments, a bispecific antibody of the present disclosure comprises at least a first binding to BCMA and at least a second binding to an immune cell. For example, and not by way of limitation, a bispecific antibody of the present disclosure comprises at least a first binding to BCMA and at least a second binding to a receptor present on the surface of an immune cell, e.g., CD3.

The bispecific molecules of the presently disclosed subject matter can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5, 5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In certain embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab)$_2$ or ligand×Fab fusion protein.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. Alternatively, the complexes can be detected using any of a variety of other immunoassays. For example, the antibody can be radioactively labeled and used in a radioimmunoassay (MA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

9. Selecting a High Affinity ScFv Against a BCMA Polypeptide

The next step is to the selection of phage that bind to the target antigen of interest with high affinity, from phage in a human phage display library that either does not bind or that binds with lower affinity. This is accomplished by iterative binding of phage to the antigen, which is bound to a solid support, for example, beads or mammalian cells followed by removal of non-bound phage and by elution of specifically bound phage. In certain embodiments, antigens are first biotinylated for immobilization to, for example, streptavidin-conjugated Dynabeads M-280. The phage library is incubated with the cells, beads or other solid support and non binding phage is removed by washing. Clones that bind are selected and tested.

Once selected, positive scFv clones are tested for their binding to BCMA (human BCMA) on live 3T3 cell surfaces by flow cytometry. Briefly, phage clones are incubated with 3T3 cells over-expressing BCMA. The cells are washed and then with a mouse anti-M13 coat protein mAb. Cells are washed again and labeled with a FITC-goat anti-mouse Ig prior to flow cytometry.

In other embodiments, the anti-BCMA antibodies can comprise one or more framework region amino acid substitutions designed to improve protein stability, antibody binding, expression levels or to introduce a site for conjugation of therapeutic agents. These scFv are then used to produce recombinant human monoclonal Igs in accordance with methods known to those of skill in the art.

10. Engineering Full Length mAb Using the Selected ScFv Fragments

Phage display technology allows for the rapid selection and production of antigen-specific scFv and Fab fragments, which are useful in and of themselves, or which can be further developed to provide complete antibodies, antigen binding proteins or antigen binding fragments thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates tha scFv and Fab, altering immune function or carrier function. Alpha emitters, for example, do not need to be internalized to kill the targets, but many drugs and toxins will benefit from internalization of the immune complex. In certain embodiments, therefore, once scFv clones specific for BCMA were obtained from phage display libraries, a full length IgG mAb using the scFv fragments was produced.

To produce recombinant human monoclonal IgG in Chinese hamster ovary (CHO) cells, a full length IgG mAb can be engineered based on a method known to those of skill in the art (Tomomatsu et al., Production of human monoclonal antibodies against FceRIa by a method combining in vitro immunization with phage display. Biosci Biotechnol Biochem 73(7): 1465-1469 2009). Briefly, antibody variable regions can be subcloned into mammalian expression vectors, with matching Lambda or Kappa light chain constant sequences and IgG1 subclass Fc (for example) (Lidija P, et al. An integrated vector system for the eukaryotic expression of antibodies or their fragments after selection from phage display libraries. Gene 1997; 187(1): 9-18; Lisa J H, et al. Crystallographic structure of an intact IgG1 monoclonal antibody. Journal of Molecular Biology 1998; 275 (5): 861-872). Kinetic binding analysis (Yasmina N A, et al. Probing the binding mechanism and affinity of tanezumab, a recombinant humanized anti-NGF monoclonal antibody, using a repertoire of biosensors. Protein Science 2008; 17(8): 1326-1335) can be used to confirm specific binding of full length IgG to BCMA, with a $K_D$ in nanomolar range.

Pharmaceutical Compositions and Methods of Treatment

Anti-BCMA antibodies of the presently disclosed subject matter can be administered for therapeutic treatments to a patient suffering from a tumor (e.g., multiple myeloma) in an amount sufficient to prevent, inhibit, or reduce the progression of the tumor. Progression includes, e.g., the growth, invasiveness, metastases and/or recurrence of the tumor. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition.

The identification of medical conditions treatable by anti-BCMA antibodies of the presently disclosed subject matter is well within the ability and knowledge of one skilled in the art. For example, human individuals who are either suffering from multiple myeloma or who are at risk of developing multiple myeloma are suitable for administration of the presently disclosed anti-BCMA antibodies. A clinician skilled in the art can readily determine, for example, by the use of clinical tests, physical examination and medical/family history, if an individual is a candidate for such treatment.

In certain embodiments, the presently disclosed subject matter provides a method of treating a tumor by administering a presently disclosed anti-BCMA antibody in combination with one or more other agents. For example, the presently disclosed subject matter provides a method of treating a tumor by administering a presently disclosed anti-BCMA antibody with an antineoplastic agent. The anti-BCMA antibody can be chemically or biosynthetically linked to one or more of the antineoplastic agents.

Non-limiting examples of suitable tumors include multiple myeloma, Non-Hodgkin Lymphoma, Hodgkin Lymphoma, Chronic Lymphocytic Leukemia (CLL), glioblastoma, and Waldenstrom's Macroglobulinemia. In certain embodiments, the tumor is multiple myeloma.

Any suitable method or route can be used to administer a presently disclosed anti-BCMA antibody, and optionally, to co-administer antineoplastic agents. Routes of administration include, for example, oral, intravenous, intraperitoneal, subcutaneous, or intramuscular administration. It should be emphasized, however, that the presently disclosed subject matter is not limited to any particular method or route of administration.

It is noted that presently disclosed anti-BCMA antibody can be administered as a conjugate, which binds specifically to the receptor and delivers a toxic, lethal payload following ligand-toxin internalization.

It is understood that anti-BCMA antibodies of the presently disclosed subject matter can be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The presently disclosed subject matter also provides use of antibodies and nucleic acids that encode them for treatment of a tumor (e.g., multiple myeloma), for diagnostic and prognostic applications as well as use as research tools for the detection of BCMA in cells and tissues. Pharmaceutical compositions comprising the disclosed antibodies and nucleic acids are encompassed by the presently disclosed subject matter. Vectors comprising the nucleic acids of the presently disclosed subject matter for antibody-based treatment by vectored immunotherapy are also contemplated by the presently disclosed subject matter. Vectors include expression vectors which enable the expression and secretion of antibodies, as well as vectors which are directed to cell surface expression of the antigen binding proteins, such as chimeric antigen receptors.

Cells comprising the nucleic acids, for example cells that have been transfected with the vectors of the invention are also encompassed by the presently disclosed subject matter.

Kits

The presently disclosed subject matter provides kits for the treatment or prevention of a tumor (e.g., multiple myeloma). In certain embodiments, the kit comprises a therapeutic composition containing an effective amount of an anti-BCMA antibody in unit dosage form. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the anti-BCMA antibody is provided together with instructions for administering the cell to a subject having or at risk of developing a tumor (e.g., multiple myeloma). The instructions will generally include information about the use of the composition for the treatment or prevention of a tumor (e.g., multiple myeloma). In other embodiments, the instructions include at least one of the following: description of the therapeutic agent; dosage schedule and administration for treatment or prevention of a neoplasia (e.g., multiple myeloma) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Methods

Flow cytometry analysis. For cell surface staining, cells can be incubated with appropriate mAbs for 30 minutes on ice, washed, and incubated with secondary antibody reagents when necessary. Flow cytometry data can be collected on a FACS Calibur (Becton Dickinson) and analyzed with FlowJo V8.7.1 and 9.4.8 software.

Selection and characterization of scFv specific for BCMA. A human scFv antibody phage display library is used for the selection of mAb clones. In brief, biotinylated antigens can be first mixed with the huma scFv phage library, then the antigen-scFv antibody complexes can be pulled down by streptavidin-conjugated Dynabeads M-280 through a magnetic rack. Bound clones can be then eluted and used to infect *E. Coli* XL1-Blue. The scFv phage clones expressed in the bacteria can be purified (Yasmina N A, et al. Probing the binding mechanism and affinity of tanezumab, a recombinant humanized anti-NGF monoclonal antibody, using a repertoire of biosensors. Protein Science 2008; 17(8): 1326-1335; Roberts W K, et al. Vaccination with CD20 peptides induces a biologically active, specific immune response in mice. Blood 2002: 99 (10): 3748-3755). Panning can be performed for 3-4 cycles to enrich scFv phage clones binding to BCMA specifically. Positive clones can be determined by standard ELISA method against biotinylated single chain BCMA. Positive clones can be further tested for their binding to BCMA on live cell surfaces by flow cytometry, using a BCMA$^+$ cell line, 3T3. The cells can be washed, and the staining can be performed in following steps.

The cells can be first stained with purified scFv phage clones, and followed by staining with a mouse anti-M13 mAb, and finally the goat anti-mouse Ig's conjugate to FITC. Each step of the staining can be done between 30-60 minutes on ice and the cells were washed twice between each step of the staining.

Engineering full length mAb using the selected ScFv fragments. Full-length human IgG1 of the selected phage clones can be produced in HEK293 and Chinese hamster ovary (CHO) cell lines, as described (Caron P C, Class K, Laird W, Co M S, Queen C, Scheinberg D A. Engineered humanized dimeric forms of IgG are more effective antibodies. J Exp Med 176:1 191-1 195. 1992). In brief, antibody variable regions can be subcloned into mammalian expression vectors, with matching human lambda or kappa light chain constant region and human IgG constant region sequences. Molecular weight of the purified full length IgG antibodies can be measured under both reducing and non-reducing conditions by electrophoresis.

Characterization of the full-length human IgG for BCMA. Initially, specificities of the fully human IgG mAbs for the BMCA can be determined by staining 3T3 cells transduced to overexpress BCMA, followed by secondary goat anti-human IgG mAb conjugate to PE or FITC. The fluorescence intensity can be measured by flow cytometry. The same method can be used to determine the binding of the mAbs to fresh tumor cells and cell lines.

Antibody-dependent cellular cytotoxicity (ADCC). Target cells used for ADCC can be 3T3 cells over-expressing BCMA. Anti-BCMA antibody or its control human IgG at various concentrations can be incubated with target cells and fresh PBMCs at different effector:target (E:T) ratio for 16 hrs. The supernatant can be harvested and the cytotoxicity can be measured by LDH release assay using Cytotox 96 nonradioactive kit from Promega following their instruction. Cytotoxicity can also be measured by standard 4 hours 51 Cr-release assay.

EXAMPLES

The following examples are put forth so as to provide those of ordinary skill in the art with a complete disclosure and description of how to make and use the antibodies, bispecific antibodies, compositions comprising thereof, screening, and therapeutic methods of the presently disclosed subject matter, and are not intended to limit the scope of what the inventors regard as their presently disclosed subject matter. It is understood that various other embodiments may be practiced, given the general description provided above.

Example 1—BCMA Expression in Various Tissues

The Expression of human BCMA was evaluated in various malignant and normal tissues by investigating gene expression profiles in databases such as the cancer cell line encyclopedia and BioGPS. As shown in FIG. 1, human BCMA was highly expressed in lymphoma and multiple myeloma, but not in other malignant tissues. Normal expression appeared limited to B-cells and plasma cells. Potential BCMA targeted CAR T cell eradication of these normal cell types may not have significant adverse effects based on inventors' patient experience with CD19 targeted CAR T cells. Any lack of physiologic antibody production can be addressed with intravenous immunoglobulin treatment.

Example 2—Selection of scFv Specific for BCMA Using a Fully Human Phage Display Library Phage display against BCMA was performed for 3 panning rounds to enrich the scFv phage clones binding to BCMA specifically. Independent pannings with 12 different phage libraries were carried out against BCMA overexpressing 3T3 cells identifying 186 clones. Individual scFv phage clones positive for the BCMA were determined by ELISA and the clones that possessed unique DNA coding sequences were subjected to further characterization. To test if the scFv bound to BCMA on live cells, the positive phage clones were tested for binding to a BCMA-positive cell line, 3T3. After sequencing, 57 unique and BCMA-Fc positive clones were found out of 79 sequenced positive clones; the unique clone rate was 72%. FACS analysis of phage antibody clones against BCMA-3T3 and parental 3T3 cell lines resulted in confirming 25 unique positive clones.

Example 3—Screening Data for Anti-BCMA Antibodies

Figure 6:
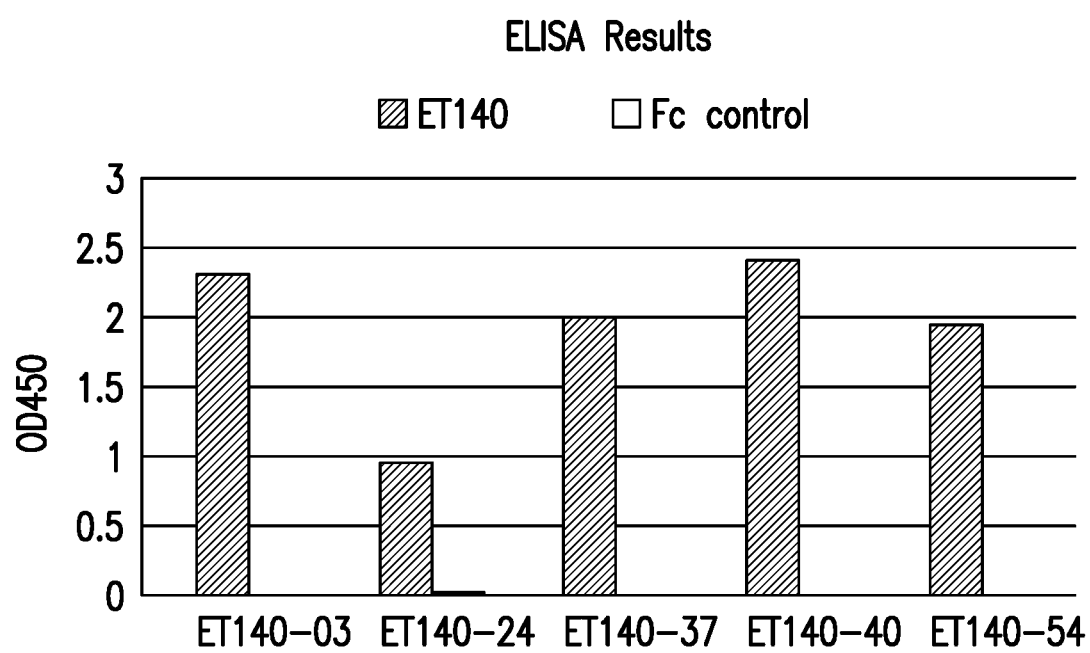
FIG. 6 depicts ELISA screening data of ET140-3, ET140-24, ET140-37, ET140-40, and ET140-54.
Figure 7A:
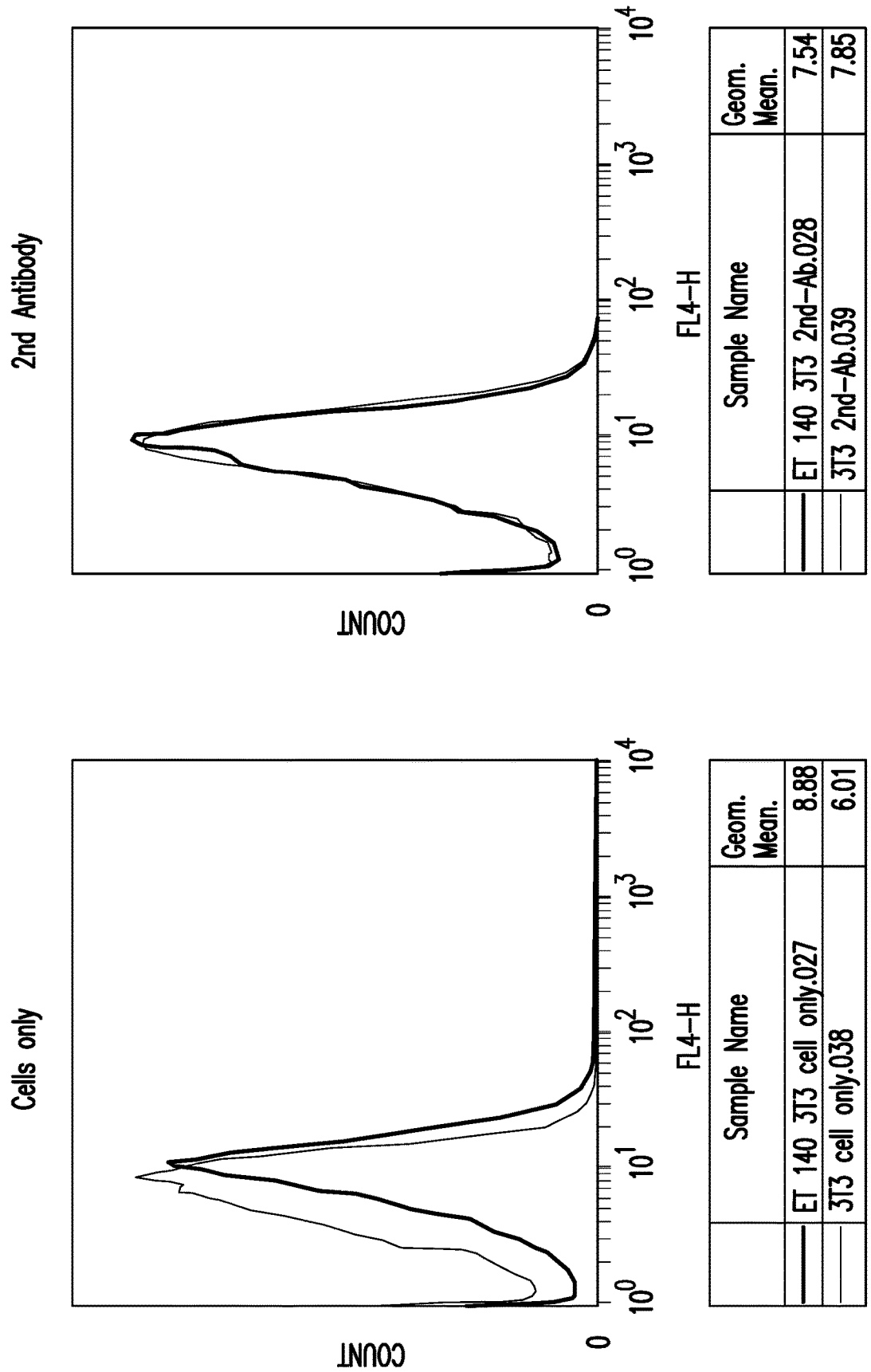
FIGS. 7A-7D depicts FACS screening data of ET140-3 (FIG. 7B), ET140-24 (FIG. 7C), ET140-37 (FIG. 7C), ET140-40 (FIG. 7D), and ET140-54 (FIG. 7D). Cells incubated with 2nd antibody alone, M13 K07 helper phage and cells only were used as negative controls (FIG. 7A).
Figure 7B:
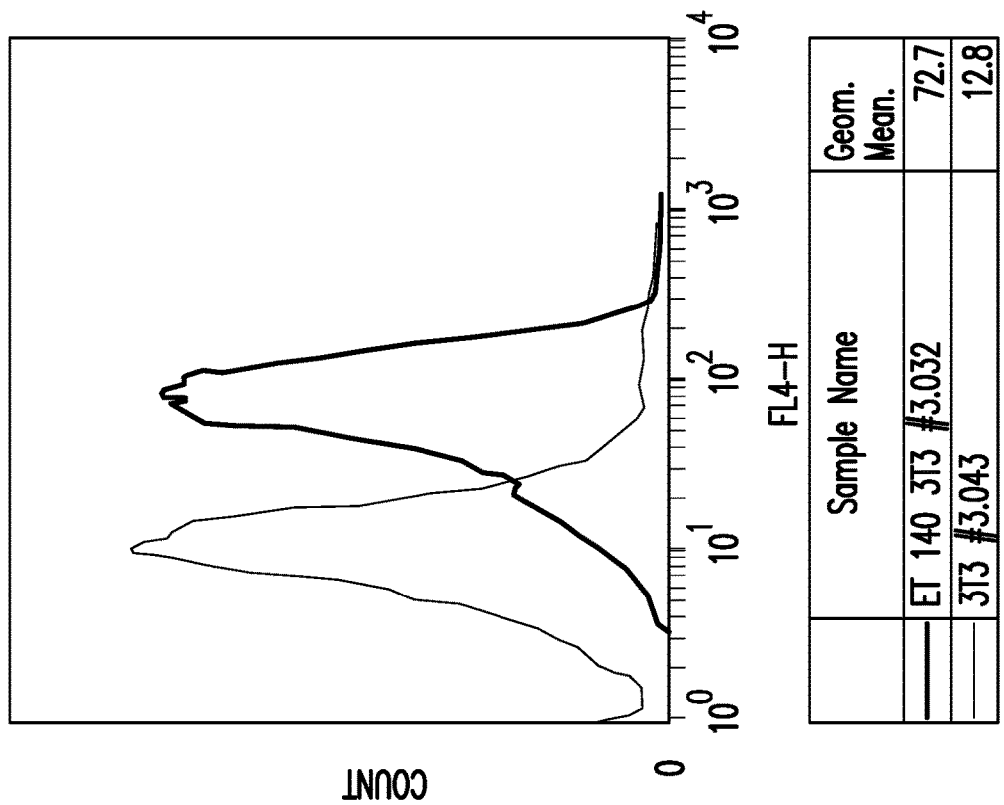
Figure 7B:
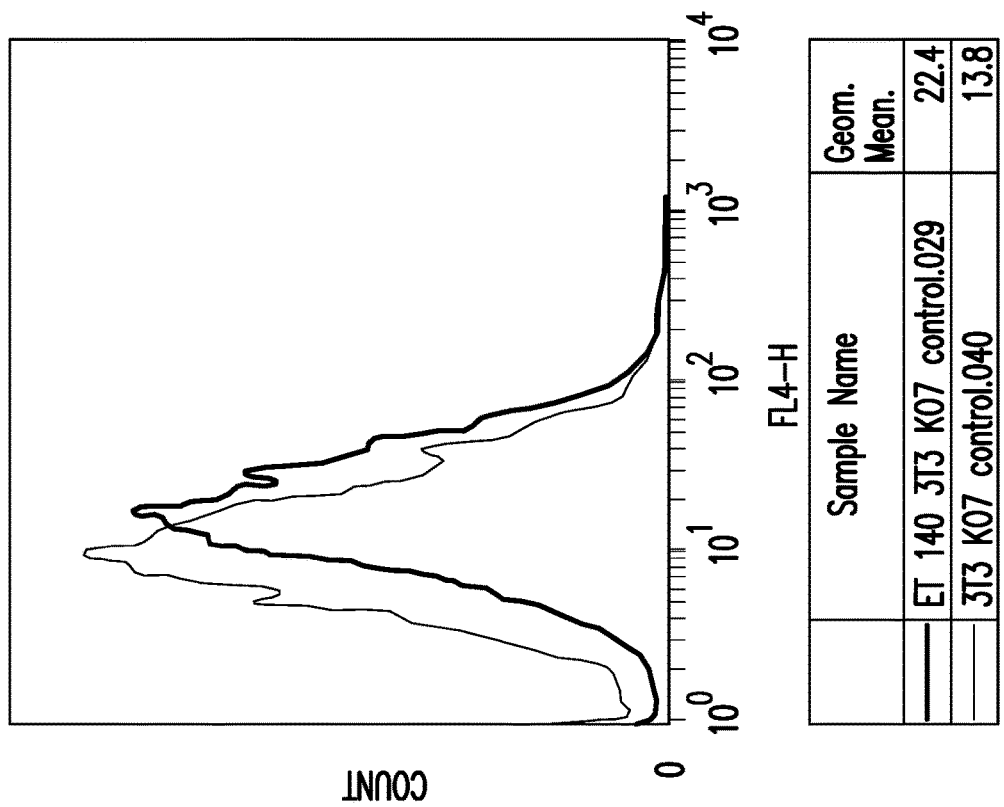
Figure 7C:
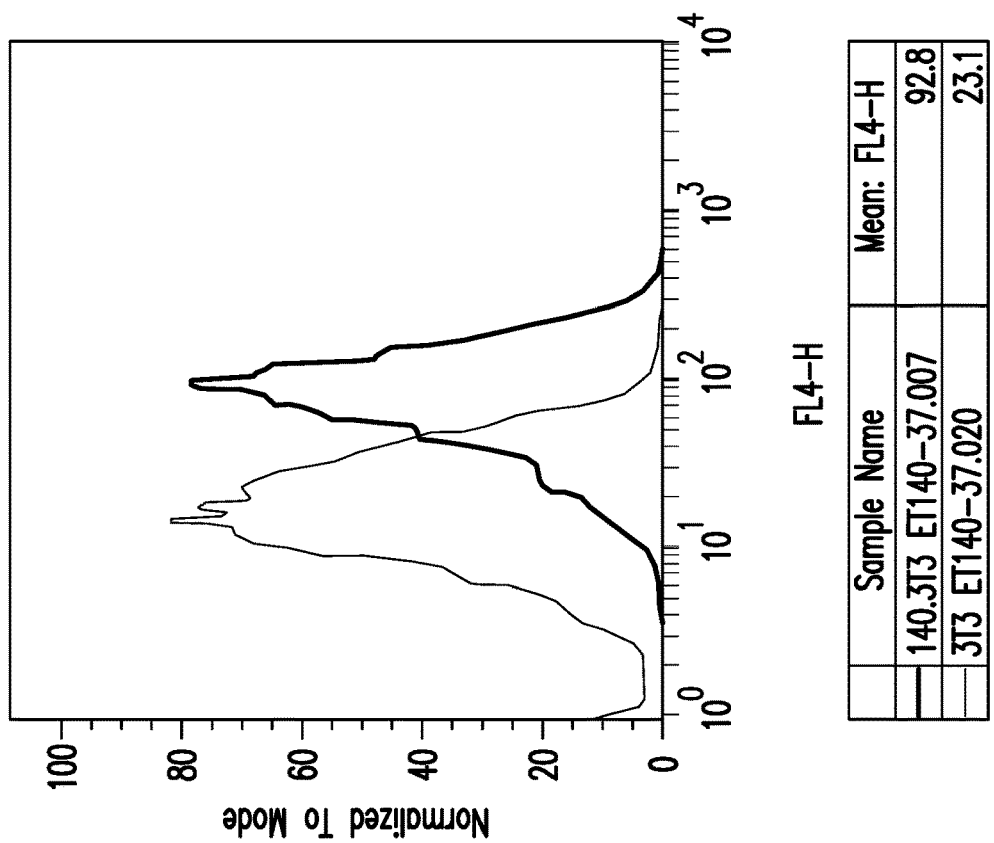
Figure 7C:
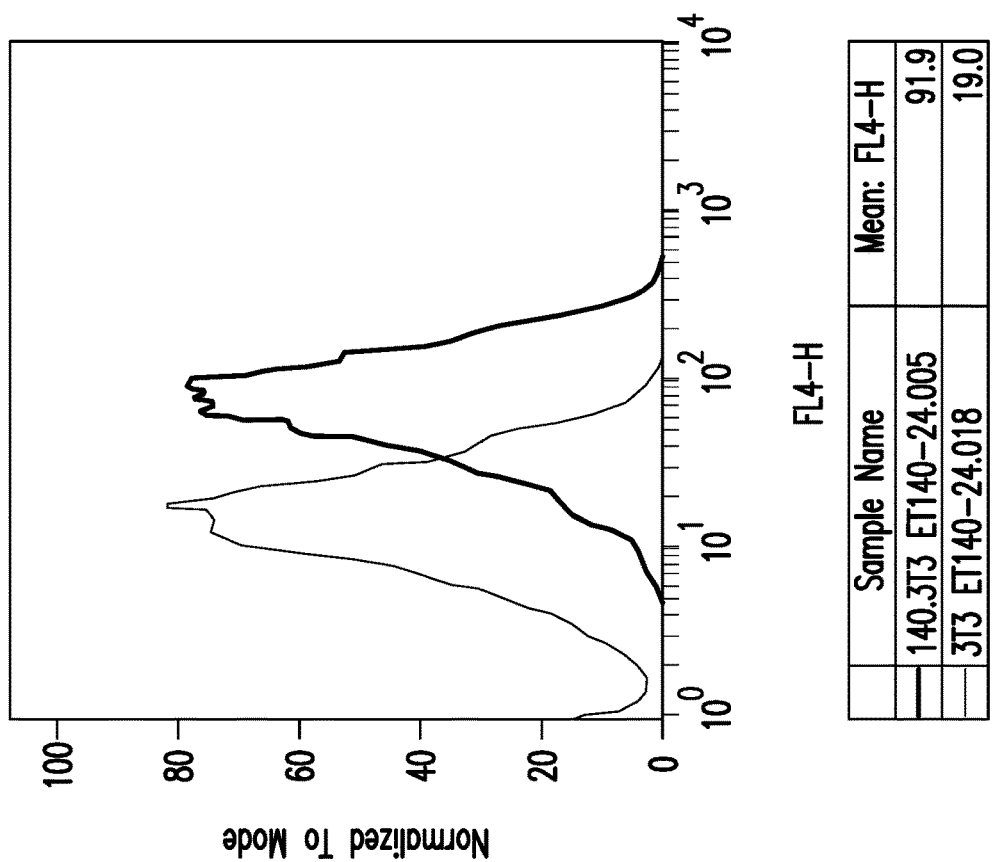
Figure 7D:
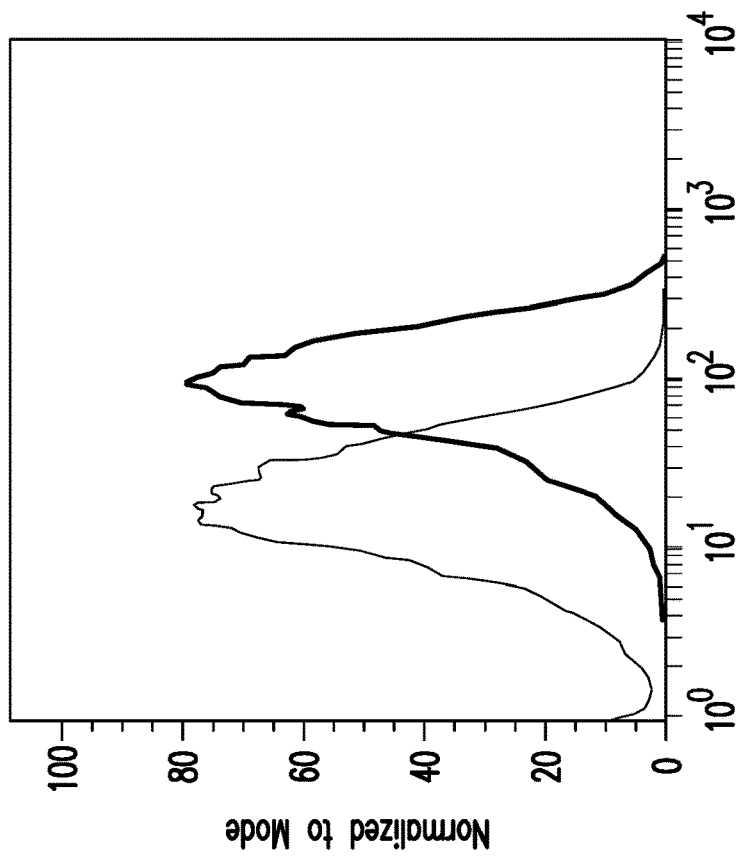
Figure 7D:
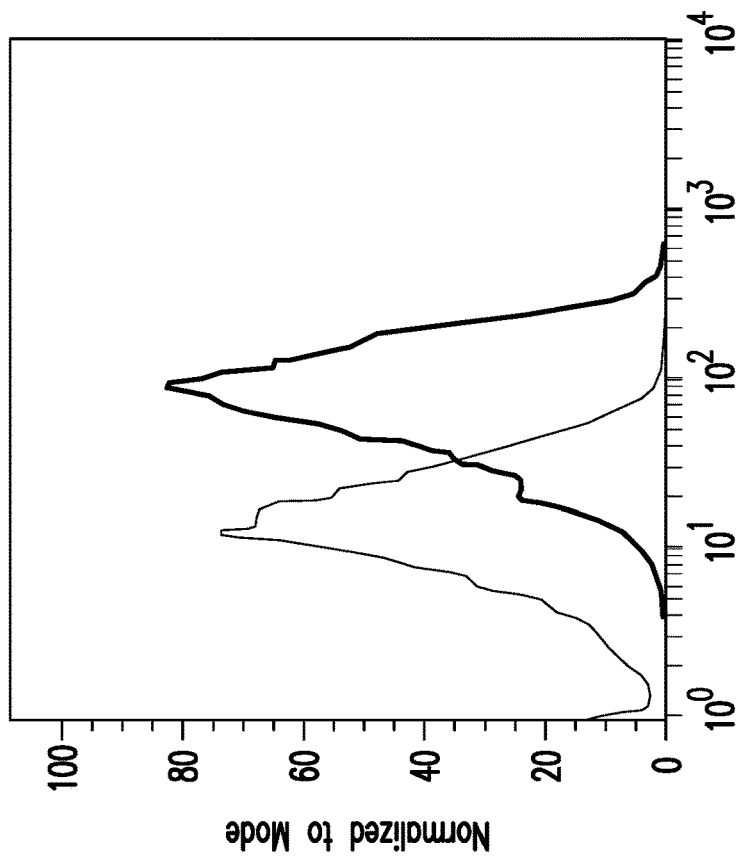

ELISA Screening: FIG. 6 shows the representative results of protein ELISA screening against BCMA antigen using specific scFv phage antibody clones (ET140-3, ET140-24, ET140-37, ET140-40 and ET140-54). ELISA plates were coated with human BCMA ECD-Fc fusion protein, control-Fc fusion protein, or PBS alone as blank control, respectively. Individual phage clones from enriched phage display panning pools against BCMA ECD-Fc fusion protein were incubated in the coated plates. Binding of the phage clones was detected by HRP-conjugated anti-M13 antibodies and developed using TMB substrate. The absorbance was read at 450 nm.

FACS Screening: FIG. 7 shows a representative figure of a FACS analysis of the BCMA-specific phage antibody clones ET140-3, ET140-24, ET140-37, ET140-40 and ET140-54. Phage clones were incubated with 3T3-BCMA cell line, then with anti-M13 mouse antibody. Finally APC-labeled anti-mouse IgG 2nd antibody was added to the reaction after washing again. The binding was measured by FACS and expressed as mean fluorescence intensity (MFI). Cells incubated with 2nd antibody alone, M13 K07 helper phage and cells only were used as negative controls.

Example 4—Epitope Mapping of Anti-BCMA Antibodies

BCMA peptides were ordered based on the ECD sequence with N-terminal Biotin+SGSG linker+15 amino acids with 1 amino acid space. The peptide library is shown in Table 19.

TABLE 19

| ET140-p1 | SGSGLQMAGQCSQNEYFDS | [SEQ ID NO: 207] |
|---|---|---|
| ET140-p2 | SGSGQMAGQCSQNEYFDSL | [SEQ ID NO: 208] |
| ET140-p3 | SGSGMAGQCSQNEYFDSLL | [SEQ ID NO: 209] |
| ET140-p4 | SGSGAGQCSQNEYFDSLLH | [SEQ ID NO: 210] |
| ET140-p5 | SGSGGQCSQNEYFDSLLHA | [SEQ ID NO: 211] |
| ET140-p6 | SGSGQCSQNEYFDSLLHAC | [SEQ ID NO: 212] |
| ET140-p7 | SGSGCSQNEYFDSLLHACI | [SEQ ID NO: 213] |
| ET140-p8 | SGSGSQNEYFDSLLHACIP | [SEQ ID NO: 214] |
| ET140-p9 | SGSGQNEYFDSLLHACIPC | [SEQ ID NO: 215] |
| ET140-p10 | SGSGNEYFDSLLHACIPCQ | [SEQ ID NO: 216] |
| ET140-p11 | SGSGEYFDSLLHACIPCQL | [SEQ ID NO: 217] |
| ET140-p12 | SGSGYFDSLLHACIPCQLR | [SEQ ID NO: 218] |
| ET140-p13 | SGSGFDSLLHACIPCQLRC | [SEQ ID NO: 219] |
| ET140-p14 | SGSGDSLLHACIPCQLRCS | [SEQ ID NO: 220] |
| ET140-p15 | SGSGSLLHACIPCQLRCSS | [SEQ ID NO: 221] |
| ET140-p16 | SGSGLLHACIPCQLRCSSN | [SEQ ID NO: 222] |
| ET140-p17 | SGSGLHACIPCQLRCSSNT | [SEQ ID NO: 223] |
| ET140-p18 | SGSGHACIPCQLRCSSNTP | [SEQ ID NO: 224] |
| ET140-p19 | SGSGACIPCQLRCSSNTPP | [SEQ ID NO: 225] |
| ET140-p20 | SGSGCIPCQLRCSSNTPPL | [SEQ ID NO: 226] |
| ET140-p21 | SGSGIPCQLRCSSNTPPLT | [SEQ ID NO: 227] |
| ET140-p22 | SGSGPCQLRCSSNTPPLTC | [SEQ ID NO: 228] |
| ET140-p23 | SGSGCQLRCSSNTPPLTCQ | [SEQ ID NO: 229] |
| ET140-p24 | SGSGQLRCSSNTPPLTCQR | [SEQ ID NO: 230] |
| ET140-p25 | SGSGLRCSSNTPPLTCQRY | [SEQ ID NO: 231] |
| ET140-p26 | SGSGRCSSNTPPLTCQRYC | [SEQ ID NO: 232] |
| ET140-p27 | SGSGCSSNTPPLTCQRYCN | [SEQ ID NO: 233] |
| ET140-p28 | SGSGSSNTPPLTCQRYCNA | [SEQ ID NO: 234] |
| ET140-p29 | SGSGSNTPPLTCQRYCNAS | [SEQ ID NO: 235] |
| ET140-p30 | SGSGNTPPLTCQRYCNASV | [SEQ ID NO: 236] |
| ET140-p31 | SGSGTPPLTCQRYCNASVT | [SEQ ID NO: 237] |
| ET140-p32 | SGSGPPLTCQRYCNASVTN | [SEQ ID NO: 238] |
| ET140-p33 | SGSGPLTCQRYCNASVTNS | [SEQ ID NO: 239] |
| ET140-p34 | SGSGLTCQRYCNASVTNSV | [SEQ ID NO: 240] |
| ET140-p35 | SGSGTCQRYCNASVTNSVK | [SEQ ID NO: 241] |
| ET140-p36 | SGSGCQRYCNASVTNSVKG | [SEQ ID NO: 242] |
| ET140-p37 | SGSGQRYCNASVTNSVKGT | [SEQ ID NO: 243] |
| ET140-p38 | SGSGRYCNASVTNSVKGTN | [SEQ ID NO: 244] |
| ET140-p39 | SGSGYCNASVTNSVKGTNA | [SEQ ID NO: 245] |

Figure 2:
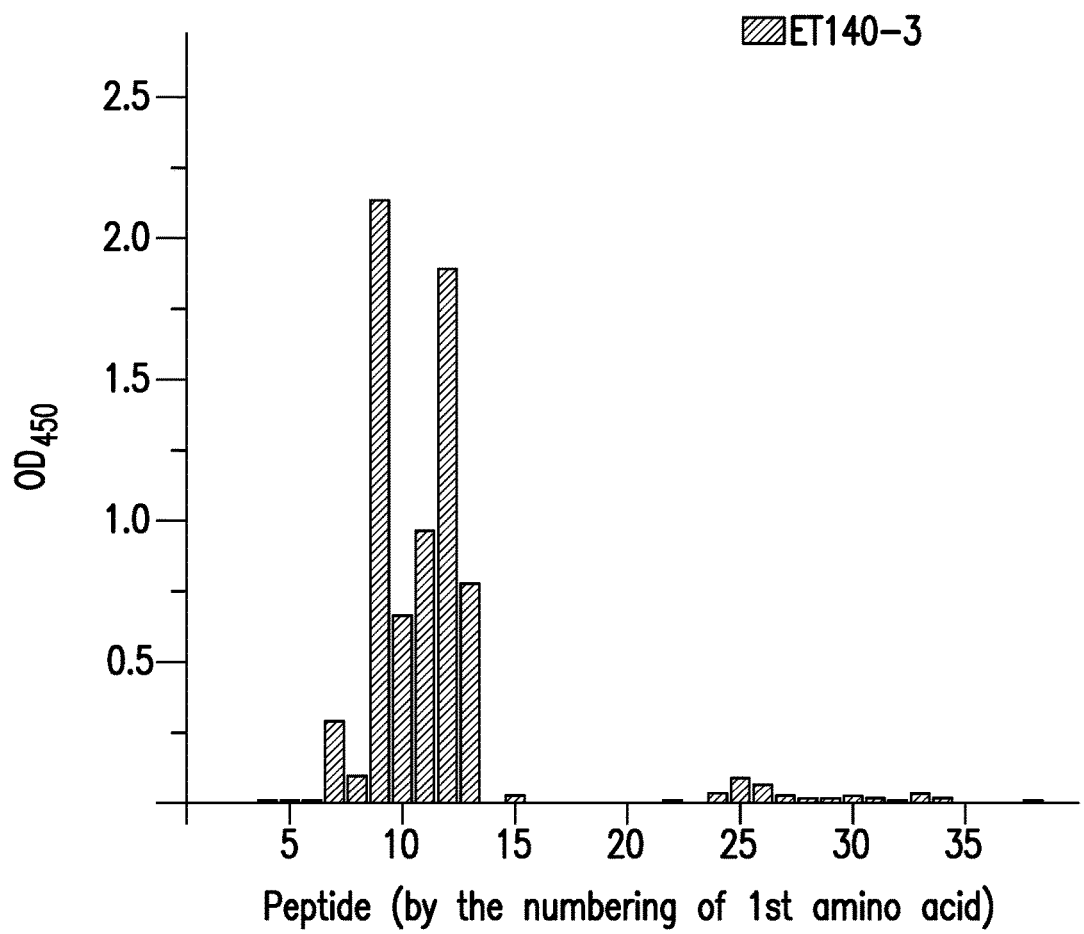
FIG. 2 depicts epitope mapping of ET140-3.
Figure 3:
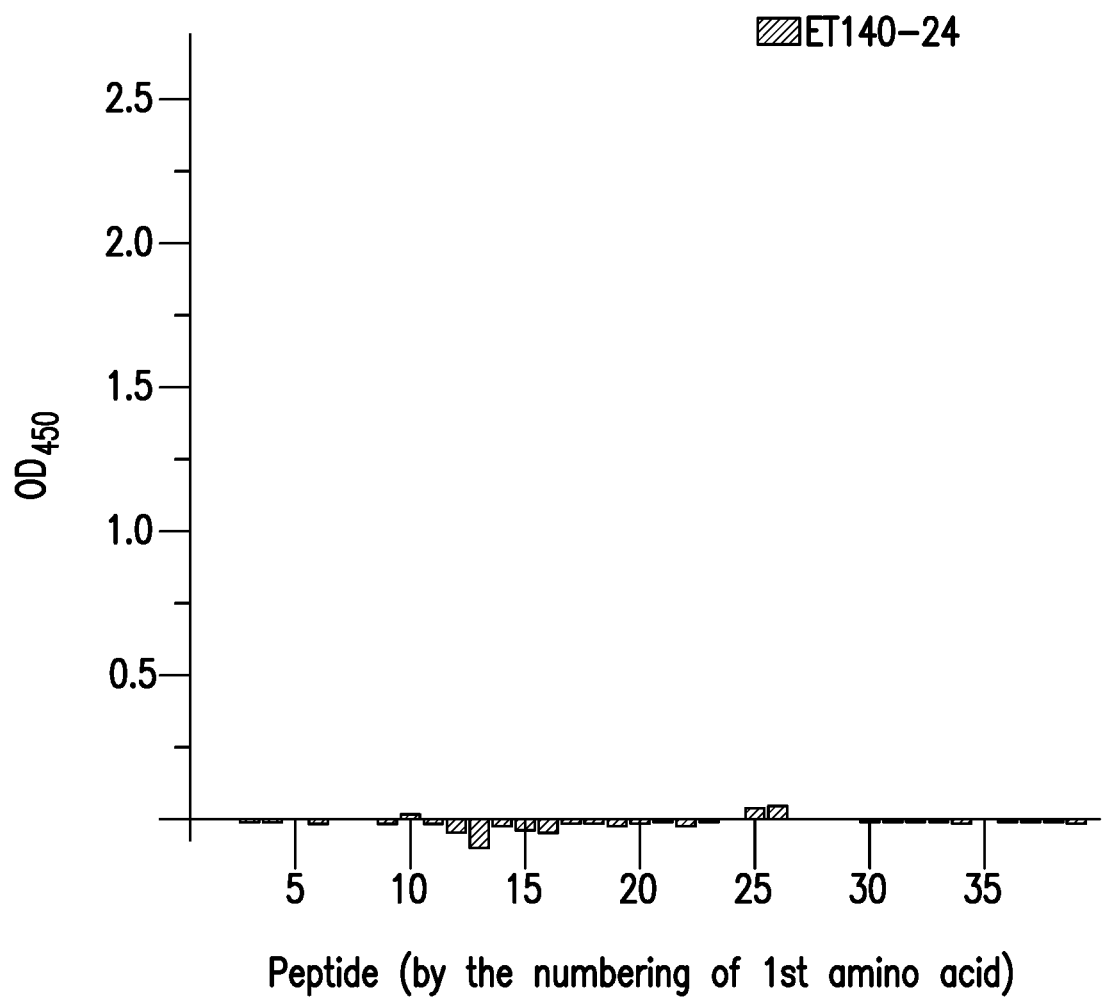
FIG. 3 depicts epitope mapping of ET140-24.
Figure 4:
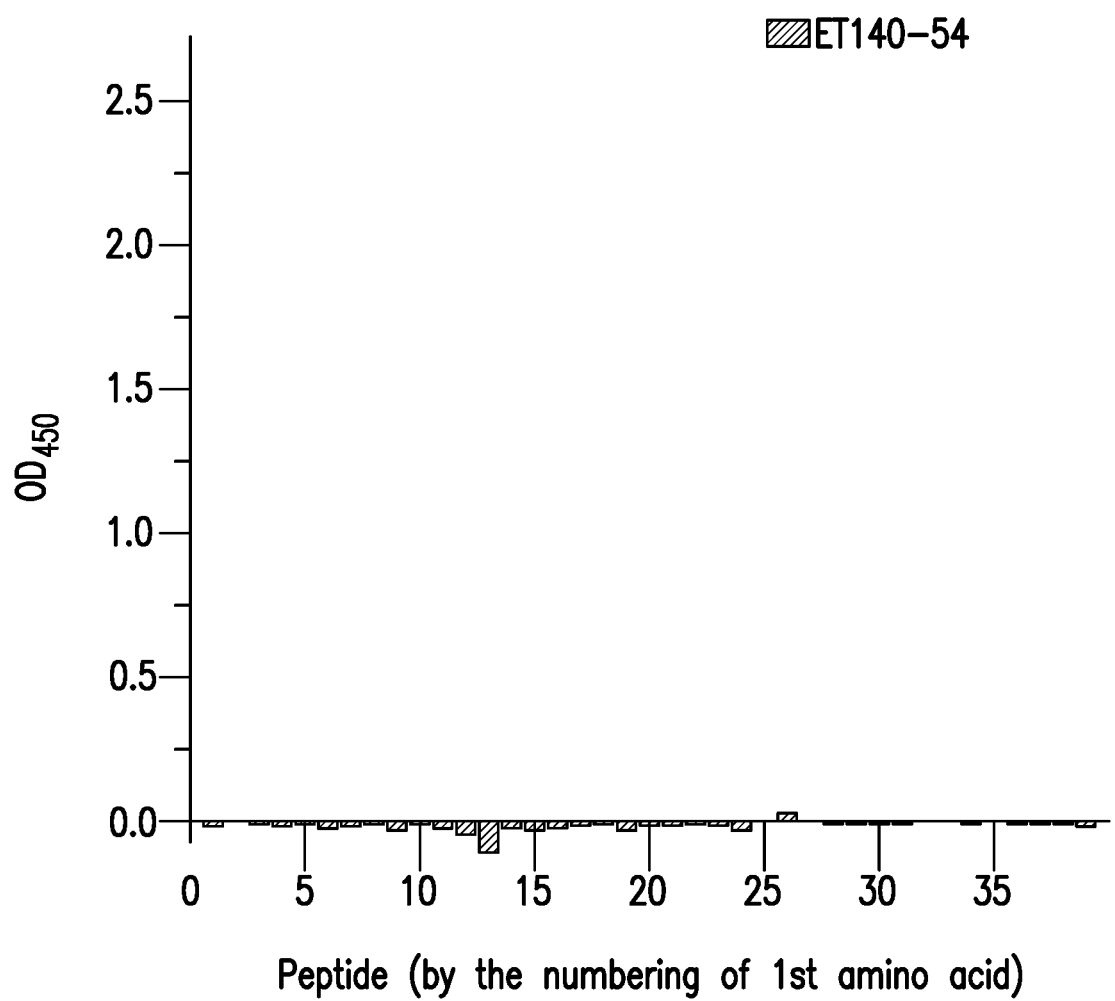
FIG. 4 depicts epitope mapping of ET140-54.

The peptides were coated onto Streptavidin plates at 2 ug/mL in PBST (PBS+0.05% Tween-20). After washing and blocking with 3% BSA. After washing, 1 ug/mL ET140-3, ET140-24, ET140-54 or ET901 mIgG1 was added to the wells, respectively. "mIgG1" used in all Examples represents that the variable region is fully human and the Fc part is mouse IgG1. Then HRP anti-mouse IgG detection antibody was added to each well. Finally, the color was developed using TMB substrate. A450 was recorded for data analysis. The results are shown in FIGS. 2-5. As shown in FIGS. 2 and 5, ET140-3 bound to peptidese 7-13 (i.e., amino acids 8-22, 9-23, 10-24, 11-25, 12-26, 13-27, and 14-28) of SEQ ID NO:71. As shown in FIGS. 3 and 4, no linear epitopes found for ET140-24 or ET140-54.

Summary: 3 ET140 antibodies (mIgG1) were tested together with isotype control ET901 mIgG1 for their binding epitope towards BCMA-ECD. A peptide library consisting of 39 peptides (N-terminal biotin+SGSG linker+15 amino acids, with 1 amino acid offset) was used for epitope mapping ELISA. This allows to search for the linear binding epitope of BCMA-ECD. ET901 mIgG1 was used as background reference for each peptide. Only ET140-3 can be identified for its epitope region: a region comprising amino acids 14-22 of SEQ ID NO:71, e.g., amino acids 8-28 of SEQ ID NO: 71.

ET140-24 and ET140-54 did not show any significant binding towards peptide library. This indicated that these two antibodies may recognize conformational epitope rather than linear epitope of BCMA.

Example 5—Anti-BCMA Antibodies Recombinant Antigen by Surface Plasmon Resonance

Kinetics of interaction between ET140-153 mIgG1 (or "ET140-3 mIgG1"), ET140-174 mIgG1 (or "ET140-24 mIgG1"), ET140-204 mIgG1 (or "ET140-54 mIgG1") and BCMA recombinant antigen was measured using a BIAcore X100 instrument. In brief, 50 μg/mL of modified streptavidin was immobilized onto a Sensor Chip CAP by flowing the Biotin CAPture Reagent through the flow cells at 2 μL/min for 5 minutes. 10 ug/mL biotinylated BCMA-Fc protein was loaded onto the flow cell at a rate of 30 μL/min for 3 minutes. Following the standard protocol for kinetics, a series of injection of ESK1 was performed between 0.6 and 15 μg/mL, each step consisting of a 3 minute injection at 30 μL/min and 3 minute disassociation. Afterwards, the surface was regenerated for 2 minutes with a solution consisting of 75% v/v of 8M guanidine-HCl and 25% v/v 1M NaOH. Kinetic constants were derived by the global fitting (1:1 Langmuir binding model) using BIAcore X100 Evaluation Software (Version 2.0.1). The binding affinity data are shown in Table 20.

TABLE 20

| Protein | KD |
|---|---|
| ET140-24 mIgG1 | KD: 4.8 nM (BiaCore) |
| ET140-54 mIgG1 | KD: 8.1 nM (BiaCore) |
| ET140-3 mIgG1 | KD: 1.2 nM (BiaCore) |

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

What is claimed:

1. A method of treating a tumor associated with B-cell maturation antigen (BCMA) in a subject, comprising administering to the subject an effective amount of an anti-BCMA single-chain variable fragment (scFv) comprising a heavy chain variable region and a light chain variable region, wherein:
   (a) the heavy chain variable region comprises the CDR1, CDR2, and CDR3 of the heavy chain variable sequence set forth in SEQ ID NO: 53, and the light chain variable region comprises the CDR1, CDR2, and CDR3 of the light chain variable region sequence set forth in SEQ ID NO: 54;
   (b) the heavy chain variable region comprises the CDR1, CDR2, and CDR3 of the heavy chain variable sequence set forth in SEQ ID NO: 65, and the light chain variable region comprises the CDR1, CDR2, and CDR3 of the light chain variable region sequence set forth in SEQ ID NO: 66;
   (c) the heavy chain variable region comprises the CDR1, CDR2, and CDR3 of the heavy chain variable sequence set forth in SEQ ID NO: 21, and the light chain variable region comprises the CDR1, CDR2, and CDR3 of the light chain variable region sequence set forth in SEQ ID NO: 22;
   (d) the heavy chain variable region comprises the CDR1, CDR2, and CDR3 of the heavy chain variable sequence set forth in SEQ ID NO: 1, and the light chain variable region comprises the CDR1, CDR2, and CDR3 of the light chain variable region sequence set forth in SEQ ID NO: 2;
   (e) the heavy chain variable region comprises the CDR1, CDR2, and CDR3 of the heavy chain variable sequence set forth in SEQ ID NO: 5, and the light chain variable region comprises the CDR1, CDR2, and CDR3 of the light chain variable region sequence set forth in SEQ ID NO: 6;
   (f) the heavy chain variable region comprises the CDR1, CDR2, and CDR3 of the heavy chain variable sequence set forth in SEQ ID NO: 9, and the light chain variable region comprises the CDR1, CDR2, and CDR3 of the light chain variable region sequence set forth in SEQ ID NO: 10;
   (g) the heavy chain variable region comprises the CDR1, CDR2, and CDR3 of the heavy chain variable sequence set forth in SEQ ID NO: 13, and the light chain variable region comprises the CDR1, CDR2, and CDR3 of the light chain variable region sequence set forth in SEQ ID NO: 14;
   (h) the heavy chain variable region comprises the CDR1, CDR2, and CDR3 of the heavy chain variable sequence set forth in SEQ ID NO: 17, and the light chain variable region comprises the CDR1, CDR2, and CDR3 of the light chain variable region sequence set forth in SEQ ID NO: 18;
   (i) the heavy chain variable region comprises the CDR1, CDR2, and CDR3 of the heavy chain variable sequence set forth in SEQ ID NO: 25, and the light chain variable region comprises the CDR1, CDR2, and CDR3 of the light chain variable region sequence set forth in SEQ ID NO: 26;
   (j) the heavy chain variable region comprises the CDR1, CDR2, and CDR3 of the heavy chain variable sequence set forth in SEQ ID NO: 29, and the light chain variable region comprises the CDR1, CDR2, and CDR3 of the light chain variable region sequence set forth in SEQ ID NO: 30;
   (k) the heavy chain variable region comprises the CDR1, CDR2, and CDR3 of the heavy chain variable sequence set forth in SEQ ID NO: 33, and the light chain variable region comprises the CDR1, CDR2, and CDR3 of the light chain variable region sequence set forth in SEQ ID NO: 34;
   (l) the heavy chain variable region comprises the CDR1, CDR2, and CDR3 of the heavy chain variable sequence set forth in SEQ ID NO: 37, and the light chain variable region comprises the CDR1, CDR2, and CDR3 of the light chain variable region sequence set forth in SEQ ID NO: 38;
   (m) the heavy chain variable region comprises the CDR1, CDR2, and CDR3 of the heavy chain variable sequence set forth in SEQ ID NO: 41, and the light chain variable region comprises the CDR1, CDR2, and CDR3 of the light chain variable region sequence set forth in SEQ ID NO: 42;
   (n) the heavy chain variable region comprises the CDR1, CDR2, and CDR3 of the heavy chain variable sequence set forth in SEQ ID NO: 45, and the light chain variable region comprises the CDR1, CDR2, and CDR3 of the light chain variable region sequence set forth in SEQ ID NO: 46;
   (o) the heavy chain variable region comprises the CDR1, CDR2, and CDR3 of the heavy chain variable sequence set forth in SEQ ID NO: 49, and the light chain variable region comprises the CDR1, CDR2, and CDR3 of the light chain variable region sequence set forth in SEQ ID NO: 50;
   (p) the heavy chain variable region comprises the CDR1, CDR2, and CDR3 of the heavy chain variable sequence set forth in SEQ ID NO: 57, and the light chain variable region comprises the CDR1, CDR2, and CDR3 of the light chain variable region sequence set forth in SEQ ID NO: 58; or
   (q) the heavy chain variable region comprises the CDR1, CDR2, and CDR3 of the heavy chain variable sequence set forth in SEQ ID NO: 61, and the light chain variable region comprises the CDR1, CDR2, and CDR3 of the light chain variable region sequence set forth in SEQ ID NO: 62.

2. The method of claim 1, wherein:
   (a) the heavy chain variable region comprises an amino acid sequence that has at least about 90% sequence identity to the amino acid sequence set forth in SEQ ID NO: 53, and the light chain variable region comprises an amino acid sequence that has at least about 90% sequence identity to the amino acid sequence set forth in SEQ ID NO: 54;
   (b) the heavy chain variable region comprises an amino acid sequence that has at least about 90% sequence identity to the amino acid sequence set forth in SEQ ID NO: 65, and the light chain variable region comprises an amino acid sequence that has at least about 90% sequence identity to the amino acid sequence set forth in SEQ ID NO: 66;
   (c) the heavy chain variable region comprises an amino acid sequence that has at least about 90% sequence identity to the amino acid sequence set forth in SEQ ID NO: 21, and the light chain variable region comprises an amino acid sequence that has at least about 90% sequence identity to the amino acid sequence set forth in SEQ ID NO: 22;
   (d) the heavy chain variable region comprises an amino acid sequence that has at least about 90% sequence identity to the amino acid sequence set forth in SEQ ID NO: 1, and the light chain variable region comprises an amino acid sequence that has at least about 90% sequence identity to the amino acid sequence set forth in SEQ ID NO: 2;

(e) the heavy chain variable region comprises an amino acid sequence that has at least about 90% sequence identity to the amino acid sequence set forth in SEQ ID NO: 5, and the light chain variable region comprises an amino acid sequence that has at least about 90% sequence identity to the amino acid sequence set forth in SEQ ID NO: 6;

(f) the heavy chain variable region comprises an amino acid sequence that has at least about 90% sequence identity to the amino acid sequence set forth in SEQ ID NO: 9, and the light chain variable region comprises an amino acid sequence that has at least about 90% sequence identity to the amino acid sequence set forth in SEQ ID NO: 10;

(g) the heavy chain variable region comprises an amino acid sequence that has at least about 90% sequence identity to the amino acid sequence set forth in SEQ ID NO: 13, and the light chain variable region comprises an amino acid sequence that has at least about 90% sequence identity to the amino acid sequence set forth in SEQ ID NO: 14;

(h) the heavy chain variable region comprises an amino acid sequence that has at least about 90% sequence identity to the amino acid sequence set forth in SEQ ID NO: 17, and the light chain variable region comprises an amino acid sequence that has at least about 90% sequence identity to the amino acid sequence set forth in SEQ ID NO: 18;

(i) the heavy chain variable region comprises an amino acid sequence that has at least about 90% sequence identity to the amino acid sequence set forth in SEQ ID NO: 25, and the light chain variable region comprises an amino acid sequence that has at least about 90% sequence identity to the amino acid sequence set forth in SEQ ID NO: 26;

(j) the heavy chain variable region comprises an amino acid sequence that has at least about 90% sequence identity to the amino acid sequence set forth in SEQ ID NO: 29, and the light chain variable region comprises an amino acid sequence that has at least about 90% sequence identity to the amino acid sequence set forth in SEQ ID NO: 30;

(k) the heavy chain variable region comprises an amino acid sequence that has at least about 90% sequence identity to the amino acid sequence set forth in SEQ ID NO: 33, and the light chain variable region comprises an amino acid sequence that has at least about 90% sequence identity to the amino acid sequence set forth in SEQ ID NO: 34;

(l) the heavy chain variable region comprises an amino acid sequence that has at least about 90% sequence identity to the amino acid sequence set forth in SEQ ID NO: 37, and the light chain variable region comprises an amino acid sequence that has at least about 90% sequence identity to the amino acid sequence set forth in SEQ ID NO: 38;

(m) the heavy chain variable region comprises an amino acid sequence that has at least about 90% sequence identity to the amino acid sequence set forth in SEQ ID NO: 41, and the light chain variable region comprises an amino acid sequence that has at least about 90% sequence identity to the amino acid sequence set forth in SEQ ID NO: 42;

(n) the heavy chain variable region comprises an amino acid sequence that has at least about 90% sequence identity to the amino acid sequence set forth in SEQ ID NO: 45, and the light chain variable region comprises an amino acid sequence that has at least about 90% sequence identity to the amino acid sequence set forth in SEQ ID NO: 46;

(o) the heavy chain variable region comprises an amino acid sequence that has at least about 90% sequence identity to the amino acid sequence set forth in SEQ ID NO: 49, and the light chain variable region comprises an amino acid sequence that has at least about 90% sequence identity to the amino acid sequence set forth in SEQ ID NO: 50;

(p) the heavy chain variable region comprises an amino acid sequence that has at least about 90% sequence identity to the amino acid sequence set forth in SEQ ID NO: 57, and the light chain variable region comprises an amino acid sequence that has at least about 90% sequence identity to the amino acid sequence set forth in SEQ ID NO: 58; or (q) the heavy chain variable region comprises an amino acid sequence that has at least about 90% sequence identity to the amino acid sequence set forth in SEQ ID NO: 61, and the light chain variable region comprises an amino acid sequence that has at least about 90% sequence identity to the amino acid sequence set forth in SEQ ID NO: 62.

3. The method of claim 1, wherein:

(a) the heavy chain variable region comprises the amino acid sequence set forth in SEQ ID NO: 53, and the light chain variable region comprises the amino acid sequence set forth in SEQ ID NO: 54;

(b) the heavy chain variable region comprises the amino acid sequence set forth in SEQ ID NO: 65, and the light chain variable region comprises the amino acid sequence set forth in SEQ ID NO: 66;

(c) the heavy chain variable region comprises the amino acid sequence set forth in SEQ ID NO: 21, and the light chain variable region comprises the amino acid sequence set forth in SEQ ID NO: 22;

(d) the heavy chain variable region comprises the amino acid sequence set forth in SEQ ID NO: 1, and the light chain variable region comprises the amino acid sequence set forth in SEQ ID NO: 2;

(e) the heavy chain variable region comprises the amino acid sequence set forth in SEQ ID NO: 5, and the light chain variable region comprises the amino acid sequence set forth in SEQ ID NO: 6;

(f) the heavy chain variable region comprises the amino acid sequence set forth in SEQ ID NO: 9, and the light chain variable region comprises the amino acid sequence set forth in SEQ ID NO: 10;

(g) the heavy chain variable region comprises the amino acid sequence set forth in SEQ ID NO: 13, and the light chain variable region comprises the amino acid sequence set forth in SEQ ID NO: 14;

(h) the heavy chain variable region comprises the amino acid sequence set forth in SEQ ID NO: 17, and the light chain variable region comprises the amino acid sequence set forth in SEQ ID NO: 18;

(i) the heavy chain variable region comprises the amino acid sequence set forth in SEQ ID NO: 25, and the light chain variable region comprises the amino acid sequence set forth in SEQ ID NO: 26;

(j) the heavy chain variable region comprises the amino acid sequence set forth in SEQ ID NO: 29, and the light chain variable region comprises the amino acid sequence set forth in SEQ ID NO: 30;
(k) the heavy chain variable region comprises the amino acid sequence set forth in SEQ ID NO: 33, and the light chain variable region comprises the amino acid sequence set forth in SEQ ID NO: 34;
(l) the heavy chain variable region comprises the amino acid sequence set forth in SEQ ID NO: 37, and the light chain variable region comprises the amino acid sequence set forth in SEQ ID NO: 38;
(m) the heavy chain variable region comprises the amino acid sequence set forth in SEQ ID NO: 41, and the light chain variable region comprises the amino acid sequence set forth in SEQ ID NO: 42;
(n) the heavy chain variable region comprises the amino acid sequence set forth in SEQ ID NO: 45, and the light chain variable region comprises the amino acid sequence set forth in SEQ ID NO: 46;
(o) the heavy chain variable region comprises the amino acid sequence set forth in SEQ ID NO: 49, and the light chain variable region comprises the amino acid sequence set forth in SEQ ID NO: 50;
(p) the heavy chain variable region comprises the amino acid sequence set forth in SEQ ID NO: 57, and the light chain variable region comprises the amino acid sequence set forth in SEQ ID NO: 58; or
(q) the heavy chain variable region comprises the amino acid sequence set forth in SEQ ID NO: 61, and the light chain variable region comprises the amino acid sequence set forth in SEQ ID NO: 62.

4. The method of claim 1, wherein the scFv comprises the amino acid sequence set forth in SEQ ID NO: 85, SEQ ID NO: 88, SEQ ID NO: 77, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 86, or SEQ ID NO: 87.

5. The method of claim 1, wherein the heavy chain variable region comprises the CDR1, CDR2, and CDR3 of the heavy chain variable sequence set forth in SEQ ID NO: 53, and the light chain variable region comprises the CDR1, CDR2, and CDR3 of the light chain variable region sequence set forth in SEQ ID NO: 54.

6. The method of claim 1, wherein the heavy chain variable region comprises the CDR1, CDR2, and CDR3 of the heavy chain variable sequence set forth in SEQ ID NO: 65, and the light chain variable region comprises the CDR1, CDR2, and CDR3 of the light chain variable region sequence set forth in SEQ ID NO: 66.

7. The method of claim 1, wherein the heavy chain variable region comprises the CDR1, CDR2, and CDR3 of the heavy chain variable sequence set forth in SEQ ID NO: 21, and the light chain variable region comprises the CDR1, CDR2, and CDR3 of the light chain variable region sequence set forth in SEQ ID NO: 22.

8. The method of claim 1, wherein the method reduces the number of tumor cells, reduces the tumor size, or eradicates the tumor in the subject.

9. The method of claim 1, wherein the tumor is selected from the group consisting of multiple myeloma, Non-Hodgkin Lymphoma, Hodgkin Lymphoma, Chronic Lymphocytic Leukemia, glioblastoma, and Waldenstrom's Macroglobulinemia.

10. The method of claim 1, wherein the tumor is multiple myeloma.

11. The method of claim 1, wherein the subject is a human.

12. A method of treating a tumor associated with B-cell maturation antigen (BCMA) in a subject, comprising administering to the subject an effective amount of an anti-BCMA single-chain variable fragment (scFv) comprising a heavy chain variable region and a light chain variable region, wherein:
(a) the heavy chain variable region comprises a CDR1, a CDR2, and a CDR3 sequence set forth in SEQ ID NOS: 167, 168, and 169, respectively; and the light chain variable region comprises a CDR1, a CDR2, and a CDR3 sequence set forth in SEQ ID NOS: 170, 171, and 172, respectively;
(b) the heavy chain variable region comprises a CDR1, a CDR2, and a CDR3 sequence set forth in SEQ ID NOS: 185, 186, and 187, respectively; and the light chain variable region comprises a CDR1, a CDR2, and a CDR3 sequence set forth in SEQ ID NOS: 188, 189, and 190, respectively;
(c) the heavy chain variable region comprises a CDR1, a CDR2, and a CDR3 sequence set forth in SEQ ID NOS: 119, 120, and 121, respectively; and the light chain variable region comprises a CDR1, a CDR2, and a CDR3 sequence set forth in SEQ ID NOS: 122, 123, and 124, respectively;
(d) the heavy chain variable region comprises a CDR1, a CDR2, and a CDR3 sequence set forth in SEQ ID NOS: 89, 90, and 91, respectively; and the light chain variable region comprises a CDR1, a CDR2, and a CDR3 sequence set forth in SEQ ID NOS: 92, 93, and 94, respectively;
(e) the heavy chain variable region comprises a CDR1, a CDR2, and a CDR3 sequence set forth in SEQ ID NOS: 95, 96, and 97, respectively; and the light chain variable region comprises a CDR1, a CDR2, and a CDR3 sequence set forth in SEQ ID NOS: 98, 99, and 100, respectively;
(f) the heavy chain variable region comprises a CDR1, a CDR2, and a CDR3 sequence set forth in SEQ ID NOS: 101, 102, and 103, respectively; and the light chain variable region comprises a CDR1, a CDR2, and a CDR3 sequence set forth in SEQ ID NOS: 104, 105, and 106, respectively;
(g) the heavy chain variable region comprises a CDR1, a CDR2, and a CDR3 sequence set forth in SEQ ID NOS: 107, 108, and 109, respectively; and the light chain variable region comprises a CDR1, a CDR2, and a CDR3 sequence set forth in SEQ ID NOS: 110, 111, and 112, respectively;
(h) the heavy chain variable region comprises a CDR1, a CDR2, and a CDR3 sequence set forth in SEQ ID NOS: 113, 114, and 115, respectively; and the light chain variable region comprises a CDR1, a CDR2, and a CDR3 sequence set forth in SEQ ID NOS: 116, 117, and 118, respectively;
(i) the heavy chain variable region comprises a CDR1, a CDR2, and a CDR3 sequence set forth in SEQ ID NOS: 125, 126, and 127, respectively; and the light chain variable region comprises a CDR1, a CDR2, and a CDR3 sequence set forth in SEQ ID NOS: 128, 129, and 130, respectively;
(j) the heavy chain variable region comprises a CDR1, a CDR2, and a CDR3 sequence set forth in SEQ ID NOS: 131, 132, and 133, respectively; and the light chain variable region comprises a CDR1, a CDR2, and a CDR3 sequence set forth in SEQ ID NOS: 134, 135, and 136, respectively;

(k) the heavy chain variable region comprises a CDR1, a CDR2, and a CDR3 sequence set forth in SEQ ID NOS: 137, 138, and 139, respectively; and the light chain variable region comprises a CDR1, a CDR2, and a CDR3 sequence set forth in SEQ ID NOS: 140, 141, and 142, respectively;

(l) the heavy chain variable region comprises a CDR1, a CDR2, and a CDR3 sequence set forth in SEQ ID NOS: 143, 144, and 145, respectively; and the light chain variable region comprises a CDR1, a CDR2, and a CDR3 sequence set forth in SEQ ID NOS: 146, 147, and 149, respectively;

(m) the heavy chain variable region comprises a CDR1, a CDR2, and a CDR3 sequence set forth in SEQ ID NOS: 149, 150, and 151, respectively; and the light chain variable region comprises a CDR1, a CDR2, and a CDR3 sequence set forth in SEQ ID NOS: 152, 152, and 154, respectively;

(n) the heavy chain variable region comprises a CDR1, a CDR2, and a CDR3 sequence set forth in SEQ ID NOS: 155, 156, and 157, respectively; and the light chain variable region comprises a CDR1, a CDR2, and a CDR3 sequence set forth in SEQ ID NOS: 158, 159, and 160, respectively;

(o) the heavy chain variable region comprises a CDR1, a CDR2, and a CDR3 sequence set forth in SEQ ID NOS: 161, 162, and 163, respectively; and the light chain variable region comprises a CDR1, a CDR2, and a CDR3 sequence set forth in SEQ ID NOS: 164, 165, and 166, respectively;

(p) the heavy chain variable region comprises a CDR1, a CDR2, and a CDR3 sequence set forth in SEQ ID NOS: 173, 174, and 175, respectively; and the light chain variable region comprises a CDR1, a CDR2, and a CDR3 sequence set forth in SEQ ID NOS: 176, 177, and 178, respectively; or (q) the heavy chain variable region comprises a CDR1, a CDR2, and a CDR3 sequence set forth in SEQ ID NOS: 179, 180, and 181, respectively; and the light chain variable region comprises a CDR1, a CDR2, and a CDR3 sequence set forth in SEQ ID NOS: 182, 183, and 184, respectively.

13. The method of claim 12, wherein:

(a) the heavy chain variable region comprises an amino acid sequence that has at least about 90% sequence identity to the amino acid sequence set forth in SEQ ID NO: 53, and the light chain variable region comprises an amino acid sequence that has at least about 90% sequence identity to the amino acid sequence set forth in SEQ ID NO: 54;

(b) the heavy chain variable region comprises an amino acid sequence that has at least about 90% sequence identity to the amino acid sequence set forth in SEQ ID NO: 65, and the light chain variable region comprises an amino acid sequence that has at least about 90% sequence identity to the amino acid sequence set forth in SEQ ID NO: 66;

(c) the heavy chain variable region comprises an amino acid sequence that has at least about 90% sequence identity to the amino acid sequence set forth in SEQ ID NO: 21, and the light chain variable region comprises an amino acid sequence that has at least about 90% sequence identity to the amino acid sequence set forth in SEQ ID NO: 22;

(d) the heavy chain variable region comprises an amino acid sequence that has at least about 90% sequence identity to the amino acid sequence set forth in SEQ ID NO: 1, and the light chain variable region comprises an amino acid sequence that has at least about 90% sequence identity to the amino acid sequence set forth in SEQ ID NO: 2;

(e) the heavy chain variable region comprises an amino acid sequence that has at least about 90% sequence identity to the amino acid sequence set forth in SEQ ID NO: 5, and the light chain variable region comprises an amino acid sequence that has at least about 90% sequence identity to the amino acid sequence set forth in SEQ ID NO: 6;

(f) the heavy chain variable region comprises an amino acid sequence that has at least about 90% sequence identity to the amino acid sequence set forth in SEQ ID NO: 9, and the light chain variable region comprises an amino acid sequence that has at least about 90% sequence identity to the amino acid sequence set forth in SEQ ID NO: 10;

(g) the heavy chain variable region comprises an amino acid sequence that has at least about 90% sequence identity to the amino acid sequence set forth in SEQ ID NO: 13, and the light chain variable region comprises an amino acid sequence that has at least about 90% sequence identity to the amino acid sequence set forth in SEQ ID NO: 14;

(h) the heavy chain variable region comprises an amino acid sequence that has at least about 90% sequence identity to the amino acid sequence set forth in SEQ ID NO: 17, and the light chain variable region comprises an amino acid sequence that has at least about 90% sequence identity to the amino acid sequence set forth in SEQ ID NO: 18;

(i) the heavy chain variable region comprises an amino acid sequence that has at least about 90% sequence identity to the amino acid sequence set forth in SEQ ID NO: 25, and the light chain variable region comprises an amino acid sequence that has at least about 90% sequence identity to the amino acid sequence set forth in SEQ ID NO: 26;

(j) the heavy chain variable region comprises an amino acid sequence that has at least about 90% sequence identity to the amino acid sequence set forth in SEQ ID NO: 29, and the light chain variable region comprises an amino acid sequence that has at least about 90% sequence identity to the amino acid sequence set forth in SEQ ID NO: 30;

(k) the heavy chain variable region comprises an amino acid sequence that has at least about 90% sequence identity to the amino acid sequence set forth in SEQ ID NO: 33, and the light chain variable region comprises an amino acid sequence that has at least about 90% sequence identity to the amino acid sequence set forth in SEQ ID NO: 34;

(l) the heavy chain variable region comprises an amino acid sequence that has at least about 90% sequence identity to the amino acid sequence set forth in SEQ ID NO: 37, and the light chain variable region comprises an amino acid sequence that has at least about 90% sequence identity to the amino acid sequence set forth in SEQ ID NO: 38;

(m) the heavy chain variable region comprises an amino acid sequence that has at least about 90% sequence identity to the amino acid sequence set forth in SEQ ID NO: 41, and the light chain variable region comprises an amino acid sequence that has at least about 90% sequence identity to the amino acid sequence set forth in SEQ ID NO: 42;

(n) the heavy chain variable region comprises an amino acid sequence that has at least about 90% sequence identity to the amino acid sequence set forth in SEQ ID NO: 45, and the light chain variable region comprises an amino acid sequence that has at least about 90% sequence identity to the amino acid sequence set forth in SEQ ID NO: 46;
(o) the heavy chain variable region comprises an amino acid sequence that has at least about 90% sequence identity to the amino acid sequence set forth in SEQ ID NO: 49, and the light chain variable region comprises an amino acid sequence that has at least about 90% sequence identity to the amino acid sequence set forth in SEQ ID NO: 50;
(p) the heavy chain variable region comprises an amino acid sequence that has at least about 90% sequence identity to the amino acid sequence set forth in SEQ ID NO: 57, and the light chain variable region comprises an amino acid sequence that has at least about 90% sequence identity to the amino acid sequence set forth in SEQ ID NO: 58; or
(q) the heavy chain variable region comprises an amino acid sequence that has at least about 90% sequence identity to the amino acid sequence set forth in SEQ ID NO: 61, and the light chain variable region comprises an amino acid sequence that has at least about 90% sequence identity to the amino acid sequence set forth in SEQ ID NO: 62.

14. The method of claim 12, wherein:
(a) the heavy chain variable region comprises the amino acid sequence set forth in SEQ ID NO: 53, and the light chain variable region comprises the amino acid sequence set forth in SEQ ID NO: 54;
(b) the heavy chain variable region comprises the amino acid sequence set forth in SEQ ID NO: 65, and the light chain variable region comprises the amino acid sequence set forth in SEQ ID NO: 66;
(c) the heavy chain variable region comprises the amino acid sequence set forth in SEQ ID NO: 21, and the light chain variable region comprises the amino acid sequence set forth in SEQ ID NO: 22;
(d) the heavy chain variable region comprises the amino acid sequence set forth in SEQ ID NO: 1, and the light chain variable region comprises the amino acid sequence set forth in SEQ ID NO: 2;
(e) the heavy chain variable region comprises the amino acid sequence set forth in SEQ ID NO: 5, and the light chain variable region comprises the amino acid sequence set forth in SEQ ID NO: 6;
(f) the heavy chain variable region comprises the amino acid sequence set forth in SEQ ID NO: 9, and the light chain variable region comprises the amino acid sequence set forth in SEQ ID NO: 10;
(g) the heavy chain variable region comprises the amino acid sequence set forth in SEQ ID NO: 13, and the light chain variable region comprises the amino acid sequence set forth in SEQ ID NO: 14;
(h) the heavy chain variable region comprises the amino acid sequence set forth in SEQ ID NO: 17, and the light chain variable region comprises the amino acid sequence set forth in SEQ ID NO: 18;
(i) the heavy chain variable region comprises the amino acid sequence set forth in SEQ ID NO: 25, and the light chain variable region comprises the amino acid sequence set forth in SEQ ID NO: 26;
(j) the heavy chain variable region comprises the amino acid sequence set forth in SEQ ID NO: 29, and the light chain variable region comprises the amino acid sequence set forth in SEQ ID NO: 30;
(k) the heavy chain variable region comprises the amino acid sequence set forth in SEQ ID NO: 33, and the light chain variable region comprises the amino acid sequence set forth in SEQ ID NO: 34;
(l) the heavy chain variable region comprises the amino acid sequence set forth in SEQ ID NO: 37, and the light chain variable region comprises the amino acid sequence set forth in SEQ ID NO: 38;
(m) the heavy chain variable region comprises the amino acid sequence set forth in SEQ ID NO: 41, and the light chain variable region comprises the amino acid sequence set forth in SEQ ID NO: 42;
(n) the heavy chain variable region comprises the amino acid sequence set forth in SEQ ID NO: 45, and the light chain variable region comprises the amino acid sequence set forth in SEQ ID NO: 46;
(o) the heavy chain variable region comprises the amino acid sequence set forth in SEQ ID NO: 49, and the light chain variable region comprises the amino acid sequence set forth in SEQ ID NO: 50;
(p) the heavy chain variable region comprises the amino acid sequence set forth in SEQ ID NO: 57, and the light chain variable region comprises the amino acid sequence set forth in SEQ ID NO: 58; or
(q) the heavy chain variable region comprises the amino acid sequence set forth in SEQ ID NO: 61, and the light chain variable region comprises the amino acid sequence set forth in SEQ ID NO: 62.

15. The method of claim 12, wherein the scFv comprises the amino acid sequence set forth in SEQ ID NO: 85, SEQ ID NO: 88, or SEQ ID NO: 77, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 86, or SEQ ID NO: 87.

16. The method of claim 12, wherein the heavy chain variable region comprises a CDR1, a CDR2, and a CDR3 sequence set forth in SEQ ID NOS: 167, 168, and 169, respectively; and the light chain variable region comprises a CDR1, a CDR2, and a CDR3 sequence set forth in SEQ ID NOS: 170, 171, and 172, respectively.

17. The method of claim 12, wherein the heavy chain variable region comprises a CDR1, a CDR2, and a CDR3 sequence set forth in SEQ ID NOS: 185, 186, and 187, respectively; and the light chain variable region comprises a CDR1, a CDR2, and a CDR3 sequence set forth in SEQ ID NOS: 188, 189, and 190, respectively.

18. The method of claim 12, wherein the heavy chain variable region comprises a CDR1, a CDR2, and a CDR3 sequence set forth in SEQ ID NOS: 119, 120, and 121, respectively; and the light chain variable region comprises a CDR1, a CDR2, and a CDR3 sequence set forth in SEQ ID NOS: 122, 123, and 124, respectively.

19. The method of claim 12, wherein the method reduces the number of tumor cells, reduces the tumor size, or eradicates the tumor in the subject.

20. The method of claim 12, wherein the tumor is selected from the group consisting of multiple myeloma, Non-Hodgkin Lymphoma, Hodgkin Lymphoma, Chronic Lymphocytic Leukemia, glioblastoma, and Waldenstrom's Macroglobulinemia.

21. The method of claim 12, wherein the tumor is multiple myeloma.

22. The method of claim 12, wherein the subject is a human.

23. An expression vector comprising a nucleic acid molecule encoding an anti-B-cell maturation antigen (BCMA) single-chain variable fragment (scFv) comprising a heavy chain variable region and a light chain variable region, wherein:
  (a) the heavy chain variable region comprises the CDR1, CDR2, and CDR3 of the heavy chain variable sequence set forth in SEQ ID NO: 53, and the light chain variable region comprises the CDR1, CDR2, and CDR3 of the light chain variable region sequence set forth in SEQ ID NO: 54;
  (b) the heavy chain variable region comprises the CDR1, CDR2, and CDR3 of the heavy chain variable sequence set forth in SEQ ID NO: 65, and the light chain variable region comprises the CDR1, CDR2, and CDR3 of the light chain variable region sequence set forth in SEQ ID NO: 66;
  (c) the heavy chain variable region comprises the CDR1, CDR2, and CDR3 of the heavy chain variable sequence set forth in SEQ ID NO: 21, and the light chain variable region comprises the CDR1, CDR2, and CDR3 of the light chain variable region sequence set forth in SEQ ID NO: 22;
  (d) the heavy chain variable region comprises the CDR1, CDR2, and CDR3 of the heavy chain variable sequence set forth in SEQ ID NO: 1, and the light chain variable region comprises the CDR1, CDR2, and CDR3 of the light chain variable region sequence set forth in SEQ ID NO: 2;
  (e) the heavy chain variable region comprises the CDR1, CDR2, and CDR3 of the heavy chain variable sequence set forth in SEQ ID NO: 5, and the light chain variable region comprises the CDR1, CDR2, and CDR3 of the light chain variable region sequence set forth in SEQ ID NO: 6;
  (f) the heavy chain variable region comprises the CDR1, CDR2, and CDR3 of the heavy chain variable sequence set forth in SEQ ID NO: 9, and the light chain variable region comprises the CDR1, CDR2, and CDR3 of the light chain variable region sequence set forth in SEQ ID NO: 10;
  (g) the heavy chain variable region comprises the CDR1, CDR2, and CDR3 of the heavy chain variable sequence set forth in SEQ ID NO: 13, and the light chain variable region comprises the CDR1, CDR2, and CDR3 of the light chain variable region sequence set forth in SEQ ID NO: 14;
  (h) the heavy chain variable region comprises the CDR1, CDR2, and CDR3 of the heavy chain variable sequence set forth in SEQ ID NO: 17, and the light chain variable region comprises the CDR1, CDR2, and CDR3 of the light chain variable region sequence set forth in SEQ ID NO: 18;
  (i) the heavy chain variable region comprises the CDR1, CDR2, and CDR3 of the heavy chain variable sequence set forth in SEQ ID NO: 25, and the light chain variable region comprises the CDR1, CDR2, and CDR3 of the light chain variable region sequence set forth in SEQ ID NO: 26;
  (j) the heavy chain variable region comprises the CDR1, CDR2, and CDR3 of the heavy chain variable sequence set forth in SEQ ID NO: 29, and the light chain variable region comprises the CDR1, CDR2, and CDR3 of the light chain variable region sequence set forth in SEQ ID NO: 30;
  (k) the heavy chain variable region comprises the CDR1, CDR2, and CDR3 of the heavy chain variable sequence set forth in SEQ ID NO: 33, and the light chain variable region comprises the CDR1, CDR2, and CDR3 of the light chain variable region sequence set forth in SEQ ID NO: 34;
  (l) the heavy chain variable region comprises the CDR1, CDR2, and CDR3 of the heavy chain variable sequence set forth in SEQ ID NO: 37, and the light chain variable region comprises the CDR1, CDR2, and CDR3 of the light chain variable region sequence set forth in SEQ ID NO: 38;
  (m) the heavy chain variable region comprises the CDR1, CDR2, and CDR3 of the heavy chain variable sequence set forth in SEQ ID NO: 41, and the light chain variable region comprises the CDR1, CDR2, and CDR3 of the light chain variable region sequence set forth in SEQ ID NO: 42;
  (n) the heavy chain variable region comprises the CDR1, CDR2, and CDR3 of the heavy chain variable sequence set forth in SEQ ID NO: 45, and the light chain variable region comprises the CDR1, CDR2, and CDR3 of the light chain variable region sequence set forth in SEQ ID NO: 46;
  (o) the heavy chain variable region comprises the CDR1, CDR2, and CDR3 of the heavy chain variable sequence set forth in SEQ ID NO: 49, and the light chain variable region comprises the CDR1, CDR2, and CDR3 of the light chain variable region sequence set forth in SEQ ID NO: 50;
  (p) the heavy chain variable region comprises the CDR1, CDR2, and CDR3 of the heavy chain variable sequence set forth in SEQ ID NO: 57, and the light chain variable region comprises the CDR1, CDR2, and CDR3 of the light chain variable region sequence set forth in SEQ ID NO: 58; or
  (q) the heavy chain variable region comprises the CDR1, CDR2, and CDR3 of the heavy chain variable sequence set forth in SEQ ID NO: 61, and the light chain variable region comprises the CDR1, CDR2, and CDR3 of the light chain variable region sequence set forth in SEQ ID NO: 62.

24. The expression vector of claim 23, wherein:
  (a) the heavy chain variable region comprises an amino acid sequence that has at least about 90% sequence identity to the amino acid sequence set forth in SEQ ID NO: 53, and the light chain variable region comprises an amino acid sequence that has at least about 90% sequence identity to the amino acid sequence set forth in SEQ ID NO: 54;
  (b) the heavy chain variable region comprises an amino acid sequence that has at least about 90% sequence identity to the amino acid sequence set forth in SEQ ID NO: 65, and the light chain variable region comprises an amino acid sequence that has at least about 90% sequence identity to the amino acid sequence set forth in SEQ ID NO: 66;
  (c) the heavy chain variable region comprises an amino acid sequence that has at least about 90% sequence identity to the amino acid sequence set forth in SEQ ID NO: 21, and the light chain variable region comprises an amino acid sequence that has at least about 90% sequence identity to the amino acid sequence set forth in SEQ ID NO: 22;
  (d) the heavy chain variable region comprises an amino acid sequence that has at least about 90% sequence identity to the amino acid sequence set forth in SEQ ID NO: 1, and the light chain variable region comprises an amino acid sequence that has at least about 90% sequence identity to the amino acid sequence set forth in SEQ ID NO: 2;

(e) the heavy chain variable region comprises an amino acid sequence that has at least about 90% sequence identity to the amino acid sequence set forth in SEQ ID NO: 5, and the light chain variable region comprises an amino acid sequence that has at least about 90% sequence identity to the amino acid sequence set forth in SEQ ID NO: 6;

(f) the heavy chain variable region comprises an amino acid sequence that has at least about 90% sequence identity to the amino acid sequence set forth in SEQ ID NO: 9, and the light chain variable region comprises an amino acid sequence that has at least about 90% sequence identity to the amino acid sequence set forth in SEQ ID NO: 10;

(g) the heavy chain variable region comprises an amino acid sequence that has at least about 90% sequence identity to the amino acid sequence set forth in SEQ ID NO: 13, and the light chain variable region comprises an amino acid sequence that has at least about 90% sequence identity to the amino acid sequence set forth in SEQ ID NO: 14;

(h) the heavy chain variable region comprises an amino acid sequence that has at least about 90% sequence identity to the amino acid sequence set forth in SEQ ID NO: 17, and the light chain variable region comprises an amino acid sequence that has at least about 90% sequence identity to the amino acid sequence set forth in SEQ ID NO: 18;

(i) the heavy chain variable region comprises an amino acid sequence that has at least about 90% sequence identity to the amino acid sequence set forth in SEQ ID NO: 25, and the light chain variable region comprises an amino acid sequence that has at least about 90% sequence identity to the amino acid sequence set forth in SEQ ID NO: 26;

(j) the heavy chain variable region comprises an amino acid sequence that has at least about 90% sequence identity to the amino acid sequence set forth in SEQ ID NO: 29, and the light chain variable region comprises an amino acid sequence that has at least about 90% sequence identity to the amino acid sequence set forth in SEQ ID NO: 30;

(k) the heavy chain variable region comprises an amino acid sequence that has at least about 90% sequence identity to the amino acid sequence set forth in SEQ ID NO: 33, and the light chain variable region comprises an amino acid sequence that has at least about 90% sequence identity to the amino acid sequence set forth in SEQ ID NO: 34;

(l) the heavy chain variable region comprises an amino acid sequence that has at least about 90% sequence identity to the amino acid sequence set forth in SEQ ID NO: 37, and the light chain variable region comprises an amino acid sequence that has at least about 90% sequence identity to the amino acid sequence set forth in SEQ ID NO: 38;

(m) the heavy chain variable region comprises an amino acid sequence that has at least about 90% sequence identity to the amino acid sequence set forth in SEQ ID NO: 41, and the light chain variable region comprises an amino acid sequence that has at least about 90% sequence identity to the amino acid sequence set forth in SEQ ID NO: 42;

(n) the heavy chain variable region comprises an amino acid sequence that has at least about 90% sequence identity to the amino acid sequence set forth in SEQ ID NO: 45, and the light chain variable region comprises an amino acid sequence that has at least about 90% sequence identity to the amino acid sequence set forth in SEQ ID NO: 46;

(o) the heavy chain variable region comprises an amino acid sequence that has at least about 90% sequence identity to the amino acid sequence set forth in SEQ ID NO: 49, and the light chain variable region comprises an amino acid sequence that has at least about 90% sequence identity to the amino acid sequence set forth in SEQ ID NO: 50;

(p) the heavy chain variable region comprises an amino acid sequence that has at least about 90% sequence identity to the amino acid sequence set forth in SEQ ID NO: 57, and the light chain variable region comprises an amino acid sequence that has at least about 90% sequence identity to the amino acid sequence set forth in SEQ ID NO: 58; or (q) the heavy chain variable region comprises an amino acid sequence that has at least about 90% sequence identity to the amino acid sequence set forth in SEQ ID NO: 61, and the light chain variable region comprises an amino acid sequence that has at least about 90% sequence identity to the amino acid sequence set forth in SEQ ID NO: 62.

25. The expression vector of claim 23, wherein:

(a) the heavy chain variable region comprises the amino acid sequence set forth in SEQ ID NO: 53, and the light chain variable region comprises the amino acid sequence set forth in SEQ ID NO: 54;

(b) the heavy chain variable region comprises the amino acid sequence set forth in SEQ ID NO: 65, and the light chain variable region comprises the amino acid sequence set forth in SEQ ID NO: 66;

(c) the heavy chain variable region comprises the amino acid sequence set forth in SEQ ID NO: 21, and the light chain variable region comprises the amino acid sequence set forth in SEQ ID NO: 22;

(d) the heavy chain variable region comprises the amino acid sequence set forth in SEQ ID NO: 1, and the light chain variable region comprises the amino acid sequence set forth in SEQ ID NO: 2;

(e) the heavy chain variable region comprises the amino acid sequence set forth in SEQ ID NO: 5, and the light chain variable region comprises the amino acid sequence set forth in SEQ ID NO: 6;

(f) the heavy chain variable region comprises the amino acid sequence set forth in SEQ ID NO: 9, and the light chain variable region comprises the amino acid sequence set forth in SEQ ID NO: 10;

(g) the heavy chain variable region comprises the amino acid sequence set forth in SEQ ID NO: 13, and the light chain variable region comprises the amino acid sequence set forth in SEQ ID NO: 14;

(h) the heavy chain variable region comprises the amino acid sequence set forth in SEQ ID NO: 17, and the light chain variable region comprises the amino acid sequence set forth in SEQ ID NO: 18;

(i) the heavy chain variable region comprises the amino acid sequence set forth in SEQ ID NO: 25, and the light chain variable region comprises the amino acid sequence set forth in SEQ ID NO: 26;

(j) the heavy chain variable region comprises the amino acid sequence set forth in SEQ ID NO: 29, and the light chain variable region comprises the amino acid sequence set forth in SEQ ID NO: 30;

(k) the heavy chain variable region comprises the amino acid sequence set forth in SEQ ID NO: 33, and the light chain variable region comprises the amino acid sequence set forth in SEQ ID NO: 34;

(l) the heavy chain variable region comprises the amino acid sequence set forth in SEQ ID NO: 37, and the light chain variable region comprises the amino acid sequence set forth in SEQ ID NO: 38;

(m) the heavy chain variable region comprises the amino acid sequence set forth in SEQ ID NO: 41, and the light chain variable region comprises the amino acid sequence set forth in SEQ ID NO: 42;

(n) the heavy chain variable region comprises the amino acid sequence set forth in SEQ ID NO: 45, and the light chain variable region comprises the amino acid sequence set forth in SEQ ID NO: 46;

(o) the heavy chain variable region comprises the amino acid sequence set forth in SEQ ID NO: 49, and the light chain variable region comprises the amino acid sequence set forth in SEQ ID NO: 50;

(p) the heavy chain variable region comprises the amino acid sequence set forth in SEQ ID NO: 57, and the light chain variable region comprises the amino acid sequence set forth in SEQ ID NO: 58; or (q) the heavy chain variable region comprises the amino acid sequence set forth in SEQ ID NO: 61, and the light chain variable region comprises the amino acid sequence set forth in SEQ ID NO: 62.

26. The expression vector of claim 23, wherein the scFv comprises the amino acid sequence set forth in SEQ ID NO: 85, SEQ ID NO: 88, or SEQ ID NO: 77, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 86, or SEQ ID NO: 87.

27. An expression vector comprising a nucleic acid molecule encoding an anti-B-cell maturation antigen (BCMA) single-chain variable fragment (scFv) comprising a heavy chain variable region and a light chain variable region, wherein:

(a) the heavy chain variable region comprises a CDR1, a CDR2, and a CDR3 sequence set forth in SEQ ID NOS: 167, 168, and 169, respectively; and the light chain variable region comprises a CDR1, a CDR2, and a CDR3 sequence set forth in SEQ ID NOS: 170, 171, and 172, respectively;

(b) the heavy chain variable region comprises a CDR1, a CDR2, and a CDR3 sequence set forth in SEQ ID NOS: 185, 186, and 187, respectively; and the light chain variable region comprises a CDR1, a CDR2, and a CDR3 sequence set forth in SEQ ID NOS: 188, 189, and 190, respectively;

(c) the heavy chain variable region comprises a CDR1, a CDR2, and a CDR3 sequence set forth in SEQ ID NOS: 119, 120, and 121, respectively; and the light chain variable region comprises a CDR1, a CDR2, and a CDR3 sequence set forth in SEQ ID NOS: 122, 123, and 124, respectively;

(d) the heavy chain variable region comprises a CDR1, a CDR2, and a CDR3 sequence set forth in SEQ ID NOS: 89, 90, and 91, respectively; and the light chain variable region comprises a CDR1, a CDR2, and a CDR3 sequence set forth in SEQ ID NOS: 92, 93, and 94, respectively;

(e) the heavy chain variable region comprises a CDR1, a CDR2, and a CDR3 sequence set forth in SEQ ID NOS: 95, 96, and 97, respectively; and the light chain variable region comprises a CDR1, a CDR2, and a CDR3 sequence set forth in SEQ ID NOS: 98, 99, and 100, respectively;

(f) the heavy chain variable region comprises a CDR1, a CDR2, and a CDR3 sequence set forth in SEQ ID NOS: 101, 102, and 103, respectively; and the light chain variable region comprises a CDR1, a CDR2, and a CDR3 sequence set forth in SEQ ID NOS: 104, 105, and 106, respectively;

(g) the heavy chain variable region comprises a CDR1, a CDR2, and a CDR3 sequence set forth in SEQ ID NOS: 107, 108, and 109, respectively; and the light chain variable region comprises a CDR1, a CDR2, and a CDR3 sequence set forth in SEQ ID NOS: 110, 111, and 112, respectively;

(h) the heavy chain variable region comprises a CDR1, a CDR2, and a CDR3 sequence set forth in SEQ ID NOS: 113, 114, and 115, respectively; and the light chain variable region comprises a CDR1, a CDR2, and a CDR3 sequence set forth in SEQ ID NOS: 116, 117, and 118, respectively;

(i) the heavy chain variable region comprises a CDR1, a CDR2, and a CDR3 sequence set forth in SEQ ID NOS: 125, 126, and 127, respectively; and the light chain variable region comprises a CDR1, a CDR2, and a CDR3 sequence set forth in SEQ ID NOS: 128, 129, and 130, respectively;

(j) the heavy chain variable region comprises a CDR1, a CDR2, and a CDR3 sequence set forth in SEQ ID NOS: 131, 132, and 133, respectively; and the light chain variable region comprises a CDR1, a CDR2, and a CDR3 sequence set forth in SEQ ID NOS: 134, 135, and 136, respectively;

(k) the heavy chain variable region comprises a CDR1, a CDR2, and a CDR3 sequence set forth in SEQ ID NOS: 137, 138, and 139, respectively; and the light chain variable region comprises a CDR1, a CDR2, and a CDR3 sequence set forth in SEQ ID NOS: 140, 141, and 142, respectively;

(l) the heavy chain variable region comprises a CDR1, a CDR2, and a CDR3 sequence set forth in SEQ ID NOS: 143, 144, and 145, respectively; and the light chain variable region comprises a CDR1, a CDR2, and a CDR3 sequence set forth in SEQ ID NOS: 146, 147, and 149, respectively;

(m) the heavy chain variable region comprises a CDR1, a CDR2, and a CDR3 sequence set forth in SEQ ID NOS: 149, 150, and 151, respectively; and the light chain variable region comprises a CDR1, a CDR2, and a CDR3 sequence set forth in SEQ ID NOS: 152, 152, and 154, respectively;

(n) the heavy chain variable region comprises a CDR1, a CDR2, and a CDR3 sequence set forth in SEQ ID NOS: 155, 156, and 157, respectively; and the light chain variable region comprises a CDR1, a CDR2, and a CDR3 sequence set forth in SEQ ID NOS: 158, 159, and 160, respectively;

(o) the heavy chain variable region comprises a CDR1, a CDR2, and a CDR3 sequence set forth in SEQ ID NOS: 161, 162, and 163, respectively; and the light chain variable region comprises a CDR1, a CDR2, and a CDR3 sequence set forth in SEQ ID NOS: 164, 165, and 166, respectively;

(p) the heavy chain variable region comprises a CDR1, a CDR2, and a CDR3 sequence set forth in SEQ ID NOS: 173, 174, and 175, respectively; and the light chain variable region comprises a CDR1, a CDR2, and a CDR3 sequence set forth in SEQ ID NOS: 176, 177, and 178, respectively; or (q) the heavy chain variable region comprises a CDR1, a CDR2, and a CDR3 sequence set forth in SEQ ID NOS: 179, 180, and 181, respectively; and the light chain variable region comprises a CDR1, a CDR2, and a CDR3 sequence set forth in SEQ ID NOS: 182, 183, and 184, respectively.

28. The expression vector of claim 27, wherein:

(a) the heavy chain variable region comprises an amino acid sequence that has at least about 90% sequence identity to the amino acid sequence set forth in SEQ ID NO: 53, and the light chain variable region comprises an amino acid sequence that has at least about 90% sequence identity to the amino acid sequence set forth in SEQ ID NO: 54;

(b) the heavy chain variable region comprises an amino acid sequence that has at least about 90% sequence identity to the amino acid sequence set forth in SEQ ID NO: 65, and the light chain variable region comprises an amino acid sequence that has at least about 90% sequence identity to the amino acid sequence set forth in SEQ ID NO: 66;

(c) the heavy chain variable region comprises an amino acid sequence that has at least about 90% sequence identity to the amino acid sequence set forth in SEQ ID NO: 21, and the light chain variable region comprises an amino acid sequence that has at least about 90% sequence identity to the amino acid sequence set forth in SEQ ID NO: 22;

(d) the heavy chain variable region comprises an amino acid sequence that has at least about 90% sequence identity to the amino acid sequence set forth in SEQ ID NO: 1, and the light chain variable region comprises an amino acid sequence that has at least about 90% sequence identity to the amino acid sequence set forth in SEQ ID NO: 2;

(e) the heavy chain variable region comprises an amino acid sequence that has at least about 90% sequence identity to the amino acid sequence set forth in SEQ ID NO: 5, and the light chain variable region comprises an amino acid sequence that has at least about 90% sequence identity to the amino acid sequence set forth in SEQ ID NO: 6;

(f) the heavy chain variable region comprises an amino acid sequence that has at least about 90% sequence identity to the amino acid sequence set forth in SEQ ID NO: 9, and the light chain variable region comprises an amino acid sequence that has at least about 90% sequence identity to the amino acid sequence set forth in SEQ ID NO: 10;

(g) the heavy chain variable region comprises an amino acid sequence that has at least about 90% sequence identity to the amino acid sequence set forth in SEQ ID NO: 13, and the light chain variable region comprises an amino acid sequence that has at least about 90% sequence identity to the amino acid sequence set forth in SEQ ID NO: 14;

(h) the heavy chain variable region comprises an amino acid sequence that has at least about 90% sequence identity to the amino acid sequence set forth in SEQ ID NO: 17, and the light chain variable region comprises an amino acid sequence that has at least about 90% sequence identity to the amino acid sequence set forth in SEQ ID NO: 18;

(i) the heavy chain variable region comprises an amino acid sequence that has at least about 90% sequence identity to the amino acid sequence set forth in SEQ ID NO: 25, and the light chain variable region comprises an amino acid sequence that has at least about 90% sequence identity to the amino acid sequence set forth in SEQ ID NO: 26;

(j) the heavy chain variable region comprises an amino acid sequence that has at least about 90% sequence identity to the amino acid sequence set forth in SEQ ID NO: 29, and the light chain variable region comprises an amino acid sequence that has at least about 90% sequence identity to the amino acid sequence set forth in SEQ ID NO: 30;

(k) the heavy chain variable region comprises an amino acid sequence that has at least about 90% sequence identity to the amino acid sequence set forth in SEQ ID NO: 33, and the light chain variable region comprises an amino acid sequence that has at least about 90% sequence identity to the amino acid sequence set forth in SEQ ID NO: 34;

(l) the heavy chain variable region comprises an amino acid sequence that has at least about 90% sequence identity to the amino acid sequence set forth in SEQ ID NO: 37, and the light chain variable region comprises an amino acid sequence that has at least about 90% sequence identity to the amino acid sequence set forth in SEQ ID NO: 38;

(m) the heavy chain variable region comprises an amino acid sequence that has at least about 90% sequence identity to the amino acid sequence set forth in SEQ ID NO: 41, and the light chain variable region comprises an amino acid sequence that has at least about 90% sequence identity to the amino acid sequence set forth in SEQ ID NO: 42;

(n) the heavy chain variable region comprises an amino acid sequence that has at least about 90% sequence identity to the amino acid sequence set forth in SEQ ID NO: 45, and the light chain variable region comprises an amino acid sequence that has at least about 90% sequence identity to the amino acid sequence set forth in SEQ ID NO: 46;

(o) the heavy chain variable region comprises an amino acid sequence that has at least about 90% sequence identity to the amino acid sequence set forth in SEQ ID NO: 49, and the light chain variable region comprises an amino acid sequence that has at least about 90% sequence identity to the amino acid sequence set forth in SEQ ID NO: 50;

(p) the heavy chain variable region comprises an amino acid sequence that has at least about 90% sequence identity to the amino acid sequence set forth in SEQ ID NO: 57, and the light chain variable region comprises an amino acid sequence that has at least about 90% sequence identity to the amino acid sequence set forth in SEQ ID NO: 58; or (q) the heavy chain variable region comprises an amino acid sequence that has at least about 90% sequence identity to the amino acid sequence set forth in SEQ ID NO: 61, and the light chain variable region comprises an amino acid sequence that has at least about 90% sequence identity to the amino acid sequence set forth in SEQ ID NO: 62.

29. The expression vector of claim 27, wherein:
(a) the heavy chain variable region comprises the amino acid sequence set forth in SEQ ID NO: 53, and the light chain variable region comprises the amino acid sequence set forth in SEQ ID NO: 54;
(b) the heavy chain variable region comprises the amino acid sequence set forth in SEQ ID NO: 65, and the light chain variable region comprises the amino acid sequence set forth in SEQ ID NO: 66; or
(c) the heavy chain variable region comprises the amino acid sequence set forth in SEQ ID NO: 21, and the light chain variable region comprises the amino acid sequence set forth in SEQ ID NO: 22;
(d) the heavy chain variable region comprises the amino acid sequence set forth in SEQ ID NO: 1, and the light chain variable region comprises the amino acid sequence set forth in SEQ ID NO: 2;
(e) the heavy chain variable region comprises the amino acid sequence set forth in SEQ ID NO: 5, and the light chain variable region comprises the amino acid sequence set forth in SEQ ID NO: 6;
(f) the heavy chain variable region comprises the amino acid sequence set forth in SEQ ID NO: 9, and the light chain variable region comprises the amino acid sequence set forth in SEQ ID NO: 10;
(g) the heavy chain variable region comprises the amino acid sequence set forth in SEQ ID NO: 13, and the light chain variable region comprises the amino acid sequence set forth in SEQ ID NO: 14;
(h) the heavy chain variable region comprises the amino acid sequence set forth in SEQ ID NO: 17, and the light chain variable region comprises the amino acid sequence set forth in SEQ ID NO: 18;
(i) the heavy chain variable region comprises the amino acid sequence set forth in SEQ ID NO: 25, and the light chain variable region comprises the amino acid sequence set forth in SEQ ID NO: 26;
(j) the heavy chain variable region comprises the amino acid sequence set forth in SEQ ID NO: 29, and the light chain variable region comprises the amino acid sequence set forth in SEQ ID NO: 30;
(k) the heavy chain variable region comprises the amino acid sequence set forth in SEQ ID NO: 33, and the light chain variable region comprises the amino acid sequence set forth in SEQ ID NO: 34;
(l) the heavy chain variable region comprises the amino acid sequence set forth in SEQ ID NO: 37, and the light chain variable region comprises the amino acid sequence set forth in SEQ ID NO: 38;
(m) the heavy chain variable region comprises the amino acid sequence set forth in SEQ ID NO: 41, and the light chain variable region comprises the amino acid sequence set forth in SEQ ID NO: 42;
(n) the heavy chain variable region comprises the amino acid sequence set forth in SEQ ID NO: 45, and the light chain variable region comprises the amino acid sequence set forth in SEQ ID NO: 46;
(o) the heavy chain variable region comprises the amino acid sequence set forth in SEQ ID NO: 49, and the light chain variable region comprises the amino acid sequence set forth in SEQ ID NO: 50;
(p) the heavy chain variable region comprises the amino acid sequence set forth in SEQ ID NO: 57, and the light chain variable region comprises the amino acid sequence set forth in SEQ ID NO: 58; or
(q) the heavy chain variable region comprises the amino acid sequence set forth in SEQ ID NO: 61, and the light chain variable region comprises the amino acid sequence set forth in SEQ ID NO: 62.

30. The expression vector of claim 27, wherein the scFv comprises the amino acid sequence set forth in SEQ ID NO: 85, SEQ ID NO: 88, or SEQ ID NO: 77, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 86, or SEQ ID NO: 87.

31. A host cell comprising an expression vector comprising a nucleic acid molecule encoding an anti-B-cell maturation antigen (BCMA) single-chain variable fragment (scFv) comprising a heavy chain variable region and a light chain variable region, wherein:
(a) the heavy chain variable region comprises the CDR1, CDR2, and CDR3 of the heavy chain variable sequence set forth in SEQ ID NO: 53, and the light chain variable region comprises the CDR1, CDR2, and CDR3 of the light chain variable region sequence set forth in SEQ ID NO: 54;
(b) the heavy chain variable region comprises the CDR1, CDR2, and CDR3 of the heavy chain variable sequence set forth in SEQ ID NO: 65, and the light chain variable region comprises the CDR1, CDR2, and CDR3 of the light chain variable region sequence set forth in SEQ ID NO: 66;
(c) the heavy chain variable region comprises the CDR1, CDR2, and CDR3 of the heavy chain variable sequence set forth in SEQ ID NO: 21, and the light chain variable region comprises the CDR1, CDR2, and CDR3 of the light chain variable region sequence set forth in SEQ ID NO: 22;
(d) the heavy chain variable region comprises the CDR1, CDR2, and CDR3 of the heavy chain variable sequence set forth in SEQ ID NO: 1, and the light chain variable region comprises the CDR1, CDR2, and CDR3 of the light chain variable region sequence set forth in SEQ ID NO: 2;
(e) the heavy chain variable region comprises the CDR1, CDR2, and CDR3 of the heavy chain variable sequence set forth in SEQ ID NO: 5, and the light chain variable region comprises the CDR1, CDR2, and CDR3 of the light chain variable region sequence set forth in SEQ ID NO: 6;
(f) the heavy chain variable region comprises the CDR1, CDR2, and CDR3 of the heavy chain variable sequence set forth in SEQ ID NO: 9, and the light chain variable region comprises the CDR1, CDR2, and CDR3 of the light chain variable region sequence set forth in SEQ ID NO: 10;
(g) the heavy chain variable region comprises the CDR1, CDR2, and CDR3 of the heavy chain variable sequence set forth in SEQ ID NO: 13, and the light chain variable region comprises the CDR1, CDR2, and CDR3 of the light chain variable region sequence set forth in SEQ ID NO: 14;
(h) the heavy chain variable region comprises the CDR1, CDR2, and CDR3 of the heavy chain variable sequence set forth in SEQ ID NO: 17, and the light chain variable region comprises the CDR1, CDR2, and CDR3 of the light chain variable region sequence set forth in SEQ ID NO: 18;
(i) the heavy chain variable region comprises the CDR1, CDR2, and CDR3 of the heavy chain variable sequence set forth in SEQ ID NO: 25, and the light chain variable region comprises the CDR1, CDR2, and CDR3 of the light chain variable region sequence set forth in SEQ ID NO: 26;

(j) the heavy chain variable region comprises the CDR1, CDR2, and CDR3 of the heavy chain variable sequence set forth in SEQ ID NO: 29, and the light chain variable region comprises the CDR1, CDR2, and CDR3 of the light chain variable region sequence set forth in SEQ ID NO: 30;

(k) the heavy chain variable region comprises the CDR1, CDR2, and CDR3 of the heavy chain variable sequence set forth in SEQ ID NO: 33, and the light chain variable region comprises the CDR1, CDR2, and CDR3 of the light chain variable region sequence set forth in SEQ ID NO: 34;

(l) the heavy chain variable region comprises the CDR1, CDR2, and CDR3 of the heavy chain variable sequence set forth in SEQ ID NO: 37, and the light chain variable region comprises the CDR1, CDR2, and CDR3 of the light chain variable region sequence set forth in SEQ ID NO: 38;

(m) the heavy chain variable region comprises the CDR1, CDR2, and CDR3 of the heavy chain variable sequence set forth in SEQ ID NO: 41, and the light chain variable region comprises the CDR1, CDR2, and CDR3 of the light chain variable region sequence set forth in SEQ ID NO: 42;

(n) the heavy chain variable region comprises the CDR1, CDR2, and CDR3 of the heavy chain variable sequence set forth in SEQ ID NO: 45, and the light chain variable region comprises the CDR1, CDR2, and CDR3 of the light chain variable region sequence set forth in SEQ ID NO: 46;

(o) the heavy chain variable region comprises the CDR1, CDR2, and CDR3 of the heavy chain variable sequence set forth in SEQ ID NO: 49, and the light chain variable region comprises the CDR1, CDR2, and CDR3 of the light chain variable region sequence set forth in SEQ ID NO: 50;

(p) the heavy chain variable region comprises the CDR1, CDR2, and CDR3 of the heavy chain variable sequence set forth in SEQ ID NO: 57, and the light chain variable region comprises the CDR1, CDR2, and CDR3 of the light chain variable region sequence set forth in SEQ ID NO: 58; or (q) the heavy chain variable region comprises the CDR1, CDR2, and CDR3 of the heavy chain variable sequence set forth in SEQ ID NO: 61, and the light chain variable region comprises the CDR1, CDR2, and CDR3 of the light chain variable region sequence set forth in SEQ ID NO: 62.

32. The host cell of claim 31, wherein:

(a) the heavy chain variable region comprises an amino acid sequence that has at least about 90% sequence identity to the amino acid sequence set forth in SEQ ID NO: 53, and the light chain variable region comprises an amino acid sequence that has at least about 90% sequence identity to the amino acid sequence set forth in SEQ ID NO: 54;

(b) the heavy chain variable region comprises an amino acid sequence that has at least about 90% sequence identity to the amino acid sequence set forth in SEQ ID NO: 65, and the light chain variable region comprises an amino acid sequence that has at least about 90% sequence identity to the amino acid sequence set forth in SEQ ID NO: 66;

(c) the heavy chain variable region comprises an amino acid sequence that has at least about 90% sequence identity to the amino acid sequence set forth in SEQ ID NO: 21, and the light chain variable region comprises an amino acid sequence that has at least about 90% sequence identity to the amino acid sequence set forth in SEQ ID NO: 22;

(d) the heavy chain variable region comprises an amino acid sequence that has at least about 90% sequence identity to the amino acid sequence set forth in SEQ ID NO: 1, and the light chain variable region comprises an amino acid sequence that has at least about 90% sequence identity to the amino acid sequence set forth in SEQ ID NO: 2;

(e) the heavy chain variable region comprises an amino acid sequence that has at least about 90% sequence identity to the amino acid sequence set forth in SEQ ID NO: 5, and the light chain variable region comprises an amino acid sequence that has at least about 90% sequence identity to the amino acid sequence set forth in SEQ ID NO: 6;

(f) the heavy chain variable region comprises an amino acid sequence that has at least about 90% sequence identity to the amino acid sequence set forth in SEQ ID NO: 9, and the light chain variable region comprises an amino acid sequence that has at least about 90% sequence identity to the amino acid sequence set forth in SEQ ID NO: 10;

(g) the heavy chain variable region comprises an amino acid sequence that has at least about 90% sequence identity to the amino acid sequence set forth in SEQ ID NO: 13, and the light chain variable region comprises an amino acid sequence that has at least about 90% sequence identity to the amino acid sequence set forth in SEQ ID NO: 14;

(h) the heavy chain variable region comprises an amino acid sequence that has at least about 90% sequence identity to the amino acid sequence set forth in SEQ ID NO: 17, and the light chain variable region comprises an amino acid sequence that has at least about 90% sequence identity to the amino acid sequence set forth in SEQ ID NO: 18;

(i) the heavy chain variable region comprises an amino acid sequence that has at least about 90% sequence identity to the amino acid sequence set forth in SEQ ID NO: 25, and the light chain variable region comprises an amino acid sequence that has at least about 90% sequence identity to the amino acid sequence set forth in SEQ ID NO: 26;

(j) the heavy chain variable region comprises an amino acid sequence that has at least about 90% sequence identity to the amino acid sequence set forth in SEQ ID NO: 29, and the light chain variable region comprises an amino acid sequence that has at least about 90% sequence identity to the amino acid sequence set forth in SEQ ID NO: 30;

(k) the heavy chain variable region comprises an amino acid sequence that has at least about 90% sequence identity to the amino acid sequence set forth in SEQ ID NO: 33, and the light chain variable region comprises an amino acid sequence that has at least about 90% sequence identity to the amino acid sequence set forth in SEQ ID NO: 34;

(l) the heavy chain variable region comprises an amino acid sequence that has at least about 90% sequence identity to the amino acid sequence set forth in SEQ ID NO: 37, and the light chain variable region comprises an amino acid sequence that has at least about 90% sequence identity to the amino acid sequence set forth in SEQ ID NO: 38;

(m) the heavy chain variable region comprises an amino acid sequence that has at least about 90% sequence identity to the amino acid sequence set forth in SEQ ID NO: 41, and the light chain variable region comprises an amino acid sequence that has at least about 90% sequence identity to the amino acid sequence set forth in SEQ ID NO: 42;

(n) the heavy chain variable region comprises an amino acid sequence that has at least about 90% sequence identity to the amino acid sequence set forth in SEQ ID NO: 45, and the light chain variable region comprises an amino acid sequence that has at least about 90% sequence identity to the amino acid sequence set forth in SEQ ID NO: 46;

(o) the heavy chain variable region comprises an amino acid sequence that has at least about 90% sequence identity to the amino acid sequence set forth in SEQ ID NO: 49, and the light chain variable region comprises an amino acid sequence that has at least about 90% sequence identity to the amino acid sequence set forth in SEQ ID NO: 50;

(p) the heavy chain variable region comprises an amino acid sequence that has at least about 90% sequence identity to the amino acid sequence set forth in SEQ ID NO: 57, and the light chain variable region comprises an amino acid sequence that has at least about 90% sequence identity to the amino acid sequence set forth in SEQ ID NO: 58; or (q) the heavy chain variable region comprises an amino acid sequence that has at least about 90% sequence identity to the amino acid sequence set forth in SEQ ID NO: 61, and the light chain variable region comprises an amino acid sequence that has at least about 90% sequence identity to the amino acid sequence set forth in SEQ ID NO: 62.

33. The host cell of claim 31, wherein:

(a) the heavy chain variable region comprises the amino acid sequence set forth in SEQ ID NO: 53, and the light chain variable region comprises the amino acid sequence set forth in SEQ ID NO: 54;

(b) the heavy chain variable region comprises the amino acid sequence set forth in SEQ ID NO: 65, and the light chain variable region comprises the amino acid sequence set forth in SEQ ID NO: 66;

(c) the heavy chain variable region comprises the amino acid sequence set forth in SEQ ID NO: 21, and the light chain variable region comprises the amino acid sequence set forth in SEQ ID NO: 22;

(d) the heavy chain variable region comprises the amino acid sequence set forth in SEQ ID NO: 1, and the light chain variable region comprises the amino acid sequence set forth in SEQ ID NO: 2;

(e) the heavy chain variable region comprises the amino acid sequence set forth in SEQ ID NO: 5, and the light chain variable region comprises the amino acid sequence set forth in SEQ ID NO: 6;

(f) the heavy chain variable region comprises the amino acid sequence set forth in SEQ ID NO: 9, and the light chain variable region comprises the amino acid sequence set forth in SEQ ID NO: 10;

(g) the heavy chain variable region comprises the amino acid sequence set forth in SEQ ID NO: 13, and the light chain variable region comprises the amino acid sequence set forth in SEQ ID NO: 14;

(h) the heavy chain variable region comprises the amino acid sequence set forth in SEQ ID NO: 17, and the light chain variable region comprises the amino acid sequence set forth in SEQ ID NO: 18;

(i) the heavy chain variable region comprises the amino acid sequence set forth in SEQ ID NO: 25, and the light chain variable region comprises the amino acid sequence set forth in SEQ ID NO: 26;

(j) the heavy chain variable region comprises the amino acid sequence set forth in SEQ ID NO: 29, and the light chain variable region comprises the amino acid sequence set forth in SEQ ID NO: 30;

(k) the heavy chain variable region comprises the amino acid sequence set forth in SEQ ID NO: 33, and the light chain variable region comprises the amino acid sequence set forth in SEQ ID NO: 34;

(l) the heavy chain variable region comprises the amino acid sequence set forth in SEQ ID NO: 37, and the light chain variable region comprises the amino acid sequence set forth in SEQ ID NO: 38;

(m) the heavy chain variable region comprises the amino acid sequence set forth in SEQ ID NO: 41, and the light chain variable region comprises the amino acid sequence set forth in SEQ ID NO: 42;

(n) the heavy chain variable region comprises the amino acid sequence set forth in SEQ ID NO: 45, and the light chain variable region comprises the amino acid sequence set forth in SEQ ID NO: 46;

(o) the heavy chain variable region comprises the amino acid sequence set forth in SEQ ID NO: 49, and the light chain variable region comprises the amino acid sequence set forth in SEQ ID NO: 50;

(p) the heavy chain variable region comprises the amino acid sequence set forth in SEQ ID NO: 57, and the light chain variable region comprises the amino acid sequence set forth in SEQ ID NO: 58; or (q) the heavy chain variable region comprises the amino acid sequence set forth in SEQ ID NO: 61, and the light chain variable region comprises the amino acid sequence set forth in SEQ ID NO: 62.

34. The host cell of claim 31, wherein the scFv comprises the amino acid sequence set forth in SEQ ID NO: 85, SEQ ID NO: 88, or SEQ ID NO: 77, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 86, or SEQ ID NO: 87.

35. The host cell of claim 31, wherein the host cell is a T cell.

36. A host cell comprising an expression vector comprising a nucleic acid molecule encoding an anti-B-cell maturation antigen (BCMA) single-chain variable fragment (scFv) comprising a heavy chain variable region and a light chain variable region, wherein:

(a) the heavy chain variable region comprises a CDR1, a CDR2, and a CDR3 sequence set forth in SEQ ID NOS: 167, 168, and 169, respectively; and the light chain variable region comprises a CDR1, a CDR2, and a CDR3 sequence set forth in SEQ ID NOS: 170, 171, and 172, respectively;

(b) the heavy chain variable region comprises a CDR1, a CDR2, and a CDR3 sequence set forth in SEQ ID NOS: 185, 186, and 187, respectively; and the light chain variable region comprises a CDR1, a CDR2, and a CDR3 sequence set forth in SEQ ID NOS: 188, 189, and 190, respectively;

(c) the heavy chain variable region comprises a CDR1, a CDR2, and a CDR3 sequence set forth in SEQ ID NOS: 119, 120, and 121, respectively; and the light chain variable region comprises a CDR1, a CDR2, and a CDR3 sequence set forth in SEQ ID NOS: 122, 123, and 124, respectively;

(d) the heavy chain variable region comprises a CDR1, a CDR2, and a CDR3 sequence set forth in SEQ ID NOS: 89, 90, and 91, respectively; and the light chain variable region comprises a CDR1, a CDR2, and a CDR3 sequence set forth in SEQ ID NOS: 92, 93, and 94, respectively;

(e) the heavy chain variable region comprises a CDR1, a CDR2, and a CDR3 sequence set forth in SEQ ID NOS: 95, 96, and 97, respectively; and the light chain variable region comprises a CDR1, a CDR2, and a CDR3 sequence set forth in SEQ ID NOS: 98, 99, and 100, respectively;

(f) the heavy chain variable region comprises a CDR1, a CDR2, and a CDR3 sequence set forth in SEQ ID NOS: 101, 102, and 103, respectively; and the light chain variable region comprises a CDR1, a CDR2, and a CDR3 sequence set forth in SEQ ID NOS: 104, 105, and 106, respectively;

(g) the heavy chain variable region comprises a CDR1, a CDR2, and a CDR3 sequence set forth in SEQ ID NOS: 107, 108, and 109, respectively; and the light chain variable region comprises a CDR1, a CDR2, and a CDR3 sequence set forth in SEQ ID NOS: 110, 111, and 112, respectively;

(h) the heavy chain variable region comprises a CDR1, a CDR2, and a CDR3 sequence set forth in SEQ ID NOS: 113, 114, and 115, respectively; and the light chain variable region comprises a CDR1, a CDR2, and a CDR3 sequence set forth in SEQ ID NOS: 116, 117, and 118, respectively;

(i) the heavy chain variable region comprises a CDR1, a CDR2, and a CDR3 sequence set forth in SEQ ID NOS: 125, 126, and 127, respectively; and the light chain variable region comprises a CDR1, a CDR2, and a CDR3 sequence set forth in SEQ ID NOS: 128, 129, and 130, respectively;

(j) the heavy chain variable region comprises a CDR1, a CDR2, and a CDR3 sequence set forth in SEQ ID NOS: 131, 132, and 133, respectively; and the light chain variable region comprises a CDR1, a CDR2, and a CDR3 sequence set forth in SEQ ID NOS: 134, 135, and 136, respectively;

(k) the heavy chain variable region comprises a CDR1, a CDR2, and a CDR3 sequence set forth in SEQ ID NOS: 137, 138, and 139, respectively; and the light chain variable region comprises a CDR1, a CDR2, and a CDR3 sequence set forth in SEQ ID NOS: 140, 141, and 142, respectively;

(l) the heavy chain variable region comprises a CDR1, a CDR2, and a CDR3 sequence set forth in SEQ ID NOS: 143, 144, and 145, respectively; and the light chain variable region comprises a CDR1, a CDR2, and a CDR3 sequence set forth in SEQ ID NOS: 146, 147, and 149, respectively;

(m) the heavy chain variable region comprises a CDR1, a CDR2, and a CDR3 sequence set forth in SEQ ID NOS: 149, 150, and 151, respectively; and the light chain variable region comprises a CDR1, a CDR2, and a CDR3 sequence set forth in SEQ ID NOS: 152, 152, and 154, respectively;

(n) the heavy chain variable region comprises a CDR1, a CDR2, and a CDR3 sequence set forth in SEQ ID NOS: 155, 156, and 157, respectively; and the light chain variable region comprises a CDR1, a CDR2, and a CDR3 sequence set forth in SEQ ID NOS: 158, 159, and 160, respectively;

(o) the heavy chain variable region comprises a CDR1, a CDR2, and a CDR3 sequence set forth in SEQ ID NOS: 161, 162, and 163, respectively; and the light chain variable region comprises a CDR1, a CDR2, and a CDR3 sequence set forth in SEQ ID NOS: 164, 165, and 166, respectively;

(p) the heavy chain variable region comprises a CDR1, a CDR2, and a CDR3 sequence set forth in SEQ ID NOS: 173, 174, and 175, respectively; and the light chain variable region comprises a CDR1, a CDR2, and a CDR3 sequence set forth in SEQ ID NOS: 176, 177, and 178, respectively; or (q) the heavy chain variable region comprises a CDR1, a CDR2, and a CDR3 sequence set forth in SEQ ID NOS: 179, 180, and 181, respectively; and the light chain variable region comprises a CDR1, a CDR2, and a CDR3 sequence set forth in SEQ ID NOS: 182, 183, and 184, respectively.

37. The host cell of claim 36, wherein:

(a) the heavy chain variable region comprises an amino acid sequence that has at least about 90% sequence identity to the amino acid sequence set forth in SEQ ID NO: 53, and the light chain variable region comprises an amino acid sequence that has at least about 90% sequence identity to the amino acid sequence set forth in SEQ ID NO: 54;

(b) the heavy chain variable region comprises an amino acid sequence that has at least about 90% sequence identity to the amino acid sequence set forth in SEQ ID NO: 65, and the light chain variable region comprises an amino acid sequence that has at least about 90% sequence identity to the amino acid sequence set forth in SEQ ID NO: 66;

(c) the heavy chain variable region comprises an amino acid sequence that has at least about 90% sequence identity to the amino acid sequence set forth in SEQ ID NO: 21, and the light chain variable region comprises an amino acid sequence that has at least about 90% sequence identity to the amino acid sequence set forth in SEQ ID NO: 22;

(d) the heavy chain variable region comprises an amino acid sequence that has at least about 90% sequence identity to the amino acid sequence set forth in SEQ ID NO: 1, and the light chain variable region comprises an amino acid sequence that has at least about 90% sequence identity to the amino acid sequence set forth in SEQ ID NO: 2;

(e) the heavy chain variable region comprises an amino acid sequence that has at least about 90% sequence identity to the amino acid sequence set forth in SEQ ID NO: 5, and the light chain variable region comprises an amino acid sequence that has at least about 90% sequence identity to the amino acid sequence set forth in SEQ ID NO: 6;

(f) the heavy chain variable region comprises an amino acid sequence that has at least about 90% sequence identity to the amino acid sequence set forth in SEQ ID NO: 9, and the light chain variable region comprises an amino acid sequence that has at least about 90% sequence identity to the amino acid sequence set forth in SEQ ID NO: 10;

(g) the heavy chain variable region comprises an amino acid sequence that has at least about 90% sequence identity to the amino acid sequence set forth in SEQ ID NO: 13, and the light chain variable region comprises an amino acid sequence that has at least about 90% sequence identity to the amino acid sequence set forth in SEQ ID NO: 14;

(h) the heavy chain variable region comprises an amino acid sequence that has at least about 90% sequence identity to the amino acid sequence set forth in SEQ ID NO: 17, and the light chain variable region comprises an amino acid sequence that has at least about 90% sequence identity to the amino acid sequence set forth in SEQ ID NO: 18;

(i) the heavy chain variable region comprises an amino acid sequence that has at least about 90% sequence identity to the amino acid sequence set forth in SEQ ID NO: 25, and the light chain variable region comprises an amino acid sequence that has at least about 90% sequence identity to the amino acid sequence set forth in SEQ ID NO: 26;

(j) the heavy chain variable region comprises an amino acid sequence that has at least about 90% sequence identity to the amino acid sequence set forth in SEQ ID NO: 29, and the light chain variable region comprises an amino acid sequence that has at least about 90% sequence identity to the amino acid sequence set forth in SEQ ID NO: 30;

(k) the heavy chain variable region comprises an amino acid sequence that has at least about 90% sequence identity to the amino acid sequence set forth in SEQ ID NO: 33, and the light chain variable region comprises an amino acid sequence that has at least about 90% sequence identity to the amino acid sequence set forth in SEQ ID NO: 34;

(l) the heavy chain variable region comprises an amino acid sequence that has at least about 90% sequence identity to the amino acid sequence set forth in SEQ ID NO: 37, and the light chain variable region comprises an amino acid sequence that has at least about 90% sequence identity to the amino acid sequence set forth in SEQ ID NO: 38;

(m) the heavy chain variable region comprises an amino acid sequence that has at least about 90% sequence identity to the amino acid sequence set forth in SEQ ID NO: 41, and the light chain variable region comprises an amino acid sequence that has at least about 90% sequence identity to the amino acid sequence set forth in SEQ ID NO: 42;

(n) the heavy chain variable region comprises an amino acid sequence that has at least about 90% sequence identity to the amino acid sequence set forth in SEQ ID NO: 45, and the light chain variable region comprises an amino acid sequence that has at least about 90% sequence identity to the amino acid sequence set forth in SEQ ID NO: 46;

(o) the heavy chain variable region comprises an amino acid sequence that has at least about 90% sequence identity to the amino acid sequence set forth in SEQ ID NO: 49, and the light chain variable region comprises an amino acid sequence that has at least about 90% sequence identity to the amino acid sequence set forth in SEQ ID NO: 50;

(p) the heavy chain variable region comprises an amino acid sequence that has at least about 90% sequence identity to the amino acid sequence set forth in SEQ ID NO: 57, and the light chain variable region comprises an amino acid sequence that has at least about 90% sequence identity to the amino acid sequence set forth in SEQ ID NO: 58; or (q) the heavy chain variable region comprises an amino acid sequence that has at least about 90% sequence identity to the amino acid sequence set forth in SEQ ID NO: 61, and the light chain variable region comprises an amino acid sequence that has at least about 90% sequence identity to the amino acid sequence set forth in SEQ ID NO: 62.

38. The host cell of claim 36, wherein:

(a) the heavy chain variable region comprises the amino acid sequence set forth in SEQ ID NO: 53, and the light chain variable region comprises the amino acid sequence set forth in SEQ ID NO: 54;

(b) the heavy chain variable region comprises the amino acid sequence set forth in SEQ ID NO: 65, and the light chain variable region comprises the amino acid sequence set forth in SEQ ID NO: 66;

(c) the heavy chain variable region comprises the amino acid sequence set forth in SEQ ID NO: 21, and the light chain variable region comprises the amino acid sequence set forth in SEQ ID NO: 22;

(d) the heavy chain variable region comprises the amino acid sequence set forth in SEQ ID NO: 1, and the light chain variable region comprises the amino acid sequence set forth in SEQ ID NO: 2;

(e) the heavy chain variable region comprises the amino acid sequence set forth in SEQ ID NO: 5, and the light chain variable region comprises the amino acid sequence set forth in SEQ ID NO: 6;

(f) the heavy chain variable region comprises the amino acid sequence set forth in SEQ ID NO: 9, and the light chain variable region comprises the amino acid sequence set forth in SEQ ID NO: 10;

(g) the heavy chain variable region comprises the amino acid sequence set forth in SEQ ID NO: 13, and the light chain variable region comprises the amino acid sequence set forth in SEQ ID NO: 14;

(h) the heavy chain variable region comprises the amino acid sequence set forth in SEQ ID NO: 17, and the light chain variable region comprises the amino acid sequence set forth in SEQ ID NO: 18;

(i) the heavy chain variable region comprises the amino acid sequence set forth in SEQ ID NO: 25, and the light chain variable region comprises the amino acid sequence set forth in SEQ ID NO: 26;

(j) the heavy chain variable region comprises the amino acid sequence set forth in SEQ ID NO: 29, and the light chain variable region comprises the amino acid sequence set forth in SEQ ID NO: 30;

(k) the heavy chain variable region comprises the amino acid sequence set forth in SEQ ID NO: 33, and the light chain variable region comprises the amino acid sequence set forth in SEQ ID NO: 34;

(l) the heavy chain variable region comprises the amino acid sequence set forth in SEQ ID NO: 37, and the light chain variable region comprises the amino acid sequence set forth in SEQ ID NO: 38;

(m) the heavy chain variable region comprises the amino acid sequence set forth in SEQ ID NO: 41, and the light chain variable region comprises the amino acid sequence set forth in SEQ ID NO: 42;

(n) the heavy chain variable region comprises the amino acid sequence set forth in SEQ ID NO: 45, and the light chain variable region comprises the amino acid sequence set forth in SEQ ID NO: 46;

(o) the heavy chain variable region comprises the amino acid sequence set forth in SEQ ID NO: 49, and the light chain variable region comprises the amino acid sequence set forth in SEQ ID NO: 50;

(p) the heavy chain variable region comprises the amino acid sequence set forth in SEQ ID NO: 57, and the light chain variable region comprises the amino acid sequence set forth in SEQ ID NO: 58; or (q) the heavy chain variable region comprises the amino acid sequence set forth in SEQ ID NO: 61, and the light chain variable region comprises the amino acid sequence set forth in SEQ ID NO: 62.

39. The host cell of claim 36, wherein the scFv comprises the amino acid sequence set forth in SEQ ID NO: 85, SEQ ID NO: 88, or SEQ ID NO: 77, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 86, or SEQ ID NO: 87.

40. The host cell of claim 36, wherein the host cell is a T cell.

* * * * *

SEQUENCE LISTING

```
<160> NUMBER OF SEQ ID NOS: 249

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Gly Tyr Ser Tyr Tyr Gly Tyr Ser Asp Val
            100                 105                 110

Trp Gly Gln Gly Thr Leu Val Thr Val Ser Ser
        115                 120

<210> SEQ ID NO 2
```

-continued

<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Pro Ser Val Ser Val Ala Pro Arg Gln
1               5                   10                  15

Arg Val Thr Ile Ser Cys Ser Gly Ser Ser Asn Ile Gly His Asn
            20                  25                  30

Asp Val Ser Trp Tyr Gln His Leu Pro Gly Lys Ala Pro Arg Leu Leu
        35                  40                  45

Ile Tyr Phe Asp Asp Leu Leu Pro Ser Gly Val Ser Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Ala Phe Val Phe Gly Thr Gly Thr Lys Val Thr Val Leu Gly
            100                 105                 110

<210> SEQ ID NO 3
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca cccagacac atccaagaac      240 cagttctccc tgcagctgaa ctctgtgact cccgaggaca cggctgtgta ttactgtgcg     300
cgccagggtt actcttacta cggttactct gatgtttggg gtcaaggtac tctggtgacc     360
gtctcctca                                                            369

<210> SEQ ID NO 4
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cagtctgtgc tgactcagcc accctcggtg tctgtagccc ccaggcagag ggtcaccatc      60
tcgtgttctg gaagcagctc caacatcgga cataatgatg taagctggta ccagcatctc     120
ccagggaagg ctcccagact cctcatctat tttgatgacc tgctgccgtc agggtctct      180 gaccgattct ctgcctccaa gtctggcacc tcagcctccc tggccatcag tgggctccag     240
tctgaggatg aggctgatta ttactgtgca gcatgggatg gcagcctgaa tgcctttgtc     300
ttcggaactg ggaccaaggt caccgtccta ggt                                  333

<210> SEQ ID NO 5
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Gly Phe Ser Gly Ser Arg Phe Tyr Asp Thr
            100                 105                 110

Trp Gly Gln Gly Thr Leu Val Thr Val Ser Ser
        115                 120
```

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Gln Pro Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu Leu Ser Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly
            100                 105                 110
```

<210> SEQ ID NO 7
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
caggtacagc tgcagcagtc aggtccagga ctggtgaagc cctcgcagac cctctcactc    60

```
acctgtgcca tctccgggga cagtgtctct agcaacagtg ctgcttggaa ctggatcagg    120
cagtccccat cgagaggcct tgagtggctg ggaaggacat actacaggtc caagtggtat    180
aatgattatg cagtatctgt gaaaagtcga ataaccatca acccagacac atccaagaac    240
cagttctccc tgcagctgaa ctctgtgact cccgaggaca cggctgtgta ttactgtgcg    300
cgctacggtt tctctggttc tcgtttctac gatacttggg gtcaaggtac tctggtgacc    360
gtctcctca                                                            369

<210> SEQ ID NO 8
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cagcctgtgc tgactcagcc accctcggtg tctgaagccc ccaggcagag ggtcaccatc     60
tcctgttctg gaagcagctc caacatcgga aataatgctg taaactggta ccagcagctc    120
ccaggaaagg ctcccaaact cctcatctat tttgatgatc tgctgtcctc agggtctct     180 gaccgattct ctggctccaa gtctggcacc tcagcctccc tggccatcag tgggctccag    240
tctgaagatg aggctgatta ttactgtgca gcatgggatg acagcctgaa tggttatgtc    300
ttcggaactg ggaccaaggt caccgtccta ggt                                 333

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Lys Ser Ile Val Ser Tyr Met Asp Tyr Trp
            100                 105                 110

Gly Gln Gly Thr Leu Val Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 10

Leu Pro Val Leu Thr Gln Pro Pro Ser Thr Ser Gly Thr Pro Gly Gln
1               5                   10                  15

Arg Val Thr Val Ser Cys Ser Gly Ser Ser Ser Asn Ile Gly Ser Asn
            20                  25                  30

Val Val Phe Trp Tyr Gln Gln Leu Pro Gly Thr Ala Pro Lys Leu Val
        35                  40                  45

Ile Tyr Arg Asn Asn Gln Arg Pro Ser Gly Val Pro Asp Arg Phe Ser
    50                  55                  60

Val Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
            100                 105                 110

<210> SEQ ID NO 11
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtccagc tggtgcagtc tggagctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatcccta tccttggtat agcaaactac      180
gcacagaagt tccagggcag agtcaccatg accgaggaca catctacaga cacagcctac     240
atggagctga gcagcctgag atctgaggac acggccgtgt attactgtgc gcgctctggt     300
tactctaaat ctatcgtttc ttacatggat tactggggtc aaggtactct ggtgaccgtc     360
tcctca                                                                366

<210> SEQ ID NO 12
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ctgcctgtgc tgactcagcc cccctccacg tctgggaccc ccgggcagag ggtcaccgtc      60
tcttgttctg gaagcagctc caacatcgga agtaatgttg tattctggta ccagcagctc     120
ccaggcacgg cccccaaact tgtcatctat aggaataatc aacgccctc a ggggtccct     180 gaccgattct ctgtctccaa gtctggcacc tcagcctccc tggccatcag tgggctccgg     240
tccgaggacg aggctgatta ttattgtgca gcttgggatg acagcctgag tggttatgtc     300
ttcggaactg ggaccaaggt caccgtccta ggt                                  333

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gln Trp Gly Gly Val Leu Asp Tyr Trp Gly Gln Gly Thr
            100                 105                 110

Leu Val Thr Val Ser Ser
            115

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ser Val Val Thr Gln Pro Pro Ser Val Ser Gly Ala Pro Gly Gln
1               5                   10                  15

Arg Val Thr Ile Ser Cys Ser Gly Ser Ser Ser Asn Ile Gly Ala Arg
            20                  25                  30

Tyr Asp Val Gln Trp Tyr Gln Gln Leu Pro Gly Thr Ala Pro Lys Leu
        35                  40                  45

Leu Ile Phe Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Gly Gly Thr Lys Leu Thr Val Leu Gly
            100                 105                 110

<210> SEQ ID NO 15
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gaggtccagc tggtacagtc tggggctgag gtgaagaagc ctggggcctc agtgaaggtt     60
tcctgcaagg catctggata caccttcacc agctactata tgcactgggt gcgacaggcc    120
cctggacaag gcttgagtg gatgggaata atcaacccta gtggtggtag cacaagctac    180
gcacagaagt tccagggcag agtcaccatg accaggaca cgtccacgag cacagtctac    240
atggagctga gcagcctgag atctgaggac acggccgtgt attactgtgc gcgctctcag    300

```
tggggtggtg ttctggatta ctggggtcaa ggtactctgg tgaccgtctc ctca        354
```

<210> SEQ ID NO 16
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
cagtctgtcg tgacgcagcc gccctcagtg tctggggccc cagggcagag ggtcaccatc    60
tcctgcagtg ggagcagctc caacatcggg gcacgttatg atgttcagtg gtaccagcag   120
cttccaggaa cagcccccaa actcctcatc tttggtaaca acaatcggcc ctcaggggtc   180
cctgaccgat tctctggctc caagtctggc acgtcagcct ccctggccat cactgggctc   240
caggctgagg atgaggctga ttattactgc cagtcctatg acagcagcct gagtgcttcg   300
gtgttcggcg gagggaccaa gctgaccgtc ctaggt                             336
```

<210> SEQ ID NO 17
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Glu Ser Trp Gly Ser Tyr Glu Val Ile Asp Arg
            100                 105                 110

Trp Gly Gln Gly Thr Leu Val Thr Val Ser Ser
        115                 120
```

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Arg Gln Leu Pro Gly Thr Ala Pro Lys Leu Leu
```

```
                35                  40                  45
Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 19
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtggagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtat agcaaactac   180
gcacagaagt tccagggcag agtcacgatt accgcggacg aatccacgag cacagcctac   240
atggagctga gcagcctgag atctgaggac acggccgtat attactgtgc gcgcactggt   300
tacgaatctt ggggttctta cgaagttatc gatcgttggg gtcaaggtac tctggtgacc   360
gtctcctca                                                           369

<210> SEQ ID NO 20
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caggctgtgc tgactcagcc accctcagcg tctgggaccc ccgggcagag ggtcaccatc    60
tcttgttctg gaagcagctc caacatcgga agtaatactg taaactggta ccggcagctc   120
ccaggaacgg ccccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctgaa tggtgtggta   300
ttcggcggag ggaccaagct gaccgtccta ggt                                333

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Ser His Asp Met Trp Ser Glu Asp Trp Gly
            100                 105                 110

Gln Gly Thr Leu Val Thr Val Ser Ser
        115                 120

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
            20                  25                  30

Ser Val Asn Trp Tyr Arg Gln Leu Pro Gly Ala Ala Pro Lys Leu Leu
        35                  40                  45

Ile Tyr Ser Asn Asn Gln Arg Pro Pro Gly Val Pro Val Arg Phe Ser
 50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110

<210> SEQ ID NO 23
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaagg atcatccctca tccttggtat agcaaactac    180
gcacagaagt tccagggcag agtcacgatt accgcggaca atccacgag cacagcctac    240 atggagctga gcagcctgag atctgaggac acggccgtgt attactgtgc gcgcggtggt    300
tactactctc atgacatgtg gtctgaagat tggggtcaag gtactctggt gaccgtctcc    360
tca                                                                  363

<210> SEQ ID NO 24
<211> LENGTH: 336
<212> TYPE: DNA

-continued

<213> ORGANISM: Artificial Sequence
<220> FEATURE:
<223> OTHER INFORMATION: Description of Artificial Sequence: Synthetic
      polynucleotide

<400> SEQUENCE: 24

```
ctgcctgtgc tgactcagcc accctcagcg tctgggaccc ccgggcagag ggtcaccatc     60
tcttgttctg gacgcagttc aacatcggg agtaattctg ttaactggta tcgacaactc    120
ccaggagcgg cccccaaact cctcatctat agtaataatc agcggccccc aggggtccct   180
gtgcgattct ctggctccaa gtctggcacc tcagcctccc tggccatcag tgggctccag   240
tctgaagatg aggccactta ttactgtgca acatgggatg acaatctgaa tgttcactat   300
gtcttcggaa ctgggaccaa ggtcaccgtc ctaggt                              336
```

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Gln Glu Ser Gly Pro Gly Leu Val Lys Pro Ser Gly
1               5                   10                  15

Thr Leu Ser Leu Thr Cys Gly Val Ser Gly Gly Ser Ile Ser Asn Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Lys Tyr Asn Pro Ser Leu
    50                  55                  60

Arg Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Asp Asn Trp Lys Thr Pro Thr Thr Lys Ile Asp Gly Phe
            100                 105                 110

Asp Ile Trp Gly Gln Gly Thr Met Val Thr Val Ser Ser
        115                 120                 125
```

<210> SEQ ID NO 26
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80
```

Lys Asn Ile Gln Glu Glu Asp Glu Gly Asp Tyr His Cys Gly Ala Asp
                85                  90                  95

His Gly Ser Gly Ser Asn Phe Val Tyr Val Phe Gly Thr Gly Thr Lys
            100                 105                 110

Val Thr Val Leu Gly
        115

<210> SEQ ID NO 27
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtgcagc tgcaggagtc gggcccagga ctggtgaagc cttcggggac cctgtccctc      60
acctgcggtg tctctggtgg ctccatcagc aatagtaact ggtggagttg ggtccgccag     120
ccccccggga aggggctgga gtggattggg gaaatctatc atagtgggag caccaagtac     180
aacccgtccc tcaggagtcg agtcaccata tcagtagaca gtccaagaac cagttctcc     240 ctaaaattga gctctgtgac cgccgcggac acggccgtat attactgtgc gagacgagat     300
aactggaaga ccccccactac caaaattgat ggttttgata tctggggcca agggacaatg     360
gtcaccgtct cttca                                                      375

<210> SEQ ID NO 28
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
cagcctgtgc tgactcagcc accttctgca tcagcctccc tgggagcctc ggtcacactc      60
acctgcaccc tgagcagcgg ctacagtaat tataaagtgg actggtacca gcagagacca     120
gggaagggcc cccggtttgt gatgcgagtg ggcactggtg ggattgtggg atccaagggg     180
gatggcatcc ctgatcgctt ctcagtcttg ggctcaggcc tgaatcggta cctgaccatc     240
aagaacatcc aggaagaaga tgagggtgac tatcactgtg gggcagacca tggcagtggg     300
agcaacttcg tgtatgtctt cggaactggg accaaggtca ccgtcctagg t              351

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe

```
                  50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Ser Gln Trp Gly Ser Ser Trp Asp Tyr Trp Gly Gln Gly Thr
            100                 105                 110

Leu Val Thr Val Ser Ser
            115

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly Thr Lys Val Glu Ile Lys Arg
            100                 105

<210> SEQ ID NO 31
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggtccagc tggtacagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaa acagtggtgg cacaaactat     180
gcacagaagt tcagggcag ggtcaccatg accagggaca cgtccatcag cacagcctac     240
atggagctga gcaggctgag atctgacgac acggccgtgt attactgtgc gcgctctcag     300
tggggttctt cttgggatta ctggggtcaa ggtactctgg tgaccgtctc ctca          354

<210> SEQ ID NO 32
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
```

```
gacatccagt tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgac gttcggccaa     300
gggaccaagg tggagatcaa acgt                                            324
```

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Ser Tyr His Leu Tyr Gly Tyr Asp Ser Trp Gly Gln Gly
            100                 105                 110

Thr Leu Val Thr Val Ser Ser
        115

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Pro Val Leu Thr Gln Pro Pro Ser Ala Ser Ala Ser Leu Gly Ala
1               5                   10                  15

Ser Val Thr Leu Thr Cys Thr Leu Ser Asn Asp Tyr Thr Asn Tyr Lys
            20                  25                  30

Val Asp Trp Tyr Gln Gln Arg Pro Gly Lys Gly Pro Arg Phe Val Met
        35                  40                  45

Arg Val Gly Pro Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Thr Gly Ser Asn Phe Val Tyr Val Phe Gly Gly Gly Thr Lys
            100                 105                 110

Leu Thr Val Leu Gly
        115

<210> SEQ ID NO 35
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gaggtgcagc tggtggagtc cgggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccccta acagtggtgg cacaaactat     180
gcacagaagt tcagggcag gtcaccatg accagggaca cgtccatcag cacagcctac     240
atggagctga gcaggctgag atctgacgac acggccgtat attactgtgc gcgctcttct     300
taccatctgt acggttacga ttcttggggt caaggtactc tggtgaccgt ctcctca       357

<210> SEQ ID NO 36
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
cagcctgtgc tgactcagcc accttctgca tcagcctccc tgggagcctc ggtcactctc      60
acctgcaccc tgagcaacga ctacactaat tataaagtgg actggtacca gcagagacca     120
gggaagggcc cccggtttgt gatgcgagtg ggccctggtg ggattgtggg atccaagggg     180
gatggcatcc ctgatcgctt ctcagtcttg ggctcaggcc tgaatcgata cctgaccatc     240
aagaacatcc aggaggagga tgagagtgac taccactgtg gggcggacca tggcaccggg     300
agcaacttcg tgtacgtgtt cggcggaggg accaagctga ccgtcctagg t            351

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Ser Thr Ala Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gln Pro Trp Thr Trp Tyr Ser Pro Tyr Asp Gln Trp Gly Gln
            100                 105                 110

Gly Thr Leu Val Thr Val Ser Ser
        115                 120

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Leu Met
        35                  40                  45

Arg Val Asp Thr Gly Gly Ile Val Gly Ser Lys Gly Asp Gly Ile Pro
    50                  55                  60

Asp Arg Phe Ser Val Ser Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val Trp Val Phe Gly Gly Gly Thr Lys
            100                 105                 110

Leu Thr Val Leu Gly
        115

<210> SEQ ID NO 39
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttagtac agcaaactac     180
gcacagaagt tccagggcag agtcaccatg accacagaca tcccacgag cacagcctac     240 atggagctga ggagcctgag atctgacgac acggccgtgt attactgtgc gcgccagccg     300
tggacttggt actctccgta cgatcagtgg ggtcaaggta ctctggtgac cgtctcctca     360

<210> SEQ ID NO 40
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cagcctgtgc tgactcagcc acctctgca tcagcctccc tgggagcctc ggtcacactc      60
acctgcaccc tgagcagcgg ctacagtaat tataaagtgg actggtatca acagagacca     120

```
gggaagggcc cccggtttct gatgcgagta gacaccggtg ggattgtggg atccaagggg    180
gatggcatcc ctgatcgctt ctcagtctcg ggctcaggtc tgaatcggta cctgaccatc    240
aagaacattc aggaagagga tgagagtgac taccactgtg gggcagacca tggcagtggg    300
agcaacttcg tgtgggtgtt cggcggaggg accaagctga ccgtcctagg t             351
```

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 41

```
Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Thr Trp Val Arg Gln Ala Pro Gly Lys Gly Leu Glu Trp Val
        35                  40                  45

Ser Ala Ile Thr Pro Gly Gly Asp Arg Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Tyr Met Ile Asp Met Trp Gly Gln Gly Thr Leu
            100                 105                 110

Val Thr Val Ser Ser
        115
```

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg
```

<210> SEQ ID NO 43

<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
gaggtgcagc tggtggagac tgggggaggc ctggtacagc ctgggggtc cctgagactc      60
tcctgtgctg cctctggatt cacctttagc acctatgcca tgacctgggt ccgccaggct    120
ccagggaagg gctggagtg gtctcagct attactcctg gtggtgatcg cacatactac      180
gcagactccg tgaagggccg tttcactatc tccagagaca attccaggaa cacgctgtat   240
ctgcaaatga acagcctgag agccgaggac acggccgtat attactgtgc gcgctactac   300
ggttacatga tcgatatgtg gggtcaaggt actctggtga ccgtctcctc a            351
```

<210> SEQ ID NO 44
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
gatgttgtga tgactcagtc tccactctcc ctgcccgtca cccctggaga gccggcctcc     60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc    240
agcagagtgg aggctgagga tgttggggtt tattactgca tgcaagctct acaaactcct   300
ctcactttcg gcggagggac caaggtggaa atcaaacgt                          339
```

<210> SEQ ID NO 45
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Val His Trp Leu Arg Gln Ala Pro Gly Gln Gly Leu Glu Trp Met
        35                  40                  45

Gly Trp Ile Asn Pro Asn Ser Gly Gly Thr Asn Asn Ala Gln Glu Phe
    50                  55                  60

Gln Gly Arg Ile Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Trp Gly Gly Thr Tyr Asp Tyr Trp Gly Gln Gly Thr
            100                 105                 110

Leu Val Thr Val Ser Ser
        115
```

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 46

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ala Ser Ala Ser Leu Ala Ile Ser Trp Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
            100                 105                 110

<210> SEQ ID NO 47
<211> LENGTH: 354
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 47
cagatgcagc tggtgcagtc tggggctgag gtgaagaagc ctggggcctc agtgaaggtc      60
tcctgcaagg cttctggata caccttcacc ggctattatg tacactggtt gcgacaggcc     120
cctggacaag gcttgagtg gatgggttgg atcaaccctaa acagtggcgg cacaaacaat      180
gcacaggagt ttcaaggcag gatcaccatg accaggaca cgtccatcaa cacagcctac      240
atggagctga gcaggctgag atctgacgac acggccgtgt attactgtgc gcgctctcag      300
tggggtggta cttacgatta ctggggtcaa ggtactctgg tgaccgtctc ctca            354

<210> SEQ ID NO 48
<211> LENGTH: 333
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 48
tcctatgtgc tgactcagcc accctcagcg tctgggaccc ccgggcagag ggtcaccatc      60
tcttgttctg gaagcagctc caacatcgga agtaatactg taaactggta ccagcaggtc     120
ccaggaacgg ccccccaaact cctcatctat agtaataatc agcggccctc agggtccct      180 gaccgattct ctggctccaa gtctggcgcc tcagcctccc tggccatcag ttggctccag     240
tctgaggatg aggctgatta ttactgtgca gcatgggatg acagcctgaa tggttgggtg     300
ttcggcggag ggaccaagct gaccgtccta ggt                                   333

```
<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asp Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Val
    50                  55                  60

Arg Gly Arg Val Thr Ile Ser Ala Asp Lys Ser Ile Asn Thr Ala Tyr
65                  70                  75                  80

Leu Gln Trp Ser Ser Leu Glu Ala Ser Asp Thr Ala Met Tyr Tyr Cys
                85                  90                  95

Ala Arg Met Trp Thr Phe Ser Gln Asp Gly Trp Gly Gln Gly Thr Leu
            100                 105                 110

Val Thr Val Ser Ser
        115

<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Tyr
            20                  25                  30

Thr Val Ser Trp Tyr Gln Gln Leu Pro Gly Thr Ala Pro Lys Phe Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly
            100                 105                 110

<210> SEQ ID NO 51
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcagc tggtgcagtc tggagcagag gtgaaaaagc cgggggagtc tctgaagatc    60
```

```
tcctgtaagg gttctggata tgactttacc acctactgga tcgggtgggt gcgccagatg    120
cccgggaagg gcctggagtg gatggggatc atctatcctg gtgactctga taccagatac    180
agcccgtccg tccgaggccg ggtcaccatc tcagccgaca agtccatcaa caccgcctat    240
ttgcagtgga gtagcctgga ggcctccgac accgccatgt attactgtgc gcgcatgtgg    300
actttctctc aggatggttg gggtcaaggt actctggtga ccgtctcctc a             351
```

<210> SEQ ID NO 52
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
caggctgtgc tgactcagcc accctcagcg tctgggaccc ccgggcagag ggtcaccatc    60
tcttgttctg gaagcagctc caacatcgga agttatactg taagctggta ccagcaactc   120
ccaggaacgg cccccaaatt cctcatctat tctaataatc agcggccctc aggggtccct   180
gaccgattct ctggctccaa gtctggcacc tcagcctccc tggccatcag tgggctccag   240
tctgaggatg aggctgatta ttactgtgct gcatgggatg acagcctgaa tggttatgtc   300
ttcggaactg ggaccaaggt caccgtccta ggt                                333
```

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115

<210> SEQ ID NO 54
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105
```

<210> SEQ ID NO 55
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
gaagtgcagc tggtgcagtc tggggctgag atgaagaagc ctggggcctc actgaagctc      60
tcctgcaagg cttctggata caccttcatc gactactatg tatactggat gcgacaggcc     120
cctggacaag gcttgagtc catgggatgg atcaaccta acagtggtgg cacaaactat      180
gcacagaagt tcagggcag ggtcaccatg accagggaca cgtccatcag cacagcctac      240
atggagctga gcaggctgag atctgacgac accgccatgt attactgtgc gcgctcccag     300
cgtgacggtt acatggatta ctggggtcaa ggtactctgg tgaccgtctc ctca           354
```

<210> SEQ ID NO 56
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
caatctgccc tgactcagcc tgcctccgtg tctgcgtctc ctggacagtc gatcgccatc      60
tcctgcactg gaaccagcag tgacgttggt tggtatcaac agcacccagg caaagccccc     120
aaactcatga tttatgagga cagtaagcgg ccctcagggg tttctaatcg cttctctggc     180
tccaagtctg gcaacacggc ctccctgacc atctctgggc tccaggctga ggacgaggct     240
gattattact gcagctcaaa tacaagaagc agcactttgg tgttcggcgg agggaccaag     300
ctgaccgtcc taggt                                                      315
```

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Gln Val Gln Leu Val Gln Ser Gly Ala Glu Val Lys Lys Pro Gly Ala

```
              1               5                  10                 15
Ser Val Lys Val Ser Cys Lys Ala Ser Gly Tyr Thr Phe Thr Asp Tyr
                20                  25                 30

Tyr Met His Trp Val Arg Gln Ala Pro Gly Gln Arg Leu Glu Trp Met
            35                  40                  45

Gly Trp Ile Asn Pro Asn Ser Gly Gly Thr Asn Tyr Ala Gln Lys Phe
    50                  55                  60

Gln Asp Arg Ile Thr Val Thr Arg Asp Thr Ser Asn Thr Gly Tyr
65                  70                  75                  80

Met Glu Leu Thr Arg Leu Arg Ser Asp Asp Thr Ala Val Tyr Tyr Cys
                85                  90                  95

Ala Arg Ser Pro Tyr Ser Gly Val Leu Asp Lys Trp Gly Gln Gly Thr
            100                 105                 110

Leu Val Thr Val Ser Ser
            115

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Phe Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

<210> SEQ ID NO 59
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
caggtccagc tggtacagtc tggggctgag gtgaagaagc ctggggcctc agtgaaggtc      60
tcctgcaagg cttctggata cacctteacc gactactata tgcactgggt gcgacaggcc    120
cctggacaac ggcttgagtg gatgggatgg atcaacccta acagtggtgg cacaaactat    180
gcacagaagt ttcaggacag gatcaccgtg accagggaca cctccagcaa cacaggctac    240
atggagctga ccaggctgag atctgacgac acggccgtgt attactgtgc gcgctctccg    300
tactctggtg ttctggataa atggggtcaa ggtactctgg tgaccgtctc ctca          354
```

<210> SEQ ID NO 60
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
cagtctgtgc tgacgcagcc gccctcagtg tctggggccc cagggcagag ggtcaccatc      60
tcctgcactg ggagcagctc caacatcggg gcaggttttg atgtacactg gtaccagcag     120
cttccaggaa cagccccaa actcctcatc tatggtaaca gcaatcggcc ctcagggtc       180 cctgaccgat tctctggctc caagtctggc acctcagcct ccctggccat cactgggctc     240
caggctgagg atgaggctga ttattactgc cagtcctatg acagcagcct gagtggttat     300
gtcttcggaa ctgggaccaa ggtcaccgtc ctaggt                                336

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Ser Tyr Arg Trp Glu Asp Ser Trp Gly Gln
            100                 105                 110

Gly Thr Leu Val Thr Val Ser Ser
        115                 120

<210> SEQ ID NO 62
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Phe Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

```
Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly
            100                 105                 110

<210> SEQ ID NO 63
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatccta tccttggtac agcaaactac     180
gcacagaagt tccagggcag agtcacgatt accgcggacg aatccacgag cacagcctac   240
atggagctga gcagcctgag atctgaggac acggccgtgt attactgtgc gcgctctggt   300
tacggttctt accgttggga agattcttgg ggtcaaggta ctctggtgac cgtctcctca   360

<210> SEQ ID NO 64
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
caggctgtgc tgactcagcc accctcagcg tctgggaccc ccgggcagag ggtcaccatc    60
tcttgttctg gaagcagctc caacatcgga agtaattacg tattctggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tgcctcttat   300
gttttcggaa ctgggaccaa ggtcaccgtc ctaggt                             336

<210> SEQ ID NO 65
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Tyr Ser Gly Ser Phe Asp Asn Trp Gly Gln Gly Thr Leu Val
            100                 105                 110

Thr Val Ser Ser
        115

<210> SEQ ID NO 66
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ser Tyr Glu Leu Thr Gln Pro Pro Ser Ala Ser Gly Thr Pro Gly Gln
  1               5                  10                  15

Arg Val Thr Met Ser Cys Ser Gly Thr Ser Ser Asn Ile Gly Ser His
                 20                  25                  30

Ser Val Asn Trp Tyr Gln Gln Leu Pro Gly Thr Ala Pro Lys Leu Leu
             35                  40                  45

Ile Tyr Thr Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Gly Ser Leu
                 85                  90                  95

Asn Gly Leu Val Phe Gly Gly Gly Thr Lys Leu Thr Val Leu Gly
            100                 105                 110

<210> SEQ ID NO 67
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca cgtcaccatc tcagctgaca gtccatcagc cactgcctac     240
ctgcagtgga gcagcctgaa ggcctcggac accgccatgt attactgtgc gcgctactct     300
ggttctttcg ataactgggg tcaaggtact ctggtgaccg tctcctca                  348

<210> SEQ ID NO 68
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
tcctatgagc tgactcagcc accctcagcg tctgggaccc ccgggcagag ggtcaccatg       60
```

```
tcttgttctg gaaccagctc caacatcgga agtcactctg taaactggta ccagcagctc    120
ccaggaacgg cccccaaact cctcatctat actaataatc agcggccctc agggtccct     180 gaccgattct ctggctccaa gtctggcacc tcagcctccc tggccatcag tggcctccag    240
tctgaggatg aggctgatta ttactgtgca gcatgggatg cagcctgaa tggtctggta     300 ttcggcggag ggaccaagct gaccgtccta ggt                                 333
```

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 70
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70

```
tctagaggtg gtggtggtag cggcggcggc ggctctggtg gtggtggatc cctcgagatg    60
gcc                                                                  63
```

<210> SEQ ID NO 71
<211> LENGTH: 184
<212> TYPE: PRT
<213> ORGANISM: Homo sapiens

<400> SEQUENCE: 71

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys

```
                145                 150                 155                 160
Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 72
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ser Val Leu Thr Gln Pro Pro Ser Val Ser Val Ala Pro Arg Gln
1               5                   10                  15

Arg Val Thr Ile Ser Cys Ser Gly Ser Ser Asn Ile Gly His Asn
            20                  25                  30

Asp Val Ser Trp Tyr Gln His Leu Pro Gly Lys Ala Pro Arg Leu Leu
            35                  40                  45

Ile Tyr Phe Asp Asp Leu Leu Pro Ser Gly Val Ser Asp Arg Phe Ser
    50                  55                  60

Ala Ser Lys Ser Gly Thr Ser Ala Ser Leu Ala Ile Ser Gly Leu Gln
65              70                  75                  80

Ser Glu Asp Glu Ala Asp Tyr Tyr Cys Ala Ala Trp Asp Gly Ser Leu
                85                  90                  95

Asn Ala Phe Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Gln Val Gln Leu Gln Gln Ser Gly Pro Gly Leu Val
    130                 135                 140

Lys Pro Ser Gln Thr Leu Ser Leu Thr Cys Ala Ile Ser Gly Asp Ser
145                 150                 155                 160

Val Ser Ser Asn Ser Ala Ala Trp Asn Trp Ile Arg Gln Ser Pro Ser
                165                 170                 175

Arg Gly Leu Glu Trp Leu Gly Arg Thr Tyr Tyr Arg Ser Lys Trp Tyr
            180                 185                 190

Asn Asp Tyr Ala Val Ser Val Lys Ser Arg Ile Thr Ile Asn Pro Asp
        195                 200                 205

Thr Ser Lys Asn Gln Phe Ser Leu Gln Leu Asn Ser Val Thr Pro Glu
    210                 215                 220

Asp Thr Ala Val Tyr Tyr Cys Ala Arg Gln Gly Tyr Ser Tyr Tyr Gly
225                 230                 235                 240

Tyr Ser Asp Val Trp Gly Gln Gly Thr Leu Val Thr Val Ser Ser
                245                 250                 255

<210> SEQ ID NO 73
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Pro Val Leu Thr Gln Pro Pro Ser Val Ser Glu Ala Pro Arg Gln
```

```
            1               5                   10                  15
Arg Val Thr Ile Ser Cys Ser Gly Ser Ser Ser Asn Ile Gly Asn Asn
                    20                  25                  30

Ala Val Asn Trp Tyr Gln Gln Leu Pro Gly Lys Ala Pro Lys Leu Leu
                    35                  40                  45

Ile Tyr Phe Asp Asp Leu Leu Ser Ser Gly Val Ser Asp Arg Phe Ser
                    50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                    85                  90                  95

Asn Gly Tyr Val Phe Gly Thr Gly Thr Lys Val Thr Val Leu Gly Ser
                    100                 105                 110

Arg Gly Gly Gly Gly Ser Gly Gly Gly Ser Gly Gly Gly Gly Ser
                    115                 120                 125

Leu Glu Met Ala Gln Val Gln Leu Gln Gln Ser Gly Pro Gly Leu Val
                    130                 135                 140

Lys Pro Ser Gln Thr Leu Ser Leu Thr Cys Ala Ile Ser Gly Asp Ser
145                 150                 155                 160

Val Ser Ser Asn Ser Ala Ala Trp Asn Trp Ile Arg Gln Ser Pro Ser
                    165                 170                 175

Arg Gly Leu Glu Trp Leu Gly Arg Thr Tyr Tyr Arg Ser Lys Trp Tyr
                    180                 185                 190

Asn Asp Tyr Ala Val Ser Val Lys Ser Arg Ile Thr Ile Asn Pro Asp
                    195                 200                 205

Thr Ser Lys Asn Gln Phe Ser Leu Gln Leu Asn Ser Val Thr Pro Glu
                    210                 215                 220

Asp Thr Ala Val Tyr Tyr Cys Ala Arg Tyr Gly Phe Ser Gly Ser Arg
225                 230                 235                 240

Phe Tyr Asp Thr Trp Gly Gln Gly Thr Leu Val Thr Val Ser Ser
                    245                 250                 255

<210> SEQ ID NO 74
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Pro Val Leu Thr Gln Pro Pro Ser Thr Ser Gly Thr Pro Gly Gln
 1               5                   10                  15

Arg Val Thr Val Ser Cys Ser Gly Ser Ser Ser Asn Ile Gly Ser Asn
                    20                  25                  30

Val Val Phe Trp Tyr Gln Gln Leu Pro Gly Thr Ala Pro Lys Leu Val
                    35                  40                  45

Ile Tyr Arg Asn Asn Gln Arg Pro Ser Gly Val Pro Asp Arg Phe Ser
                    50                  55                  60

Val Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                    85                  90                  95

Ser Gly Tyr Val Phe Gly Thr Gly Thr Lys Val Thr Val Leu Gly Ser
                    100                 105                 110
```

```
Arg Gly Gly Gly Ser Gly Gly Gly Ser Gly Gly Gly Ser
    115                 120                 125

Leu Glu Met Ala Glu Val Gln Leu Val Gln Ser Gly Ala Glu Val Lys
130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Leu Gly Ile Ala Asn Tyr
            180                 185                 190

Ala Gln Lys Phe Gln Gly Arg Val Thr Met Thr Glu Asp Thr Ser Thr
        195                 200                 205

Asp Thr Ala Tyr Met Glu Leu Ser Ser Leu Arg Ser Glu Asp Thr Ala
    210                 215                 220

Val Tyr Tyr Cys Ala Arg Ser Gly Tyr Ser Lys Ser Ile Val Ser Tyr
225                 230                 235                 240

Met Asp Tyr Trp Gly Gln Gly Thr Leu Val Thr Val Ser Ser
                245                 250

<210> SEQ ID NO 75
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ser Val Val Thr Gln Pro Pro Ser Val Ser Gly Ala Pro Gly Gln
1               5                   10                  15

Arg Val Thr Ile Ser Cys Ser Gly Ser Ser Ser Asn Ile Gly Ala Arg
            20                  25                  30

Tyr Asp Val Gln Trp Tyr Gln Gln Leu Pro Gly Thr Ala Pro Lys Leu
        35                  40                  45

Leu Ile Phe Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Ala Ser Val Lys Val Ser Cys Lys Ala Ser Gly Tyr
145                 150                 155                 160

Thr Phe Thr Ser Tyr Tyr Met His Trp Val Arg Gln Ala Pro Gly Gln
                165                 170                 175

Gly Leu Glu Trp Met Gly Ile Ile Asn Pro Ser Gly Gly Ser Thr Ser
            180                 185                 190

Tyr Ala Gln Lys Phe Gln Gly Arg Val Thr Met Thr Arg Asp Thr Ser
        195                 200                 205

Thr Ser Thr Val Tyr Met Glu Leu Ser Ser Leu Arg Ser Glu Asp Thr
    210                 215                 220
```

```
Ala Val Tyr Tyr Cys Ala Arg Ser Gln Trp Gly Val Leu Asp Tyr
225                 230                 235                 240

Trp Gly Gln Gly Thr Leu Val Thr Val Ser Ser
            245                 250
```

<210> SEQ ID NO 76
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Arg Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Val Gln Leu Val Glu Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Leu Gly Ile Ala Asn Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Thr Gly Tyr Glu Ser Trp Gly Ser Tyr Glu
225                 230                 235                 240

Val Ile Asp Arg Trp Gly Gln Gly Thr Leu Val Thr Val Ser Ser
                245                 250                 255
```

<210> SEQ ID NO 77
<211> LENGTH: 254
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Leu Pro Val Leu Thr Gln Pro Pro Ser Ala Ser Gly Thr Pro Gly Gln
1               5                   10                  15
```

```
Arg Val Thr Ile Ser Cys Ser Gly Arg Ser Ser Asn Ile Gly Ser Asn
         20                  25                  30

Ser Val Asn Trp Tyr Arg Gln Leu Pro Gly Ala Ala Pro Lys Leu Leu
         35                  40                  45

Ile Tyr Ser Asn Asn Gln Arg Pro Pro Gly Val Pro Val Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Thr Tyr Tyr Cys Ala Thr Trp Asp Asp Asn Leu
             85                  90                  95

Asn Val His Tyr Val Phe Gly Thr Gly Thr Lys Val Thr Val Leu Gly
            100                 105                 110

Ser Arg Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Ile Ala Asn
            180                 185                 190

Tyr Ala Gln Lys Phe Gln Gly Arg Val Thr Ile Thr Ala Asp Lys Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Gly Gly Tyr Tyr Ser His Asp Met Trp
225                 230                 235                 240

Ser Glu Asp Trp Gly Gln Gly Thr Leu Val Thr Val Ser Ser
                245                 250

<210> SEQ ID NO 78
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Pro Val Leu Thr Gln Pro Pro Ser Ala Ser Ala Ser Leu Gly Ala
1               5                  10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
         35                  40                  45

Arg Val Gly Thr Gly Gly Ile Val Gly Ser Lys Gly Asp Gly Ile Pro
 50                  55                  60

Asp Arg Phe Ser Val Leu Gly Ser Gly Leu Asn Arg Tyr Leu Thr Ile
 65                  70                  75                  80

Lys Asn Ile Gln Glu Glu Asp Glu Gly Asp Tyr His Cys Gly Ala Asp
             85                  90                  95

His Gly Ser Gly Ser Asn Phe Val Tyr Val Phe Gly Thr Gly Thr Lys
            100                 105                 110

Val Thr Val Leu Gly Ser Arg Gly Gly Gly Ser Gly Gly Gly Gly
```

```
            115                 120                 125
Ser Gly Gly Gly Ser Leu Glu Met Ala Gln Val Gln Leu Gln Glu
    130                 135                 140
Ser Gly Pro Gly Leu Val Lys Pro Ser Gly Thr Leu Ser Leu Thr Cys
145                 150                 155                 160
Gly Val Ser Gly Ser Ile Ser Asn Ser Asn Trp Trp Ser Trp Val
                165                 170                 175
Arg Gln Pro Pro Gly Lys Gly Leu Glu Trp Ile Gly Glu Ile Tyr His
            180                 185                 190
Ser Gly Ser Thr Lys Tyr Asn Pro Ser Leu Arg Ser Arg Val Thr Ile
            195                 200                 205
Ser Val Asp Lys Ser Lys Asn Gln Phe Ser Leu Lys Leu Ser Ser Val
    210                 215                 220
Thr Ala Ala Asp Thr Ala Val Tyr Tyr Cys Ala Arg Arg Asp Asn Trp
225                 230                 235                 240
Lys Thr Pro Thr Thr Lys Ile Asp Gly Phe Asp Ile Trp Gly Gln Gly
                245                 250                 255
Thr Met Val Thr Val Ser Ser
                260
```

<210> SEQ ID NO 79
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Pro
                85                  90                  95
Thr Phe Gly Gln Gly Thr Lys Val Glu Ile Lys Arg Ser Arg Gly Gly
            100                 105                 110
Gly Gly Ser Gly Gly Gly Gly Ser Gly Gly Gly Gly Ser Leu Glu Met
        115                 120                 125
Ala Gln Val Gln Leu Val Gln Ser Gly Ala Glu Val Lys Lys Pro Gly
    130                 135                 140
Ala Ser Val Lys Val Ser Cys Lys Ala Ser Gly Tyr Thr Phe Thr Gly
145                 150                 155                 160
Tyr Tyr Met His Trp Val Arg Gln Ala Pro Gly Gln Gly Leu Glu Trp
                165                 170                 175
Met Gly Trp Ile Asn Pro Asn Ser Gly Gly Thr Asn Tyr Ala Gln Lys
            180                 185                 190
Phe Gln Gly Arg Val Thr Met Thr Arg Asp Thr Ser Ile Ser Thr Ala
        195                 200                 205
```

```
Tyr Met Glu Leu Ser Arg Leu Arg Ser Asp Asp Thr Ala Val Tyr Tyr
    210                 215                 220

Cys Ala Arg Ser Gln Trp Gly Ser Ser Trp Asp Tyr Trp Gly Gln Gly
225                 230                 235                 240

Thr Leu Val Thr Val Ser Ser
                245
```

<210> SEQ ID NO 80
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Gln Pro Val Leu Thr Gln Pro Pro Ser Ala Ser Ala Ser Leu Gly Ala
1               5                   10                  15

Ser Val Thr Leu Thr Cys Thr Leu Ser Asn Asp Tyr Thr Asn Tyr Lys
            20                  25                  30

Val Asp Trp Tyr Gln Gln Arg Pro Gly Lys Gly Pro Arg Phe Val Met
        35                  40                  45

Arg Val Gly Pro Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Thr Gly Ser Asn Phe Val Tyr Val Phe Gly Gly Thr Lys
            100                 105                 110

Leu Thr Val Leu Gly Ser Arg Gly Gly Gly Ser Gly Gly Gly Gly
        115                 120                 125

Ser Gly Gly Gly Gly Ser Leu Glu Met Ala Glu Val Gln Leu Val Glu
130                 135                 140

Ser Gly Ala Glu Val Lys Lys Pro Gly Ala Ser Val Lys Val Ser Cys
145                 150                 155                 160

Lys Ala Ser Gly Tyr Thr Phe Thr Gly Tyr Tyr Met His Trp Val Arg
                165                 170                 175

Gln Ala Pro Gly Gln Gly Leu Glu Trp Met Gly Trp Ile Asn Pro Asn
            180                 185                 190

Ser Gly Gly Thr Asn Tyr Ala Gln Lys Phe Gln Gly Arg Val Thr Met
        195                 200                 205

Thr Arg Asp Thr Ser Ile Ser Thr Ala Tyr Met Glu Leu Ser Arg Leu
    210                 215                 220

Arg Ser Asp Asp Thr Ala Val Tyr Tyr Cys Ala Arg Ser Ser Tyr His
225                 230                 235                 240

Leu Tyr Gly Tyr Asp Ser Trp Gly Gln Gly Thr Leu Val Thr Val Ser
                245                 250                 255

Ser
```

<210> SEQ ID NO 81
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Pro Val Leu Thr Gln Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Leu Met
        35                  40                  45

Arg Val Asp Thr Gly Gly Ile Val Gly Ser Lys Gly Asp Gly Ile Pro
    50                  55                  60

Asp Arg Phe Ser Val Ser Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val Trp Val Phe Gly Gly Gly Thr Lys
            100                 105                 110

Leu Thr Val Leu Gly Ser Arg Gly Gly Gly Ser Gly Gly Gly Gly
        115                 120                 125

Ser Gly Gly Gly Gly Ser Leu Glu Met Ala Gln Val Gln Leu Val Gln
130                 135                 140

Ser Gly Ala Glu Val Lys Lys Pro Gly Ser Ser Val Lys Val Ser Cys
145                 150                 155                 160

Lys Ala Ser Gly Gly Thr Phe Ser Ser Tyr Ala Ile Ser Trp Val Arg
            165                 170                 175

Gln Ala Pro Gly Gln Gly Leu Glu Trp Met Gly Gly Ile Ile Pro Ile
        180                 185                 190

Phe Ser Thr Ala Asn Tyr Ala Gln Lys Phe Gln Gly Arg Val Thr Met
    195                 200                 205

Thr Thr Asp Thr Ser Thr Ser Thr Ala Tyr Met Glu Leu Arg Ser Leu
210                 215                 220

Arg Ser Asp Asp Thr Ala Val Tyr Tyr Cys Ala Arg Gln Pro Trp Thr
225                 230                 235                 240

Trp Tyr Ser Pro Tyr Asp Gln Trp Gly Gln Gly Thr Leu Val Thr Val
            245                 250                 255

Ser Ser

<210> SEQ ID NO 82
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala

```
                    85                  90                  95
Leu Gln Thr Pro Leu Thr Phe Gly Gly Gly Thr Lys Val Glu Ile Lys
                100                 105                 110

Arg Ser Arg Gly Gly Gly Ser Gly Gly Gly Ser Gly Gly Gly
            115                 120                 125

Gly Ser Leu Glu Met Ala Glu Val Gln Leu Val Glu Thr Gly Gly Gly
        130                 135                 140

Leu Val Gln Pro Gly Gly Ser Leu Arg Leu Ser Cys Ala Ala Ser Gly
145                 150                 155                 160

Phe Thr Phe Ser Thr Tyr Ala Met Thr Trp Val Arg Gln Ala Pro Gly
                165                 170                 175

Lys Gly Leu Glu Trp Val Ser Ala Ile Thr Pro Gly Gly Asp Arg Thr
            180                 185                 190

Tyr Tyr Ala Asp Ser Val Lys Gly Arg Phe Thr Ile Ser Arg Asp Asn
        195                 200                 205

Ser Arg Asn Thr Leu Tyr Leu Gln Met Asn Ser Leu Arg Ala Glu Asp
    210                 215                 220

Thr Ala Val Tyr Tyr Cys Ala Arg Tyr Tyr Gly Tyr Met Ile Asp Met
225                 230                 235                 240

Trp Gly Gln Gly Thr Leu Val Thr Val Ser Ser
                245                 250

<210> SEQ ID NO 83
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ala Ser Ala Ser Leu Ala Ile Ser Trp Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Ser
            100                 105                 110

Arg Gly Gly Gly Ser Gly Gly Gly Ser Gly Gly Gly Ser
        115                 120                 125

Leu Glu Met Ala Gln Met Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Gly Tyr Tyr Val His Trp Leu Arg Gln Ala Pro Gly Gln Gly
                165                 170                 175

Leu Glu Trp Met Gly Trp Ile Asn Pro Asn Ser Gly Gly Thr Asn Asn
            180                 185                 190
```

```
Ala Gln Glu Phe Gln Gly Arg Ile Thr Met Thr Arg Asp Thr Ser Ile
            195                 200                 205

Asn Thr Ala Tyr Met Glu Leu Ser Arg Leu Arg Ser Asp Asp Thr Ala
    210                 215                 220

Val Tyr Tyr Cys Ala Arg Ser Gln Trp Gly Thr Tyr Asp Tyr Trp
225                 230                 235                 240

Gly Gln Gly Thr Leu Val Thr Val Ser Ser
                245                 250

<210> SEQ ID NO 84
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Tyr
            20                  25                  30

Thr Val Ser Trp Tyr Gln Gln Leu Pro Gly Thr Ala Pro Lys Phe Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Asp
145                 150                 155                 160

Phe Thr Thr Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Val Arg Gly Arg Val Thr Ile Ser Ala Asp Lys Ser Ile
        195                 200                 205

Asn Thr Ala Tyr Leu Gln Trp Ser Ser Leu Glu Ala Ser Asp Thr Ala
    210                 215                 220

Met Tyr Tyr Cys Ala Arg Met Trp Thr Phe Ser Gln Asp Gly Trp Gly
225                 230                 235                 240

Gln Gly Thr Leu Val Thr Val Ser Ser
                245

<210> SEQ ID NO 85
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 85

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
            115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser

<210> SEQ ID NO 86
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

```
Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly
        115                 120                 125

Ser Leu Glu Met Ala Gln Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Asp Tyr Tyr Met His Trp Val Arg Gln Ala Pro Gly Gln
                165                 170                 175

Arg Leu Glu Trp Met Gly Trp Ile Asn Pro Asn Ser Gly Gly Thr Asn
            180                 185                 190

Tyr Ala Gln Lys Phe Gln Asp Arg Ile Thr Val Thr Arg Asp Thr Ser
        195                 200                 205

Ser Asn Thr Gly Tyr Met Glu Leu Thr Arg Leu Arg Ser Asp Asp Thr
    210                 215                 220

Ala Val Tyr Tyr Cys Ala Arg Ser Pro Tyr Ser Gly Val Leu Asp Lys
225                 230                 235                 240

Trp Gly Gln Gly Thr Leu Val Thr Val Ser Ser
                245                 250
```

<210> SEQ ID NO 87
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Phe Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly
            100                 105                 110

Ser Arg Gly Gly Gly Gly Ser Gly Gly Gly Ser Gly Gly Gly
        115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Thr Ala Asn
            180                 185                 190

Tyr Ala Gln Lys Phe Gln Gly Arg Val Thr Ile Thr Ala Asp Glu Ser
        195                 200                 205
```

Thr Ser Thr Ala Tyr Met Glu Leu Ser Ser Leu Arg Ser Glu Asp Thr
    210                 215                 220

Ala Val Tyr Tyr Cys Ala Arg Ser Gly Tyr Gly Ser Tyr Arg Trp Glu
225                 230                 235                 240

Asp Ser Trp Gly Gln Gly Thr Leu Val Thr Val Ser Ser
                245                 250

<210> SEQ ID NO 88
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser
                245

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Val Ser Ser Asn Ser Ala Ala Trp Asn
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Tyr Arg Ser Lys Trp Tyr Asn
1               5

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Gln Gly Tyr Ser Tyr Tyr Gly Tyr Ser Asp Val
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Ser Asn Ile Gly His Asn Asp
1               5

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Asp Asp
1

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ala Trp Asp Gly Ser Leu Asn Ala Phe Val
1               5                   10

<210> SEQ ID NO 95
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 95

Val Ser Ser Asn Ser Ala Ala Trp Asn
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Arg Ser Lys Trp Tyr Asn
1               5

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Tyr Gly Phe Ser Gly Ser Arg Phe Tyr Asp Thr
1               5                   10

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ser Asn Ile Gly Asn Asn Ala
1               5

<210> SEQ ID NO 99
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Phe Asp Asp
1

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ala Trp Asp Asp Ser Leu Asn Gly Tyr Val
1               5                   10
```

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Thr Phe Ser Ser Tyr Ala
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Ile Pro Ile Leu Gly Ile Ala
1               5

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Arg Ser Gly Tyr Ser Lys Ser Ile Val Ser Tyr Met Asp Tyr
1               5                   10                  15

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ser Asn Ile Gly Ser Asn Val
1               5

<210> SEQ ID NO 105
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Asn Asn
1

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 106

Ala Ala Trp Asp Asp Ser Leu Ser Gly Tyr Val
1               5                   10

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Tyr Thr Phe Thr Ser Tyr Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Asn Pro Ser Gly Gly Ser Thr
1               5

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Arg Ser Gln Trp Gly Gly Val Leu Asp Tyr
1               5                   10

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Ser Asn Ile Gly Ala Arg Tyr Asp
1               5

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Asn Asn
1

<210> SEQ ID NO 112
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 112

Gln Ser Tyr Asp Ser Ser Leu Ser Ala Ser Val
1               5                   10

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Thr Phe Ser Ser Tyr Ala
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Ile Pro Ile Leu Gly Ile Ala
1               5

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Arg Thr Gly Tyr Glu Ser Trp Gly Ser Tyr Glu Val Ile Asp Arg
1               5                   10                  15

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Ser Asn Ile Gly Ser Asn Thr
1               5

<210> SEQ ID NO 117
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Asn Asn
1
```

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Ala Trp Asp Asp Ser Leu Asn Gly Val Val
1               5                   10

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Gly Thr Phe Ser Ser Tyr Ala
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Ile Pro Ile Leu Gly Ile Ala
1               5

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Arg Gly Gly Tyr Tyr Ser His Asp Met Trp Ser Glu Asp
1               5                   10

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Ser Asn Ile Gly Ser Asn Ser
1               5

<210> SEQ ID NO 123
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 123

Ser Asn Asn
1

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Thr Trp Asp Asp Asn Leu Asn Val His Tyr Val
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Gly Ser Ile Ser Asn Ser Asn Trp
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ile Tyr His Ser Gly Ser Thr
1               5

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Arg Arg Asp Asn Trp Lys Thr Pro Thr Thr Lys Ile Asp Gly Phe
1               5                   10                  15

Asp Ile

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Gly Tyr Ser Asn Tyr Lys
1               5
```

```
<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Val Gly Thr Gly Gly Ile Val Gly
1               5

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Ala Asp His Gly Ser Gly Ser Asn Phe Val Tyr Val
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Tyr Thr Phe Thr Gly Tyr Tyr
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Asn Pro Asn Ser Gly Gly Thr
1               5

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Arg Ser Gln Trp Gly Ser Ser Trp Asp Tyr
1               5                   10

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134
```

```
Gln Ser Ile Ser Ser Tyr
1               5

<210> SEQ ID NO 135
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ala Ser
1

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Gln Ser Tyr Ser Thr Pro Pro Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Tyr Thr Phe Thr Gly Tyr Tyr
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Asn Pro Asn Ser Gly Gly Thr
1               5

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Arg Ser Ser Tyr His Leu Tyr Gly Tyr Asp Ser
1               5                   10

<210> SEQ ID NO 140
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 140

Asn Asp Tyr Thr Asn Tyr Lys
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Val Gly Pro Gly Gly Ile Val Gly
1               5

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Ala Asp His Gly Thr Gly Ser Asn Phe Val Tyr Val
1               5                   10

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Thr Phe Ser Ser Tyr Ala
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ile Ile Pro Ile Phe Ser Thr Ala
1               5

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Arg Gln Pro Trp Thr Trp Tyr Ser Pro Tyr Asp Gln
1               5                   10
```

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Gly Tyr Ser Asn Tyr Lys
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Asp Thr Gly Gly Ile Val Gly
1               5

<210> SEQ ID NO 148
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ala Asp His Gly Ser Gly Ser Asn Phe Val Trp Val
1               5                   10

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Phe Thr Phe Ser Thr Tyr Ala
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Thr Pro Gly Gly Asp Arg Thr
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 151

Ala Arg Tyr Tyr Gly Tyr Met Ile Asp Met
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Ser Leu Leu His Ser Asn Gly Tyr Asn Tyr
1               5                   10

<210> SEQ ID NO 153
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Leu Gly Ser
1

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Met Gln Ala Leu Gln Thr Pro Leu Thr
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Tyr Thr Phe Thr Gly Tyr Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Asn Pro Asn Ser Gly Gly Thr
1               5

<210> SEQ ID NO 157
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 157

Ala Arg Ser Gln Trp Gly Gly Thr Tyr Asp Tyr
1               5                   10

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Ser Asn Ile Gly Ser Asn Thr
1               5

<210> SEQ ID NO 159
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Asn Asn
1

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Ala Trp Asp Asp Ser Leu Asn Gly Trp Val
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Tyr Asp Phe Thr Thr Tyr Trp
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ile Tyr Pro Gly Asp Ser Asp Thr
1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Arg Met Trp Thr Phe Ser Gln Asp Gly
1               5                   10

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ser Asn Ile Gly Ser Tyr Thr
1               5

<210> SEQ ID NO 165
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Asn Asn
1

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ala Trp Asp Asp Ser Leu Asn Gly Tyr Val
1               5                   10

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Tyr Thr Phe Ile Asp Tyr Tyr
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 168

Ile Asn Pro Asn Ser Gly Gly Thr
1               5

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Arg Ser Gln Arg Asp Gly Tyr Met Asp Tyr
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ile Ser Cys Thr Gly Thr Ser Ser Asp
1               5

<210> SEQ ID NO 171
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Glu Asp Ser
1

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Ser Asn Thr Arg Ser Ser Thr Leu Val
1               5                   10

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Tyr Thr Phe Thr Asp Tyr Tyr
1               5

<210> SEQ ID NO 174
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ile Asn Pro Asn Ser Gly Gly Thr
1               5

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Arg Ser Pro Tyr Ser Gly Val Leu Asp Lys
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Ser Asn Ile Gly Ala Gly Phe Asp
1               5

<210> SEQ ID NO 177
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Asn Ser
1

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gln Ser Tyr Asp Ser Ser Leu Ser Gly Tyr Val
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Gly Thr Phe Ser Ser Tyr Ala
```

```
1               5
```

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Ile Ile Pro Ile Leu Gly Thr Ala
1               5
```

<210> SEQ ID NO 181
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Ala Arg Ser Gly Tyr Gly Ser Tyr Arg Trp Glu Asp Ser
1               5                   10
```

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Ser Ser Asn Ile Gly Ser Asn Tyr
1               5
```

<210> SEQ ID NO 183
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Ser Asn Asn
1
```

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Ala Ala Trp Asp Asp Ser Leu Ser Ala Ser Tyr Val
1               5                   10
```

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Gly Tyr Ser Phe Thr Ser Tyr Trp
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Tyr Pro Gly Asp Ser Asp Thr
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Arg Tyr Ser Gly Ser Phe Asp Asn
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Ser Asn Ile Gly Ser His Ser
1               5

<210> SEQ ID NO 189
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Thr Asn Asn
1

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Ala Trp Asp Gly Ser Leu Asn Gly Leu Val
1               5                   10

<210> SEQ ID NO 191

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Gly Gly Gly Ser Gly Gly Gly Ser Gly Gly Gly Gly Ser
1               5                   10                  15

<210> SEQ ID NO 192
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ggtggaggtg gatcaggtgg aggtggatct ggtggaggtg gatct                45

<210> SEQ ID NO 193
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Gly Gly Gly Ser
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Gly Gly Ser Gly Gly Ser
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Gly Gly Gly Ser Gly Gly Gly Ser
1               5

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Gly Gly Gly Ser Gly Gly Gly Gly Ser
```

```
1               5                   10
```

<210> SEQ ID NO 197
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Gly Gly Gly Gly Ser Gly Gly Gly Ser Gly Gly Gly Gly Gly
1               5                   10                  15

Gly Ser
```

<210> SEQ ID NO 198
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 199
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 200
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 201
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

```
Gly Gly Gly Gly Ser Gly Gly Gly Ser Gly Gly Gly Ser Gly
1               5                  10                 15

Gly Gly Gly Ser Gly Gly Gly Ser Gly Gly Gly Ser Gly Gly
                20                  25                  30

Gly Gly Ser
        35

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Glu Pro Lys Ser Cys Asp Lys Thr His Thr Cys Pro Pro Cys Pro
1               5                  10                  15

<210> SEQ ID NO 203
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Gly Gly Ser Gly Gly Gly Ser Glu Pro Lys Ser Cys Asp Lys
1               5                  10                  15

Thr His Thr Cys Pro Pro Cys Pro
            20

<210> SEQ ID NO 204
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Leu Lys Thr Pro Leu Gly Asp Thr Thr His Thr Cys Pro Arg Cys
1               5                  10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
        50                  55                  60

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Ser Gly Ser Gly Ser
1               5
```

```
<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ala Ala Ala
1

<210> SEQ ID NO 207
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Gly Ser Gly Leu Gln Met Ala Gly Gln Cys Ser Gln Asn Glu Tyr
1               5                   10                  15

Phe Asp Ser

<210> SEQ ID NO 208
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Gly Ser Gly Gln Met Ala Gly Gln Cys Ser Gln Asn Glu Tyr Phe
1               5                   10                  15

Asp Ser Leu

<210> SEQ ID NO 209
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Gly Ser Gly Met Ala Gly Gln Cys Ser Gln Asn Glu Tyr Phe Asp
1               5                   10                  15

Ser Leu Leu

<210> SEQ ID NO 210
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ser Gly Ser Gly Ala Gly Gln Cys Ser Gln Asn Glu Tyr Phe Asp Ser
1               5                   10                  15

Leu Leu His

<210> SEQ ID NO 211
```

<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Gly Ser Gly Gly Gln Cys Ser Gln Asn Glu Tyr Phe Asp Ser Leu
1               5                   10                  15

Leu His Ala

<210> SEQ ID NO 212
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Gly Ser Gly Gln Cys Ser Gln Asn Glu Tyr Phe Asp Ser Leu Leu
1               5                   10                  15

His Ala Cys

<210> SEQ ID NO 213
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Gly Ser Gly Cys Ser Gln Asn Glu Tyr Phe Asp Ser Leu Leu His
1               5                   10                  15

Ala Cys Ile

<210> SEQ ID NO 214
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Gly Ser Gly Ser Gln Asn Glu Tyr Phe Asp Ser Leu Leu His Ala
1               5                   10                  15

Cys Ile Pro

<210> SEQ ID NO 215
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Gly Ser Gly Gln Asn Glu Tyr Phe Asp Ser Leu Leu His Ala Cys
1               5                   10                  15

Ile Pro Cys

```
<210> SEQ ID NO 216
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Gly Ser Gly Asn Glu Tyr Phe Asp Ser Leu Leu His Ala Cys Ile
1               5                   10                  15

Pro Cys Gln

<210> SEQ ID NO 217
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ser Gly Ser Gly Glu Tyr Phe Asp Ser Leu Leu His Ala Cys Ile Pro
1               5                   10                  15

Cys Gln Leu

<210> SEQ ID NO 218
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Gly Ser Gly Tyr Phe Asp Ser Leu Leu His Ala Cys Ile Pro Cys
1               5                   10                  15

Gln Leu Arg

<210> SEQ ID NO 219
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Gly Ser Gly Phe Asp Ser Leu Leu His Ala Cys Ile Pro Cys Gln
1               5                   10                  15

Leu Arg Cys

<210> SEQ ID NO 220
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Gly Ser Gly Asp Ser Leu Leu His Ala Cys Ile Pro Cys Gln Leu
1               5                   10                  15

Arg Cys Ser
```

<210> SEQ ID NO 221
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Ser Gly Ser Gly Ser Leu Leu His Ala Cys Ile Pro Cys Gln Leu Arg
1               5                   10                  15

Cys Ser Ser

<210> SEQ ID NO 222
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Ser Gly Ser Gly Leu Leu His Ala Cys Ile Pro Cys Gln Leu Arg Cys
1               5                   10                  15

Ser Ser Asn

<210> SEQ ID NO 223
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Ser Gly Ser Gly Leu His Ala Cys Ile Pro Cys Gln Leu Arg Cys Ser
1               5                   10                  15

Ser Asn Thr

<210> SEQ ID NO 224
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Ser Gly Ser Gly His Ala Cys Ile Pro Cys Gln Leu Arg Cys Ser Ser
1               5                   10                  15

Asn Thr Pro

<210> SEQ ID NO 225
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Ser Gly Ser Gly Ala Cys Ile Pro Cys Gln Leu Arg Cys Ser Ser Asn
1               5                   10                  15

Thr Pro Pro

<210> SEQ ID NO 226
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ser Gly Ser Gly Cys Ile Pro Cys Gln Leu Arg Cys Ser Ser Asn Thr
1               5                   10                  15

Pro Pro Leu

<210> SEQ ID NO 227
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Gly Ser Gly Ile Pro Cys Gln Leu Arg Cys Ser Ser Asn Thr Pro
1               5                   10                  15

Pro Leu Thr

<210> SEQ ID NO 228
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ser Gly Ser Gly Pro Cys Gln Leu Arg Cys Ser Ser Asn Thr Pro Pro
1               5                   10                  15

Leu Thr Cys

<210> SEQ ID NO 229
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Gly Ser Gly Cys Gln Leu Arg Cys Ser Ser Asn Thr Pro Pro Leu
1               5                   10                  15

Thr Cys Gln

<210> SEQ ID NO 230
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Gly Ser Gly Gln Leu Arg Cys Ser Ser Asn Thr Pro Pro Leu Thr
1               5                   10                  15

-continued

Cys Gln Arg

<210> SEQ ID NO 231
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ser Gly Ser Gly Leu Arg Cys Ser Ser Asn Thr Pro Pro Leu Thr Cys
1               5                   10                  15

Gln Arg Tyr

<210> SEQ ID NO 232
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Gly Ser Gly Arg Cys Ser Ser Asn Thr Pro Pro Leu Thr Cys Gln
1               5                   10                  15

Arg Tyr Cys

<210> SEQ ID NO 233
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Gly Ser Gly Cys Ser Ser Asn Thr Pro Pro Leu Thr Cys Gln Arg
1               5                   10                  15

Tyr Cys Asn

<210> SEQ ID NO 234
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Gly Ser Gly Ser Ser Asn Thr Pro Pro Leu Thr Cys Gln Arg Tyr
1               5                   10                  15

Cys Asn Ala

<210> SEQ ID NO 235
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Gly Ser Gly Ser Asn Thr Pro Pro Leu Thr Cys Gln Arg Tyr Cys
1               5                   10                  15

Asn Ala Ser

<210> SEQ ID NO 236
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Gly Ser Gly Asn Thr Pro Pro Leu Thr Cys Gln Arg Tyr Cys Asn
1               5                   10                  15

Ala Ser Val

<210> SEQ ID NO 237
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Gly Ser Gly Thr Pro Pro Leu Thr Cys Gln Arg Tyr Cys Asn Ala
1               5                   10                  15

Ser Val Thr

<210> SEQ ID NO 238
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Gly Ser Gly Pro Pro Leu Thr Cys Gln Arg Tyr Cys Asn Ala Ser
1               5                   10                  15

Val Thr Asn

<210> SEQ ID NO 239
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Gly Ser Gly Pro Leu Thr Cys Gln Arg Tyr Cys Asn Ala Ser Val
1               5                   10                  15

Thr Asn Ser

<210> SEQ ID NO 240
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ser Gly Ser Gly Leu Thr Cys Gln Arg Tyr Cys Asn Ala Ser Val Thr

-continued

```
1               5                   10                  15

Asn Ser Val

<210> SEQ ID NO 241
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Gly Ser Gly Thr Cys Gln Arg Tyr Cys Asn Ala Ser Val Thr Asn
1               5                   10                  15

Ser Val Lys

<210> SEQ ID NO 242
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Gly Ser Gly Cys Gln Arg Tyr Cys Asn Ala Ser Val Thr Asn Ser
1               5                   10                  15

Val Lys Gly

<210> SEQ ID NO 243
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Gly Ser Gly Gln Arg Tyr Cys Asn Ala Ser Val Thr Asn Ser Val
1               5                   10                  15

Lys Gly Thr

<210> SEQ ID NO 244
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ser Gly Ser Gly Arg Tyr Cys Asn Ala Ser Val Thr Asn Ser Val Lys
1               5                   10                  15

Gly Thr Asn

<210> SEQ ID NO 245
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245
```

```
Ser Gly Ser Gly Tyr Cys Asn Ala Ser Val Thr Asn Ser Val Lys Gly
1               5                   10                  15

Thr Asn Ala

<210> SEQ ID NO 246
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Ser Gly Gln Ala Gly Gln His His His His His His Gly Ala Tyr
1               5                   10                  15

Pro Tyr Asp Val Pro Asp Tyr Ala Ser
            20                  25

<210> SEQ ID NO 247
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
actagtggcc aggccggcca gcaccatcac catcaccatg gcgcataccc gtacgacgtt    60
ccggactacg cttct                                                    75

<210> SEQ ID NO 248
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ser Gly Ser Gly
1

<210> SEQ ID NO 249
<211> LENGTH: 53
<212> TYPE: PRT
<213> ORGANISM: Homo sapiens

<400> SEQUENCE: 249

Leu Gln Met Ala Gly Gln Cys Ser Gln Asn Glu Tyr Phe Asp Ser Leu
1               5                   10                  15

Leu His Ala Cys Ile Pro Cys Gln Leu Arg Cys Ser Ser Asn Thr Pro
            20                  25                  30

Pro Leu Thr Cys Gln Arg Tyr Cys Asn Ala Ser Val Thr Asn Ser Val
        35                  40                  45

Lys Gly Thr Asn Ala
        50
```